(12) United States Patent
Sidhu et al.

(10) Patent No.: US 12,240,909 B2
(45) Date of Patent: Mar. 4, 2025

(54) HUMAN ANTIBODIES TO HUMAN INTERLEUKIN 18 RECEPTOR ALPHA OR BETA

(71) Applicants: ShanghaiTech University, Pudong New Area (CN); The Governing Council of the University of Toronto, Toronto (CA)

(72) Inventors: Sachedv S. Sidhu, Toronto (CA); Donghui Wu, Shanghai (CN); Guohua James Pan, Toronto (CA); Shusu Liu, Shanghai (CN); Shane Miersch, Toronto (CA); Haiming Huang, Toronto (CA)

(73) Assignees: ShanghaiTech University, Shanghai (CN); The Governing Council of the University of Toronto, Toronto (CA)

( * ) Notice: Subject to any disclaimer, the term of this patent is extended or adjusted under 35 U.S.C. 154(b) by 70 days.

(21) Appl. No.: 17/254,248

(22) PCT Filed: Jun. 19, 2019

(86) PCT No.: PCT/CN2019/091936
§ 371 (c)(1),
(2) Date: Dec. 18, 2020

(87) PCT Pub. No.: WO2019/242655
PCT Pub. Date: Dec. 26, 2019

(65) Prior Publication Data
US 2024/0262919 A1  Aug. 8, 2024

(30) Foreign Application Priority Data

Jun. 19, 2018 (WO) ............... PCT/CN2018/091780

(51) Int. Cl.
C07K 16/28 (2006.01)
(52) U.S. Cl.
CPC ...... *C07K 16/2866* (2013.01); *C07K 2317/31* (2013.01); *C07K 2317/55* (2013.01); *C07K 2317/565* (2013.01); *C07K 2317/92* (2013.01)
(58) Field of Classification Search
CPC .............. C07K 16/2866; C07K 2317/565
USPC ......................... 424/133.1, 139, 1
See application file for complete search history.

(56) References Cited

U.S. PATENT DOCUMENTS

| 6,600,022 | B1 | 7/2003 | Torigoe et al. |
| 2002/0068060 | A1 | 6/2002 | Abrams |
| 2008/0063644 | A1 | 3/2008 | Sekiyama |
| 2011/0069187 | A1 | 11/2011 | Yokota |

FOREIGN PATENT DOCUMENTS

| CA | 3104362 A1 | * | 12/2019 |
| CN | 101835489 A | | 9/2010 |
| JP | 2006-206524 | | 8/2006 |
| WO | WO 2009/015284 A2 | | 1/2009 |
| WO | WO 2012/015662 A1 | | 2/2012 |
| WO | WO 2012/025536 A1 | | 3/2012 |
| WO | WO 2015/032932 A1 | | 3/2015 |
| WO | WO 2023133842 | * | 7/2023 |
| WO | WO 2023134767 | * | 7/2023 |

OTHER PUBLICATIONS

Hamasaki et al (J Biochem Oct. 2005;138(4):433-42).*
Edwards et al., J Mol Biol 334:103-118 (2003).*
Marchalonis et al., Dev & Comp Immunol. 30:223-247 (2006).*
Lippow et al., Nature Biotechnology, 25(10):1171-1176 (2007).*
Sulea et al., Scientific Reports, 8(260): 1-11 (2018).*
Hasegawa et al., MABS, vol. 9, No. 5, pp. 854-873 (2017).*
Altshuler et al., Biochemistry (Moscow), 75(13): 1584-1605 (2010).*
Vajda et al., Current Opinion in Structural Biology, 67 pp. 226-231 (2021).*
Marks et al., J. Biol. Chem. 295(29) 9823-9837 (2020).*
Akbar et al., Cell Reports 34, 108856, Mar. 16, 2021).*
Lo et al., BMC Genomics vol. 22, Article No. 116 (2021).*
Creative Biolabs (product data sheet: Human Anti-IL18RAP Recombinant Antibody (clone 3131); pp. 1-2; Oct. 28, 2024)).*
Desroches, C.V. et al. Monoclonal antibodies specific for the IL-18 receptor. Cellular Immunology. Sep. 12, 2005 (Sep. 12, 2005) vol. 236 abstract, p. 102.
UniProtKB-095256 (I18RA_HUMAN) Uniprot. May 1, 1999.
European Search Report and Opinion dated Mar. 11, 2022 for EP Application No. 19823445.2. 12 pages.
Bardelli, et al. Epitope mapping by solution NMR spectroscopy. Journal of Molecular Recognition. Feb. 2015; 28(6):393-400.
Simonyan, et al. Conformational Epitope Mapping by Cross-link Mass Spectrometry: Analysis of Ipilimumab, Nivolumab and Pembrolizumab. Nov. 15, 2017.https://covalx.com/pdf/171113-CovalX-XLMS%20Xray%20Comparions-PEGSEU17.pdf. 1 page.

* cited by examiner

*Primary Examiner* — Lynn A Bristol
(74) *Attorney, Agent, or Firm* — Sheppard Mullin & Hampton LLP

(57) ABSTRACT

Provided are antibodies or fragments thereof having binding specificity to anti-IL-18 receptor alpha or beta. Methods of using the antibodies or fragments thereof for treating and diagnosing diseases such as cancer and inflammatory and autoimmune diseases are also provided.

6 Claims, 12 Drawing Sheets

Specification includes a Sequence Listing.

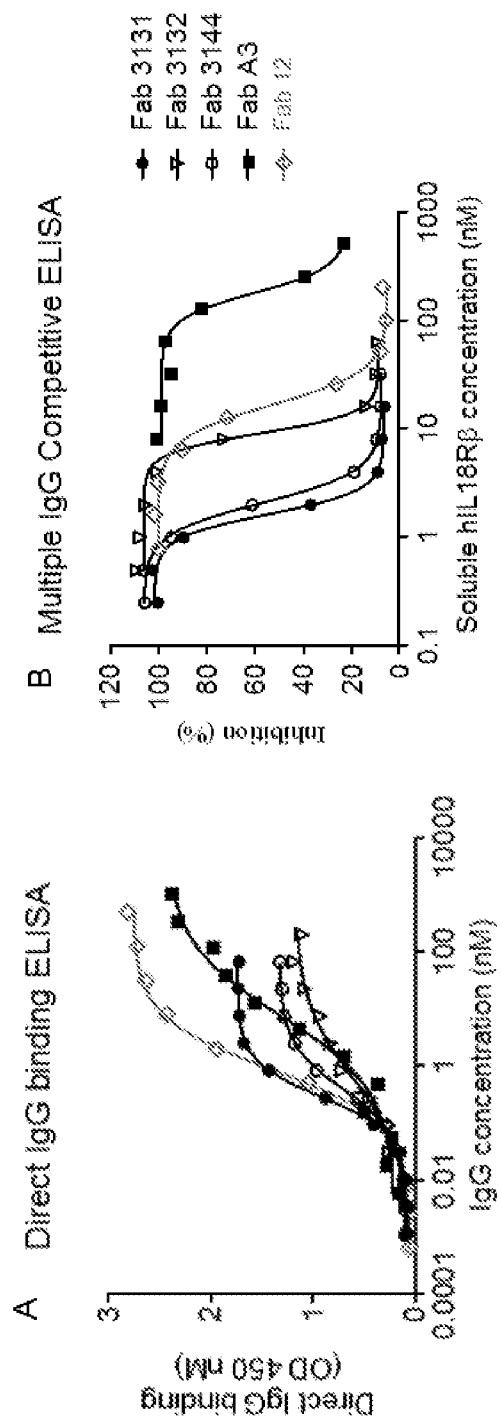
FIG. 2A-B

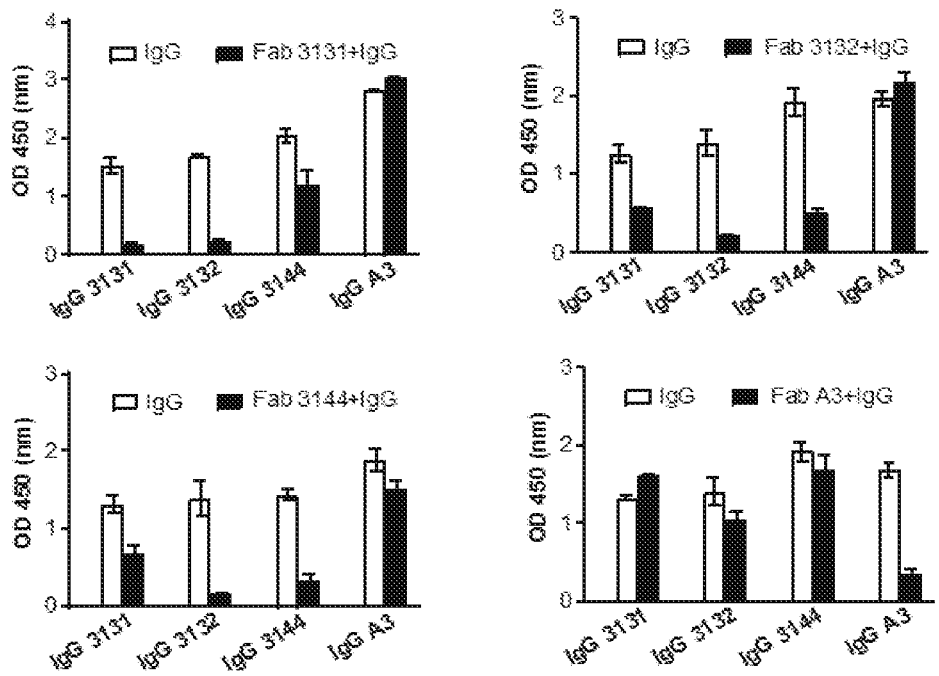
FIG. 2C-D

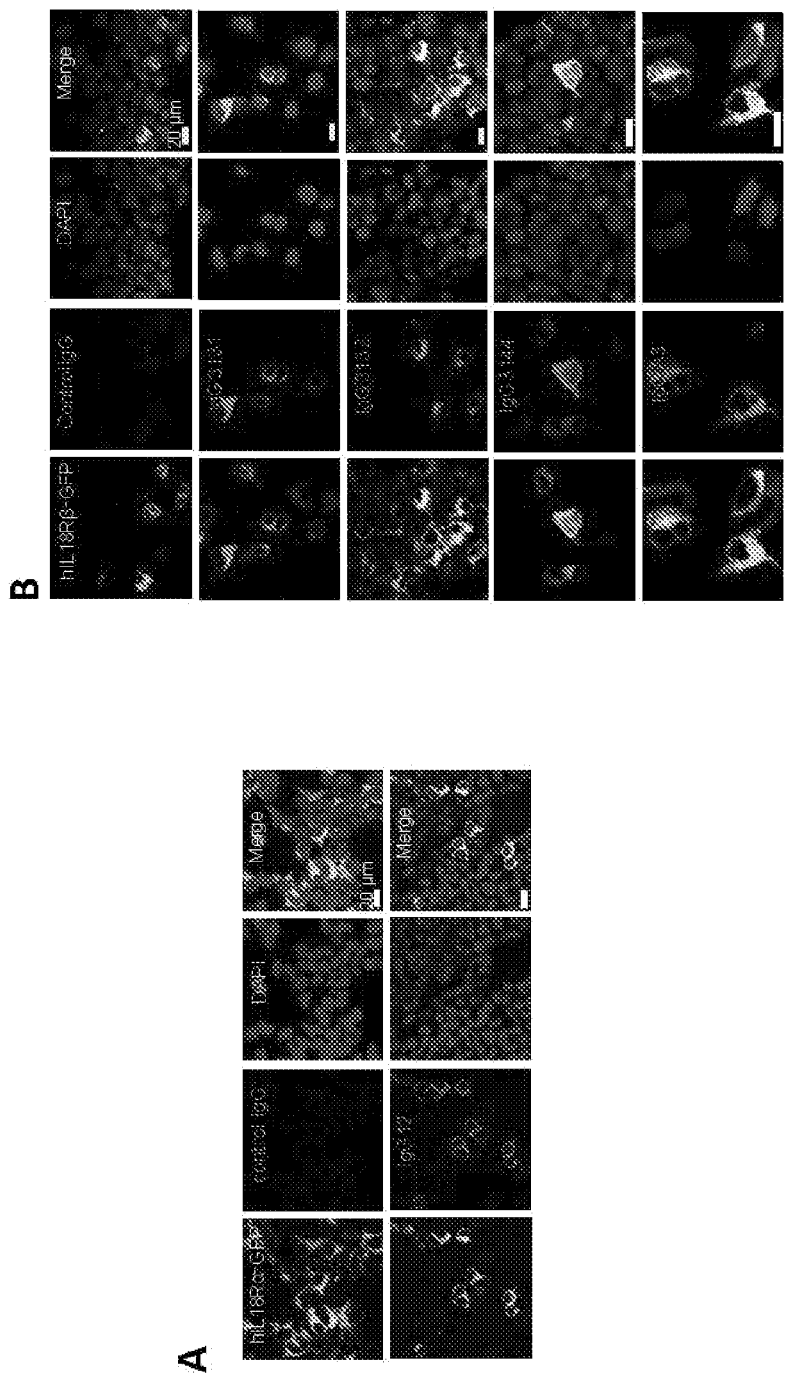
FIG. 3A-B

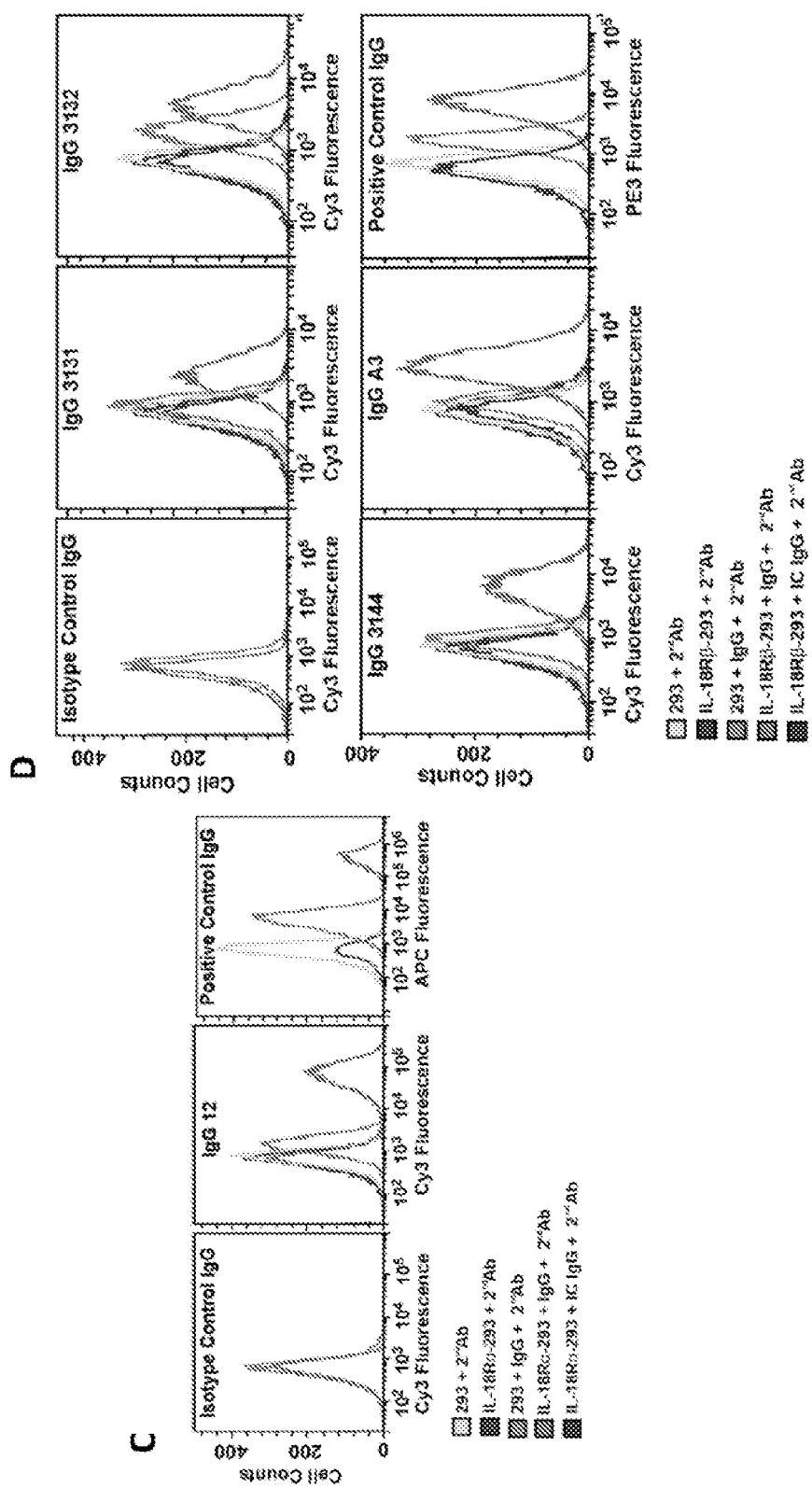
FIG. 3C-D

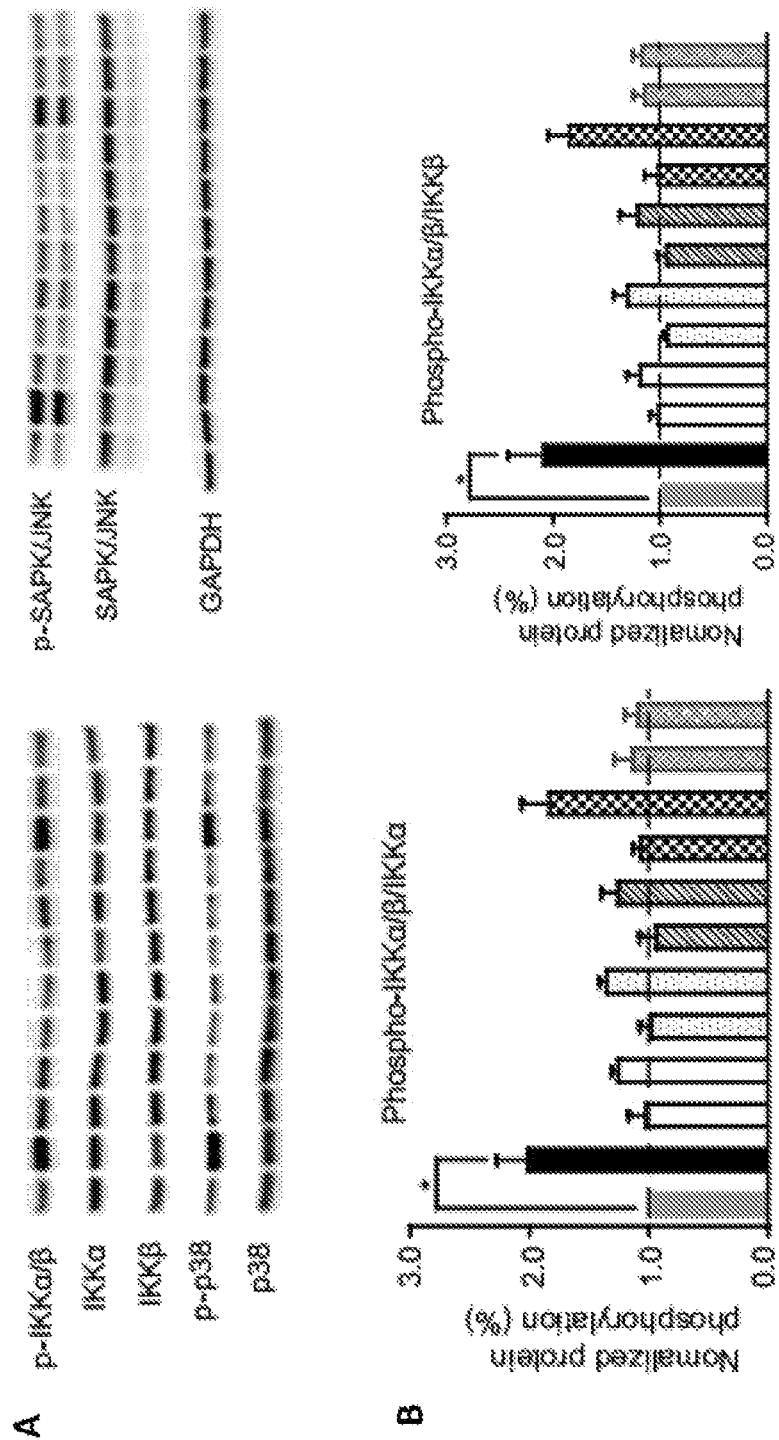
FIG. 4A-B

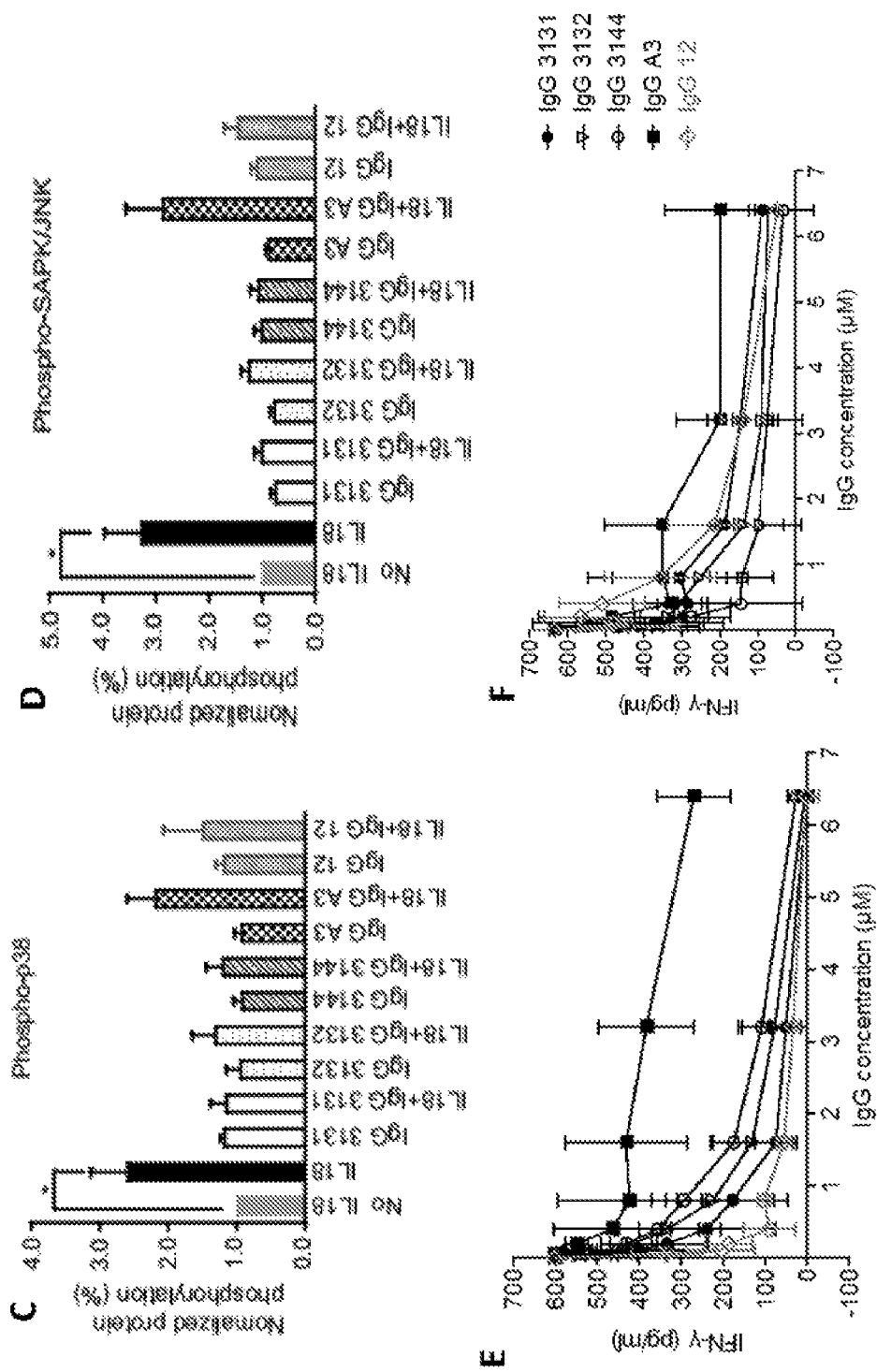
FIG. 4C-F

SEQUENCE LISTING

<160> NUMBER OF SEQ ID NOS: 352

<210> SEQ ID NO 1
<211> LENGTH: 696
<212> TYPE: DNA
<213> ORGANISM: Artificial Sequence
<220> FEATURE:
<223> OTHER INFORMATION: Synthetic

<400> SEQUENCE: 1
gaggttcagc tggtggagtc tggcggtggc ctggtgcagc cagggggctc actccgtttg      60
tcctgtgcag cttctggctt caacctctat tattcttcta tgcactgggt gcgtcaggcc     120
ccgggtaagg gcctggaatg ggttgcatct atttattctt cttatggcta tacttattat     180
gccgatagcg tcaagggccg tttcactata agcgcagaca catccaaaaa cacagcctac     240
ctacaaatga acagcttaag agctgaggac actgccgtct attattgtgc tcgctcttct     300
ttctctcatg gttacggttg gtacggtttg gactactggg gtcaaggaac cctggtcacc     360
gtctcctcgg cctccaccaa gggtccatcg gtcttccccc tggcaccctc ctccaagagc     420
acctctgggg gcacagcggc cctgggctgc ctggtcaagg actacttccc cgaaccggtg     480
acggtgtcgt ggaactcagg cgccctgacc agcggcgtgc acaccttccc ggctgtccta     540
cagtcctcag gactctactc cctcagcagc gtggtgaccg tgccctccag cagcttgggc     600
acccagacct acatctgcaa cgtgaatcac aagcccagca caccaaggt cgacaagaaa     660 gttgagccca atcttgtga caaaactcac acataa                                696

<210> SEQ ID NO 2
<211> LENGTH: 231
<212> TYPE: PRT
<213> ORGANISM: Artificial Sequence
<220> FEATURE:
<223> OTHER INFORMATION: Synthetic

<400> SEQUENCE: 2

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Leu Tyr Tyr Ser
            20                  25                  30

Ser Met His Trp Val Arg Gln Ala Pro Gly Lys Gly Leu Glu Trp Val
        35                  40                  45

Ala Ser Ile Tyr Ser Ser Tyr Gly Tyr Thr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ser Ser Phe Ser His Gly Tyr Gly Trp Tyr Gly Leu Asp Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Val Val
                180                 185                 190

Thr Val Pro Ser Ser Leu Gly Thr Gln Thr Tyr Ile Cys Asn Val
            195                 200                 205

Asn His Lys Pro Ser Asn Thr Lys Val Asp Lys Lys Val Glu Pro Lys
        210                 215                 220

Ser Cys Asp Lys Thr His Thr
225                 230

<210> SEQ ID NO 3
<211> LENGTH: 687
<212> TYPE: DNA
<213> ORGANISM: Artificial Sequence
<220> FEATURE:
<223> OTHER INFORMATION: Synthetic

<400> SEQUENCE: 3

```
gatatccaga tgacccagtc cccgagctcc ctgtccgcct ctgtgggcga tagggtcacc      60
atcacctgcc gtgccagtca gtccgtgtcc agcgctgtag cctggtatca acagaaacca    120
ggaaaagctc cgaagcttct gatttactcg gcatccagcc tctactctgg agtcccttct    180
cgcttctctg gtagccgttc cgggacggat ttcactctga ccatcagcag tctgcagccg    240
gaagacttcg caacttatta ctgtcagcaa tacggttacc attacgctgg tctgatcacg    300
ttcggacagg gtaccaaggt ggagatcaaa cgaactgtgg ctgcaccatc tgtcttcatc    360
ttcccgccat ctgattcaca gttgaaatct ggaactgcct ctgttgtgtg cctgctgaat    420
aacttctatc ccagagaggc caaagtacag tggaaggtgg ataacgccct ccaatcgggt    480
aactcccagg agagtgtcac agagcaggac agcaaggaca gcacctacag cctcagcagc    540
accctgacgc tgagcaaagc agactacgaa aacataaag tctacgcctg cgaagtcacc    600
catcagggcc tgagctcgcc cgtcacaaag agcttcaaca ggggagagtg tggtggttct    660
gattacaaag atgacgatga caaataa                                        687
```

<210> SEQ ID NO 4
<211> LENGTH: 228
<212> TYPE: PRT
<213> ORGANISM: Artificial Sequence
<220> FEATURE:
<223> OTHER INFORMATION: Synthetic

<400> SEQUENCE: 4

Asp Ile Gln Met Thr Gln Ser Pro Ser Ser Leu Ser Ala Ser Val Gly
1               5                  10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Gly Tyr His Tyr Ala
                85                  90                  95

Gly Leu Ile Thr Phe Gly Gln Gly Thr Lys Val Glu Ile Lys Arg Thr
            100                 105                 110

Val Ala Ala Pro Ser Val Phe Ile Phe Pro Pro Ser Asp Ser Gln Leu
        115                 120                 125

-continued

Lys Ser Gly Thr Ala Ser Val Cys Leu Leu Asn Asn Phe Tyr Pro
            130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys Gly Gly Ser Tyr Lys Asp
    210                 215                 220

Asp Asp Asp Lys
225

<210> SEQ ID NO 5
<211> LENGTH: 672
<212> TYPE: DNA
<213> ORGANISM: Artificial Sequence
<220> FEATURE:
<223> OTHER INFORMATION: Synthetic

<400> SEQUENCE: 5
gaggttcagc tggtggagtc tggcggtggc ctggtgcagc caggggggctc actccgtttg      60 tcctgtgcag cttctggctt caacatctct tattattata tccactgggt gcgtcaggcc     120
ccgggtaagg gcctggaatg ggttgcatct atttattctt attctggcta tacttcttat     180
gccgatagcg tcaagggccg tttcactata agcgcagaca catccaaaaa cacagcctac     240
ctacaaatga acagcttaag agctgaggac actgccgtct attattgtgc tcgcgcttct     300
gctatggact actggggtca aggaaccctg gtcaccgtct cctcggcctc caccaagggt     360
ccatcggtct tccccctggc accctcctcc aagagcacct ctgggggcac agcggccctg     420
ggctgcctgg tcaaggacta cttccccgaa ccggtgacgg tgtcgtggaa ctcaggcgcc     480
ctgaccagcg gcgtgcacac cttcccggct gtcctacagt cctcaggact ctactccctc     540
agcagcgtgg tgaccgtgcc ctccagcagc ttgggcaccc agacctacat ctgcaacgtg     600
aatcacaagc ccagcaacac caaggtcgac aagaaagttg agcccaaatc ttgtgacaaa     660
actcacacat aa                                                          672

<210> SEQ ID NO 6
<211> LENGTH: 223
<212> TYPE: PRT
<213> ORGANISM: Artificial Sequence
<220> FEATURE:
<223> OTHER INFORMATION: Synthetic

<400> SEQUENCE: 6

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Ser Tyr Tyr
            20                  25                  30

Tyr Ile His Trp Val Arg Gln Ala Pro Gly Lys Gly Leu Glu Trp Val
        35                  40                  45

Ala Ser Ile Tyr Ser Tyr Ser Gly Tyr Thr Ser Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
            85                  90                  95

Ala Arg Ala Ser Ala Met Asp Tyr Trp Gly Gln Gly Thr Leu Val Thr
        100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
            165                 170                 175

Leu Tyr Ser Leu Ser Ser Val Val Thr Val Pro Ser Ser Ser Leu Gly
        180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr
    210                 215                 220

<210> SEQ ID NO 7
<211> LENGTH: 687
<212> TYPE: DNA
<213> ORGANISM: Artificial Sequence
<220> FEATURE:
<223> OTHER INFORMATION: Synthetic

<400> SEQUENCE: 7
gatatccaga tgacccagtc cccgagctcc ctgtccgcct ctgtgggcga tagggtcacc      60
atcacctgcc gtgccagtca gtccgtgtcc agcgctgtag cctggtatca acagaaacca    120
ggaaaagctc cgaagcttct gatttactcg gcatccagcc tctactctgg agtcccttct    180
cgcttctctg gtagccgttc cgggacggat ttcactctga ccatcagcag tctgcagccg    240
gaagacttcg caacttatta ctgtcagcaa cattgtgggg cttctgttcc gccgttcacg    300
ttcggacagg gtaccaaggt ggagatcaaa cgaactgtgg ctgcaccatc tgtcttcatc    360
ttcccgccat ctgattcaca gttgaaatct ggaactgcct ctgttgtgtg cctgctgaat    420
aacttctatc ccagagaggc caaagtacag tggaaggtgg ataacgccct ccaatcgggt    480
aactcccagg agagtgtcac agagcaggac agcaaggaca gcacctacag cctcagcagc    540
accctgacgc tgagcaaagc agactacgaa aaacataaag tctacgcctg cgaagtcacc    600
catcagggcc tgagctcgcc cgtcacaaag agcttcaaca ggggagagtg tggtggttct    660
gattacaaag atgacgatga caaataa                                        687

<210> SEQ ID NO 8
<211> LENGTH: 228
<212> TYPE: PRT
<213> ORGANISM: Artificial Sequence
<220> FEATURE:
<223> OTHER INFORMATION: Synthetic

<400> SEQUENCE: 8

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Trp Trp Ala Ser Val
                85                  90                  95

Pro Pro Phe Thr Phe Gly Gln Gly Thr Lys Val Glu Ile Lys Arg Thr
            100                 105                 110

Val Ala Ala Pro Ser Val Phe Ile Phe Pro Pro Ser Asp Ser Gln Leu
            115                 120                 125

Lys Ser Gly Thr Ala Ser Val Val Cys Leu Leu Asn Asn Phe Tyr Pro
130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys Gly Gly Ser Asp Tyr Lys Asp
    210                 215                 220

Asp Asp Asp Lys
225

<210> SEQ ID NO 9
<211> LENGTH: 672
<212> TYPE: DNA
<213> ORGANISM: Artificial Sequence
<220> FEATURE:
<223> OTHER INFORMATION: Synthetic

<400> SEQUENCE: 9
gaggttcagc tggtggagtc tggcggtggc ctggtgcagc caggggggctc actccgtttg      60 tcctgtgcag cttctggctt caacctctct tattattcta tccactgggt gcgtcaggcc     120
ccgggtaagg gcctggaatg ggttgcatct atttattctt attctggcta tacttcttat     180
gccgatagcg tcaagggccg tttcactata agcgcagaca catccaaaaa cacagcctac     240
ctacaaatga acagcttaag agctgaggac actgccgtct attattgtgc tcgctcttct     300
gctatggact actggggtca aggaaccctg gtcaccgtct cctcggcctc caccaagggt     360
ccatcggtct tcccctggc accctcctcc aagagcacct ctgggggcac agcggccctg     420
ggctgcctgg tcaaggacta cttccccgaa ccggtgacgg tgtcgtggaa ctcaggcgcc     480
ctgaccagcg gcgtgcacac cttcccggct gtcctacagt cctcaggact ctactccctc     540
agcagcgtgg tgaccgtgcc ctccagcagc ttgggcaccc agacctacat ctgcaacgtg     600
aatcacaagc ccagcaacac caaggtcgac aagaaagttg agcccaaatc ttgtgacaaa     660
actcacacat aa                                                         672

<210> SEQ ID NO 10

<211> LENGTH: 223
<212> TYPE: PRT
<213> ORGANISM: Artificial Sequence
<220> FEATURE:
<223> OTHER INFORMATION: Synthetic

<400> SEQUENCE: 10

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Leu Ser Tyr Tyr
            20                  25                  30

Ser Ile His Trp Val Arg Gln Ala Pro Gly Lys Gly Leu Glu Trp Val
        35                  40                  45

Ala Ser Ile Tyr Ser Tyr Ser Gly Tyr Thr Ser Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ser Ser Ala Met Asp Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr
    210                 215                 220
```

<210> SEQ ID NO 11
<211> LENGTH: 684
<212> TYPE: DNA
<213> ORGANISM: Artificial Sequence
<220> FEATURE:
<223> OTHER INFORMATION: Synthetic

<400> SEQUENCE: 11

```
gatatccaga tgacccagtc cccgagctcc ctgtccgcct ctgtgggcga tagggtcacc      60
atcacctgcc gtgccagtca gtccgtgtcc agcgctgtag cctggtatca acagaaacca    120
ggaaaagctc cgaagcttct gatttactcg gcatccagcc tctactctgg agtcccttct    180
cgcttctctg gtagccgttc cgggacggat ttcactctga ccatcagcag tctgcagccg    240
gaagacttcg caacttatta ctgtcagcaa cattggtggg ttacccgct gatcacgttc      300 ggacagggta ccaaggtgga gatcaaacga actgtggctg caccatctgt cttcatcttc    360
ccgccatctg attcacagtt gaaatctgga actgcctctg ttgtgtgcct gctgaataac    420
ttctatccca gagaggccaa agtacagtgg aaggtggata cgccctcca atcgggtaac    480 tcccaggaga gtgtcacaga gcaggacagc aaggacagca cctacagcct cagcagcacc    540
ctgacgctga gcaaagcaga ctacgaaaaa cataaagtct acgcctgcga agtcacccat    600
```

-continued cagggcctga gctcgcccgt cacaaagagc ttcaacaggg gagagtgtgg tggttctgat    660
tacaaagatg acgatgacaa ataa    684

<210> SEQ ID NO 12
<211> LENGTH: 227
<212> TYPE: PRT
<213> ORGANISM: Artificial Sequence
<220> FEATURE:
<223> OTHER INFORMATION: Synthetic

<400> SEQUENCE: 12

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Trp Trp Gly Tyr Pro
                85                  90                  95

Leu Ile Thr Phe Gly Gln Gly Thr Lys Val Glu Ile Lys Arg Thr Val
            100                 105                 110

Ala Ala Pro Ser Val Phe Ile Phe Pro Pro Ser Asp Ser Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys Gly Gly Ser Asp Tyr Lys Asp Asp
    210                 215                 220

Asp Asp Lys
225

<210> SEQ ID NO 13
<211> LENGTH: 702
<212> TYPE: DNA
<213> ORGANISM: Artificial Sequence
<220> FEATURE:
<223> OTHER INFORMATION: Synthetic

<400> SEQUENCE: 13
gaggttcagc tggtggagtc tggcggtggc ctggtgcagc cagggggctc actccgtttg    60
tcctgtgcag cttctggctt caacctctat tcttcttata ccactgggt gcgtcaggcc    120 ccgggtaagg gcctggaatg ggttgcatct atttattctt cttctggcta tacttattat    180
gccgatagcg tcaagggccg tttcactata agcgcagaca catccaaaaa cacagcctac    240
ctacaaatga acagcttaag agctgaggac actgccgtct attattgtgc tcgctctgtt    300

-continued

```
cattcttact actcttctgc tgcttactac gctatggact actggggtca aggaaccctg    360
gtcaccgtct cctcggcctc caccaagggt ccatcggtct tcccctggc acctcctcc      420 aagagcacct ctgggggcac agcggccctg ggctgcctgg tcaaggacta cttccccgaa    480
ccggtgacgg tgtcgtggaa ctcaggcgcc ctgaccagcg gcgtgcacac cttcccggct    540
gtcctacagt cctcaggact ctactccctc agcagcgtgg tgaccgtgcc ctccagcagc    600
ttgggcaccc agacctacat ctgcaacgtg aatcacaagc ccagcaacac caaggtcgac    660
aagaaagttg agcccaaatc ttgtgacaaa actcacacat aa                       702
```

```
<210> SEQ ID NO 14
<211> LENGTH: 233
<212> TYPE: PRT
<213> ORGANISM: Artificial Sequence
<220> FEATURE:
<223> OTHER INFORMATION: Synthetic

<400> SEQUENCE: 14
```

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Leu Tyr Ser Ser
            20                  25                  30

Tyr Ile His Trp Val Arg Gln Ala Pro Gly Lys Gly Leu Glu Trp Val
        35                  40                  45

Ala Ser Ile Tyr Ser Ser Gly Tyr Thr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ser Val His Ser Tyr Tyr Ser Ser Ala Ala Tyr Tyr Ala Met
            100                 105                 110

Asp Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Asp Lys Thr His Thr
225                 230

```
<210> SEQ ID NO 15
<211> LENGTH: 675
<212> TYPE: DNA
<213> ORGANISM: Artificial Sequence
<220> FEATURE:
<223> OTHER INFORMATION: Synthetic
```

<400> SEQUENCE: 15

```
gatatccaga tgacccagtc cccgagctcc ctgtccgcct ctgtgggcga tagggtcacc        60
atcacctgcc gtgccagtca gtccgtgtcc agcgctgtag cctggtatca acagaaacca       120
ggaaaagctc cgaagcttct gatttactcg gcatccagcc tctactctgg agtcccttct       180
cgcttctctg gtagccgttc cgggacggat ttcactctga ccatcagcag tctgcagccg       240
gaagacttcg caacttatta ctgtcagcaa tcttacttcc tgatcacgtt cggacagggt       300
accaaggtgg agatcaaacg aactgtggct gcaccatctg tcttcatctt cccgccatct       360
gattcacagt tgaaatctgg aactgcctct gttgtgtgcc tgctgaataa cttctatccc       420
agagaggcca agtacagtg gaaggtggat aacgccctcc aatcgggtaa ctcccaggag        480
agtgtcacag agcaggacag caaggacagc acctacagcc tcagcagcac cctgacgctg       540
agcaaagcag actacgaaaa acataaagtc tacgcctgcg aagtcaccca tcagggcctg       600
agctcgcccg tcacaaagag cttcaacagg ggagagtgtg gtggttctga ttacaaagat       660
gacgatgaca aataa                                                        675
```

```
<210> SEQ ID NO 16
<211> LENGTH: 224
<212> TYPE: PRT
<213> ORGANISM: Artificial Sequence
<220> FEATURE:
<223> OTHER INFORMATION: Synthetic
```

<400> SEQUENCE: 16

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Phe Leu Ile Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Ser Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys Gly Gly Ser Asp Tyr Lys Asp Asp Asp Lys
    210                 215                 220
```

<210> SEQ ID NO 17
<211> LENGTH: 696
<212> TYPE: DNA
<213> ORGANISM: Artificial Sequence
<220> FEATURE:
<223> OTHER INFORMATION: Synthetic

<400> SEQUENCE: 17

```
gaggttcagc tggtggagtc tggcggtggc ctggtgcagc cagggggctc actccgtttg      60
tcctgtgcag cttctggctt caaccccctat tattcttcca ttcactgggt gcgtcaggcc    120
ccgggtaagg gcctggaatg ggttgcatct atttctcctt cttatagctc tacttattat    180
gccgatagcg tcaagggccg tttcactata agcgcagaca catccaaaaa cacagcctac    240
ctacaaatga acagcttaag agctgaggac actgccgtct attattgtgc tcgctcttct    300
tgctctcata gttgccgttt ttacggtttg gactactggg gtcaaggaac cctggtcacc    360
gtctcctcgg cctccaccaa gggtccatcg gtcttccccc tggcaccctc ctccaagagc    420
acctctgggg gcacagcggc cctgggctgc ctggtcaagg actacttccc cgaaccggtg    480
acggtgtcgt ggaactcagg cgccctgacc agcggcgtgc acaccttccc ggctgtccta    540
cagtcctcag gactctactc cctcagcagc gtggtgaccg tgccctccag cagcttgggc    600
acccagacct acatctgcaa cgtgaatcac aagcccagca acaccaaggt cgacaagaaa    660
gttgagccca atcttgtga caaaactcac acataa                                 696
```

<210> SEQ ID NO 18
<211> LENGTH: 231
<212> TYPE: PRT
<213> ORGANISM: Artificial Sequence
<220> FEATURE:
<223> OTHER INFORMATION: Synthetic

<400> SEQUENCE: 18

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Pro Tyr Tyr Ser
            20                  25                  30

Ser Ile His Trp Val Arg Gln Ala Pro Gly Lys Gly Leu Glu Trp Val
        35                  40                  45

Ala Ser Ile Ser Pro Ser Tyr Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ser Ser Cys Ser His Ser Cys Arg Phe Tyr Gly Leu Asp Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190
```

Thr Val Pro Ser Ser Leu Gly Thr Gln Thr Tyr Ile Cys Asn Val
            195                 200                 205

Asn His Lys Pro Ser Asn Thr Lys Val Asp Lys Val Glu Pro Lys
    210                 215                 220

Ser Cys Asp Lys Thr His Thr
225                 230

<210> SEQ ID NO 19
<211> LENGTH: 705
<212> TYPE: DNA
<213> ORGANISM: Artificial Sequence
<220> FEATURE:
<223> OTHER INFORMATION: Synthetic

<400> SEQUENCE: 19

```
gatatccaga tgacccagtc cccgagctcc ctgtccgcct ctgtgggcga tagggtcacc     60
atcacctgcc gtgccagtca gtccgtgtcc agcgctgtag cctggtatca acagaaacca    120
ggaaaagctc cgaagcttct gatttactcg gcatccagcc tctactctgg agtcccttct    180
cgcttctctg gtagccgttc cgggacggat ttcactctga ccatcagcag tctgcagccg    240
gaagacttcg caacttatta ctgtcagcaa tacgcttacc atgagcccgg tttgctctct    300
tcttattctc tgatcacgtt cggacagggt accaaggtgg agatcaaacg aactgtggct    360
gcaccatctg tcttcatctt cccgccatct gattcacagt tgaaatctgg aactgcctct    420
gttgtgtgcc tgctgaataa cttctatccc agagaggcca agtacagtg aaggtggat     480
aacgccctcc aatcgggtaa ctcccaggag agtgtcacag agcaggacag caaggacagc    540
acctacagcc tcagcagcac cctgacgctg agcaaagcag actacgaaaa acataaagtc    600
tacgcctgcg aagtcaccca tcagggcctg agctcgcccg tcacaaagag cttcaacagg    660
ggagagtgtg tggttctga ttacaaagat gacgatgaca aataa                     705
```

<210> SEQ ID NO 20
<211> LENGTH: 228
<212> TYPE: PRT
<213> ORGANISM: Artificial Sequence
<220> FEATURE:
<223> OTHER INFORMATION: Synthetic

<400> SEQUENCE: 20

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ala Tyr His Glu Pro
                85                  90                  95

Gly Leu Leu Thr Phe Gly Gln Gly Thr Lys Val Glu Ile Lys Arg Thr
            100                 105                 110

Val Ala Ala Pro Ser Val Phe Ile Phe Pro Pro Ser Asp Ser Gln Leu
        115                 120                 125

Lys Ser Gly Thr Ala Ser Val Val Cys Leu Leu Asn Asn Phe Tyr Pro
130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
            165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys Gly Gly Ser Tyr Lys Asp
    210                 215                 220

Asp Asp Asp Lys
225

<210> SEQ ID NO 21
<211> LENGTH: 699
<212> TYPE: DNA
<213> ORGANISM: Artificial Sequence
<220> FEATURE:
<223> OTHER INFORMATION: Synthetic

<400> SEQUENCE: 21
gaggttcagc tggtggagtc tggcggtggc ctggtgcagc caggggctc actccgtttg       60 tcctgtgcag cttctggctt caacttctat tattcttcga ttcactgggt gcgtcaggcc    120
ccgggtaagg gcctggaatg ggttgcatct tcgatttctt cggctactgg aaatacttct    180
tatgccgata gcgtcaaggg ccgtttcact ataagcgcag acacatccaa aaacacagcc    240
tacctacaaa tgaacagctt aagagctgag gacactgccg tctattattg tgctcgctct    300
tcttactctc atggtcatag ttggtacggt ttggactact ggggtcaagg aaccctggtc    360
accgtctcct cggcctccac caagggtcca tcggtcttcc ccctggcacc ctcctccaag    420
agcacctctg gggcacagc ggccctgggc tgcctggtca aggactactt ccccgaaccg    480
gtgacggtgt cgtggaactc aggcgccctg accagcggcg tgcacacctt cccggctgtc    540
ctacagtcct caggactcta ctccctcagc agcgtggtga ccgtgccctc agcagcttg    600 ggcacccaga cctacatctg caacgtgaat cacaagccca gcaacaccaa ggtcgacaag    660
aaagttgagc ccaaatcttg tgacaaaact cacacataa                           699

<210> SEQ ID NO 22
<211> LENGTH: 232
<212> TYPE: PRT
<213> ORGANISM: Artificial Sequence
<220> FEATURE:
<223> OTHER INFORMATION: Synthetic

<400> SEQUENCE: 22

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Phe Tyr Tyr Ser
            20                  25                  30

Ser Ile His Trp Val Arg Gln Ala Pro Gly Lys Gly Leu Glu Trp Val
        35                  40                  45

Ala Ser Ser Ile Ser Ser Ala Thr Gly Asn Thr Ser Tyr Ala Asp Ser
    50                  55                  60

Val Lys Gly Arg Phe Thr Ile Ser Ala Asp Thr Ser Lys Asn Thr Ala
65                  70                  75                  80

Tyr Leu Gln Met Asn Ser Leu Arg Ala Glu Asp Thr Ala Val Tyr Tyr
                85                  90                  95

Cys Ala Arg Ser Ser Tyr Ser His Gly His Ser Trp Tyr Gly Leu Asp
            100                 105                 110

Tyr Trp Gly Gln Gly Thr Leu Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Leu Gly Thr Gln Thr Tyr Ile Cys Asn
        195                 200                 205

Val Asn His Lys Pro Ser Asn Thr Lys Val Asp Lys Lys Val Glu Pro
    210                 215                 220

Lys Ser Cys Asp Lys Thr His Thr
225                 230

<210> SEQ ID NO 23
<211> LENGTH: 687
<212> TYPE: DNA
<213> ORGANISM: Artificial Sequence
<220> FEATURE:
<223> OTHER INFORMATION: Synthetic

<400> SEQUENCE: 23

```
gatatccaga tgacccagtc cccgagctcc ctgtccgcct ctgtgggcga tagggtcacc      60
atcacctgcc gtgccagtca gtccgtgtcc agcgctgtag cctggtatca acagaaacca    120
ggaaaagctc cgaagcttct gatttactcg gcatccagcc tctactctgg agtcccttct    180
cgcttctctg gtagccgttc cgggacggat ttcactctga ccatcagcag tctgcagccg    240
gaagacttcg caacttatta ctgtcagcaa tggggttacc ggtacgcacc cctggtcacg    300
ttcggacagg gtaccaaggt ggagatcaaa cgaactgtgg ctgcaccatc tgtcttcatc    360
ttcccgccat ctgattcaca gttgaaatct ggaactgcct ctgttgtgtg cctgctgaat    420
aacttctatc ccagagaggc caaagtacag tggaaggtgg ataacgccct ccaatcgggt    480
aactcccagg agagtgtcac agagcaggac agcaaggaca gcacctacag cctcagcagc    540
accctgacgc tgagcaaagc agactacgaa aaacataaag tctacgcctg cgaagtcacc    600
catcagggcc tgagctcgcc cgtcacaaag agcttcaaca ggggagagtg tggtggttct    660
gattacaaag atgacgatga caaataa                                        687
```

<210> SEQ ID NO 24
<211> LENGTH: 228
<212> TYPE: PRT
<213> ORGANISM: Artificial Sequence
<220> FEATURE:
<223> OTHER INFORMATION: Synthetic -continued

<400> SEQUENCE: 24

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Trp Gly Tyr Arg Tyr Ala
                85                  90                  95

Pro Leu Val Thr Phe Gly Gln Gly Thr Lys Val Glu Ile Lys Arg Thr
            100                 105                 110

Val Ala Ala Pro Ser Val Phe Ile Phe Pro Pro Ser Asp Ser Gln Leu
        115                 120                 125

Lys Ser Gly Thr Ala Ser Val Val Cys Leu Leu Asn Asn Phe Tyr Pro
130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys Gly Gly Ser Asp Tyr Lys Asp
    210                 215                 220

Asp Asp Lys
225

<210> SEQ ID NO 25
<211> LENGTH: 695
<212> TYPE: DNA
<213> ORGANISM: Artificial Sequence
<220> FEATURE:
<223> OTHER INFORMATION: Synthetic

<400> SEQUENCE: 25
gaggttcagc tggtggagtc tggcggtggc ctggtgcagc cagggggctc actccgtttg      60
tcctgtgcag cttctggctt caacctcact tggtggtcta tcctccactt gggtggtcta     120
tccactgggt gcgtcaggcc ccgggtaagg gcctggaatg ggttgcatct actattttt      180 ctggttttc ctatacttct tatgccgata gcgtcaaggg ccgtttcact ataagcgcag      240
acacatccaa aaacacagcc tacctacaaa tgaacagctt aagagctgag acactgccg      300 tctattattg tgctcgctct tctgctatgg actactgggg tcaaggaacc ctggtcaccg     360
tctcctcggc ctccaccaag ggtccatcgg tcttcccccct ggcaccctcc tccaagagca    420
cctctggggg cacagcggcc ctgggctgcc tggtcaagga ctacttcccc gaaccggtga    480
cggtgtcgtg gaactcaggc gccctgacca gcggcgtgca ccttcccg gctgtcctac      540 agtcctcagg actctactcc ctcagcagcg tggtgaccgt gccctccagc agcttgggca    600

-continued

```
cccagaccta catctgcaac gtgaatcaca agcccagcaa caccaaggtc gacaagaaag    660
ttgagcccaa atcttgtgac aaaactcaca cataa                               695
```

<210> SEQ ID NO 26
<211> LENGTH: 224
<212> TYPE: PRT
<213> ORGANISM: Artificial Sequence
<220> FEATURE:
<223> OTHER INFORMATION: Synthetic

<400> SEQUENCE: 26

| | | | | | | | | | | | | | | |
|---|---|---|---|---|---|---|---|---|---|---|---|---|---|---|
| Glu | Val | Gln | Leu | Val | Glu | Ser | Gly | Gly | Gly | Leu | Val | Gln | Pro | Gly | Gly |
| 1 | | | | 5 | | | | | 10 | | | | | 15 | |
| Ser | Leu | Arg | Leu | Ser | Cys | Ala | Ala | Ser | Gly | Phe | Asn | Leu | Thr | Trp | Trp |
| | | | 20 | | | | | 25 | | | | | 30 | | |
| Ser | Ile | His | Trp | Val | Arg | Gln | Ala | Pro | Gly | Lys | Gly | Leu | Glu | Trp | Val |
| | | 35 | | | | | 40 | | | | | 45 | | | |
| Ala | Ser | Thr | Ile | Phe | Ser | Gly | Phe | Ser | Tyr | Thr | Ser | Tyr | Ala | Asp | Ser |
| | 50 | | | | | 55 | | | | | 60 | | | | |
| Val | Lys | Gly | Arg | Phe | Thr | Ile | Ser | Ala | Asp | Thr | Ser | Lys | Asn | Thr | Ala |
| 65 | | | | | 70 | | | | | 75 | | | | | 80 |
| Tyr | Leu | Gln | Met | Asn | Ser | Leu | Arg | Ala | Glu | Asp | Thr | Ala | Val | Tyr | Tyr |
| | | | | 85 | | | | | 90 | | | | | 95 | |
| Cys | Ala | Arg | Ser | Ser | Ala | Met | Asp | Tyr | Trp | Gly | Gln | Gly | Thr | Leu | Val |
| | | | 100 | | | | | 105 | | | | | 110 | | |
| Thr | Val | Ser | Ser | Ala | Ser | Thr | Lys | Gly | Pro | Ser | Val | Phe | Pro | Leu | Ala |
| | | | 115 | | | | | 120 | | | | | 125 | | |
| Pro | Ser | Ser | Lys | Ser | Thr | Ser | Gly | Gly | Thr | Ala | Ala | Leu | Gly | Cys | Leu |
| | 130 | | | | | 135 | | | | | 140 | | | | |
| Val | Lys | Asp | Tyr | Phe | Pro | Glu | Pro | Val | Thr | Val | Ser | Trp | Asn | Ser | Gly |
| 145 | | | | | 150 | | | | | 155 | | | | | 160 |
| Ala | Leu | Thr | Ser | Gly | Val | His | Thr | Phe | Pro | Ala | Val | Leu | Gln | Ser | Ser |
| | | | | 165 | | | | | 170 | | | | | 175 | |
| Gly | Leu | Tyr | Ser | Leu | Ser | Ser | Val | Val | Thr | Val | Pro | Ser | Ser | Ser | Leu |
| | | | 180 | | | | | 185 | | | | | 190 | | |
| Gly | Thr | Gln | Thr | Tyr | Ile | Cys | Asn | Val | Asn | His | Lys | Pro | Ser | Asn | Thr |
| | | | 195 | | | | | 200 | | | | | 205 | | |
| Lys | Val | Asp | Lys | Lys | Val | Glu | Pro | Lys | Ser | Cys | Asp | Lys | Thr | His | Thr |
| | 210 | | | | | 215 | | | | | 220 | | | | |

<210> SEQ ID NO 27
<211> LENGTH: 684
<212> TYPE: DNA
<213> ORGANISM: Artificial Sequence
<220> FEATURE:
<223> OTHER INFORMATION: Synthetic

<400> SEQUENCE: 27

```
gatatccaga tgacccagtc cccgagctcc ctgtccgcct ctgtgggcga tagggtcacc     60
atcacctgcc gtgccagtca gtccgtgtcc agcgctgtag cctggtatca acagaaacca    120
ggaaaagctc cgaagcttct gatttactcg gcatccagcc tctactctgg agtcccttct    180
cgcttctctg gtagccgttc cgggacggat ttcactctga ccatcagcag tctgcagccg    240
gaagacttcg caacttatta ctgtcagcaa cattcatggg catacccgat gataacgttc    300
ggacagggta ccaaggtgga gatcaaacga actgtggctg caccatctgt cttcatcttc    360
```

```
ccgccatctg attcacagtt gaaatctgga actgcctctg ttgtgtgcct gctgaataac    420
ttctatccca gagaggccaa agtacagtgg aaggtggata cgccctcca atcgggtaac     480 tcccaggaga gtgtcacaga gcaggacagc aaggacagca cctacagcct cagcagcacc    540
ctgacgctga gcaaagcaga ctacgaaaaa cataaagtct acgcctgcga agtcacccat    600
cagggcctga gctcgcccgt cacaaagagc ttcaacaggg gagagtgtgg tggttctgat    660
tacaaagatg acgatgacaa ataa                                           684
```

<210> SEQ ID NO 28
<211> LENGTH: 227
<212> TYPE: PRT
<213> ORGANISM: Artificial Sequence
<220> FEATURE:
<223> OTHER INFORMATION: Synthetic

<400> SEQUENCE: 28

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Ser Trp Ala Tyr Pro
                85                  90                  95

Met Ile Thr Phe Gly Gln Gly Thr Lys Val Glu Ile Lys Arg Thr Val
            100                 105                 110

Ala Ala Pro Ser Val Phe Ile Phe Pro Pro Ser Asp Ser Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys Gly Gly Ser Asp Tyr Lys Asp Asp
    210                 215                 220

Asp Asp Lys
225
```

<210> SEQ ID NO 29
<211> LENGTH: 672
<212> TYPE: DNA
<213> ORGANISM: Artificial Sequence
<220> FEATURE:
<223> OTHER INFORMATION: Synthetic

<400> SEQUENCE: 29

```
gaggttcagc tggtggagtc tggcggtggc ctggtgcagc caggggggctc actccgtttg    60
tcctgtgcag cttctggctt caacatctct cagtatacta tccactgggt gcgtcaggcc   120
ccgggtaagg gcctggaatg ggttgcatct atttatgctc gttctaggtt tacttcttat   180
gccgatagcg tcaagggccg tttcactata agcgcagaca catccaaaaa cacagcctac   240
ctacaaatga acagcttaag agctgaggac actgccgtct attattgtgc cgctcttct   300
cgtatggact actggggtca aggaaccctg gtcaccgtct cctcggcctc caccaagggt   360
ccatcggtct tccccctggc accctcctcc aagagcacct ctgggggcac agcggccctg   420
ggctgcctgg tcaaggacta cttccccgaa ccggtgacgg tgtcgtggaa ctcaggcgcc   480
ctgaccagcg gcgtgcacac cttcccggct gtcctacagt cctcaggact ctactccctc   540
agcagcgtgg tgaccgtgcc ctccagcagc ttgggcaccc agacctacat ctgcaacgtg   600
aatcacaagc ccagcaacac caaggtcgac aagaaagttg agcccaaatc ttgtgacaaa   660
actcacacat aa                                                      672
```

<210> SEQ ID NO 30
<211> LENGTH: 223
<212> TYPE: PRT
<213> ORGANISM: Artificial Sequence
<220> FEATURE:
<223> OTHER INFORMATION: Synthetic

<400> SEQUENCE: 30

```
Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Asn Ile Ser Gln Tyr
            20                  25                  30
Thr Ile His Trp Val Arg Gln Ala Pro Gly Lys Gly Leu Glu Trp Val
        35                  40                  45
Ala Ser Ile Tyr Ala Arg Ser Arg Phe Thr Ser Tyr Ala Asp Ser Val
    50                  55                  60
Lys Gly Arg Phe Thr Ile Ser Ala Asp Thr Ser Lys Asn Thr Ala Tyr
65                  70                  75                  80
Leu Gln Met Asn Ser Leu Arg Ala Glu Asp Thr Ala Val Tyr Tyr Cys
                85                  90                  95
Ala Arg Ser Ser Arg Met Asp Tyr Trp Gly Gln Gly Thr Leu Val Thr
            100                 105                 110
Val Ser Ser Ala Ser Thr Lys Gly Pro Ser Val Phe Pro Leu Ala Pro
        115                 120                 125
Ser Ser Lys Ser Thr Ser Gly Gly Thr Ala Ala Leu Gly Cys Leu Val
    130                 135                 140
Lys Asp Tyr Phe Pro Glu Pro Val Thr Val Ser Trp Asn Ser Gly Ala
145                 150                 155                 160
Leu Thr Ser Gly Val His Thr Phe Pro Ala Val Leu Gln Ser Ser Gly
                165                 170                 175
Leu Tyr Ser Leu Ser Ser Val Val Thr Val Pro Ser Ser Ser Leu Gly
            180                 185                 190
Thr Gln Thr Tyr Ile Cys Asn Val Asn His Lys Pro Ser Asn Thr Lys
        195                 200                 205
Val Asp Lys Lys Val Glu Pro Lys Ser Cys Asp Lys Thr His Thr
    210                 215                 220
```

<210> SEQ ID NO 31
<211> LENGTH: 702
<212> TYPE: DNA
<213> ORGANISM: Artificial Sequence
<220> FEATURE:
<223> OTHER INFORMATION: Synthetic

<400> SEQUENCE: 31

```
gatatccaga tgacccagtc cccgagctcc ctgtccgcct ctgtgggcga tagggtcacc      60
atcacctgcc gtgccagtca gtccgtgtcc agcgctgtag cctggtatca acagaaacca     120
ggaaaagctc cgaagcttct gatttactcg gcatccagcc tctactctgg agtccctcct    180
cgcttctctg gtagccgttc cgggacggat ttcactctga ccatcagcag tctgcagccg     240
gaagacttcg caacttatta ctgtcagcaa cattggtttg gtatccccagc ggtatcttct    300
tattctctga tcacgttcgg acagggtacc aaggtggaga tcaaacgaac tgtggctgca     360
ccatctgtct tcatcttccc gccatctgat tcacagttga aatctggaac tgcctctgtt     420
gtgtgcctgc tgaataactt ctatcccaga gaggccaaag tacagtggaa ggtggataac     480
gccctccaat cgggtaactc ccaggagagt gtcacagagc aggacagcaa ggacagcacc     540
tacagcctca gcagcaccct gacgctgagc aaagcagact acgaaaaaca taagagtctac    600
gcctgcgaag tcacccatca gggcctgagc tcgcccgtca caagagctt caacagggga     660
gagtgtggtg gttctgatta caaagatgac gatgacaaat aa                        702
```

<210> SEQ ID NO 32
<211> LENGTH: 227
<212> TYPE: PRT
<213> ORGANISM: Artificial Sequence
<220> FEATURE:
<223> OTHER INFORMATION: Synthetic

<400> SEQUENCE: 32

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Trp Phe Gly Tyr Pro
                85                  90                  95

Ala Val Thr Phe Gly Gln Gly Thr Lys Val Glu Ile Lys Arg Thr Val
            100                 105                 110

Ala Ala Pro Ser Val Phe Ile Phe Pro Pro Ser Asp Ser Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190
```

```
Val Tyr Ala Cys Glu Val Thr His Gln Gly Leu Ser Ser Pro Val Thr
        195                 200                 205

Lys Ser Phe Asn Arg Gly Glu Cys Gly Gly Ser Asp Tyr Lys Asp Asp
        210                 215                 220

Asp Asp Lys
225

<210> SEQ ID NO 33
<211> LENGTH: 675
<212> TYPE: DNA
<213> ORGANISM: Artificial Sequence
<220> FEATURE:
<223> OTHER INFORMATION: Synthetic

<400> SEQUENCE: 33
gaggttcagc tggtggagtc tggcggtggc ctggtgcagc caggggctc actccgtttg      60 tcctgtgcag cttctggctt caacatctct tattatacta tccactgggt gcgtcaggcc     120
ccgggtaagg gcctggaatg ggttgcatcc tctatttatt cttattctct ctatacttct     180
tatgccgata gcgtcaaggg ccgtttcact ataagcgcag acacatccaa aaacacagcc     240
tacctacaaa tgaacagctt aagagctgag gacactgccg tctattattg tgctcgctct     300
tctgctatgg actactgggg tcaaggaacc ctggtcaccg tctcctcggc tccaccaag      360 ggtccatcgg tcttccccct ggcacccctcc tccaagagca cctctggggg cacagcggcc     420
ctgggctgcc tggtcaagga ctacttcccc gaaccggtga cggtgtcgtg gaactcaggc     480
gccctgacca gcggcgtgca caccttcccg gctgtcctac agtcctcagg actctactcc     540
ctcagcagcg tggtgaccgt gccctccagc agcttgggca cccagaccta catctgcaac     600
gtgaatcaca agcccagcaa caccaaggtc gacaagaaag ttgagcccaa atcttgtgac     660
aaaactcaca cataa                                                     675

<210> SEQ ID NO 34
<211> LENGTH: 224
<212> TYPE: PRT
<213> ORGANISM: Artificial Sequence
<220> FEATURE:
<223> OTHER INFORMATION: Synthetic

<400> SEQUENCE: 34

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Ser Tyr Tyr
            20                  25                  30

Thr Ile His Trp Val Arg Gln Ala Pro Gly Lys Gly Leu Glu Trp Val
        35                  40                  45

Ala Ser Ser Ile Tyr Ser Tyr Ser Leu Tyr Thr Ser Tyr Ala Asp Ser
    50                  55                  60

Val Lys Gly Arg Phe Thr Ile Ser Ala Asp Thr Ser Lys Asn Thr Ala
65                  70                  75                  80

Tyr Leu Gln Met Asn Ser Leu Arg Ala Glu Asp Thr Ala Val Tyr Tyr
                85                  90                  95

Cys Ala Arg Ser Ser Ala Met Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125
```

Pro Ser Ser Lys Ser Thr Ser Gly Gly Thr Ala Ala Leu Gly Cys Leu
        130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

<210> SEQ ID NO 35
<211> LENGTH: 684
<212> TYPE: DNA
<213> ORGANISM: Artificial Sequence
<220> FEATURE:
<223> OTHER INFORMATION: Synthetic

<400> SEQUENCE: 35
gatatccaga tgacccagtc cccgagctcc ctgtccgcct ctgtgggcga tagggtcacc      60
atcacctgcc gtgccagtca gtccgtgtcc agcgctgtag cctggtatca acagaaacca    120
ggaaaagctc cgaagcttct gatttactcg gcatccagcc tctactctgg agtcccttct    180
cgcttctctg gtagccgttc cgggacggat ttcactctga ccatcagcag tctgcagccg    240
gaagacttcg caacttatta ctgtcagcaa cattggtggg gttaccctat gatcacgttc    300
ggacagggta ccaaggtgga gatcaaacga actgtggctg caccatctgt cttcatcttc    360
ccgccatctg attcacagtt gaaatctgga actgcctctg ttgtgtgcct gctgaataac    420
ttctatccca gagaggccaa agtacagtgg aaggtggata acgccctcca atcgggtaac    480
tcccaggaga gtgtcacaga gcaggacagc aaggacagca cctacagcct cagcagcacc    540
ctgacgctga gcaaagcaga ctacgaaaaa cataaagtct acgcctgcga agtcaccccat   600 cagggcctga gctcgcccgt cacaaagagc ttcaacaggg gagagtgtgg tggttctgat    660
tacaaagatg acgatgacaa ataa                                            684

<210> SEQ ID NO 36
<211> LENGTH: 227
<212> TYPE: PRT
<213> ORGANISM: Artificial Sequence
<220> FEATURE:
<223> OTHER INFORMATION: Synthetic

<400> SEQUENCE: 36

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Trp Trp Gly Tyr Pro
                85                  90                  95

Met Ile Thr Phe Gly Gln Gly Thr Lys Val Glu Ile Lys Arg Thr Val
            100                 105                 110

Ala Ala Pro Ser Val Phe Ile Phe Pro Pro Ser Asp Ser Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys Gly Gly Ser Asp Tyr Lys Asp Asp
    210                 215                 220

Asp Asp Lys
225

<210> SEQ ID NO 37
<211> LENGTH: 675
<212> TYPE: DNA
<213> ORGANISM: Artificial Sequence
<220> FEATURE:
<223> OTHER INFORMATION: Synthetic

<400> SEQUENCE: 37
gaggttcagc tggtggagtc tggcggtggc ctggtgcagc caggggctc actccgtttg      60 tcctgtgcag cttctggctt caacctctct tcttattcta tccactgggt gcgtcaggcc     120
ccgggtaagg gcctggaatg ggttgcatct gcaatttatg ctggtttcgg ctcaactacg     180
tatgccgata cgtcaagggg ccgtttcact ataagcgcag acacatccaa aaacacagcc     240
tacctacaaa tgaacagctt aagagctgag gacactgccg tctattattg tgctcgctct     300
tcagctatgg actactgggg tcaaggaacc ctggtcaccg tctcctcggc ctccaccaag     360
ggtccatcgg tcttcccct ggcacccctcc tccaagagca cctctggggg cacagcggcc     420
ctgggctgcc tggtcaagga ctacttcccc gaaccggtga cggtgtcgtg gaactcaggc     480
gccctgacca gcggcgtgca caccttcccg gctgtcctac agtcctcagg actctactcc     540
ctcagcagcg tggtgaccgt gccctccagc agcttgggca cccagaccta catctgcaac     600
gtgaatcaca gcccagcaa caccaaggtc gacaagaaag ttgagcccaa atcttgtgac     660
aaaactcaca cataa                                                       675

<210> SEQ ID NO 38
<211> LENGTH: 224
<212> TYPE: PRT
<213> ORGANISM: Artificial Sequence
<220> FEATURE:
<223> OTHER INFORMATION: Synthetic

<400> SEQUENCE: 38

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Leu Ser Ser Tyr
            20                  25                  30

Ser Ile His Trp Val Arg Gln Ala Pro Gly Lys Gly Leu Glu Trp Val
        35                  40                  45

Ala Ser Ala Ile Tyr Ala Gly Phe Gly Ser Thr Thr Tyr Ala Asp Ser
50                  55                  60

Val Lys Gly Arg Phe Thr Ile Ser Ala Asp Thr Ser Lys Asn Thr Ala
65                  70                  75                  80

Tyr Leu Gln Met Asn Ser Leu Arg Ala Glu Asp Thr Ala Val Tyr Tyr
                85                  90                  95

Cys Ala Arg Ser Ser Ala Met Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

<210> SEQ ID NO 39
<211> LENGTH: 684
<212> TYPE: DNA
<213> ORGANISM: Artificial Sequence
<220> FEATURE:
<223> OTHER INFORMATION: Synthetic

<400> SEQUENCE: 39
gatatccaga tgacccagtc cccgagctcc ctgtccgcct ctgtgggcga tagggtcacc      60
atcacctgcc gtgccagtca gtccgtgtcc agcgctgtag cctggtatca acagaaacca    120
ggaaaagctc cgaagcttct gatttactcg gcatccagcc tctactctgg agtcccttct    180
cgcttctctg gtagccgttc cgggacggat ttcactctga ccatcagcag tctgcagccg    240
gaagacttcg caacttatta ctgtcagcaa cattcttggc ggtacccgct gattacgttc    300
ggacagggta ccaaggtgga gatcaaacga actgtggctg caccatctgt cttcatcttc    360
ccgccatctg attcacagtt gaaatctgga actgcctctg ttgtgtgcct gctgaataac    420
ttctatccca gagaggccaa agtacagtgg aaggtggata acgccctcca atcgggtaac    480
tcccaggaga gtgtcacaga gcaggacagc aaggacagca cctacagcct cagcagcacc    540
ctgacgctga gcaaagcaga ctacgaaaaa cataaagtct acgcctgcga agtcacccat    600
cagggcctga gctcgcccgt cacaaagagc ttcaacaggg gagagtgtgg tggttctgat    660
tacaaagatg acgatgacaa ataa                                            684

<210> SEQ ID NO 40
<211> LENGTH: 227
<212> TYPE: PRT
<213> ORGANISM: Artificial Sequence
<220> FEATURE:
<223> OTHER INFORMATION: Synthetic

<400> SEQUENCE: 40

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Ser Trp Arg Tyr Pro
                85                  90                  95

Leu Ile Thr Phe Gly Gln Gly Thr Lys Val Glu Ile Lys Arg Thr Val
            100                 105                 110

Ala Ala Pro Ser Val Phe Ile Phe Pro Pro Ser Asp Ser Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys Gly Gly Ser Asp Tyr Lys Asp Asp
    210                 215                 220

Asp Asp Lys
225

<210> SEQ ID NO 41
<211> LENGTH: 669
<212> TYPE: DNA
<213> ORGANISM: Artificial Sequence
<220> FEATURE:
<223> OTHER INFORMATION: Synthetic

<400> SEQUENCE: 41
gaggttcagc tggtggagtc tggcggtggc ctggtgcagc cagggggctc actccgtttg      60
tcctgtgcag cttctggctt caacatctct tcttcttcta tccactgggt gcgtcaggcc     120
ccgggtaagg gcctggaatg ggttgcatct atttctcctt cttatagctc tacttattat     180
gccgatagcg tcaagggccg tttcactata agcgcagaca catccaaaaa cacagcctac     240
ctacaaatga acagcttaag agctgaggac actgccgtct attattgtgc tcgcggtgct     300
tttgactact ggggtcaagg aaccctggtc accgtctcct cggcctccac caagggtcca     360
tcggtcttcc ccctggcacc ctcctccaag agcacctctg ggggcacagc ggccctgggc     420
tgcctggtca aggactactt ccccgaaccg gtgacggtgt cgtggaactc aggcgccctg     480
accagcggcg tgcacacctt cccggctgtc ctacagtcct caggactcta ctccctcagc     540
agcgtggtga ccgtgccctc agcagcttgg gcacccaga cctacatctg caacgtgaat     600

```
cacaagccca gcaacaccaa ggtcgacaag aaagttgagc ccaaatcttg tgacaaaact    660
cacacataa                                                           669
```

<210> SEQ ID NO 42
<211> LENGTH: 222
<212> TYPE: PRT
<213> ORGANISM: Artificial Sequence
<220> FEATURE:
<223> OTHER INFORMATION: Synthetic

<400> SEQUENCE: 42

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Ser Ser Ser
            20                  25                  30

Ser Ile His Trp Val Arg Gln Ala Pro Gly Lys Gly Leu Glu Trp Val
        35                  40                  45

Ala Ser Ile Ser Pro Ser Tyr Ser Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Ala Phe Asp Tyr Trp Gly Gln Gly Thr Leu Val Thr Val
            100                 105                 110

Ser Ser Ala Ser Thr Lys Gly Pro Ser Val Phe Pro Leu Ala Pro Ser
        115                 120                 125

Ser Lys Ser Thr Ser Gly Gly Thr Ala Ala Leu Gly Cys Leu Val Lys
    130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190

Gln Thr Tyr Ile Cys Asn Val Asn His Lys Pro Ser Asn Thr Lys Val
        195                 200                 205

Asp Lys Lys Val Glu Pro Lys Ser Cys Asp Lys Thr His Thr
    210                 215                 220
```

<210> SEQ ID NO 43
<211> LENGTH: 675
<212> TYPE: DNA
<213> ORGANISM: Artificial Sequence
<220> FEATURE:
<223> OTHER INFORMATION: Synthetic

<400> SEQUENCE: 43

```
gatatccaga tgacccagtc cccgagctcc ctgtccgcct ctgtgggcga tagggtcacc    60
atcacctgcc gtgccagtca gtccgtgtcc agcgctgtag cctggtatca acagaaacca   120
ggaaaagctc cgaagcttct gatttactcg gcatccagcc tctactctgg agtcccttct   180
cgcttctctg gtagccgttc cgggacggat tcactctga ccatcagcag tctgcagccg   240
gaagacttcg caacttatta ctgtcagcaa tactggcatc cgttcacgtt cggacagggt   300
accaaggtgg agatcaaacg aactgtggct gcaccatctg tcttcatctt cccgccatct   360
```

-continued

```
gattcacagt tgaaatctgg aactgcctct gttgtgtgcc tgctgaataa cttctatccc    420
agagaggcca agtacagtg gaaggtggat aacgccctcc aatcgggtaa ctcccaggag     480
agtgtcacag agcaggacag caaggacagc acctacagcc tcagcagcac cctgacgctg    540
agcaaagcag actacgaaaa acataaagtc tacgcctgcg aagtcaccca tcagggcctg    600
agctcgcccg tcacaaagag cttcaacagg ggagagtgtg gtggttctga ttacaaagat    660
gacgatgaca aataa                                                    675
```

<210> SEQ ID NO 44
<211> LENGTH: 224
<212> TYPE: PRT
<213> ORGANISM: Artificial Sequence
<220> FEATURE:
<223> OTHER INFORMATION: Synthetic

<400> SEQUENCE: 44

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Trp His Pro Phe Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Ser Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys Gly Gly Ser Asp Tyr Lys Asp Asp Asp Asp Lys
    210                 215                 220
```

<210> SEQ ID NO 45
<211> LENGTH: 6
<212> TYPE: PRT
<213> ORGANISM: Artificial Sequence
<220> FEATURE:
<223> OTHER INFORMATION: Synthetic

<400> SEQUENCE: 45

```
Gln Ser Val Ser Ser Ala
1               5
```

<210> SEQ ID NO 46

```
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Xaa is any amino acid

<400> SEQUENCE: 46

Ser Ala Ser Xaa
1

<210> SEQ ID NO 47
<211> LENGTH: 12
<212> TYPE: PRT
<213> ORGANISM: Artificial Sequence
<220> FEATURE:
<223> OTHER INFORMATION: Synthetic

<400> SEQUENCE: 47

Gln Gln Tyr Gly Tyr His Tyr Ala Gly Leu Ile Thr
1               5                   10

<210> SEQ ID NO 48
<211> LENGTH: 12
<212> TYPE: PRT
<213> ORGANISM: Artificial Sequence
<220> FEATURE:
<223> OTHER INFORMATION: Synthetic

<400> SEQUENCE: 48

Gln Gln His Trp Trp Ala Ser Val Pro Pro Phe Thr
1               5                   10

<210> SEQ ID NO 49
<211> LENGTH: 10
<212> TYPE: PRT
<213> ORGANISM: Artificial Sequence
<220> FEATURE:
<223> OTHER INFORMATION: Synthetic

<400> SEQUENCE: 49

Gln Gln His Tyr Trp Gly Tyr Leu Ile Thr
1               5                   10

<210> SEQ ID NO 50
<211> LENGTH: 10
<212> TYPE: PRT
<213> ORGANISM: Artificial Sequence
<220> FEATURE:
<223> OTHER INFORMATION: Synthetic

<400> SEQUENCE: 50

Gln Gln His His Trp Ser Tyr Pro Ile Thr
1               5                   10

<210> SEQ ID NO 51
<211> LENGTH: 11
<212> TYPE: PRT
<213> ORGANISM: Artificial Sequence
<220> FEATURE:
<223> OTHER INFORMATION: Synthetic

<400> SEQUENCE: 51

Gln Gln His His His Trp Ala Val Leu Ile Thr
1               5                   10
```

```
<210> SEQ ID NO 52
<211> LENGTH: 10
<212> TYPE: PRT
<213> ORGANISM: Artificial Sequence
<220> FEATURE:
<223> OTHER INFORMATION: Synthetic

<400> SEQUENCE: 52

Gln Gln His Tyr Trp Gly Gly Pro Ile Thr
1               5                   10

<210> SEQ ID NO 53
<211> LENGTH: 11
<212> TYPE: PRT
<213> ORGANISM: Artificial Sequence
<220> FEATURE:
<223> OTHER INFORMATION: Synthetic

<400> SEQUENCE: 53

Gln Gln Ser Trp Gly Trp Ser Trp Leu Ile Thr
1               5                   10

<210> SEQ ID NO 54
<211> LENGTH: 11
<212> TYPE: PRT
<213> ORGANISM: Artificial Sequence
<220> FEATURE:
<223> OTHER INFORMATION: Synthetic

<400> SEQUENCE: 54

Gln Gln His Ser Phe His Ser Gly Leu Ile Thr
1               5                   10

<210> SEQ ID NO 55
<211> LENGTH: 12
<212> TYPE: PRT
<213> ORGANISM: Artificial Sequence
<220> FEATURE:
<223> OTHER INFORMATION: Synthetic

<400> SEQUENCE: 55

Gln Gln Ser His Gly Trp Trp Gly Phe Pro Phe Thr
1               5                   10

<210> SEQ ID NO 56
<211> LENGTH: 11
<212> TYPE: PRT
<213> ORGANISM: Artificial Sequence
<220> FEATURE:
<223> OTHER INFORMATION: Synthetic

<400> SEQUENCE: 56

Gln Gln Tyr Tyr Trp Ala Ser Tyr Pro Phe Thr
1               5                   10

<210> SEQ ID NO 57
<211> LENGTH: 11
<212> TYPE: PRT
<213> ORGANISM: Artificial Sequence
<220> FEATURE:
<223> OTHER INFORMATION: Synthetic

<400> SEQUENCE: 57

Gln Gln Tyr Tyr Tyr Ser Ala Ala Leu Ile Thr
1               5                   10
```

<210> SEQ ID NO 58
<211> LENGTH: 12
<212> TYPE: PRT
<213> ORGANISM: Artificial Sequence
<220> FEATURE:
<223> OTHER INFORMATION: Synthetic

<400> SEQUENCE: 58

Gln Gln Trp Trp Gly Gly Pro Tyr Val Leu Ile Thr
1               5                   10

<210> SEQ ID NO 59
<211> LENGTH: 12
<212> TYPE: PRT
<213> ORGANISM: Artificial Sequence
<220> FEATURE:
<223> OTHER INFORMATION: Synthetic

<400> SEQUENCE: 59

Gln Gln Tyr His Trp Gly Ser Tyr Tyr Pro Phe Thr
1               5                   10

<210> SEQ ID NO 60
<211> LENGTH: 11
<212> TYPE: PRT
<213> ORGANISM: Artificial Sequence
<220> FEATURE:
<223> OTHER INFORMATION: Synthetic

<400> SEQUENCE: 60

Gln Gln His Trp Trp Gly Tyr Pro Leu Ile Thr
1               5                   10

<210> SEQ ID NO 61
<211> LENGTH: 12
<212> TYPE: PRT
<213> ORGANISM: Artificial Sequence
<220> FEATURE:
<223> OTHER INFORMATION: Synthetic

<400> SEQUENCE: 61

Gln Gln His Tyr Tyr Gly Ser Phe Pro Pro Ile Thr
1               5                   10

<210> SEQ ID NO 62
<211> LENGTH: 10
<212> TYPE: PRT
<213> ORGANISM: Artificial Sequence
<220> FEATURE:
<223> OTHER INFORMATION: Synthetic

<400> SEQUENCE: 62

Gln Gln His Trp Trp Ala Ala Leu Ile Thr
1               5                   10

<210> SEQ ID NO 63
<211> LENGTH: 10
<212> TYPE: PRT
<213> ORGANISM: Artificial Sequence
<220> FEATURE:
<223> OTHER INFORMATION: Synthetic

<400> SEQUENCE: 63

Gln Gln His Tyr Tyr Ser Ser Leu Ile Thr
1               5                   10

```
<210> SEQ ID NO 64
<211> LENGTH: 10
<212> TYPE: PRT
<213> ORGANISM: Artificial Sequence
<220> FEATURE:
<223> OTHER INFORMATION: Synthetic

<400> SEQUENCE: 64

Gln Gln His Ser Trp Ala Val Pro Ile Thr
1               5                   10

<210> SEQ ID NO 65
<211> LENGTH: 11
<212> TYPE: PRT
<213> ORGANISM: Artificial Sequence
<220> FEATURE:
<223> OTHER INFORMATION: Synthetic

<400> SEQUENCE: 65

Gln Gln His Ser Tyr Ser Ala Pro Leu Ile Thr
1               5                   10

<210> SEQ ID NO 66
<211> LENGTH: 8
<212> TYPE: PRT
<213> ORGANISM: Artificial Sequence
<220> FEATURE:
<223> OTHER INFORMATION: Synthetic

<400> SEQUENCE: 66

Gln Gln Ser Tyr Phe Leu Ile Thr
1               5

<210> SEQ ID NO 67
<211> LENGTH: 12
<212> TYPE: PRT
<213> ORGANISM: Artificial Sequence
<220> FEATURE:
<223> OTHER INFORMATION: Synthetic

<400> SEQUENCE: 67

Gln Gln Tyr Pro Ser Ala Ser His Tyr Leu Ile Thr
1               5                   10

<210> SEQ ID NO 68
<211> LENGTH: 12
<212> TYPE: PRT
<213> ORGANISM: Artificial Sequence
<220> FEATURE:
<223> OTHER INFORMATION: Synthetic

<400> SEQUENCE: 68

Gln Gln Tyr Ala Tyr His Glu Pro Gly Leu Leu Thr
1               5                   10

<210> SEQ ID NO 69
<211> LENGTH: 12
<212> TYPE: PRT
<213> ORGANISM: Artificial Sequence
<220> FEATURE:
<223> OTHER INFORMATION: Synthetic

<400> SEQUENCE: 69

Gln Gln Trp Gly Tyr Arg Tyr Ala Pro Leu Val Thr
1               5                   10

<210> SEQ ID NO 70
```

```
<211> LENGTH: 11
<212> TYPE: PRT
<213> ORGANISM: Artificial Sequence
<220> FEATURE:
<223> OTHER INFORMATION: Synthetic

<400> SEQUENCE: 70

Gln Gln His Ser Trp Ala Tyr Pro Met Ile Thr
1               5                   10

<210> SEQ ID NO 71
<211> LENGTH: 11
<212> TYPE: PRT
<213> ORGANISM: Artificial Sequence
<220> FEATURE:
<223> OTHER INFORMATION: Synthetic

<400> SEQUENCE: 71

Gln Gln His Trp Phe Gly Tyr Pro Ala Val Thr
1               5                   10

<210> SEQ ID NO 72
<211> LENGTH: 11
<212> TYPE: PRT
<213> ORGANISM: Artificial Sequence
<220> FEATURE:
<223> OTHER INFORMATION: Synthetic

<400> SEQUENCE: 72

Gln Gln His Trp Trp Gly Tyr Pro Met Ile Thr
1               5                   10

<210> SEQ ID NO 73
<211> LENGTH: 11
<212> TYPE: PRT
<213> ORGANISM: Artificial Sequence
<220> FEATURE:
<223> OTHER INFORMATION: Synthetic

<400> SEQUENCE: 73

Gln Gln His Ser Trp Arg Tyr Pro Leu Ile Thr
1               5                   10

<210> SEQ ID NO 74
<211> LENGTH: 9
<212> TYPE: PRT
<213> ORGANISM: Artificial Sequence
<220> FEATURE:
<223> OTHER INFORMATION: Synthetic

<400> SEQUENCE: 74

Gly Phe Asn Leu Tyr Tyr Ser Ser Met
1               5

<210> SEQ ID NO 75
<211> LENGTH: 9
<212> TYPE: PRT
<213> ORGANISM: Artificial Sequence
<220> FEATURE:
<223> OTHER INFORMATION: Synthetic

<400> SEQUENCE: 75

Gly Phe Asn Ile Ser Tyr Tyr Tyr Ile
1               5

<210> SEQ ID NO 76
<211> LENGTH: 9
```

```
<212> TYPE: PRT
<213> ORGANISM: Artificial Sequence
<220> FEATURE:
<223> OTHER INFORMATION: Synthetic

<400> SEQUENCE: 76

Gly Phe Asn Leu Ser Tyr Tyr Ser Ile
1               5

<210> SEQ ID NO 77
<211> LENGTH: 9
<212> TYPE: PRT
<213> ORGANISM: Artificial Sequence
<220> FEATURE:
<223> OTHER INFORMATION: Synthetic

<400> SEQUENCE: 77

Gly Phe Asn Ile Tyr Ser Tyr Ser Ile
1               5

<210> SEQ ID NO 78
<211> LENGTH: 9
<212> TYPE: PRT
<213> ORGANISM: Artificial Sequence
<220> FEATURE:
<223> OTHER INFORMATION: Synthetic

<400> SEQUENCE: 78

Gly Phe Asn Phe Tyr Ser Tyr Ser Met
1               5

<210> SEQ ID NO 79
<211> LENGTH: 9
<212> TYPE: PRT
<213> ORGANISM: Artificial Sequence
<220> FEATURE:
<223> OTHER INFORMATION: Synthetic

<400> SEQUENCE: 79

Gly Phe Asn Ile Ser Ser Tyr Ser Met
1               5

<210> SEQ ID NO 80
<211> LENGTH: 9
<212> TYPE: PRT
<213> ORGANISM: Artificial Sequence
<220> FEATURE:
<223> OTHER INFORMATION: Synthetic

<400> SEQUENCE: 80

Gly Phe Asn Leu Ser Ser Tyr Ser Ile
1               5

<210> SEQ ID NO 81
<211> LENGTH: 9
<212> TYPE: PRT
<213> ORGANISM: Artificial Sequence
<220> FEATURE:
<223> OTHER INFORMATION: Synthetic

<400> SEQUENCE: 81

Gly Phe Asn Leu Tyr Ser Tyr Ser Met
1               5

<210> SEQ ID NO 82
<211> LENGTH: 9
<212> TYPE: PRT
```

```
<213> ORGANISM: Artificial Sequence
<220> FEATURE:
<223> OTHER INFORMATION: Synthetic

<400> SEQUENCE: 82

Gly Phe Asn Ile Ser Ser Tyr Ser Ile
1               5

<210> SEQ ID NO 83
<211> LENGTH: 9
<212> TYPE: PRT
<213> ORGANISM: Artificial Sequence
<220> FEATURE:
<223> OTHER INFORMATION: Synthetic

<400> SEQUENCE: 83

Gly Phe Asn Ile Tyr Tyr Ser Ser Met
1               5

<210> SEQ ID NO 84
<211> LENGTH: 9
<212> TYPE: PRT
<213> ORGANISM: Artificial Sequence
<220> FEATURE:
<223> OTHER INFORMATION: Synthetic

<400> SEQUENCE: 84

Gly Phe Asn Leu Ser Tyr Ser Ser Met
1               5

<210> SEQ ID NO 85
<211> LENGTH: 9
<212> TYPE: PRT
<213> ORGANISM: Artificial Sequence
<220> FEATURE:
<223> OTHER INFORMATION: Synthetic

<400> SEQUENCE: 85

Gly Phe Asn Leu Ser Ser Tyr Tyr Met
1               5

<210> SEQ ID NO 86
<211> LENGTH: 9
<212> TYPE: PRT
<213> ORGANISM: Artificial Sequence
<220> FEATURE:
<223> OTHER INFORMATION: Synthetic

<400> SEQUENCE: 86

Gly Phe Asn Ile Tyr Ser Tyr Ser Met
1               5

<210> SEQ ID NO 87
<211> LENGTH: 9
<212> TYPE: PRT
<213> ORGANISM: Artificial Sequence
<220> FEATURE:
<223> OTHER INFORMATION: Synthetic

<400> SEQUENCE: 87

Gly Phe Asn Leu Ser Ser Tyr Ser Met
1               5

<210> SEQ ID NO 88
<211> LENGTH: 9
<212> TYPE: PRT
<213> ORGANISM: Artificial Sequence
```

```
<220> FEATURE:
<223> OTHER INFORMATION: Synthetic

<400> SEQUENCE: 88

Gly Phe Asn Leu Tyr Ser Ser Tyr Ile
1               5

<210> SEQ ID NO 89
<211> LENGTH: 9
<212> TYPE: PRT
<213> ORGANISM: Artificial Sequence
<220> FEATURE:
<223> OTHER INFORMATION: Synthetic

<400> SEQUENCE: 89

Gly Phe Asn Leu Tyr Tyr Tyr Tyr Met
1               5

<210> SEQ ID NO 90
<211> LENGTH: 9
<212> TYPE: PRT
<213> ORGANISM: Artificial Sequence
<220> FEATURE:
<223> OTHER INFORMATION: Synthetic

<400> SEQUENCE: 90

Gly Phe Asn Pro Tyr Tyr Ser Ser Ile
1               5

<210> SEQ ID NO 91
<211> LENGTH: 9
<212> TYPE: PRT
<213> ORGANISM: Artificial Sequence
<220> FEATURE:
<223> OTHER INFORMATION: Synthetic

<400> SEQUENCE: 91

Gly Phe Asn Phe Tyr Tyr Ser Ser Ile
1               5

<210> SEQ ID NO 92
<211> LENGTH: 9
<212> TYPE: PRT
<213> ORGANISM: Artificial Sequence
<220> FEATURE:
<223> OTHER INFORMATION: Synthetic

<400> SEQUENCE: 92

Gly Phe Asn Leu Thr Trp Trp Ser Ile
1               5

<210> SEQ ID NO 93
<211> LENGTH: 9
<212> TYPE: PRT
<213> ORGANISM: Artificial Sequence
<220> FEATURE:
<223> OTHER INFORMATION: Synthetic

<400> SEQUENCE: 93

Gly Phe Asn Ile Ser Gln Tyr Thr Ile
1               5

<210> SEQ ID NO 94
<211> LENGTH: 9
<212> TYPE: PRT
<213> ORGANISM: Artificial Sequence
<220> FEATURE:
```

<223> OTHER INFORMATION: Synthetic

<400> SEQUENCE: 94

Gly Phe Asn Ile Ser Tyr Tyr Thr Ile
1               5

<210> SEQ ID NO 95
<211> LENGTH: 10
<212> TYPE: PRT
<213> ORGANISM: Artificial Sequence
<220> FEATURE:
<223> OTHER INFORMATION: Synthetic

<400> SEQUENCE: 95

Ser Ile Tyr Ser Ser Tyr Gly Tyr Thr Tyr
1               5                   10

<210> SEQ ID NO 96
<211> LENGTH: 10
<212> TYPE: PRT
<213> ORGANISM: Artificial Sequence
<220> FEATURE:
<223> OTHER INFORMATION: Synthetic

<400> SEQUENCE: 96

Ser Ile Tyr Ser Tyr Ser Gly Tyr Thr Ser
1               5                   10

<210> SEQ ID NO 97
<211> LENGTH: 10
<212> TYPE: PRT
<213> ORGANISM: Artificial Sequence
<220> FEATURE:
<223> OTHER INFORMATION: Synthetic

<400> SEQUENCE: 97

Ser Ile Tyr Ser Ser Tyr Gly Tyr Thr Ser
1               5                   10

<210> SEQ ID NO 98
<211> LENGTH: 10
<212> TYPE: PRT
<213> ORGANISM: Artificial Sequence
<220> FEATURE:
<223> OTHER INFORMATION: Synthetic

<400> SEQUENCE: 98

Ser Ile Tyr Pro Ser Tyr Gly Tyr Thr Ser
1               5                   10

<210> SEQ ID NO 99
<211> LENGTH: 10
<212> TYPE: PRT
<213> ORGANISM: Artificial Sequence
<220> FEATURE:
<223> OTHER INFORMATION: Synthetic

<400> SEQUENCE: 99

Tyr Ile Tyr Pro Tyr Ser Gly Tyr Thr Ser
1               5                   10

<210> SEQ ID NO 100
<211> LENGTH: 10
<212> TYPE: PRT
<213> ORGANISM: Artificial Sequence
<220> FEATURE:
<223> OTHER INFORMATION: Synthetic

<400> SEQUENCE: 100

Ser Ile Tyr Ser Tyr Tyr Ser Tyr Thr Ser
1               5                   10

<210> SEQ ID NO 101
<211> LENGTH: 10
<212> TYPE: PRT
<213> ORGANISM: Artificial Sequence
<220> FEATURE:
<223> OTHER INFORMATION: Synthetic

<400> SEQUENCE: 101

Tyr Ile Tyr Pro Ser Tyr Gly Ser Thr Tyr
1               5                   10

<210> SEQ ID NO 102
<211> LENGTH: 10
<212> TYPE: PRT
<213> ORGANISM: Artificial Sequence
<220> FEATURE:
<223> OTHER INFORMATION: Synthetic

<400> SEQUENCE: 102

Tyr Ile Tyr Ser Tyr Ser Gly Tyr Thr Ser
1               5                   10

<210> SEQ ID NO 103
<211> LENGTH: 10
<212> TYPE: PRT
<213> ORGANISM: Artificial Sequence
<220> FEATURE:
<223> OTHER INFORMATION: Synthetic

<400> SEQUENCE: 103

Ser Ile Tyr Pro Tyr Tyr Gly Tyr Thr Tyr
1               5                   10

<210> SEQ ID NO 104
<211> LENGTH: 10
<212> TYPE: PRT
<213> ORGANISM: Artificial Sequence
<220> FEATURE:
<223> OTHER INFORMATION: Synthetic

<400> SEQUENCE: 104

Ser Ile Tyr Pro Ser Ser Ser Ser Thr Tyr
1               5                   10

<210> SEQ ID NO 105
<211> LENGTH: 10
<212> TYPE: PRT
<213> ORGANISM: Artificial Sequence
<220> FEATURE:
<223> OTHER INFORMATION: Synthetic

<400> SEQUENCE: 105

Ser Ile Tyr Ser Tyr Tyr Gly Tyr Thr Ser
1               5                   10

<210> SEQ ID NO 106
<211> LENGTH: 10
<212> TYPE: PRT
<213> ORGANISM: Artificial Sequence
<220> FEATURE:
<223> OTHER INFORMATION: Synthetic

```
<400> SEQUENCE: 106

Tyr Ile Tyr Ser Ser Tyr Gly Tyr Thr Ser
1               5                   10

<210> SEQ ID NO 107
<211> LENGTH: 10
<212> TYPE: PRT
<213> ORGANISM: Artificial Sequence
<220> FEATURE:
<223> OTHER INFORMATION: Synthetic

<400> SEQUENCE: 107

Ser Ile Tyr Pro Tyr Tyr Ser Ser Thr Tyr
1               5                   10

<210> SEQ ID NO 108
<211> LENGTH: 10
<212> TYPE: PRT
<213> ORGANISM: Artificial Sequence
<220> FEATURE:
<223> OTHER INFORMATION: Synthetic

<400> SEQUENCE: 108

Ser Ile Tyr Pro Tyr Tyr Gly Tyr Thr Ser
1               5                   10

<210> SEQ ID NO 109
<211> LENGTH: 10
<212> TYPE: PRT
<213> ORGANISM: Artificial Sequence
<220> FEATURE:
<223> OTHER INFORMATION: Synthetic

<400> SEQUENCE: 109

Ser Ile Tyr Pro Ser Tyr Ser Tyr Thr Ser
1               5                   10

<210> SEQ ID NO 110
<211> LENGTH: 10
<212> TYPE: PRT
<213> ORGANISM: Artificial Sequence
<220> FEATURE:
<223> OTHER INFORMATION: Synthetic

<400> SEQUENCE: 110

Ser Ile Tyr Ser Ser Ser Gly Tyr Thr Tyr
1               5                   10

<210> SEQ ID NO 111
<211> LENGTH: 10
<212> TYPE: PRT
<213> ORGANISM: Artificial Sequence
<220> FEATURE:
<223> OTHER INFORMATION: Synthetic

<400> SEQUENCE: 111

Ser Ile Ser Pro Ser Tyr Ser Ser Thr Tyr
1               5                   10

<210> SEQ ID NO 112
<211> LENGTH: 10
<212> TYPE: PRT
<213> ORGANISM: Artificial Sequence
<220> FEATURE:
<223> OTHER INFORMATION: Synthetic
```

<400> SEQUENCE: 112

Ser Ile Ser Ser Ala Thr Gly Asn Thr Ser
1               5                   10

<210> SEQ ID NO 113
<211> LENGTH: 10
<212> TYPE: PRT
<213> ORGANISM: Artificial Sequence
<220> FEATURE:
<223> OTHER INFORMATION: Synthetic

<400> SEQUENCE: 113

Thr Ile Phe Ser Gly Phe Ser Tyr Thr Ser
1               5                   10

<210> SEQ ID NO 114
<211> LENGTH: 10
<212> TYPE: PRT
<213> ORGANISM: Artificial Sequence
<220> FEATURE:
<223> OTHER INFORMATION: Synthetic

<400> SEQUENCE: 114

Ser Ile Tyr Ala Arg Ser Arg Phe Thr Ser
1               5                   10

<210> SEQ ID NO 115
<211> LENGTH: 10
<212> TYPE: PRT
<213> ORGANISM: Artificial Sequence
<220> FEATURE:
<223> OTHER INFORMATION: Synthetic

<400> SEQUENCE: 115

Ser Ile Tyr Ser Tyr Ser Leu Tyr Thr Ser
1               5                   10

<210> SEQ ID NO 116
<211> LENGTH: 10
<212> TYPE: PRT
<213> ORGANISM: Artificial Sequence
<220> FEATURE:
<223> OTHER INFORMATION: Synthetic

<400> SEQUENCE: 116

Ala Ile Tyr Ala Gly Phe Gly Ser Thr Thr
1               5                   10

<210> SEQ ID NO 117
<211> LENGTH: 16
<212> TYPE: PRT
<213> ORGANISM: Artificial Sequence
<220> FEATURE:
<223> OTHER INFORMATION: Synthetic

<400> SEQUENCE: 117

Ala Arg Ser Ser Phe Ser His Gly Tyr Gly Trp Tyr Gly Leu Asp Tyr
1               5                   10                  15

<210> SEQ ID NO 118
<211> LENGTH: 8
<212> TYPE: PRT
<213> ORGANISM: Artificial Sequence
<220> FEATURE:
<223> OTHER INFORMATION: Synthetic

```
<400> SEQUENCE: 118

Ala Arg Ala Ser Ala Met Asp Tyr
1               5

<210> SEQ ID NO 119
<211> LENGTH: 8
<212> TYPE: PRT
<213> ORGANISM: Artificial Sequence
<220> FEATURE:
<223> OTHER INFORMATION: Synthetic

<400> SEQUENCE: 119

Ala Arg Ser Tyr Gly Leu Asp Tyr
1               5

<210> SEQ ID NO 120
<211> LENGTH: 8
<212> TYPE: PRT
<213> ORGANISM: Artificial Sequence
<220> FEATURE:
<223> OTHER INFORMATION: Synthetic

<400> SEQUENCE: 120

Ala Arg Ser Phe Gly Leu Asp Tyr
1               5

<210> SEQ ID NO 121
<211> LENGTH: 8
<212> TYPE: PRT
<213> ORGANISM: Artificial Sequence
<220> FEATURE:
<223> OTHER INFORMATION: Synthetic

<400> SEQUENCE: 121

Ala Arg Ser Phe Ala Met Asp Tyr
1               5

<210> SEQ ID NO 122
<211> LENGTH: 8
<212> TYPE: PRT
<213> ORGANISM: Artificial Sequence
<220> FEATURE:
<223> OTHER INFORMATION: Synthetic

<400> SEQUENCE: 122

Ala Arg Ser Tyr Ala Met Asp Tyr
1               5

<210> SEQ ID NO 123
<211> LENGTH: 8
<212> TYPE: PRT
<213> ORGANISM: Artificial Sequence
<220> FEATURE:
<223> OTHER INFORMATION: Synthetic

<400> SEQUENCE: 123

Ala Arg Ser Tyr Ala Leu Asp Tyr
1               5

<210> SEQ ID NO 124
<211> LENGTH: 8
<212> TYPE: PRT
<213> ORGANISM: Artificial Sequence
<220> FEATURE:
<223> OTHER INFORMATION: Synthetic
```

<400> SEQUENCE: 124

Ala Arg Gly Phe Ala Leu Asp Tyr
1               5

<210> SEQ ID NO 125
<211> LENGTH: 8
<212> TYPE: PRT
<213> ORGANISM: Artificial Sequence
<220> FEATURE:
<223> OTHER INFORMATION: Synthetic

<400> SEQUENCE: 125

Ala Arg Ser Trp Ala Met Asp Tyr
1               5

<210> SEQ ID NO 126
<211> LENGTH: 8
<212> TYPE: PRT
<213> ORGANISM: Artificial Sequence
<220> FEATURE:
<223> OTHER INFORMATION: Synthetic

<400> SEQUENCE: 126

Ala Arg Ser Phe Gly Phe Asp Tyr
1               5

<210> SEQ ID NO 127
<211> LENGTH: 8
<212> TYPE: PRT
<213> ORGANISM: Artificial Sequence
<220> FEATURE:
<223> OTHER INFORMATION: Synthetic

<400> SEQUENCE: 127

Ala Arg Tyr Phe Ala Met Asp Tyr
1               5

<210> SEQ ID NO 128
<211> LENGTH: 16
<212> TYPE: PRT
<213> ORGANISM: Artificial Sequence
<220> FEATURE:
<223> OTHER INFORMATION: Synthetic

<400> SEQUENCE: 128

Ala Arg Ser Ser His Ser His Gly Tyr Tyr Phe Tyr Gly Ile Asp Tyr
1               5                   10                  15

<210> SEQ ID NO 129
<211> LENGTH: 8
<212> TYPE: PRT
<213> ORGANISM: Artificial Sequence
<220> FEATURE:
<223> OTHER INFORMATION: Synthetic

<400> SEQUENCE: 129

Ala Arg Ser Ser Ala Met Asp Tyr
1               5

<210> SEQ ID NO 130
<211> LENGTH: 8
<212> TYPE: PRT
<213> ORGANISM: Artificial Sequence
<220> FEATURE:
<223> OTHER INFORMATION: Synthetic

<400> SEQUENCE: 130

Ala Arg Ser Phe Gly Met Asp Tyr
1               5

<210> SEQ ID NO 131
<211> LENGTH: 8
<212> TYPE: PRT
<213> ORGANISM: Artificial Sequence
<220> FEATURE:
<223> OTHER INFORMATION: Synthetic

<400> SEQUENCE: 131

Ala Arg Ser Ser Ala Phe Asp Tyr
1               5

<210> SEQ ID NO 132
<211> LENGTH: 18
<212> TYPE: PRT
<213> ORGANISM: Artificial Sequence
<220> FEATURE:
<223> OTHER INFORMATION: Synthetic

<400> SEQUENCE: 132

Ala Arg Ser Val His Ser Tyr Tyr Ser Ser Ala Ala Tyr Tyr Ala Met
1               5                   10                  15

Asp Tyr

<210> SEQ ID NO 133
<211> LENGTH: 16
<212> TYPE: PRT
<213> ORGANISM: Artificial Sequence
<220> FEATURE:
<223> OTHER INFORMATION: Synthetic

<400> SEQUENCE: 133

Ala Arg Ser Tyr Pro Ser Ser Ser Trp Gly Ser Val Ala Leu Asp Tyr
1               5                   10                  15

<210> SEQ ID NO 134
<211> LENGTH: 16
<212> TYPE: PRT
<213> ORGANISM: Artificial Sequence
<220> FEATURE:
<223> OTHER INFORMATION: Synthetic

<400> SEQUENCE: 134

Ala Arg Ser Ser Cys Ser His Ser Cys Arg Phe Tyr Gly Leu Asp Tyr
1               5                   10                  15

<210> SEQ ID NO 135
<211> LENGTH: 16
<212> TYPE: PRT
<213> ORGANISM: Artificial Sequence
<220> FEATURE:
<223> OTHER INFORMATION: Synthetic

<400> SEQUENCE: 135

Ala Arg Ser Ser Tyr Ser His Gly His Ser Trp Tyr Gly Leu Asp Tyr
1               5                   10                  15

<210> SEQ ID NO 136
<211> LENGTH: 8
<212> TYPE: PRT
<213> ORGANISM: Artificial Sequence
<220> FEATURE:
<223> OTHER INFORMATION: Synthetic

```
<400> SEQUENCE: 136

Ala Arg Ser Ser Arg Met Asp Tyr
1               5

<210> SEQ ID NO 137
<211> LENGTH: 8
<212> TYPE: PRT
<213> ORGANISM: Artificial Sequence
<220> FEATURE:
<223> OTHER INFORMATION: Synthetic

<400> SEQUENCE: 137

Gln Gln Tyr Tyr Ser Pro Phe Thr
1               5

<210> SEQ ID NO 138
<211> LENGTH: 8
<212> TYPE: PRT
<213> ORGANISM: Artificial Sequence
<220> FEATURE:
<223> OTHER INFORMATION: Synthetic

<400> SEQUENCE: 138

Gln Gln Tyr Ala Ser Pro Phe Thr
1               5

<210> SEQ ID NO 139
<211> LENGTH: 8
<212> TYPE: PRT
<213> ORGANISM: Artificial Sequence
<220> FEATURE:
<223> OTHER INFORMATION: Synthetic

<400> SEQUENCE: 139

Gln Gln Tyr Tyr Val Pro Phe Thr
1               5

<210> SEQ ID NO 140
<211> LENGTH: 8
<212> TYPE: PRT
<213> ORGANISM: Artificial Sequence
<220> FEATURE:
<223> OTHER INFORMATION: Synthetic

<400> SEQUENCE: 140

Gln Gln Tyr Tyr His Pro Phe Thr
1               5

<210> SEQ ID NO 141
<211> LENGTH: 8
<212> TYPE: PRT
<213> ORGANISM: Artificial Sequence
<220> FEATURE:
<223> OTHER INFORMATION: Synthetic

<400> SEQUENCE: 141

Gln Gln Tyr Phe His Pro Phe Thr
1               5

<210> SEQ ID NO 142
<211> LENGTH: 9
<212> TYPE: PRT
<213> ORGANISM: Artificial Sequence
<220> FEATURE:
<223> OTHER INFORMATION: Synthetic
```

```
<400> SEQUENCE: 142

Gln Gln Gly Phe Phe His Pro Ile Thr
1               5

<210> SEQ ID NO 143
<211> LENGTH: 8
<212> TYPE: PRT
<213> ORGANISM: Artificial Sequence
<220> FEATURE:
<223> OTHER INFORMATION: Synthetic

<400> SEQUENCE: 143

Gln Gln Tyr Trp His Pro Phe Thr
1               5

<210> SEQ ID NO 144
<211> LENGTH: 8
<212> TYPE: PRT
<213> ORGANISM: Artificial Sequence
<220> FEATURE:
<223> OTHER INFORMATION: Synthetic

<400> SEQUENCE: 144

Gln Gln Ala Gly Tyr Ser Ile Thr
1               5

<210> SEQ ID NO 145
<211> LENGTH: 9
<212> TYPE: PRT
<213> ORGANISM: Artificial Sequence
<220> FEATURE:
<223> OTHER INFORMATION: Synthetic

<400> SEQUENCE: 145

Gly Phe Asn Ile Tyr Tyr Ser Ser Ile
1               5

<210> SEQ ID NO 146
<211> LENGTH: 9
<212> TYPE: PRT
<213> ORGANISM: Artificial Sequence
<220> FEATURE:
<223> OTHER INFORMATION: Synthetic

<400> SEQUENCE: 146

Gly Phe Asn Ile Ser Ser Ser Ser Met
1               5

<210> SEQ ID NO 147
<211> LENGTH: 9
<212> TYPE: PRT
<213> ORGANISM: Artificial Sequence
<220> FEATURE:
<223> OTHER INFORMATION: Synthetic

<400> SEQUENCE: 147

Gly Phe Asn Leu Ser Ser Ser Ser Ile
1               5

<210> SEQ ID NO 148
<211> LENGTH: 9
<212> TYPE: PRT
<213> ORGANISM: Artificial Sequence
<220> FEATURE:
<223> OTHER INFORMATION: Synthetic
```

<400> SEQUENCE: 148

Gly Phe Asn Ile Ser Ser Ser Ser Ile
1               5

<210> SEQ ID NO 149
<211> LENGTH: 9
<212> TYPE: PRT
<213> ORGANISM: Artificial Sequence
<220> FEATURE:
<223> OTHER INFORMATION: Synthetic

<400> SEQUENCE: 149

Gly Phe Asn Phe Ser Ser Ser Ser Ile
1               5

<210> SEQ ID NO 150
<211> LENGTH: 10
<212> TYPE: PRT
<213> ORGANISM: Artificial Sequence
<220> FEATURE:
<223> OTHER INFORMATION: Synthetic

<400> SEQUENCE: 150

Ser Ile Ser Ser Tyr Tyr Gly Ser Thr Tyr
1               5                   10

<210> SEQ ID NO 151
<211> LENGTH: 10
<212> TYPE: PRT
<213> ORGANISM: Artificial Sequence
<220> FEATURE:
<223> OTHER INFORMATION: Synthetic

<400> SEQUENCE: 151

Ser Ile Ser Ser Ser Tyr Ser Ser Thr Ser
1               5                   10

<210> SEQ ID NO 152
<211> LENGTH: 10
<212> TYPE: PRT
<213> ORGANISM: Artificial Sequence
<220> FEATURE:
<223> OTHER INFORMATION: Synthetic

<400> SEQUENCE: 152

Ser Ile Ser Ser Ser Tyr Gly Ser Thr Tyr
1               5                   10

<210> SEQ ID NO 153
<211> LENGTH: 10
<212> TYPE: PRT
<213> ORGANISM: Artificial Sequence
<220> FEATURE:
<223> OTHER INFORMATION: Synthetic

<400> SEQUENCE: 153

Ser Ile Ser Ser Ser Tyr Ser Ser Thr Tyr
1               5                   10

<210> SEQ ID NO 154
<211> LENGTH: 10
<212> TYPE: PRT
<213> ORGANISM: Artificial Sequence
<220> FEATURE:
<223> OTHER INFORMATION: Synthetic

```
<400> SEQUENCE: 154

Ser Ile Tyr Ser Tyr Tyr Gly Ser Thr Ser
1               5                   10

<210> SEQ ID NO 155
<211> LENGTH: 10
<212> TYPE: PRT
<213> ORGANISM: Artificial Sequence
<220> FEATURE:
<223> OTHER INFORMATION: Synthetic

<400> SEQUENCE: 155

Tyr Ile Ser Ser Tyr Tyr Gly Ser Thr Ser
1               5                   10

<210> SEQ ID NO 156
<211> LENGTH: 7
<212> TYPE: PRT
<213> ORGANISM: Artificial Sequence
<220> FEATURE:
<223> OTHER INFORMATION: Synthetic

<400> SEQUENCE: 156

Ala Arg Gly Ala Phe Asp Tyr
1               5

<210> SEQ ID NO 157
<211> LENGTH: 7
<212> TYPE: PRT
<213> ORGANISM: Artificial Sequence
<220> FEATURE:
<223> OTHER INFORMATION: Synthetic

<400> SEQUENCE: 157

Ala Arg Gly Ala Met Asp Tyr
1               5

<210> SEQ ID NO 158
<211> LENGTH: 7
<212> TYPE: PRT
<213> ORGANISM: Artificial Sequence
<220> FEATURE:
<223> OTHER INFORMATION: Synthetic

<400> SEQUENCE: 158

Ala Arg Gly Ala Leu Asp Tyr
1               5

<210> SEQ ID NO 159
<211> LENGTH: 22
<212> TYPE: PRT
<213> ORGANISM: Artificial Sequence
<220> FEATURE:
<223> OTHER INFORMATION: Synthetic

<400> SEQUENCE: 159

Ala Arg Tyr Tyr His Gly Tyr Trp Gly Ser Tyr Ser Ala Gly Ser Ser
1               5                   10                  15

Ala Trp Gly Phe Asp Tyr
            20

<210> SEQ ID NO 160
<211> LENGTH: 18
<212> TYPE: PRT
<213> ORGANISM: Artificial Sequence
<220> FEATURE:
```

<223> OTHER INFORMATION: Synthetic

<400> SEQUENCE: 160

Ala Arg Ser Val Val Tyr Gly Tyr Trp Tyr Gly Gly Trp Val Gly Phe
1               5                   10                  15

Asp Tyr

<210> SEQ ID NO 161
<211> LENGTH: 599
<212> TYPE: PRT
<213> ORGANISM: Artificial Sequence
<220> FEATURE:
<223> OTHER INFORMATION: Synthetic

<400> SEQUENCE: 161

Met Leu Cys Leu Gly Trp Ile Phe Leu Trp Leu Val Ala Gly Glu Arg
1               5                   10                  15

Ile Lys Gly Phe Asn Ile Ser Gly Cys Ser Thr Lys Lys Leu Leu Trp
            20                  25                  30

Thr Tyr Ser Thr Arg Ser Glu Glu Glu Phe Val Leu Phe Cys Asp Leu
        35                  40                  45

Pro Glu Pro Gln Lys Ser His Phe Cys His Arg Asn Arg Leu Ser Pro
50                  55                  60

Lys Gln Val Pro Glu His Leu Pro Phe Met Gly Ser Asn Asp Leu Ser
65                  70                  75                  80

Asp Val Gln Trp Tyr Gln Gln Pro Ser Asn Gly Asp Pro Leu Glu Asp
                85                  90                  95

Ile Arg Lys Ser Tyr Pro His Ile Ile Gln Asp Lys Cys Thr Leu His
            100                 105                 110

Phe Leu Thr Pro Gly Val Asn Asn Ser Gly Ser Tyr Ile Cys Arg Pro
        115                 120                 125

Lys Met Ile Lys Ser Pro Tyr Asp Val Ala Cys Cys Val Lys Met Ile
130                 135                 140

Leu Glu Val Lys Pro Gln Thr Asn Ala Ser Cys Glu Tyr Ser Ala Ser
145                 150                 155                 160

His Lys Gln Asp Leu Leu Leu Gly Ser Thr Gly Ser Ile Ser Cys Pro
                165                 170                 175

Ser Leu Ser Cys Gln Ser Asp Ala Gln Ser Pro Ala Val Thr Trp Tyr
            180                 185                 190

Lys Asn Gly Lys Leu Leu Ser Val Glu Arg Ser Asn Arg Ile Val Val
        195                 200                 205

Asp Glu Val Tyr Asp Tyr His Gln Gly Thr Tyr Val Cys Asp Tyr Thr
210                 215                 220

Gln Ser Asp Thr Val Ser Ser Trp Thr Val Arg Ala Val Val Gln Val
225                 230                 235                 240

Arg Thr Ile Val Gly Asp Thr Lys Leu Lys Pro Asp Ile Leu Asp Pro
                245                 250                 255

Val Glu Asp Thr Leu Glu Val Glu Leu Gly Lys Pro Leu Thr Ile Ser
            260                 265                 270

Cys Lys Ala Arg Phe Gly Phe Glu Arg Val Phe Asn Pro Val Ile Lys
        275                 280                 285

Trp Tyr Ile Lys Asp Ser Asp Leu Glu Trp Glu Val Ser Val Pro Glu
290                 295                 300

Ala Lys Ser Ile Lys Ser Thr Leu Lys Asp Glu Ile Ile Glu Arg Asn
305                 310                 315                 320

```
Ile Ile Leu Glu Lys Val Thr Gln Arg Asp Leu Arg Arg Lys Phe Val
            325                 330                 335

Cys Phe Val Gln Asn Ser Ile Gly Asn Thr Thr Gln Ser Val Gln Leu
            340                 345                 350

Lys Glu Lys Arg Gly Val Val Leu Leu Tyr Ile Leu Leu Gly Thr Ile
            355                 360                 365

Gly Thr Leu Val Ala Val Leu Ala Ala Ser Ala Leu Leu Tyr Arg His
        370                 375                 380

Trp Ile Glu Ile Val Leu Leu Tyr Arg Thr Tyr Gln Ser Lys Asp Gln
385                 390                 395                 400

Thr Leu Gly Asp Lys Lys Asp Phe Asp Ala Phe Val Ser Tyr Ala Lys
            405                 410                 415

Trp Ser Ser Phe Pro Ser Glu Ala Thr Ser Ser Leu Ser Glu Glu His
            420                 425                 430

Leu Ala Leu Ser Leu Phe Pro Asp Val Leu Glu Asn Lys Tyr Gly Tyr
            435                 440                 445

Ser Leu Cys Leu Leu Glu Arg Asp Val Ala Pro Gly Gly Val Tyr Ala
        450                 455                 460

Glu Asp Ile Val Ser Ile Ile Lys Arg Ser Arg Arg Gly Ile Phe Ile
465                 470                 475                 480

Leu Ser Pro Asn Tyr Val Asn Gly Pro Ser Ile Phe Glu Leu Gln Ala
            485                 490                 495

Ala Val Asn Leu Ala Leu Asp Asp Gln Thr Leu Lys Leu Ile Leu Ile
            500                 505                 510

Lys Phe Cys Tyr Phe Gln Glu Pro Glu Ser Leu Pro His Leu Val Lys
            515                 520                 525

Lys Ala Leu Arg Val Leu Pro Thr Val Thr Trp Arg Gly Leu Lys Ser
        530                 535                 540

Val Pro Pro Asn Ser Arg Phe Trp Ala Lys Met Arg Tyr His Met Pro
545                 550                 555                 560

Val Lys Asn Ser Gln Gly Phe Thr Trp Asn Gln Leu Arg Ile Thr Ser
            565                 570                 575

Arg Ile Phe Gln Trp Lys Gly Leu Ser Arg Thr Glu Thr Thr Gly Arg
            580                 585                 590

Ser Ser Gln Pro Lys Glu Trp
            595

<210> SEQ ID NO 162
<211> LENGTH: 110
<212> TYPE: PRT
<213> ORGANISM: Artificial Sequence
<220> FEATURE:
<223> OTHER INFORMATION: Synthetic

<400> SEQUENCE: 162

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80
```

```
Glu Asp Phe Ala Thr Tyr Tyr Cys Gln Gln Tyr Gly Tyr His His Ala
                85                  90                  95

Gly Leu Ile Thr Phe Gly Gln Gly Thr Lys Val Glu Ile Lys
            100                 105                 110

<210> SEQ ID NO 163
<211> LENGTH: 123
<212> TYPE: PRT
<213> ORGANISM: Artificial Sequence
<220> FEATURE:
<223> OTHER INFORMATION: Synthetic

<400> SEQUENCE: 163

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Leu Tyr Tyr Ser
            20                  25                  30

Ser Met His Trp Val Arg Gln Ala Pro Gly Lys Gly Leu Glu Trp Val
        35                  40                  45

Ala Ser Ile Tyr Ser Ser Tyr Gly Tyr Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ser Ser Phe Ser His Gly Tyr Gly Trp Tyr Gly Leu Asp Tyr
            100                 105                 110

Trp Gly Gln Gly Thr Leu Val Thr Val Ser Ser
        115                 120

<210> SEQ ID NO 164
<211> LENGTH: 110
<212> TYPE: PRT
<213> ORGANISM: Artificial Sequence
<220> FEATURE:
<223> OTHER INFORMATION: Synthetic

<400> SEQUENCE: 164

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Arg Asp Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Gly Tyr His Tyr Ala
                85                  90                  95

Gly Leu Ile Thr Phe Gly Gln Gly Thr Lys Val Glu Ile Lys
            100                 105                 110

<210> SEQ ID NO 165
<211> LENGTH: 123
<212> TYPE: PRT
<213> ORGANISM: Artificial Sequence
<220> FEATURE:
<223> OTHER INFORMATION: Synthetic
```

-continued

<400> SEQUENCE: 165

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Leu Tyr Tyr Ser
            20                  25                  30

Ser Met His Trp Val Arg Gln Ala Pro Gly Lys Gly Leu Glu Trp Val
        35                  40                  45

Ala Ser Ile Tyr Ser Ser His Gly Arg Thr Gly Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ser Ser Phe Ser His Gly Tyr Gly Trp Tyr Gly Leu Asp Tyr
            100                 105                 110

Trp Gly Gln Gly Thr Leu Val Thr Val Ser Ser
        115                 120

<210> SEQ ID NO 166
<211> LENGTH: 110
<212> TYPE: PRT
<213> ORGANISM: Artificial Sequence
<220> FEATURE:
<223> OTHER INFORMATION: Synthetic

<400> SEQUENCE: 166

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Gly Tyr His Tyr Ala
                85                  90                  95

Gly Leu Ile Thr Phe Gly Gln Gly Thr Lys Val Glu Ile Lys
            100                 105                 110

<210> SEQ ID NO 167
<211> LENGTH: 123
<212> TYPE: PRT
<213> ORGANISM: Artificial Sequence
<220> FEATURE:
<223> OTHER INFORMATION: Synthetic

<400> SEQUENCE: 167

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Leu Tyr Tyr Ser
            20                  25                  30

Ser Met His Trp Val Arg Gln Ala Pro Gly Lys Gly Leu Glu Trp Val
        35                  40                  45

Ala Ser Ile Tyr Ser Ser Ser Gly Tyr Thr Ser Tyr Ala Asp Ser Val
    50                  55                  60

-continued

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ser Ser Phe Ser His Gly Tyr Gly Trp Tyr Gly Leu Asp Tyr
            100                 105                 110

Trp Gly Gln Gly Thr Leu Val Thr Val Ser Ser
        115                 120

<210> SEQ ID NO 168
<211> LENGTH: 110
<212> TYPE: PRT
<213> ORGANISM: Artificial Sequence
<220> FEATURE:
<223> OTHER INFORMATION: Synthetic

<400> SEQUENCE: 168

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Gly Tyr His Tyr Ala
                85                  90                  95

Gly Leu Ile Thr Phe Gly Gln Gly Thr Lys Val Glu Ile Lys
            100                 105                 110

<210> SEQ ID NO 169
<211> LENGTH: 123
<212> TYPE: PRT
<213> ORGANISM: Artificial Sequence
<220> FEATURE:
<223> OTHER INFORMATION: Synthetic

<400> SEQUENCE: 169

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Leu Tyr Tyr Ser
            20                  25                  30

Ser Met His Trp Val Arg Gln Ala Pro Gly Lys Gly Leu Glu Trp Val
        35                  40                  45

Ala Ser Ile Tyr Ser Ser Ser Gly Ser Thr Cys Tyr Ala Asp Ser Val
50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ser Ser Phe Ser His Gly Tyr Gly Trp Tyr Gly Leu Asp Tyr
            100                 105                 110

Trp Gly Gln Gly Thr Leu Val Thr Val Ser Ser
        115                 120

<210> SEQ ID NO 170

```
<211> LENGTH: 110
<212> TYPE: PRT
<213> ORGANISM: Artificial Sequence
<220> FEATURE:
<223> OTHER INFORMATION: Synthetic

<400> SEQUENCE: 170

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Gly Tyr His Tyr Ala
                85                  90                  95

Gly Leu Ile Thr Phe Gly Gln Gly Thr Lys Val Glu Ile Lys
            100                 105                 110

<210> SEQ ID NO 171
<211> LENGTH: 123
<212> TYPE: PRT
<213> ORGANISM: Artificial Sequence
<220> FEATURE:
<223> OTHER INFORMATION: Synthetic

<400> SEQUENCE: 171

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Leu Tyr Tyr Ser
            20                  25                  30

Ser Met His Trp Val Arg Gln Ala Pro Gly Lys Gly Leu Glu Trp Val
        35                  40                  45

Ala Ser Ile Tyr Ser Ser Ser Gly Asp Thr His Tyr Ala Asp Ser Val
50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ser Ser Phe Ser His Gly Tyr Gly Trp Tyr Gly Leu Asp Tyr
            100                 105                 110

Trp Gly Gln Gly Thr Leu Val Thr Val Ser Ser
        115                 120

<210> SEQ ID NO 172
<211> LENGTH: 110
<212> TYPE: PRT
<213> ORGANISM: Artificial Sequence
<220> FEATURE:
<223> OTHER INFORMATION: Synthetic

<400> SEQUENCE: 172

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30
```

Val Ala Trp Tyr Gln Gln Lys Pro Gly Lys Ala Pro Lys Leu Leu Ile
            35                  40                  45

Tyr Ser Ala Ser Ser Leu Tyr Ser Gly Val Pro Ser Arg Phe Ser Gly
 50                  55                  60

Ser Arg Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Gly Tyr His Tyr Ala
                 85                  90                  95

Gly Leu Ile Thr Phe Gly Gln Gly Thr Lys Val Glu Ile Lys
                100                 105                 110

<210> SEQ ID NO 173
<211> LENGTH: 123
<212> TYPE: PRT
<213> ORGANISM: Artificial Sequence
<220> FEATURE:
<223> OTHER INFORMATION: Synthetic

<400> SEQUENCE: 173

Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Asn Leu Tyr Tyr Ser
                 20                  25                  30

Ser Met His Trp Val Arg Gln Ala Pro Gly Lys Gly Leu Glu Trp Val
             35                  40                  45

Ala Ser Ile Tyr Ser Ser His Gly Gly Thr Asn Tyr Ala Asp Ser Val
 50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Arg Ser Ser Phe Ser His Gly Tyr Gly Trp Tyr Gly Leu Asp Tyr
                100                 105                 110

Trp Gly Gln Gly Thr Leu Val Thr Val Ser Ser
            115                 120

<210> SEQ ID NO 174
<211> LENGTH: 110
<212> TYPE: PRT
<213> ORGANISM: Artificial Sequence
<220> FEATURE:
<223> OTHER INFORMATION: Synthetic

<400> SEQUENCE: 174

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Ser Val Ser Ser Ala
                 20                  25                  30

Val Ala Trp Tyr Gln Gln Lys Pro Gly Lys Ala Pro Lys Leu Leu Ile
            35                  40                  45

Tyr Ser Ala Ser Ser Leu Tyr Ser Gly Val Pro Ser Arg Phe Ser Gly
 50                  55                  60

Ser Arg Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Gly Tyr His Asp Ala
                 85                  90                  95

Gly Leu Ile Thr Phe Gly Gln Gly Thr Lys Val Glu Ile Lys
                100                 105                 110

<210> SEQ ID NO 175
<211> LENGTH: 123
<212> TYPE: PRT
<213> ORGANISM: Artificial Sequence
<220> FEATURE:
<223> OTHER INFORMATION: Synthetic

<400> SEQUENCE: 175

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Leu Tyr Tyr Ser
            20                  25                  30

Ser Met His Trp Val Arg Gln Ala Pro Gly Lys Gly Leu Glu Trp Val
        35                  40                  45

Ala Ser Ile Tyr Ser Ser His Gly Gly Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ser Ser Phe Ser His Gly Tyr Gly Trp Tyr Gly Leu Asp Tyr
            100                 105                 110

Trp Gly Gln Gly Thr Leu Val Thr Val Ser Ser
        115                 120

<210> SEQ ID NO 176
<211> LENGTH: 110
<212> TYPE: PRT
<213> ORGANISM: Artificial Sequence
<220> FEATURE:
<223> OTHER INFORMATION: Synthetic

<400> SEQUENCE: 176

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Gly Tyr His Tyr Ala
                85                  90                  95

Gly Leu Ile Thr Phe Gly Gln Gly Thr Lys Val Glu Ile Lys
            100                 105                 110

<210> SEQ ID NO 177
<211> LENGTH: 123
<212> TYPE: PRT
<213> ORGANISM: Artificial Sequence
<220> FEATURE:
<223> OTHER INFORMATION: Synthetic

<400> SEQUENCE: 177

Glu Val Gln Leu Val Glu Ser Gly Gly Gly Leu Val Gln Pro Gly Gly
1               5                   10                  15

```
Ser Leu Arg Leu Ser Cys Ala Ala Ser Gly Phe Asn Leu Tyr Tyr Ser
            20                  25                  30

Ser Met His Trp Val Arg Gln Ala Pro Gly Lys Gly Leu Glu Trp Val
        35                  40                  45

Ala Ser Ile Tyr Ser Ser Asn Gly Arg Thr Tyr Tyr Ala Asp Ser Val
 50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                85                  90                  95

Ala Arg Ser Ser Phe Ser His Gly Tyr Gly Trp Tyr Gly Leu Asp Tyr
            100                 105                 110

Trp Gly Gln Gly Thr Leu Val Thr Val Ser Ser
            115                 120
```

```
<210> SEQ ID NO 178
<211> LENGTH: 110
<212> TYPE: PRT
<213> ORGANISM: Artificial Sequence
<220> FEATURE:
<223> OTHER INFORMATION: Synthetic

<400> SEQUENCE: 178

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
 50                  55                  60

Ser Arg Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Gly Tyr His Asn Ala
                85                  90                  95

Gly Leu Ile Thr Phe Gly Gln Gly Thr Lys Val Glu Ile Lys
            100                 105                 110
```

```
<210> SEQ ID NO 179
<211> LENGTH: 123
<212> TYPE: PRT
<213> ORGANISM: Artificial Sequence
<220> FEATURE:
<223> OTHER INFORMATION: Synthetic

<400> SEQUENCE: 179

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Asn Leu Tyr Tyr Ser
            20                  25                  30

Ser Met His Trp Val Arg Gln Ala Pro Gly Lys Gly Leu Glu Trp Val
        35                  40                  45

Ala Ser Ile Tyr Ser Ser Tyr Gly Tyr Thr Tyr Tyr Ala Asp Ser Val
 50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                85                  90                  95
```

Ala Arg Ser Ser Phe Ser His Gly Tyr Gly Trp Tyr Gly Leu Asp Tyr
            100                 105                 110

Trp Gly Gln Gly Thr Leu Val Thr Val Ser Ser
        115                 120

<210> SEQ ID NO 180
<211> LENGTH: 110
<212> TYPE: PRT
<213> ORGANISM: Artificial Sequence
<220> FEATURE:
<223> OTHER INFORMATION: Synthetic

<400> SEQUENCE: 180

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Gly Tyr His Tyr Ala
                85                  90                  95

Gly Leu Ile Thr Phe Gly Gln Gly Thr Lys Val Glu Ile Lys
            100                 105                 110

<210> SEQ ID NO 181
<211> LENGTH: 123
<212> TYPE: PRT
<213> ORGANISM: Artificial Sequence
<220> FEATURE:
<223> OTHER INFORMATION: Synthetic

<400> SEQUENCE: 181

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Leu Tyr Tyr Ser
            20                  25                  30

Ser Met His Trp Val Arg Gln Ala Pro Gly Lys Gly Leu Glu Trp Val
        35                  40                  45

Ala Ser Ile Tyr Ser Ser Asn Gly Asn Thr Gly Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ser Ser Phe Ser His Gly Tyr Gly Trp Tyr Gly Leu Asp Tyr
            100                 105                 110

Trp Gly Gln Gly Thr Leu Val Thr Val Ser Ser
        115                 120

<210> SEQ ID NO 182
<211> LENGTH: 110
<212> TYPE: PRT
<213> ORGANISM: Artificial Sequence
<220> FEATURE:
<223> OTHER INFORMATION: Synthetic

<400> SEQUENCE: 182

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Gly Tyr His Tyr Ala
                85                  90                  95

Gly Leu Ile Thr Phe Gly Gln Gly Thr Lys Val Glu Ile Lys
            100                 105                 110

<210> SEQ ID NO 183
<211> LENGTH: 123
<212> TYPE: PRT
<213> ORGANISM: Artificial Sequence
<220> FEATURE:
<223> OTHER INFORMATION: Synthetic

<400> SEQUENCE: 183

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Leu Tyr Tyr Ser
            20                  25                  30

Ser Met His Trp Val Arg Gln Ala Pro Gly Lys Gly Leu Glu Trp Val
        35                  40                  45

Ala Ser Ile Tyr Ser Ser Asn Gly Asn Thr Gly Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ser Ser Phe Ser His Gly Tyr Gly Trp Tyr Gly Leu Asp Tyr
            100                 105                 110

Trp Gly Gln Gly Thr Leu Val Thr Val Ser Ser
        115                 120

<210> SEQ ID NO 184
<211> LENGTH: 110
<212> TYPE: PRT
<213> ORGANISM: Artificial Sequence
<220> FEATURE:
<223> OTHER INFORMATION: Synthetic

<400> SEQUENCE: 184

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
    50                  55                  60

```
Ser Arg Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Gly Tyr His Asp Ala
                 85                  90                  95

Gly Leu Ile Thr Phe Gly Gln Gly Thr Lys Val Glu Ile Lys
            100                 105                 110
```

<210> SEQ ID NO 185
<211> LENGTH: 123
<212> TYPE: PRT
<213> ORGANISM: Artificial Sequence
<220> FEATURE:
<223> OTHER INFORMATION: Synthetic

<400> SEQUENCE: 185

```
Glu Val Gln Leu Val Glu Ser Gly Gly Gly Leu Val Gln Pro Gly Gly
 1               5                   10                  15

Ser Leu Arg Leu Ser Cys Ala Ala Ser Gly Phe Asn Leu Tyr Tyr Ser
             20                  25                  30

Ser Met His Trp Val Arg Gln Ala Pro Gly Lys Gly Leu Glu Trp Val
         35                  40                  45

Ala Ser Ile Tyr Ser Ser Tyr Gly Tyr Thr Tyr Tyr Ala Asp Ser Val
     50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Arg Ser Ser Phe Ser His Gly Tyr Gly Trp Tyr Gly Leu Asp Tyr
            100                 105                 110

Trp Gly Gln Gly Thr Leu Val Thr Val Ser Ser
        115                 120
```

<210> SEQ ID NO 186
<211> LENGTH: 110
<212> TYPE: PRT
<213> ORGANISM: Artificial Sequence
<220> FEATURE:
<223> OTHER INFORMATION: Synthetic

<400> SEQUENCE: 186

```
Asp Ile Gln Met Thr Gln Ser Pro Ser Ser Leu Ser Ala Ser Val Gly
 1               5                   10                  15

Asp Arg Val Thr Ile Thr Cys Arg Ala Ser Gln Ser Val Ser Ser Ala
             20                  25                  30

Val Ala Trp Tyr Gln Gln Lys Pro Gly Lys Ala Pro Lys Leu Leu Ile
         35                  40                  45

Tyr Ser Ala Ser Ser Leu Tyr Ser Gly Val Pro Ser Arg Phe Ser Gly
     50                  55                  60

Ser Arg Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Gly Tyr His Gly Ala
                 85                  90                  95

Gly Leu Ile Thr Phe Gly Gln Gly Thr Lys Val Glu Ile Lys
            100                 105                 110
```

<210> SEQ ID NO 187
<211> LENGTH: 123
<212> TYPE: PRT

```
<213> ORGANISM: Artificial Sequence
<220> FEATURE:
<223> OTHER INFORMATION: Synthetic

<400> SEQUENCE: 187

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Leu Tyr Tyr Ser
            20                  25                  30

Ser Met His Trp Val Arg Gln Ala Pro Gly Lys Gly Leu Glu Trp Val
        35                  40                  45

Ala Ser Ile Tyr Ser Ser Tyr Gly Tyr Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ser Ser Phe Ser His Gly Tyr Gly Trp Tyr Gly Leu Asp Tyr
            100                 105                 110

Trp Gly Gln Gly Thr Leu Val Thr Val Ser Ser
        115                 120

<210> SEQ ID NO 188
<211> LENGTH: 110
<212> TYPE: PRT
<213> ORGANISM: Artificial Sequence
<220> FEATURE:
<223> OTHER INFORMATION: Synthetic

<400> SEQUENCE: 188

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Gly Tyr His Tyr Ala
                85                  90                  95

Gly Leu Ile Thr Phe Gly Gln Gly Thr Lys Val Glu Ile Lys
            100                 105                 110

<210> SEQ ID NO 189
<211> LENGTH: 123
<212> TYPE: PRT
<213> ORGANISM: Artificial Sequence
<220> FEATURE:
<223> OTHER INFORMATION: Synthetic

<400> SEQUENCE: 189

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Leu Tyr Tyr Ser
            20                  25                  30

Ser Met His Trp Val Arg Gln Ala Pro Gly Lys Gly Leu Glu Trp Val
        35                  40                  45
```

```
Ala Ser Ile Tyr Ser Ser Gly Asp Thr Gly Tyr Ala Asp Ser Val
        50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Arg Ser Ser Phe Ser His Gly Tyr Gly Trp Tyr Gly Leu Asp Tyr
            100                 105                 110

Trp Gly Gln Gly Thr Leu Val Thr Val Ser Ser
            115                 120
```

<210> SEQ ID NO 190
<211> LENGTH: 110
<212> TYPE: PRT
<213> ORGANISM: Artificial Sequence
<220> FEATURE:
<223> OTHER INFORMATION: Synthetic

<400> SEQUENCE: 190

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Thr Ser Ser Leu Tyr Ser Gly Val Pro Ser Arg Phe Ser Gly
 50                  55                  60

Ser Arg Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Gly Tyr His Tyr Ala
                 85                  90                  95

Gly Leu Ile Thr Phe Gly Gln Gly Thr Lys Val Glu Ile Lys
            100                 105                 110
```

<210> SEQ ID NO 191
<211> LENGTH: 123
<212> TYPE: PRT
<213> ORGANISM: Artificial Sequence
<220> FEATURE:
<223> OTHER INFORMATION: Synthetic

<400> SEQUENCE: 191

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Asn Leu Tyr Tyr Ser
            20                  25                  30

Ser Met His Trp Val Arg Gln Ala Pro Gly Lys Gly Leu Glu Trp Val
        35                  40                  45

Ala Ser Ile Tyr Ser Ser Tyr Gly Tyr Thr Tyr Tyr Ala Asp Ser Val
 50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Arg Ser Ser Phe Ser His Gly Tyr Gly Trp Tyr Gly Leu Asp Tyr
            100                 105                 110
```

Trp Gly Gln Gly Thr Leu Val Thr Val Ser Ser
        115                 120

<210> SEQ ID NO 192
<211> LENGTH: 110
<212> TYPE: PRT
<213> ORGANISM: Artificial Sequence
<220> FEATURE:
<223> OTHER INFORMATION: Synthetic

<400> SEQUENCE: 192

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Gly Tyr His Tyr Ala
                85                  90                  95

Gly Leu Ile Thr Phe Gly Gln Gly Thr Lys Val Glu Ile Lys
            100                 105                 110

<210> SEQ ID NO 193
<211> LENGTH: 123
<212> TYPE: PRT
<213> ORGANISM: Artificial Sequence
<220> FEATURE:
<223> OTHER INFORMATION: Synthetic

<400> SEQUENCE: 193

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Leu Tyr Tyr Ser
            20                  25                  30

Ser Met His Trp Val Arg Gln Ala Pro Gly Lys Gly Leu Glu Trp Val
        35                  40                  45

Ala Ser Ile Tyr Ser Ser His Gly Asn Thr Asp Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ser Ser Phe Ser His Gly Tyr Gly Trp Tyr Gly Leu Asp Tyr
            100                 105                 110

Trp Gly Gln Gly Thr Leu Val Thr Val Ser Ser
        115                 120

<210> SEQ ID NO 194
<211> LENGTH: 110
<212> TYPE: PRT
<213> ORGANISM: Artificial Sequence
<220> FEATURE:
<223> OTHER INFORMATION: Synthetic

<400> SEQUENCE: 194

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Gly Tyr His Tyr Ala
                85                  90                  95

Gly Leu Ile Thr Phe Gly Gln Gly Thr Lys Val Glu Ile Lys
            100                 105                 110

<210> SEQ ID NO 195
<211> LENGTH: 123
<212> TYPE: PRT
<213> ORGANISM: Artificial Sequence
<220> FEATURE:
<223> OTHER INFORMATION: Synthetic

<400> SEQUENCE: 195

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Leu Tyr Tyr Ser
            20                  25                  30

Ser Met His Trp Val Arg Gln Ala Pro Gly Lys Gly Leu Glu Trp Val
        35                  40                  45

Ala Ser Ile Tyr Ser Ser Gly Gly Ser Thr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ser Ser Phe Ser His Gly Tyr Gly Trp Tyr Gly Leu Asp Tyr
            100                 105                 110

Trp Gly Gln Gly Thr Leu Val Thr Val Ser Ser
        115                 120

<210> SEQ ID NO 196
<211> LENGTH: 110
<212> TYPE: PRT
<213> ORGANISM: Artificial Sequence
<220> FEATURE:
<223> OTHER INFORMATION: Synthetic

<400> SEQUENCE: 196

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Gly Ser Ser Gly Arg Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Gly Tyr His Tyr Ala
                85                  90                  95

Gly Leu Ile Thr Phe Gly Gln Gly Thr Lys Val Glu Ile Lys
            100                 105                 110

<210> SEQ ID NO 197
<211> LENGTH: 123
<212> TYPE: PRT
<213> ORGANISM: Artificial Sequence
<220> FEATURE:
<223> OTHER INFORMATION: Synthetic

<400> SEQUENCE: 197

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Leu Tyr Tyr Ser
            20                  25                  30

Ser Met His Trp Val Arg Gln Ala Pro Gly Lys Gly Leu Glu Trp Val
        35                  40                  45

Ala Ser Ile Tyr Ser Ser Tyr Gly Tyr Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ser Ser Phe Ser His Gly Tyr Gly Trp Tyr Gly Leu Asp Tyr
            100                 105                 110

Trp Gly Gln Gly Thr Leu Val Thr Val Ser Ser
        115                 120

<210> SEQ ID NO 198
<211> LENGTH: 110
<212> TYPE: PRT
<213> ORGANISM: Artificial Sequence
<220> FEATURE:
<223> OTHER INFORMATION: Synthetic

<400> SEQUENCE: 198

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Asp Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Gly Tyr His Tyr Ala
                85                  90                  95

Gly Leu Ile Thr Phe Gly Gln Gly Thr Lys Val Glu Ile Lys
            100                 105                 110

<210> SEQ ID NO 199
<211> LENGTH: 123
<212> TYPE: PRT

<213> ORGANISM: Artificial Sequence
<220> FEATURE:
<223> OTHER INFORMATION: Synthetic

<400> SEQUENCE: 199

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Leu Tyr Tyr Ser
            20                  25                  30

Ser Met His Trp Val Arg Gln Ala Pro Gly Lys Gly Leu Glu Trp Val
        35                  40                  45

Ala Ser Ile Tyr Ser Ser Tyr Gly Tyr Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ser Ser Phe Ser His Gly Tyr Gly Trp Tyr Gly Leu Asp Tyr
            100                 105                 110

Trp Gly Gln Gly Thr Leu Val Thr Val Ser Ser
        115                 120

<210> SEQ ID NO 200
<211> LENGTH: 110
<212> TYPE: PRT
<213> ORGANISM: Artificial Sequence
<220> FEATURE:
<223> OTHER INFORMATION: Synthetic

<400> SEQUENCE: 200

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Arg Asp Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Gly Tyr His Tyr Ala
                85                  90                  95

Gly Leu Ile Thr Phe Gly Gln Gly Thr Lys Val Glu Ile Lys
            100                 105                 110

<210> SEQ ID NO 201
<211> LENGTH: 123
<212> TYPE: PRT
<213> ORGANISM: Artificial Sequence
<220> FEATURE:
<223> OTHER INFORMATION: Synthetic

<400> SEQUENCE: 201

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Leu Tyr Tyr Ser
            20                  25                  30

Ser Met His Trp Val Arg Gln Ala Pro Gly Lys Gly Leu Glu Trp Val
        35                  40                  45

```
Ala Ser Ile Tyr Ser Ser Tyr Gly Tyr Thr Tyr Tyr Ala Asp Ser Val
        50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                85                  90                  95

Ala Arg Ser Ser Phe Ser His Gly Tyr Gly Trp Tyr Gly Leu Asp Tyr
            100                 105                 110

Trp Gly Gln Gly Thr Leu Val Thr Val Ser Ser
        115                 120

<210> SEQ ID NO 202
<211> LENGTH: 110
<212> TYPE: PRT
<213> ORGANISM: Artificial Sequence
<220> FEATURE:
<223> OTHER INFORMATION: Synthetic

<400> SEQUENCE: 202

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Ser Val Ser Ser Ala
                 20                  25                  30

Val Ala Trp Tyr Gln Gln Lys Pro Gly Lys Ala Pro Lys Leu Leu Ile
             35                  40                  45

Tyr Ser Glu Ser Ser Leu Ser Gly Val Pro Ser Arg Phe Ser Gly
         50                  55                  60

Ser Arg Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Gly Tyr His Tyr Ala
                85                  90                  95

Gly Leu Ile Thr Phe Gly Gln Gly Thr Lys Val Glu Ile Lys
            100                 105                 110

<210> SEQ ID NO 203
<211> LENGTH: 123
<212> TYPE: PRT
<213> ORGANISM: Artificial Sequence
<220> FEATURE:
<223> OTHER INFORMATION: Synthetic

<400> SEQUENCE: 203

Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Asn Leu Tyr Tyr Ser
                 20                  25                  30

Ser Met His Trp Val Arg Gln Ala Pro Gly Lys Gly Leu Glu Trp Val
             35                  40                  45

Ala Ser Ile Tyr Ser Ser Tyr Gly Tyr Thr Tyr Tyr Ala Asp Ser Val
        50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                85                  90                  95
```

Ala Arg Ser Ser Phe Ser His Gly Tyr Gly Trp Tyr Gly Leu Asp Tyr
            100                 105                 110

Trp Gly Gln Gly Thr Leu Val Thr Val Ser Ser
        115                 120

<210> SEQ ID NO 204
<211> LENGTH: 110
<212> TYPE: PRT
<213> ORGANISM: Artificial Sequence
<220> FEATURE:
<223> OTHER INFORMATION: Synthetic

<400> SEQUENCE: 204

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Arg Ser Ser Asp Ser Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Gly Tyr His Tyr Ala
                85                  90                  95

Gly Leu Ile Thr Phe Gly Gln Gly Thr Lys Val Glu Ile Lys
            100                 105                 110

<210> SEQ ID NO 205
<211> LENGTH: 123
<212> TYPE: PRT
<213> ORGANISM: Artificial Sequence
<220> FEATURE:
<223> OTHER INFORMATION: Synthetic

<400> SEQUENCE: 205

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Leu Tyr Tyr Ser
            20                  25                  30

Ser Met His Trp Val Arg Gln Ala Pro Gly Lys Gly Leu Glu Trp Val
        35                  40                  45

Ala Ser Ile Tyr Ser Ser Tyr Gly Tyr Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ser Ser Phe Ser His Gly Tyr Gly Trp Tyr Gly Leu Asp Tyr
            100                 105                 110

Trp Gly Gln Gly Thr Leu Val Thr Val Ser Ser
        115                 120

<210> SEQ ID NO 206
<211> LENGTH: 110
<212> TYPE: PRT
<213> ORGANISM: Artificial Sequence
<220> FEATURE:
<223> OTHER INFORMATION: Synthetic

<400> SEQUENCE: 206

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Thr Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Gly Tyr His Tyr Ala
                85                  90                  95

Gly Leu Ile Thr Phe Gly Gln Gly Thr Lys Val Glu Ile Lys
            100                 105                 110

<210> SEQ ID NO 207
<211> LENGTH: 123
<212> TYPE: PRT
<213> ORGANISM: Artificial Sequence
<220> FEATURE:
<223> OTHER INFORMATION: Synthetic

<400> SEQUENCE: 207

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Leu Tyr Tyr Ser
            20                  25                  30

Ser Met His Trp Val Arg Gln Ala Pro Gly Lys Gly Leu Glu Trp Val
        35                  40                  45

Ala Ser Ile Tyr Ser Ser Tyr Gly Tyr Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ser Ser Phe Ser His Gly Tyr Gly Trp Tyr Gly Leu Asp Tyr
            100                 105                 110

Trp Gly Gln Gly Thr Leu Val Thr Val Ser Ser
        115                 120

<210> SEQ ID NO 208
<211> LENGTH: 110
<212> TYPE: PRT
<213> ORGANISM: Artificial Sequence
<220> FEATURE:
<223> OTHER INFORMATION: Synthetic

<400> SEQUENCE: 208

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Glu Arg Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Gly Tyr His Tyr Ala
                85                  90                  95

Gly Leu Ile Thr Phe Gly Gln Gly Thr Lys Val Glu Ile Lys
            100                 105                 110

<210> SEQ ID NO 209
<211> LENGTH: 123
<212> TYPE: PRT
<213> ORGANISM: Artificial Sequence
<220> FEATURE:
<223> OTHER INFORMATION: Synthetic

<400> SEQUENCE: 209

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Leu Tyr Tyr Ser
            20                  25                  30

Ser Met His Trp Val Arg Gln Ala Pro Gly Lys Gly Leu Glu Trp Val
        35                  40                  45

Ala Ser Ile Tyr Ser Ser Tyr Gly Tyr Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ser Ser Phe Ser His Gly Tyr Gly Trp Tyr Gly Leu Asp Tyr
            100                 105                 110

Trp Gly Gln Gly Thr Leu Val Thr Val Ser Ser
        115                 120

<210> SEQ ID NO 210
<211> LENGTH: 110
<212> TYPE: PRT
<213> ORGANISM: Artificial Sequence
<220> FEATURE:
<223> OTHER INFORMATION: Synthetic

<400> SEQUENCE: 210

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Glu Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Gly Tyr His Tyr Ala
                85                  90                  95

Gly Leu Ile Thr Phe Gly Gln Gly Thr Lys Val Glu Ile Lys
            100                 105                 110

<210> SEQ ID NO 211
<211> LENGTH: 123
<212> TYPE: PRT

```
<213> ORGANISM: Artificial Sequence
<220> FEATURE:
<223> OTHER INFORMATION: Synthetic

<400> SEQUENCE: 211

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Leu Tyr Tyr Ser
            20                  25                  30

Ser Met His Trp Val Arg Gln Ala Pro Gly Lys Gly Leu Glu Trp Val
        35                  40                  45

Ala Ser Ile Tyr Ser Ser Tyr Gly Tyr Thr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ser Ser Phe Ser His Gly Tyr Gly Trp Tyr Gly Leu Asp Tyr
            100                 105                 110

Trp Gly Gln Gly Thr Leu Val Thr Val Ser Ser
        115                 120

<210> SEQ ID NO 212
<211> LENGTH: 110
<212> TYPE: PRT
<213> ORGANISM: Artificial Sequence
<220> FEATURE:
<223> OTHER INFORMATION: Synthetic

<400> SEQUENCE: 212

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ser Ser Val Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Gly Tyr His Tyr Ala
                85                  90                  95

Gly Leu Ile Thr Phe Gly Gln Gly Thr Lys Val Glu Ile Lys
            100                 105                 110

<210> SEQ ID NO 213
<211> LENGTH: 123
<212> TYPE: PRT
<213> ORGANISM: Artificial Sequence
<220> FEATURE:
<223> OTHER INFORMATION: Synthetic

<400> SEQUENCE: 213

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Leu Tyr Tyr Ser
            20                  25                  30

Ser Met His Trp Val Arg Gln Ala Pro Gly Lys Gly Leu Glu Trp Val
        35                  40                  45
```

```
Ala Ser Ile Tyr Ser Ser Tyr Gly Tyr Thr Tyr Ala Asp Ser Val
        50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                85                  90                  95

Ala Arg Ser Ser Phe Ser His Gly Tyr Gly Trp Tyr Gly Leu Asp Tyr
                100                 105                 110

Trp Gly Gln Gly Thr Leu Val Thr Val Ser Ser
            115                 120
```

<210> SEQ ID NO 214
<211> LENGTH: 110
<212> TYPE: PRT
<213> ORGANISM: Artificial Sequence
<220> FEATURE:
<223> OTHER INFORMATION: Synthetic

<400> SEQUENCE: 214

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Val Ser Ser Ala
                20                  25                  30

Val Ala Trp Tyr Gln Gln Lys Pro Gly Lys Ala Pro Lys Leu Leu Ile
            35                  40                  45

Tyr Ser Ala Ser Ser Leu Tyr Ser Gly Val Pro Ser Arg Phe Ser Gly
        50                  55                  60

Ser Arg Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Gly Tyr His Tyr Ala
                85                  90                  95

Gly Leu Ile Thr Phe Gly Gln Gly Thr Lys Val Glu Ile Lys
                100                 105                 110
```

<210> SEQ ID NO 215
<211> LENGTH: 123
<212> TYPE: PRT
<213> ORGANISM: Artificial Sequence
<220> FEATURE:
<223> OTHER INFORMATION: Synthetic

<400> SEQUENCE: 215

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Asn Leu Tyr Tyr Ser
                20                  25                  30

Ser Met His Trp Val Arg Gln Ala Pro Gly Lys Gly Leu Glu Trp Val
            35                  40                  45

Ala Ser Ile Tyr Ser Ser Tyr Gly His Thr Ser Tyr Ala Asp Ser Val
        50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                85                  90                  95
```

Ala Arg Ser Ser Phe Ser His Gly Tyr Gly Trp Tyr Gly Leu Asp Tyr
            100                 105                 110

Trp Gly Gln Gly Thr Leu Val Thr Val Ser Ser
        115                 120

<210> SEQ ID NO 216
<211> LENGTH: 110
<212> TYPE: PRT
<213> ORGANISM: Artificial Sequence
<220> FEATURE:
<223> OTHER INFORMATION: Synthetic

<400> SEQUENCE: 216

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Gly Tyr His Ser Ala
                85                  90                  95

Gly Leu Ile Thr Phe Gly Gln Gly Thr Lys Val Glu Ile Lys
            100                 105                 110

<210> SEQ ID NO 217
<211> LENGTH: 123
<212> TYPE: PRT
<213> ORGANISM: Artificial Sequence
<220> FEATURE:
<223> OTHER INFORMATION: Synthetic

<400> SEQUENCE: 217

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Leu Tyr Tyr Ser
            20                  25                  30

Ser Met His Trp Val Arg Gln Ala Pro Gly Lys Gly Leu Glu Trp Val
        35                  40                  45

Ala Ser Ile Tyr Ser Ser Tyr Gly Tyr Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ser Ser Phe Ser His Gly Tyr Gly Trp Tyr Gly Leu Asp Tyr
            100                 105                 110

Trp Gly Gln Gly Thr Leu Val Thr Val Ser Ser
        115                 120

<210> SEQ ID NO 218
<211> LENGTH: 110
<212> TYPE: PRT
<213> ORGANISM: Artificial Sequence
<220> FEATURE:
<223> OTHER INFORMATION: Synthetic

<400> SEQUENCE: 218

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Gly Tyr His Tyr Ala
                85                  90                  95

Gly Leu Ile Thr Phe Gly Gln Gly Thr Lys Val Glu Ile Lys
            100                 105                 110

<210> SEQ ID NO 219
<211> LENGTH: 123
<212> TYPE: PRT
<213> ORGANISM: Artificial Sequence
<220> FEATURE:
<223> OTHER INFORMATION: Synthetic

<400> SEQUENCE: 219

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Leu Tyr Tyr Ser
            20                  25                  30

Ser Met His Trp Val Arg Gln Ala Pro Gly Lys Gly Leu Glu Trp Val
        35                  40                  45

Ala Ser Ile Tyr Ser Ser Gly Ser Thr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ser Ser Phe Ser His Gly Tyr Gly Trp Tyr Gly Leu Asp Tyr
            100                 105                 110

Trp Gly Gln Gly Thr Leu Val Thr Val Ser Ser
        115                 120

<210> SEQ ID NO 220
<211> LENGTH: 110
<212> TYPE: PRT
<213> ORGANISM: Artificial Sequence
<220> FEATURE:
<223> OTHER INFORMATION: Synthetic

<400> SEQUENCE: 220

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Gly Tyr His Ser Ala
                85                  90                  95

Gly Leu Ile Thr Phe Gly Gln Gly Thr Lys Val Glu Ile Lys
            100                 105                 110

<210> SEQ ID NO 221
<211> LENGTH: 123
<212> TYPE: PRT
<213> ORGANISM: Artificial Sequence
<220> FEATURE:
<223> OTHER INFORMATION: Synthetic

<400> SEQUENCE: 221

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Leu Tyr Tyr Ser
            20                  25                  30

Ser Met His Trp Val Arg Gln Ala Pro Gly Lys Gly Leu Glu Trp Val
        35                  40                  45

Ala Ser Ile Tyr Ser Ser Ser Gly Ser Thr Ser Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ser Ser Phe Ser His Gly Tyr Gly Trp Tyr Gly Leu Asp Tyr
            100                 105                 110

Trp Gly Gln Gly Thr Leu Val Thr Val Ser Ser
        115                 120

<210> SEQ ID NO 222
<211> LENGTH: 110
<212> TYPE: PRT
<213> ORGANISM: Artificial Sequence
<220> FEATURE:
<223> OTHER INFORMATION: Synthetic

<400> SEQUENCE: 222

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Gly Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Gly Tyr His Tyr Ala
                85                  90                  95

Gly Leu Ile Thr Phe Gly Gln Gly Thr Lys Val Glu Ile Lys
            100                 105                 110

<210> SEQ ID NO 223
<211> LENGTH: 123
<212> TYPE: PRT

```
<213> ORGANISM: Artificial Sequence
<220> FEATURE:
<223> OTHER INFORMATION: Synthetic

<400> SEQUENCE: 223

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Leu Tyr Tyr Ser
            20                  25                  30

Ser Met His Trp Val Arg Gln Ala Pro Gly Lys Gly Leu Glu Trp Val
        35                  40                  45

Ala Ser Ile Tyr Ser Ser Tyr Gly Tyr Thr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ser Ser Phe Ser His Gly Tyr Gly Trp Tyr Gly Leu Asp Tyr
            100                 105                 110

Trp Gly Gln Gly Thr Leu Val Thr Val Ser Ser
        115                 120

<210> SEQ ID NO 224
<211> LENGTH: 110
<212> TYPE: PRT
<213> ORGANISM: Artificial Sequence
<220> FEATURE:
<223> OTHER INFORMATION: Synthetic

<400> SEQUENCE: 224

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Thr Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Gly Tyr His Tyr Ala
                85                  90                  95

Gly Leu Ile Thr Phe Gly Gln Gly Thr Lys Val Glu Ile Lys
            100                 105                 110

<210> SEQ ID NO 225
<211> LENGTH: 123
<212> TYPE: PRT
<213> ORGANISM: Artificial Sequence
<220> FEATURE:
<223> OTHER INFORMATION: Synthetic

<400> SEQUENCE: 225

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Leu Tyr Tyr Ser
            20                  25                  30

Ser Met His Trp Val Arg Gln Ala Pro Gly Lys Gly Leu Glu Trp Val
        35                  40                  45
```

```
Ala Ser Ile Tyr Ser Ser Tyr Gly Tyr Thr Tyr Tyr Ala Asp Ser Val
        50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                85                  90                  95

Ala Arg Ser Ser Phe Ser His Gly Tyr Gly Trp Tyr Gly Leu Asp Tyr
            100                 105                 110

Trp Gly Gln Gly Thr Leu Val Thr Val Ser Ser
            115                 120

<210> SEQ ID NO 226
<211> LENGTH: 110
<212> TYPE: PRT
<213> ORGANISM: Artificial Sequence
<220> FEATURE:
<223> OTHER INFORMATION: Synthetic

<400> SEQUENCE: 226

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Val Ser Ser Ala
                20                  25                  30

Val Ala Trp Tyr Gln Gln Lys Pro Gly Lys Ala Pro Lys Leu Leu Ile
            35                  40                  45

Tyr His Ala Ser Ser Leu Tyr Ser Gly Val Pro Ser Arg Phe Ser Gly
        50                  55                  60

Ser Arg Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Gly Tyr His Tyr Ala
                85                  90                  95

Gly Leu Ile Thr Phe Gly Gln Gly Thr Lys Val Glu Ile Lys
            100                 105                 110

<210> SEQ ID NO 227
<211> LENGTH: 123
<212> TYPE: PRT
<213> ORGANISM: Artificial Sequence
<220> FEATURE:
<223> OTHER INFORMATION: Synthetic

<400> SEQUENCE: 227

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Asn Leu Tyr Tyr Ser
                20                  25                  30

Ser Met His Trp Val Arg Gln Ala Pro Gly Lys Gly Leu Glu Trp Val
            35                  40                  45

Ala Ser Ile Tyr Ser Ser Tyr Gly Tyr Thr Tyr Tyr Ala Asp Ser Val
        50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                85                  90                  95
```

Ala Arg Ser Ser Phe Ser His Gly Tyr Gly Trp Tyr Gly Leu Asp Tyr
            100                 105                 110

Trp Gly Gln Gly Thr Leu Val Thr Val Ser Ser
        115                 120

<210> SEQ ID NO 228
<211> LENGTH: 110
<212> TYPE: PRT
<213> ORGANISM: Artificial Sequence
<220> FEATURE:
<223> OTHER INFORMATION: Synthetic

<400> SEQUENCE: 228

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Tyr Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Gly Tyr His Tyr Ala
                85                  90                  95

Gly Leu Ile Thr Phe Gly Gln Gly Thr Lys Val Glu Ile Lys
            100                 105                 110

<210> SEQ ID NO 229
<211> LENGTH: 123
<212> TYPE: PRT
<213> ORGANISM: Artificial Sequence
<220> FEATURE:
<223> OTHER INFORMATION: Synthetic

<400> SEQUENCE: 229

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Leu Tyr Tyr Ser
            20                  25                  30

Ser Met His Trp Val Arg Gln Ala Pro Gly Lys Gly Leu Glu Trp Val
        35                  40                  45

Ala Ser Ile Tyr Ser Ser Tyr Gly Tyr Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ser Ser Phe Ser His Gly Tyr Gly Trp Tyr Gly Leu Asp Tyr
            100                 105                 110

Trp Gly Gln Gly Thr Leu Val Thr Val Ser Ser
        115                 120

<210> SEQ ID NO 230
<211> LENGTH: 110
<212> TYPE: PRT
<213> ORGANISM: Artificial Sequence
<220> FEATURE:
<223> OTHER INFORMATION: Synthetic -continued

<400> SEQUENCE: 230

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Arg Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Gly Tyr His Tyr Ala
                85                  90                  95

Gly Leu Ile Thr Phe Gly Gln Gly Thr Lys Val Glu Ile Lys
            100                 105                 110

<210> SEQ ID NO 231
<211> LENGTH: 123
<212> TYPE: PRT
<213> ORGANISM: Artificial Sequence
<220> FEATURE:
<223> OTHER INFORMATION: Synthetic

<400> SEQUENCE: 231

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Tyr Tyr Ser
            20                  25                  30

Ser Met His Trp Val Arg Gln Ala Pro Gly Lys Gly Leu Glu Trp Val
        35                  40                  45

Ala Ser Ile Tyr Ser Ser Gly Gly Ser Thr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ser Ser Phe Ser His Gly Tyr Gly Trp Tyr Gly Leu Asp Tyr
            100                 105                 110

Trp Gly Gln Gly Thr Leu Val Thr Val Ser Ser
        115                 120

<210> SEQ ID NO 232
<211> LENGTH: 110
<212> TYPE: PRT
<213> ORGANISM: Artificial Sequence
<220> FEATURE:
<223> OTHER INFORMATION: Synthetic

<400> SEQUENCE: 232

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Arg Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Gly Tyr His Tyr Ala
                 85                  90                  95

Gly Leu Ile Thr Phe Gly Gln Gly Thr Lys Val Glu Ile Lys
            100                 105                 110

<210> SEQ ID NO 233
<211> LENGTH: 123
<212> TYPE: PRT
<213> ORGANISM: Artificial Sequence
<220> FEATURE:
<223> OTHER INFORMATION: Synthetic

<400> SEQUENCE: 233

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asp Leu Tyr Tyr Ser
            20                  25                  30

Ser Met His Trp Val Arg Gln Ala Pro Gly Lys Gly Leu Glu Trp Val
        35                  40                  45

Ala Ser Ile Tyr Ser Ser Gly Gly Ser Thr Ser Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ser Ser Phe Ser His Gly Tyr Gly Trp Tyr Gly Leu Asp Tyr
            100                 105                 110

Trp Gly Gln Gly Thr Leu Val Thr Val Ser Ser
        115                 120

<210> SEQ ID NO 234
<211> LENGTH: 110
<212> TYPE: PRT
<213> ORGANISM: Artificial Sequence
<220> FEATURE:
<223> OTHER INFORMATION: Synthetic

<400> SEQUENCE: 234

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Arg Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Gly Tyr His Tyr Ala
                85                  90                  95

Gly Leu Ile Thr Phe Gly Gln Gly Thr Lys Val Glu Ile Lys
            100                 105                 110

<210> SEQ ID NO 235
<211> LENGTH: 123
<212> TYPE: PRT

<213> ORGANISM: Artificial Sequence
<220> FEATURE:
<223> OTHER INFORMATION: Synthetic

<400> SEQUENCE: 235

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Tyr Tyr Ser
            20                  25                  30

Ser Met His Trp Val Arg Gln Ala Pro Gly Lys Gly Leu Glu Trp Val
        35                  40                  45

Ala Ser Ile Tyr Ser Ser Gly Gly Ser Thr Ser Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ser Ser Phe Ser His Gly Tyr Gly Trp Tyr Gly Leu Asp Tyr
            100                 105                 110

Trp Gly Gln Gly Thr Leu Val Thr Val Ser Ser
        115                 120

<210> SEQ ID NO 236
<211> LENGTH: 110
<212> TYPE: PRT
<213> ORGANISM: Artificial Sequence
<220> FEATURE:
<223> OTHER INFORMATION: Synthetic

<400> SEQUENCE: 236

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Arg Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Gly Tyr His Tyr Ala
                85                  90                  95

Gly Leu Ile Thr Phe Gly Gln Gly Thr Lys Val Glu Ile Lys
            100                 105                 110

<210> SEQ ID NO 237
<211> LENGTH: 123
<212> TYPE: PRT
<213> ORGANISM: Artificial Sequence
<220> FEATURE:
<223> OTHER INFORMATION: Synthetic

<400> SEQUENCE: 237

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Tyr Tyr Ser
            20                  25                  30

Ser Met His Trp Val Arg Gln Ala Pro Gly Lys Gly Leu Glu Trp Val
        35                  40                  45

Ala Ser Ile Tyr Ser Ser Gly Asp Thr His Tyr Ala Asp Ser Val
            50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Arg Ser Ser Phe Ser His Gly Tyr Gly Trp Tyr Gly Leu Asp Tyr
            100                 105                 110

Trp Gly Gln Gly Thr Leu Val Thr Val Ser Ser
            115                 120

<210> SEQ ID NO 238
<211> LENGTH: 110
<212> TYPE: PRT
<213> ORGANISM: Artificial Sequence
<220> FEATURE:
<223> OTHER INFORMATION: Synthetic

<400> SEQUENCE: 238

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Val Ser Ser Ala
             20                  25                  30

Val Ala Trp Tyr Gln Gln Lys Pro Gly Lys Ala Pro Arg Leu Leu Ile
         35                  40                  45

Tyr Ser Ala Ser Ser Leu Tyr Ser Gly Val Pro Ser Arg Phe Ser Gly
     50                  55                  60

Ser Arg Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Gly Tyr His Tyr Ala
                 85                  90                  95

Gly Leu Ile Thr Phe Gly Gln Gly Thr Lys Val Glu Ile Lys
            100                 105                 110

<210> SEQ ID NO 239
<211> LENGTH: 123
<212> TYPE: PRT
<213> ORGANISM: Artificial Sequence
<220> FEATURE:
<223> OTHER INFORMATION: Synthetic

<400> SEQUENCE: 239

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Asp Leu Tyr Tyr Ser
             20                  25                  30

Ser Met His Trp Val Arg Gln Ala Pro Gly Lys Gly Leu Glu Trp Val
         35                  40                  45

Ala Ser Ile Tyr Ser Ser Gly Asp Thr His Tyr Ala Asp Ser Val
     50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

```
Ala Arg Ser Ser Phe Ser His Gly Tyr Gly Trp Tyr Gly Leu Asp Tyr
            100                 105                 110

Trp Gly Gln Gly Thr Leu Val Thr Val Ser Ser
        115                 120
```

<210> SEQ ID NO 240
<211> LENGTH: 110
<212> TYPE: PRT
<213> ORGANISM: Artificial Sequence
<220> FEATURE:
<223> OTHER INFORMATION: Synthetic

<400> SEQUENCE: 240

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Arg Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Gly Tyr His Tyr Ala
                85                  90                  95

Gly Leu Ile Thr Phe Gly Gln Gly Thr Lys Val Glu Ile Lys
            100                 105                 110
```

<210> SEQ ID NO 241
<211> LENGTH: 123
<212> TYPE: PRT
<213> ORGANISM: Artificial Sequence
<220> FEATURE:
<223> OTHER INFORMATION: Synthetic

<400> SEQUENCE: 241

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Tyr Tyr Ser
            20                  25                  30

Ser Met His Trp Val Arg Gln Ala Pro Gly Lys Gly Leu Glu Trp Val
        35                  40                  45

Ala Ser Ile Tyr Ser Ser Ser Gly Asp Thr His Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ser Ser Phe Ser His Gly Tyr Gly Trp Tyr Gly Leu Asp Tyr
            100                 105                 110

Trp Gly Gln Gly Thr Leu Val Thr Val Ser Ser
        115                 120
```

<210> SEQ ID NO 242
<211> LENGTH: 110
<212> TYPE: PRT
<213> ORGANISM: Artificial Sequence
<220> FEATURE:
<223> OTHER INFORMATION: Synthetic

<400> SEQUENCE: 242

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Arg Leu Leu Ile
        35                  40                  45

Tyr Gly Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Gly Tyr His Tyr Ala
                85                  90                  95

Gly Leu Ile Thr Phe Gly Gln Gly Thr Lys Val Glu Ile Lys
            100                 105                 110

<210> SEQ ID NO 243
<211> LENGTH: 123
<212> TYPE: PRT
<213> ORGANISM: Artificial Sequence
<220> FEATURE:
<223> OTHER INFORMATION: Synthetic

<400> SEQUENCE: 243

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Leu Tyr Tyr Ser
            20                  25                  30

Ser Met His Trp Val Arg Gln Ala Pro Gly Lys Gly Leu Glu Trp Val
        35                  40                  45

Ala Ser Ile Tyr Ser Ser Gly Gly Ser Thr Ser Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ser Ser Phe Ser His Gly Tyr Gly Trp Tyr Gly Leu Asp Tyr
            100                 105                 110

Trp Gly Gln Gly Thr Leu Val Thr Val Ser Ser
        115                 120

<210> SEQ ID NO 244
<211> LENGTH: 110
<212> TYPE: PRT
<213> ORGANISM: Artificial Sequence
<220> FEATURE:
<223> OTHER INFORMATION: Synthetic

<400> SEQUENCE: 244

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Arg Leu Leu Ile
        35                  40                  45

Tyr Gly Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Gly Tyr His Tyr Ala
                85                  90                  95

Gly Leu Ile Thr Phe Gly Gln Gly Thr Lys Val Glu Ile Lys
            100                 105                 110

<210> SEQ ID NO 245
<211> LENGTH: 123
<212> TYPE: PRT
<213> ORGANISM: Artificial Sequence
<220> FEATURE:
<223> OTHER INFORMATION: Synthetic

<400> SEQUENCE: 245

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Tyr Tyr Ser
            20                  25                  30

Ser Met His Trp Val Arg Gln Ala Pro Gly Lys Gly Leu Glu Trp Val
        35                  40                  45

Ala Ser Ile Tyr Ser Ser Gly Gly Ser Thr Ser Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ser Ser Phe Ser His Gly Tyr Gly Trp Tyr Gly Leu Asp Tyr
            100                 105                 110

Trp Gly Gln Gly Thr Leu Val Thr Val Ser Ser
        115                 120

<210> SEQ ID NO 246
<211> LENGTH: 110
<212> TYPE: PRT
<213> ORGANISM: Artificial Sequence
<220> FEATURE:
<223> OTHER INFORMATION: Synthetic

<400> SEQUENCE: 246

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Arg Leu Leu Ile
        35                  40                  45

Tyr Gly Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Gly Tyr His Tyr Ala
                85                  90                  95

Gly Leu Ile Thr Phe Gly Gln Gly Thr Lys Val Glu Ile Lys
            100                 105                 110

<210> SEQ ID NO 247
<211> LENGTH: 123
<212> TYPE: PRT

```
<213> ORGANISM: Artificial Sequence
<220> FEATURE:
<223> OTHER INFORMATION: Synthetic

<400> SEQUENCE: 247

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asp Leu Tyr Tyr Ser
            20                  25                  30

Ser Met His Trp Val Arg Gln Ala Pro Gly Lys Gly Leu Glu Trp Val
        35                  40                  45

Ala Ser Ile Tyr Ser Ser Gly Gly Ser Thr Ser Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ser Ser Phe Ser His Gly Tyr Gly Trp Tyr Gly Leu Asp Tyr
            100                 105                 110

Trp Gly Gln Gly Thr Leu Val Thr Val Ser Ser
        115                 120

<210> SEQ ID NO 248
<211> LENGTH: 110
<212> TYPE: PRT
<213> ORGANISM: Artificial Sequence
<220> FEATURE:
<223> OTHER INFORMATION: Synthetic

<400> SEQUENCE: 248

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Arg Leu Leu Ile
        35                  40                  45

Tyr Gly Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Gly Tyr His Tyr Ala
                85                  90                  95

Gly Leu Ile Thr Phe Gly Gln Gly Thr Lys Val Glu Ile Lys
            100                 105                 110

<210> SEQ ID NO 249
<211> LENGTH: 123
<212> TYPE: PRT
<213> ORGANISM: Artificial Sequence
<220> FEATURE:
<223> OTHER INFORMATION: Synthetic

<400> SEQUENCE: 249

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Tyr Tyr Ser
            20                  25                  30

Ser Met His Trp Val Arg Gln Ala Pro Gly Lys Gly Leu Glu Trp Val
        35                  40                  45
```

```
Ala Ser Ile Tyr Ser Ser Gly Gly Ser Thr Ser Tyr Ala Asp Ser Val
        50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Arg Ser Ser Phe Ser His Gly Tyr Gly Trp Tyr Gly Leu Asp Tyr
            100                 105                 110

Trp Gly Gln Gly Thr Leu Val Thr Val Ser Ser
            115                 120

<210> SEQ ID NO 250
<211> LENGTH: 110
<212> TYPE: PRT
<213> ORGANISM: Artificial Sequence
<220> FEATURE:
<223> OTHER INFORMATION: Synthetic

<400> SEQUENCE: 250

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Arg Leu Leu Ile
        35                  40                  45

Tyr Gly Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Gly Tyr His Tyr Ala
                 85                  90                  95

Gly Leu Ile Thr Phe Gly Gln Gly Thr Lys Val Glu Ile Lys
            100                 105                 110

<210> SEQ ID NO 251
<211> LENGTH: 123
<212> TYPE: PRT
<213> ORGANISM: Artificial Sequence
<220> FEATURE:
<223> OTHER INFORMATION: Synthetic

<400> SEQUENCE: 251

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Asn Leu Tyr Tyr Ser
            20                  25                  30

Ser Met His Trp Val Arg Gln Ala Pro Gly Lys Gly Leu Glu Trp Val
        35                  40                  45

Ala Ser Ile Tyr Ser Ser Gly Asp Thr His Tyr Ala Asp Ser Val
    50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95
```

```
Ala Arg Ser Ser Phe Ser His Gly Tyr Gly Trp Tyr Gly Leu Asp Tyr
            100                 105                 110

Trp Gly Gln Gly Thr Leu Val Thr Val Ser Ser
        115                 120
```

<210> SEQ ID NO 252
<211> LENGTH: 110
<212> TYPE: PRT
<213> ORGANISM: Artificial Sequence
<220> FEATURE:
<223> OTHER INFORMATION: Synthetic

<400> SEQUENCE: 252

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Arg Leu Leu Ile
        35                  40                  45

Tyr Gly Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Gly Tyr His Tyr Ala
                85                  90                  95

Gly Leu Ile Thr Phe Gly Gln Gly Thr Lys Val Glu Ile Lys
            100                 105                 110
```

<210> SEQ ID NO 253
<211> LENGTH: 123
<212> TYPE: PRT
<213> ORGANISM: Artificial Sequence
<220> FEATURE:
<223> OTHER INFORMATION: Synthetic

<400> SEQUENCE: 253

```
Glu Val Gln Leu Val Glu Ser Gly Gly Leu Val Gln Pro Gly Gly
1               5                   10                  15

Ser Leu Arg Leu Ser Cys Ala Ala Ser Gly Phe Thr Leu Tyr Tyr Ser
            20                  25                  30

Ser Met His Trp Val Arg Gln Ala Pro Gly Lys Gly Leu Glu Trp Val
        35                  40                  45

Ala Ser Ile Tyr Ser Ser Ser Gly Asp Thr His Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ser Ser Phe Ser His Gly Tyr Gly Trp Tyr Gly Leu Asp Tyr
            100                 105                 110

Trp Gly Gln Gly Thr Leu Val Thr Val Ser Ser
        115                 120
```

<210> SEQ ID NO 254
<211> LENGTH: 110
<212> TYPE: PRT
<213> ORGANISM: Artificial Sequence
<220> FEATURE:
<223> OTHER INFORMATION: Synthetic

<400> SEQUENCE: 254

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Arg Leu Leu Ile
        35                  40                  45

Tyr Gly Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Gly Tyr His Tyr Ala
                85                  90                  95

Gly Leu Ile Thr Phe Gly Gln Gly Thr Lys Val Glu Ile Lys
            100                 105                 110

<210> SEQ ID NO 255
<211> LENGTH: 123
<212> TYPE: PRT
<213> ORGANISM: Artificial Sequence
<220> FEATURE:
<223> OTHER INFORMATION: Synthetic

<400> SEQUENCE: 255

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asp Leu Tyr Tyr Ser
            20                  25                  30

Ser Met His Trp Val Arg Gln Ala Pro Gly Lys Gly Leu Glu Trp Val
        35                  40                  45

Ala Ser Ile Tyr Ser Ser Gly Asp Thr His Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ser Ser Phe Ser His Gly Tyr Gly Trp Tyr Gly Leu Asp Tyr
            100                 105                 110

Trp Gly Gln Gly Thr Leu Val Thr Val Ser Ser
        115                 120

<210> SEQ ID NO 256
<211> LENGTH: 110
<212> TYPE: PRT
<213> ORGANISM: Artificial Sequence
<220> FEATURE:
<223> OTHER INFORMATION: Synthetic

<400> SEQUENCE: 256

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Arg Leu Leu Ile
        35                  40                  45

Tyr Gly Ala Ser Ser Leu Tyr Ser Gly Val Pro Ser Arg Phe Ser Gly
    50                  55                  60

```
Ser Arg Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Gly Tyr His Tyr Ala
                 85                  90                  95

Gly Leu Ile Thr Phe Gly Gln Gly Thr Lys Val Glu Ile Lys
            100                 105                 110
```

<210> SEQ ID NO 257
<211> LENGTH: 123
<212> TYPE: PRT
<213> ORGANISM: Artificial Sequence
<220> FEATURE:
<223> OTHER INFORMATION: Synthetic

<400> SEQUENCE: 257

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Ser Leu Tyr Tyr Ser
             20                  25                  30

Ser Met His Trp Val Arg Gln Ala Pro Gly Lys Gly Leu Glu Trp Val
         35                  40                  45

Ala Ser Ile Tyr Ser Ser Ser Gly Asp Thr His Tyr Ala Asp Ser Val
     50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Arg Ser Ser Phe Ser His Gly Tyr Gly Trp Tyr Gly Leu Asp Tyr
            100                 105                 110

Trp Gly Gln Gly Thr Leu Val Thr Val Ser Ser
        115                 120
```

<210> SEQ ID NO 258
<211> LENGTH: 110
<212> TYPE: PRT
<213> ORGANISM: Artificial Sequence
<220> FEATURE:
<223> OTHER INFORMATION: Synthetic

<400> SEQUENCE: 258

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Val Ser Ser Ala
             20                  25                  30

Val Ala Trp Tyr Gln Gln Lys Pro Gly Lys Ala Pro Arg Leu Leu Ile
         35                  40                  45

Tyr Ser Ala Ser Ser Leu Tyr Ser Gly Val Pro Ser Arg Phe Ser Gly
     50                  55                  60

Ser Arg Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Gly Tyr His Asp Ala
                 85                  90                  95

Gly Leu Ile Thr Phe Gly Gln Gly Thr Lys Val Glu Ile Lys
            100                 105                 110
```

<210> SEQ ID NO 259
<211> LENGTH: 123
<212> TYPE: PRT

<213> ORGANISM: Artificial Sequence
<220> FEATURE:
<223> OTHER INFORMATION: Synthetic

<400> SEQUENCE: 259

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Leu Tyr Tyr Ser
            20                  25                  30

Ser Met His Trp Val Arg Gln Ala Pro Gly Lys Gly Leu Glu Trp Val
        35                  40                  45

Ala Ser Ile Tyr Ser Ser Gly Gly Ser Thr Ser Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ser Ser Phe Ser His Gly Tyr Gly Trp Tyr Gly Leu Asp Tyr
            100                 105                 110

Trp Gly Gln Gly Thr Leu Val Thr Val Ser Ser
        115                 120
```

<210> SEQ ID NO 260
<211> LENGTH: 110
<212> TYPE: PRT
<213> ORGANISM: Artificial Sequence
<220> FEATURE:
<223> OTHER INFORMATION: Synthetic

<400> SEQUENCE: 260

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Arg Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Gly Tyr His Asp Ala
                85                  90                  95

Gly Leu Ile Thr Phe Gly Gln Gly Thr Lys Val Glu Ile Lys
            100                 105                 110
```

<210> SEQ ID NO 261
<211> LENGTH: 123
<212> TYPE: PRT
<213> ORGANISM: Artificial Sequence
<220> FEATURE:
<223> OTHER INFORMATION: Synthetic

<400> SEQUENCE: 261

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Tyr Tyr Ser
            20                  25                  30

Ser Met His Trp Val Arg Gln Ala Pro Gly Lys Gly Leu Glu Trp Val
        35                  40                  45
```

```
Ala Ser Ile Tyr Ser Ser Gly Gly Ser Thr Ser Tyr Ala Asp Ser Val
        50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                85                  90                  95

Ala Arg Ser Ser Phe Ser His Gly Tyr Gly Trp Tyr Gly Leu Asp Tyr
            100                 105                 110

Trp Gly Gln Gly Thr Leu Val Thr Val Ser Ser
        115                 120
```

<210> SEQ ID NO 262
<211> LENGTH: 110
<212> TYPE: PRT
<213> ORGANISM: Artificial Sequence
<220> FEATURE:
<223> OTHER INFORMATION: Synthetic

<400> SEQUENCE: 262

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Val Ser Ser Ala
                20                  25                  30

Val Ala Trp Tyr Gln Gln Lys Pro Gly Lys Ala Pro Arg Leu Leu Ile
            35                  40                  45

Tyr Ser Ala Ser Ser Leu Tyr Ser Gly Val Pro Ser Arg Phe Ser Gly
 50                  55                  60

Ser Arg Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Gly Tyr His Asp Ala
                85                  90                  95

Gly Leu Ile Thr Phe Gly Gln Gly Thr Lys Val Glu Ile Lys
            100                 105                 110
```

<210> SEQ ID NO 263
<211> LENGTH: 123
<212> TYPE: PRT
<213> ORGANISM: Artificial Sequence
<220> FEATURE:
<223> OTHER INFORMATION: Synthetic

<400> SEQUENCE: 263

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Asp Leu Tyr Tyr Ser
                20                  25                  30

Ser Met His Trp Val Arg Gln Ala Pro Gly Lys Gly Leu Glu Trp Val
            35                  40                  45

Ala Ser Ile Tyr Ser Ser Gly Gly Ser Thr Ser Tyr Ala Asp Ser Val
 50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                85                  90                  95
```

```
Ala Arg Ser Ser Phe Ser His Gly Tyr Gly Trp Tyr Gly Leu Asp Tyr
            100                 105                 110

Trp Gly Gln Gly Thr Leu Val Thr Val Ser Ser
        115                 120
```

<210> SEQ ID NO 264
<211> LENGTH: 110
<212> TYPE: PRT
<213> ORGANISM: Artificial Sequence
<220> FEATURE:
<223> OTHER INFORMATION: Synthetic

<400> SEQUENCE: 264

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Arg Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Gly Tyr His Asp Ala
                85                  90                  95

Gly Leu Ile Thr Phe Gly Gln Gly Thr Lys Val Glu Ile Lys
            100                 105                 110
```

<210> SEQ ID NO 265
<211> LENGTH: 123
<212> TYPE: PRT
<213> ORGANISM: Artificial Sequence
<220> FEATURE:
<223> OTHER INFORMATION: Synthetic

<400> SEQUENCE: 265

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Tyr Tyr Ser
            20                  25                  30

Ser Met His Trp Val Arg Gln Ala Pro Gly Lys Gly Leu Glu Trp Val
        35                  40                  45

Ala Ser Ile Tyr Ser Ser Gly Gly Ser Thr Ser Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ser Ser Phe Ser His Gly Tyr Gly Trp Tyr Gly Leu Asp Tyr
            100                 105                 110

Trp Gly Gln Gly Thr Leu Val Thr Val Ser Ser
        115                 120
```

<210> SEQ ID NO 266
<211> LENGTH: 110
<212> TYPE: PRT
<213> ORGANISM: Artificial Sequence
<220> FEATURE:
<223> OTHER INFORMATION: Synthetic

<400> SEQUENCE: 266

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Arg Leu Leu Ile
        35                  40                  45

Tyr Ser Ala Ser Ser Leu Tyr Ser Gly Val Pro Ser Arg Phe Ser Gly
50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Gly Tyr His Asp Ala
                85                  90                  95

Gly Leu Ile Thr Phe Gly Gln Gly Thr Lys Val Glu Ile Lys
            100                 105                 110

<210> SEQ ID NO 267
<211> LENGTH: 123
<212> TYPE: PRT
<213> ORGANISM: Artificial Sequence
<220> FEATURE:
<223> OTHER INFORMATION: Synthetic

<400> SEQUENCE: 267

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Leu Tyr Tyr Ser
            20                  25                  30

Ser Met His Trp Val Arg Gln Ala Pro Gly Lys Gly Leu Glu Trp Val
        35                  40                  45

Ala Ser Ile Tyr Ser Ser Gly Asp Thr His Tyr Ala Asp Ser Val
50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ser Ser Phe Ser His Gly Tyr Gly Trp Tyr Gly Leu Asp Tyr
            100                 105                 110

Trp Gly Gln Gly Thr Leu Val Thr Val Ser Ser
        115                 120

<210> SEQ ID NO 268
<211> LENGTH: 110
<212> TYPE: PRT
<213> ORGANISM: Artificial Sequence
<220> FEATURE:
<223> OTHER INFORMATION: Synthetic

<400> SEQUENCE: 268

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Arg Leu Leu Ile
        35                  40                  45

Tyr Ser Ala Ser Ser Leu Tyr Ser Gly Val Pro Ser Arg Phe Ser Gly
50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Gly Tyr His Asp Ala
                85                  90                  95

Gly Leu Ile Thr Phe Gly Gln Gly Thr Lys Val Glu Ile Lys
            100                 105                 110

<210> SEQ ID NO 269
<211> LENGTH: 123
<212> TYPE: PRT
<213> ORGANISM: Artificial Sequence
<220> FEATURE:
<223> OTHER INFORMATION: Synthetic

<400> SEQUENCE: 269

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Tyr Tyr Ser
            20                  25                  30

Ser Met His Trp Val Arg Gln Ala Pro Gly Lys Gly Leu Glu Trp Val
        35                  40                  45

Ala Ser Ile Tyr Ser Ser Ser Gly Asp Thr His Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ser Ser Phe Ser His Gly Tyr Gly Trp Tyr Gly Leu Asp Tyr
            100                 105                 110

Trp Gly Gln Gly Thr Leu Val Thr Val Ser Ser
        115                 120

<210> SEQ ID NO 270
<211> LENGTH: 110
<212> TYPE: PRT
<213> ORGANISM: Artificial Sequence
<220> FEATURE:
<223> OTHER INFORMATION: Synthetic

<400> SEQUENCE: 270

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Arg Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Gly Tyr His Asp Ala
                85                  90                  95

Gly Leu Ile Thr Phe Gly Gln Gly Thr Lys Val Glu Ile Lys
            100                 105                 110

<210> SEQ ID NO 271
<211> LENGTH: 123
<212> TYPE: PRT

<213> ORGANISM: Artificial Sequence
<220> FEATURE:
<223> OTHER INFORMATION: Synthetic

<400> SEQUENCE: 271

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asp Leu Tyr Tyr Ser
            20                  25                  30

Ser Met His Trp Val Arg Gln Ala Pro Gly Lys Gly Leu Glu Trp Val
        35                  40                  45

Ala Ser Ile Tyr Ser Ser Gly Asp Thr His Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ser Ser Phe Ser His Gly Tyr Gly Trp Tyr Gly Leu Asp Tyr
            100                 105                 110

Trp Gly Gln Gly Thr Leu Val Thr Val Ser Ser
        115                 120

<210> SEQ ID NO 272
<211> LENGTH: 110
<212> TYPE: PRT
<213> ORGANISM: Artificial Sequence
<220> FEATURE:
<223> OTHER INFORMATION: Synthetic

<400> SEQUENCE: 272

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Arg Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Gly Tyr His Asp Ala
                85                  90                  95

Gly Leu Ile Thr Phe Gly Gln Gly Thr Lys Val Glu Ile Lys
            100                 105                 110

<210> SEQ ID NO 273
<211> LENGTH: 123
<212> TYPE: PRT
<213> ORGANISM: Artificial Sequence
<220> FEATURE:
<223> OTHER INFORMATION: Synthetic

<400> SEQUENCE: 273

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Tyr Tyr Ser
            20                  25                  30

Ser Met His Trp Val Arg Gln Ala Pro Gly Lys Gly Leu Glu Trp Val
        35                  40                  45

Ala Ser Ile Tyr Ser Ser Gly Asp Thr His Tyr Ala Asp Ser Val
            50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                85                  90                  95

Ala Arg Ser Ser Phe Ser His Gly Tyr Gly Trp Tyr Gly Leu Asp Tyr
                100                 105                 110

Trp Gly Gln Gly Thr Leu Val Thr Val Ser Ser
            115                 120

<210> SEQ ID NO 274
<211> LENGTH: 110
<212> TYPE: PRT
<213> ORGANISM: Artificial Sequence
<220> FEATURE:
<223> OTHER INFORMATION: Synthetic

<400> SEQUENCE: 274

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Val Ser Ser Ala
                20                  25                  30

Val Ala Trp Tyr Gln Gln Lys Pro Gly Lys Ala Pro Arg Leu Leu Ile
            35                  40                  45

Tyr Gly Ala Ser Ser Leu Tyr Ser Gly Val Pro Ser Arg Phe Ser Gly
        50                  55                  60

Ser Arg Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Gly Tyr His Asp Ala
                85                  90                  95

Gly Leu Ile Thr Phe Gly Gln Gly Thr Lys Val Glu Ile Lys
                100                 105                 110

<210> SEQ ID NO 275
<211> LENGTH: 123
<212> TYPE: PRT
<213> ORGANISM: Artificial Sequence
<220> FEATURE:
<223> OTHER INFORMATION: Synthetic

<400> SEQUENCE: 275

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Asn Leu Tyr Tyr Ser
                20                  25                  30

Ser Met His Trp Val Arg Gln Ala Pro Gly Lys Gly Leu Glu Trp Val
            35                  40                  45

Ala Ser Ile Tyr Ser Ser Gly Gly Ser Thr Tyr Ala Asp Ser Val
        50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                85                  90                  95

Ala Arg Ser Ser Phe Ser His Gly Tyr Gly Trp Tyr Gly Leu Asp Tyr
            100                 105                 110

Trp Gly Gln Gly Thr Leu Val Thr Val Ser Ser
        115                 120

<210> SEQ ID NO 276
<211> LENGTH: 110
<212> TYPE: PRT
<213> ORGANISM: Artificial Sequence
<220> FEATURE:
<223> OTHER INFORMATION: Synthetic

<400> SEQUENCE: 276

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Arg Leu Leu Ile
        35                  40                  45

Tyr Gly Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Gly Tyr His Asp Ala
                85                  90                  95

Gly Leu Ile Thr Phe Gly Gln Gly Thr Lys Val Glu Ile Lys
            100                 105                 110

<210> SEQ ID NO 277
<211> LENGTH: 123
<212> TYPE: PRT
<213> ORGANISM: Artificial Sequence
<220> FEATURE:
<223> OTHER INFORMATION: Synthetic

<400> SEQUENCE: 277

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Tyr Tyr Ser
            20                  25                  30

Ser Met His Trp Val Arg Gln Ala Pro Gly Lys Gly Leu Glu Trp Val
        35                  40                  45

Ala Ser Ile Tyr Ser Ser Gly Gly Ser Thr Ser Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ser Ser Phe Ser His Gly Tyr Gly Trp Tyr Gly Leu Asp Tyr
            100                 105                 110

Trp Gly Gln Gly Thr Leu Val Thr Val Ser Ser
        115                 120

<210> SEQ ID NO 278
<211> LENGTH: 110
<212> TYPE: PRT
<213> ORGANISM: Artificial Sequence
<220> FEATURE:
<223> OTHER INFORMATION: Synthetic

<400> SEQUENCE: 278

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Arg Leu Leu Ile
        35                  40                  45

Tyr Gly Ala Ser Ser Leu Tyr Ser Gly Val Pro Ser Arg Phe Ser Gly
50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Gly Tyr His Asp Ala
                85                  90                  95

Gly Leu Ile Thr Phe Gly Gln Gly Thr Lys Val Glu Ile Lys
            100                 105                 110

<210> SEQ ID NO 279
<211> LENGTH: 123
<212> TYPE: PRT
<213> ORGANISM: Artificial Sequence
<220> FEATURE:
<223> OTHER INFORMATION: Synthetic

<400> SEQUENCE: 279

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asp Leu Tyr Tyr Ser
            20                  25                  30

Ser Met His Trp Val Arg Gln Ala Pro Gly Lys Gly Leu Glu Trp Val
        35                  40                  45

Ala Ser Ile Tyr Ser Ser Gly Gly Ser Thr Ser Tyr Ala Asp Ser Val
50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ser Ser Phe Ser His Gly Tyr Gly Trp Tyr Gly Leu Asp Tyr
            100                 105                 110

Trp Gly Gln Gly Thr Leu Val Thr Val Ser Ser
        115                 120

<210> SEQ ID NO 280
<211> LENGTH: 110
<212> TYPE: PRT
<213> ORGANISM: Artificial Sequence
<220> FEATURE:
<223> OTHER INFORMATION: Synthetic

<400> SEQUENCE: 280

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Arg Leu Leu Ile
        35                  40                  45

Tyr Gly Ala Ser Ser Leu Tyr Ser Gly Val Pro Ser Arg Phe Ser Gly
50                  55                  60

```
Ser Arg Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Gly Tyr His Asp Ala
                 85                  90                  95

Gly Leu Ile Thr Phe Gly Gln Gly Thr Lys Val Glu Ile Lys
            100                 105                 110

<210> SEQ ID NO 281
<211> LENGTH: 123
<212> TYPE: PRT
<213> ORGANISM: Artificial Sequence
<220> FEATURE:
<223> OTHER INFORMATION: Synthetic

<400> SEQUENCE: 281

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Ser Leu Tyr Tyr Ser
            20                  25                  30

Ser Met His Trp Val Arg Gln Ala Pro Gly Lys Gly Leu Glu Trp Val
        35                  40                  45

Ala Ser Ile Tyr Ser Ser Gly Gly Ser Thr Ser Tyr Ala Asp Ser Val
    50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Arg Ser Ser Phe Ser His Gly Tyr Gly Trp Tyr Gly Leu Asp Tyr
            100                 105                 110

Trp Gly Gln Gly Thr Leu Val Thr Val Ser Ser
        115                 120

<210> SEQ ID NO 282
<211> LENGTH: 110
<212> TYPE: PRT
<213> ORGANISM: Artificial Sequence
<220> FEATURE:
<223> OTHER INFORMATION: Synthetic

<400> SEQUENCE: 282

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Arg Leu Leu Ile
        35                  40                  45

Tyr Gly Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Gly Tyr His Asp Ala
                 85                  90                  95

Gly Leu Ile Thr Phe Gly Gln Gly Thr Lys Val Glu Ile Lys
            100                 105                 110

<210> SEQ ID NO 283
<211> LENGTH: 123
<212> TYPE: PRT
```

<213> ORGANISM: Artificial Sequence
<220> FEATURE:
<223> OTHER INFORMATION: Synthetic

<400> SEQUENCE: 283

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Leu Tyr Tyr Ser
            20                  25                  30

Ser Met His Trp Val Arg Gln Ala Pro Gly Lys Gly Leu Glu Trp Val
        35                  40                  45

Ala Ser Ile Tyr Ser Ser Gly Asp Thr His Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ser Ser Phe Ser His Gly Tyr Gly Trp Tyr Gly Leu Asp Tyr
            100                 105                 110

Trp Gly Gln Gly Thr Leu Val Thr Val Ser Ser
        115                 120

<210> SEQ ID NO 284
<211> LENGTH: 110
<212> TYPE: PRT
<213> ORGANISM: Artificial Sequence
<220> FEATURE:
<223> OTHER INFORMATION: Synthetic

<400> SEQUENCE: 284

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Arg Leu Leu Ile
        35                  40                  45

Tyr Gly Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Gly Tyr His Asp Ala
                85                  90                  95

Gly Leu Ile Thr Phe Gly Gln Gly Thr Lys Val Glu Ile Lys
            100                 105                 110

<210> SEQ ID NO 285
<211> LENGTH: 123
<212> TYPE: PRT
<213> ORGANISM: Artificial Sequence
<220> FEATURE:
<223> OTHER INFORMATION: Synthetic

<400> SEQUENCE: 285

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Tyr Tyr Ser
            20                  25                  30

Ser Met His Trp Val Arg Gln Ala Pro Gly Lys Gly Leu Glu Trp Val
        35                  40                  45

Ala Ser Ile Tyr Ser Ser Gly Asp Thr His Tyr Ala Asp Ser Val
            50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Arg Ser Ser Phe Ser His Gly Tyr Gly Trp Tyr Gly Leu Asp Tyr
            100                 105                 110

Trp Gly Gln Gly Thr Leu Val Thr Val Ser Ser
            115                 120

<210> SEQ ID NO 286
<211> LENGTH: 110
<212> TYPE: PRT
<213> ORGANISM: Artificial Sequence
<220> FEATURE:
<223> OTHER INFORMATION: Synthetic

<400> SEQUENCE: 286

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Val Ser Ser Ala
             20                  25                  30

Val Ala Trp Tyr Gln Gln Lys Pro Gly Lys Ala Pro Arg Leu Leu Ile
         35                  40                  45

Tyr Gly Ala Ser Ser Leu Tyr Ser Gly Val Pro Ser Arg Phe Ser Gly
     50                  55                  60

Ser Arg Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Gly Tyr His Asp Ala
                 85                  90                  95

Gly Leu Ile Thr Phe Gly Gln Gly Thr Lys Val Glu Ile Lys
            100                 105                 110

<210> SEQ ID NO 287
<211> LENGTH: 123
<212> TYPE: PRT
<213> ORGANISM: Artificial Sequence
<220> FEATURE:
<223> OTHER INFORMATION: Synthetic

<400> SEQUENCE: 287

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Asp Leu Tyr Tyr Ser
             20                  25                  30

Ser Met His Trp Val Arg Gln Ala Pro Gly Lys Gly Leu Glu Trp Val
         35                  40                  45

Ala Ser Ile Tyr Ser Ser Gly Asp Thr His Tyr Ala Asp Ser Val
     50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

```
Ala Arg Ser Ser Phe Ser His Gly Tyr Gly Trp Tyr Gly Leu Asp Tyr
            100                 105                 110

Trp Gly Gln Gly Thr Leu Val Thr Val Ser Ser
        115                 120
```

<210> SEQ ID NO 288
<211> LENGTH: 110
<212> TYPE: PRT
<213> ORGANISM: Artificial Sequence
<220> FEATURE:
<223> OTHER INFORMATION: Synthetic

<400> SEQUENCE: 288

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Arg Leu Leu Ile
        35                  40                  45

Tyr Gly Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Gly Tyr His Asp Ala
                85                  90                  95

Gly Leu Ile Thr Phe Gly Gln Gly Thr Lys Val Glu Ile Lys
            100                 105                 110
```

<210> SEQ ID NO 289
<211> LENGTH: 123
<212> TYPE: PRT
<213> ORGANISM: Artificial Sequence
<220> FEATURE:
<223> OTHER INFORMATION: Synthetic

<400> SEQUENCE: 289

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Tyr Tyr Ser
            20                  25                  30

Ser Met His Trp Val Arg Gln Ala Pro Gly Lys Gly Leu Glu Trp Val
        35                  40                  45

Ala Ser Ile Tyr Ser Ser Ser Gly Asp Thr His Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ser Ser Phe Ser His Gly Tyr Gly Trp Tyr Gly Leu Asp Tyr
            100                 105                 110

Trp Gly Gln Gly Thr Leu Val Thr Val Ser Ser
        115                 120
```

<210> SEQ ID NO 290
<211> LENGTH: 110
<212> TYPE: PRT
<213> ORGANISM: Artificial Sequence
<220> FEATURE:
<223> OTHER INFORMATION: Synthetic

<400> SEQUENCE: 290

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Arg Leu Leu Ile
        35                  40                  45

Tyr Ser Ala Ser Ser Leu Tyr Ser Gly Val Pro Ser Arg Phe Ser Gly
50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Gly Tyr His Gly Ala
                85                  90                  95

Gly Leu Ile Thr Phe Gly Gln Gly Thr Lys Val Glu Ile Lys
            100                 105                 110

<210> SEQ ID NO 291
<211> LENGTH: 123
<212> TYPE: PRT
<213> ORGANISM: Artificial Sequence
<220> FEATURE:
<223> OTHER INFORMATION: Synthetic

<400> SEQUENCE: 291

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Leu Tyr Tyr Ser
            20                  25                  30

Ser Met His Trp Val Arg Gln Ala Pro Gly Lys Gly Leu Glu Trp Val
        35                  40                  45

Ala Ser Ile Tyr Ser Ser Gly Gly Ser Thr Tyr Ala Asp Ser Val
50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ser Ser Phe Ser His Gly Tyr Gly Trp Tyr Gly Leu Asp Tyr
            100                 105                 110

Trp Gly Gln Gly Thr Leu Val Thr Val Ser Ser
        115                 120

<210> SEQ ID NO 292
<211> LENGTH: 110
<212> TYPE: PRT
<213> ORGANISM: Artificial Sequence
<220> FEATURE:
<223> OTHER INFORMATION: Synthetic

<400> SEQUENCE: 292

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Arg Leu Leu Ile
        35                  40                  45

Tyr Ser Ala Ser Ser Leu Tyr Ser Gly Val Pro Ser Arg Phe Ser Gly
50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Gly Tyr His Gly Ala
                85                  90                  95

Gly Leu Ile Thr Phe Gly Gln Gly Thr Lys Val Glu Ile Lys
            100                 105                 110

<210> SEQ ID NO 293
<211> LENGTH: 123
<212> TYPE: PRT
<213> ORGANISM: Artificial Sequence
<220> FEATURE:
<223> OTHER INFORMATION: Synthetic

<400> SEQUENCE: 293

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Tyr Tyr Ser
            20                  25                  30

Ser Met His Trp Val Arg Gln Ala Pro Gly Lys Gly Leu Glu Trp Val
        35                  40                  45

Ala Ser Ile Tyr Ser Ser Gly Gly Ser Thr Ser Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ser Ser Phe Ser His Gly Tyr Gly Trp Tyr Gly Leu Asp Tyr
            100                 105                 110

Trp Gly Gln Gly Thr Leu Val Thr Val Ser Ser
        115                 120

<210> SEQ ID NO 294
<211> LENGTH: 110
<212> TYPE: PRT
<213> ORGANISM: Artificial Sequence
<220> FEATURE:
<223> OTHER INFORMATION: Synthetic

<400> SEQUENCE: 294

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Arg Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Gly Tyr His Gly Ala
                85                  90                  95

Gly Leu Ile Thr Phe Gly Gln Gly Thr Lys Val Glu Ile Lys
            100                 105                 110

<210> SEQ ID NO 295
<211> LENGTH: 123
<212> TYPE: PRT

```
<213> ORGANISM: Artificial Sequence
<220> FEATURE:
<223> OTHER INFORMATION: Synthetic

<400> SEQUENCE: 295

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asp Leu Tyr Tyr Ser
            20                  25                  30

Ser Met His Trp Val Arg Gln Ala Pro Gly Lys Gly Leu Glu Trp Val
        35                  40                  45

Ala Ser Ile Tyr Ser Ser Gly Gly Ser Thr Ser Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ser Ser Phe Ser His Gly Tyr Gly Trp Tyr Gly Leu Asp Tyr
            100                 105                 110

Trp Gly Gln Gly Thr Leu Val Thr Val Ser Ser
        115                 120

<210> SEQ ID NO 296
<211> LENGTH: 110
<212> TYPE: PRT
<213> ORGANISM: Artificial Sequence
<220> FEATURE:
<223> OTHER INFORMATION: Synthetic

<400> SEQUENCE: 296

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Arg Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Gly Tyr His Gly Ala
                85                  90                  95

Gly Leu Ile Thr Phe Gly Gln Gly Thr Lys Val Glu Ile Lys
            100                 105                 110

<210> SEQ ID NO 297
<211> LENGTH: 123
<212> TYPE: PRT
<213> ORGANISM: Artificial Sequence
<220> FEATURE:
<223> OTHER INFORMATION: Synthetic

<400> SEQUENCE: 297

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Tyr Tyr Ser
            20                  25                  30

Ser Met His Trp Val Arg Gln Ala Pro Gly Lys Gly Leu Glu Trp Val
        35                  40                  45
```

```
Ala Ser Ile Tyr Ser Ser Gly Gly Ser Thr Ser Tyr Ala Asp Ser Val
        50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Arg Ser Ser Phe Ser His Gly Tyr Gly Trp Tyr Gly Leu Asp Tyr
            100                 105                 110

Trp Gly Gln Gly Thr Leu Val Thr Val Ser Ser
            115                 120

<210> SEQ ID NO 298
<211> LENGTH: 110
<212> TYPE: PRT
<213> ORGANISM: Artificial Sequence
<220> FEATURE:
<223> OTHER INFORMATION: Synthetic

<400> SEQUENCE: 298

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Val Ser Ser Ala
                 20                  25                  30

Val Ala Trp Tyr Gln Gln Lys Pro Gly Lys Ala Pro Arg Leu Leu Ile
            35                  40                  45

Tyr Ser Ala Ser Ser Leu Tyr Ser Gly Val Pro Ser Arg Phe Ser Gly
        50                  55                  60

Ser Arg Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Gly Tyr His Gly Ala
                 85                  90                  95

Gly Leu Ile Thr Phe Gly Gln Gly Thr Lys Val Glu Ile Lys
            100                 105                 110

<210> SEQ ID NO 299
<211> LENGTH: 123
<212> TYPE: PRT
<213> ORGANISM: Artificial Sequence
<220> FEATURE:
<223> OTHER INFORMATION: Synthetic

<400> SEQUENCE: 299

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Asn Leu Tyr Tyr Ser
                 20                  25                  30

Ser Met His Trp Val Arg Gln Ala Pro Gly Lys Gly Leu Glu Trp Val
            35                  40                  45

Ala Ser Ile Tyr Ser Ser Ser Gly Asp Thr His Tyr Ala Asp Ser Val
        50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95
```

Ala Arg Ser Ser Phe Ser His Gly Tyr Gly Trp Tyr Gly Leu Asp Tyr
            100                 105                 110

Trp Gly Gln Gly Thr Leu Val Thr Val Ser Ser
        115                 120

<210> SEQ ID NO 300
<211> LENGTH: 110
<212> TYPE: PRT
<213> ORGANISM: Artificial Sequence
<220> FEATURE:
<223> OTHER INFORMATION: Synthetic

<400> SEQUENCE: 300

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Arg Leu Leu Ile
        35                  40                  45

Tyr Ser Ala Ser Ser Leu Tyr Ser Gly Val Pro Ser Arg Phe Ser Gly
50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Gly Tyr His Gly Ala
                85                  90                  95

Gly Leu Ile Thr Phe Gly Gln Gly Thr Lys Val Glu Ile Lys
            100                 105                 110

<210> SEQ ID NO 301
<211> LENGTH: 123
<212> TYPE: PRT
<213> ORGANISM: Artificial Sequence
<220> FEATURE:
<223> OTHER INFORMATION: Synthetic

<400> SEQUENCE: 301

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Tyr Tyr Ser
            20                  25                  30

Ser Met His Trp Val Arg Gln Ala Pro Gly Lys Gly Leu Glu Trp Val
        35                  40                  45

Ala Ser Ile Tyr Ser Ser Ser Gly Asp Thr His Tyr Ala Asp Ser Val
50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ser Ser Phe Ser His Gly Tyr Gly Trp Tyr Gly Leu Asp Tyr
            100                 105                 110

Trp Gly Gln Gly Thr Leu Val Thr Val Ser Ser
        115                 120

<210> SEQ ID NO 302
<211> LENGTH: 110
<212> TYPE: PRT
<213> ORGANISM: Artificial Sequence
<220> FEATURE:
<223> OTHER INFORMATION: Synthetic

<400> SEQUENCE: 302

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Arg Leu Leu Ile
        35                  40                  45

Tyr Ser Ala Ser Ser Leu Tyr Ser Gly Val Pro Ser Arg Phe Ser Gly
50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Gly Tyr His Gly Ala
                85                  90                  95

Gly Leu Ile Thr Phe Gly Gln Gly Thr Lys Val Glu Ile Lys
            100                 105                 110

<210> SEQ ID NO 303
<211> LENGTH: 123
<212> TYPE: PRT
<213> ORGANISM: Artificial Sequence
<220> FEATURE:
<223> OTHER INFORMATION: Synthetic

<400> SEQUENCE: 303

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asp Leu Tyr Tyr Ser
            20                  25                  30

Ser Met His Trp Val Arg Gln Ala Pro Gly Lys Gly Leu Glu Trp Val
        35                  40                  45

Ala Ser Ile Tyr Ser Ser Gly Asp Thr His Tyr Ala Asp Ser Val
50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ser Ser Phe Ser His Gly Tyr Gly Trp Tyr Gly Leu Asp Tyr
            100                 105                 110

Trp Gly Gln Gly Thr Leu Val Thr Val Ser Ser
        115                 120

<210> SEQ ID NO 304
<211> LENGTH: 110
<212> TYPE: PRT
<213> ORGANISM: Artificial Sequence
<220> FEATURE:
<223> OTHER INFORMATION: Synthetic

<400> SEQUENCE: 304

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Arg Leu Leu Ile
        35                  40                  45

Tyr Ser Ala Ser Ser Leu Tyr Ser Gly Val Pro Ser Arg Phe Ser Gly
50                  55                  60

```
Ser Arg Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Gly Tyr His Gly Ala
                 85                  90                  95

Gly Leu Ile Thr Phe Gly Gln Gly Thr Lys Val Glu Ile Lys
            100                 105                 110
```

<210> SEQ ID NO 305
<211> LENGTH: 123
<212> TYPE: PRT
<213> ORGANISM: Artificial Sequence
<220> FEATURE:
<223> OTHER INFORMATION: Synthetic

<400> SEQUENCE: 305

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Ser Leu Tyr Tyr Ser
            20                  25                  30

Ser Met His Trp Val Arg Gln Ala Pro Gly Lys Gly Leu Glu Trp Val
        35                  40                  45

Ala Ser Ile Tyr Ser Ser Ser Gly Asp Thr His Tyr Ala Asp Ser Val
    50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Arg Ser Ser Phe Ser His Gly Tyr Gly Trp Tyr Gly Leu Asp Tyr
            100                 105                 110

Trp Gly Gln Gly Thr Leu Val Thr Val Ser Ser
        115                 120
```

<210> SEQ ID NO 306
<211> LENGTH: 110
<212> TYPE: PRT
<213> ORGANISM: Artificial Sequence
<220> FEATURE:
<223> OTHER INFORMATION: Synthetic

<400> SEQUENCE: 306

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Arg Leu Leu Ile
        35                  40                  45

Tyr Gly Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Gly Tyr His Gly Ala
                 85                  90                  95

Gly Leu Ile Thr Phe Gly Gln Gly Thr Lys Val Glu Ile Lys
            100                 105                 110
```

<210> SEQ ID NO 307
<211> LENGTH: 123
<212> TYPE: PRT

```
<213> ORGANISM: Artificial Sequence
<220> FEATURE:
<223> OTHER INFORMATION: Synthetic

<400> SEQUENCE: 307

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Asn Leu Tyr Tyr Ser
            20                  25                  30

Ser Met His Trp Val Arg Gln Ala Pro Gly Lys Gly Leu Glu Trp Val
        35                  40                  45

Ala Ser Ile Tyr Ser Ser Gly Gly Ser Thr Ser Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ser Ser Phe Ser His Gly Tyr Gly Trp Tyr Gly Leu Asp Tyr
            100                 105                 110

Trp Gly Gln Gly Thr Leu Val Thr Val Ser Ser
        115                 120

<210> SEQ ID NO 308
<211> LENGTH: 110
<212> TYPE: PRT
<213> ORGANISM: Artificial Sequence
<220> FEATURE:
<223> OTHER INFORMATION: Synthetic

<400> SEQUENCE: 308

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Arg Leu Leu Ile
        35                  40                  45

Tyr Gly Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Gly Tyr His Gly Ala
                85                  90                  95

Gly Leu Ile Thr Phe Gly Gln Gly Thr Lys Val Glu Ile Lys
            100                 105                 110

<210> SEQ ID NO 309
<211> LENGTH: 123
<212> TYPE: PRT
<213> ORGANISM: Artificial Sequence
<220> FEATURE:
<223> OTHER INFORMATION: Synthetic

<400> SEQUENCE: 309

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Leu Tyr Tyr Ser
            20                  25                  30

Ser Met His Trp Val Arg Gln Ala Pro Gly Lys Gly Leu Glu Trp Val
        35                  40                  45
```

Ala Ser Ile Tyr Ser Ser Gly Gly Ser Thr Ser Tyr Ala Asp Ser Val
            50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                     85                  90                  95

Ala Arg Ser Ser Phe Ser His Gly Tyr Gly Trp Tyr Gly Leu Asp Tyr
                100                 105                 110

Trp Gly Gln Gly Thr Leu Val Thr Val Ser Ser
            115                 120

<210> SEQ ID NO 310
<211> LENGTH: 110
<212> TYPE: PRT
<213> ORGANISM: Artificial Sequence
<220> FEATURE:
<223> OTHER INFORMATION: Synthetic

<400> SEQUENCE: 310

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Ser Val Ser Ser Ala
                 20                  25                  30

Val Ala Trp Tyr Gln Gln Lys Pro Gly Lys Ala Pro Arg Leu Leu Ile
             35                  40                  45

Tyr Gly Ala Ser Ser Leu Tyr Ser Gly Val Pro Ser Arg Phe Ser Gly
 50                  55                  60

Ser Arg Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Gly Tyr His Gly Ala
                 85                  90                  95

Gly Leu Ile Thr Phe Gly Gln Gly Thr Lys Val Glu Ile Lys
                100                 105                 110

<210> SEQ ID NO 311
<211> LENGTH: 123
<212> TYPE: PRT
<213> ORGANISM: Artificial Sequence
<220> FEATURE:
<223> OTHER INFORMATION: Synthetic

<400> SEQUENCE: 311

Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Asp Leu Tyr Tyr Ser
                 20                  25                  30

Ser Met His Trp Val Arg Gln Ala Pro Gly Lys Gly Leu Glu Trp Val
             35                  40                  45

Ala Ser Ile Tyr Ser Ser Gly Gly Ser Thr Tyr Ala Asp Ser Val
 50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

```
Ala Arg Ser Ser Phe Ser His Gly Tyr Gly Trp Tyr Gly Leu Asp Tyr
            100                 105                 110

Trp Gly Gln Gly Thr Leu Val Thr Val Ser Ser
        115                 120
```

<210> SEQ ID NO 312
<211> LENGTH: 110
<212> TYPE: PRT
<213> ORGANISM: Artificial Sequence
<220> FEATURE:
<223> OTHER INFORMATION: Synthetic

<400> SEQUENCE: 312

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Arg Leu Leu Ile
        35                  40                  45

Tyr Gly Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Gly Tyr His Gly Ala
                85                  90                  95

Gly Leu Ile Thr Phe Gly Gln Gly Thr Lys Val Glu Ile Lys
            100                 105                 110
```

<210> SEQ ID NO 313
<211> LENGTH: 123
<212> TYPE: PRT
<213> ORGANISM: Artificial Sequence
<220> FEATURE:
<223> OTHER INFORMATION: Synthetic

<400> SEQUENCE: 313

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Tyr Tyr Ser
            20                  25                  30

Ser Met His Trp Val Arg Gln Ala Pro Gly Lys Gly Leu Glu Trp Val
        35                  40                  45

Ala Ser Ile Tyr Ser Ser Gly Gly Ser Thr Ser Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ser Ser Phe Ser His Gly Tyr Gly Trp Tyr Gly Leu Asp Tyr
            100                 105                 110

Trp Gly Gln Gly Thr Leu Val Thr Val Ser Ser
        115                 120
```

<210> SEQ ID NO 314
<211> LENGTH: 110
<212> TYPE: PRT
<213> ORGANISM: Artificial Sequence
<220> FEATURE:
<223> OTHER INFORMATION: Synthetic

<400> SEQUENCE: 314

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Arg Leu Leu Ile
        35                  40                  45

Tyr Gly Ala Ser Ser Leu Tyr Ser Gly Val Pro Ser Arg Phe Ser Gly
50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Gly Tyr His Gly Ala
                85                  90                  95

Gly Leu Ile Thr Phe Gly Gln Gly Thr Lys Val Glu Ile Lys
            100                 105                 110

<210> SEQ ID NO 315
<211> LENGTH: 123
<212> TYPE: PRT
<213> ORGANISM: Artificial Sequence
<220> FEATURE:
<223> OTHER INFORMATION: Synthetic

<400> SEQUENCE: 315

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Leu Tyr Tyr Ser
            20                  25                  30

Ser Met His Trp Val Arg Gln Ala Pro Gly Lys Gly Leu Glu Trp Val
        35                  40                  45

Ala Ser Ile Tyr Ser Ser Gly Asp Thr His Tyr Ala Asp Ser Val
50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ser Ser Phe Ser His Gly Tyr Gly Trp Tyr Gly Leu Asp Tyr
            100                 105                 110

Trp Gly Gln Gly Thr Leu Val Thr Val Ser Ser
        115                 120

<210> SEQ ID NO 316
<211> LENGTH: 110
<212> TYPE: PRT
<213> ORGANISM: Artificial Sequence
<220> FEATURE:
<223> OTHER INFORMATION: Synthetic

<400> SEQUENCE: 316

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Arg Leu Leu Ile
        35                  40                  45

Tyr Gly Ala Ser Ser Leu Tyr Ser Gly Val Pro Ser Arg Phe Ser Gly
50                  55                  60

```
Ser Arg Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Gly Tyr His Gly Ala
                 85                  90                  95

Gly Leu Ile Thr Phe Gly Gln Gly Thr Lys Val Glu Ile Lys
            100                 105                 110

<210> SEQ ID NO 317
<211> LENGTH: 123
<212> TYPE: PRT
<213> ORGANISM: Artificial Sequence
<220> FEATURE:
<223> OTHER INFORMATION: Synthetic

<400> SEQUENCE: 317

Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Leu Tyr Tyr Ser
             20                  25                  30

Ser Met His Trp Val Arg Gln Ala Pro Gly Lys Gly Leu Glu Trp Val
         35                  40                  45

Ala Ser Ile Tyr Ser Ser Gly Asp Thr His Tyr Ala Asp Ser Val
     50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Arg Ser Ser Phe Ser His Gly Tyr Gly Trp Tyr Gly Leu Asp Tyr
            100                 105                 110

Trp Gly Gln Gly Thr Leu Val Thr Val Ser Ser
        115                 120

<210> SEQ ID NO 318
<211> LENGTH: 110
<212> TYPE: PRT
<213> ORGANISM: Artificial Sequence
<220> FEATURE:
<223> OTHER INFORMATION: Synthetic

<400> SEQUENCE: 318

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Ser Val Ser Ser Ala
             20                  25                  30

Val Ala Trp Tyr Gln Gln Lys Pro Gly Lys Ala Pro Arg Leu Leu Ile
         35                  40                  45

Tyr Gly Ala Ser Ser Leu Tyr Ser Gly Val Pro Ser Arg Phe Ser Gly
     50                  55                  60

Ser Arg Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Gly Tyr His Gly Ala
                 85                  90                  95

Gly Leu Ile Thr Phe Gly Gln Gly Thr Lys Val Glu Ile Lys
            100                 105                 110

<210> SEQ ID NO 319
<211> LENGTH: 123
<212> TYPE: PRT
```

```
<213> ORGANISM: Artificial Sequence
<220> FEATURE:
<223> OTHER INFORMATION: Synthetic

<400> SEQUENCE: 319

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asp Leu Tyr Tyr Ser
            20                  25                  30

Ser Met His Trp Val Arg Gln Ala Pro Gly Lys Gly Leu Glu Trp Val
        35                  40                  45

Ala Ser Ile Tyr Ser Ser Gly Asp Thr His Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ser Ser Phe Ser His Gly Tyr Gly Trp Tyr Gly Leu Asp Tyr
            100                 105                 110

Trp Gly Gln Gly Thr Leu Val Thr Val Ser Ser
        115                 120

<210> SEQ ID NO 320
<211> LENGTH: 110
<212> TYPE: PRT
<213> ORGANISM: Artificial Sequence
<220> FEATURE:
<223> OTHER INFORMATION: Synthetic

<400> SEQUENCE: 320

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Arg Leu Leu Ile
        35                  40                  45

Tyr Gly Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Gly Tyr His Gly Ala
                85                  90                  95

Gly Leu Ile Thr Phe Gly Gln Gly Thr Lys Val Glu Ile Lys
            100                 105                 110

<210> SEQ ID NO 321
<211> LENGTH: 123
<212> TYPE: PRT
<213> ORGANISM: Artificial Sequence
<220> FEATURE:
<223> OTHER INFORMATION: Synthetic

<400> SEQUENCE: 321

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Tyr Tyr Ser
            20                  25                  30

Ser Met His Trp Val Arg Gln Ala Pro Gly Lys Gly Leu Glu Trp Val
        35                  40                  45
```

```
Ala Ser Ile Tyr Ser Ser Gly Asp Thr His Tyr Ala Asp Ser Val
     50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                     85                  90                  95

Ala Arg Ser Ser Phe Ser His Gly Tyr Gly Trp Tyr Gly Leu Asp Tyr
                100                 105                 110

Trp Gly Gln Gly Thr Leu Val Thr Val Ser Ser
            115                 120
```

```
<210> SEQ ID NO 322
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Xaa is any amino acid

<400> SEQUENCE: 322

Ser Thr Ser Xaa
1

<210> SEQ ID NO 323
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Xaa is any amino acid

<400> SEQUENCE: 323

Ser Gly Ser Xaa
1

<210> SEQ ID NO 324
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Xaa is any amino acid

<400> SEQUENCE: 324

Ser Asp Ser Xaa
1

<210> SEQ ID NO 325
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Xaa is any amino acid
```

```
<400> SEQUENCE: 325

Ser Glu Ser Xaa
1

<210> SEQ ID NO 326
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Xaa is any amino acid

<400> SEQUENCE: 326

Ser Arg Ser Xaa
1

<210> SEQ ID NO 327
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Xaa is any amino acid

<400> SEQUENCE: 327

Ser Ser Ser Xaa
1

<210> SEQ ID NO 328
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Xaa is any amino acid

<400> SEQUENCE: 328

Gly Ala Ser Xaa
1

<210> SEQ ID NO 329
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Xaa is any amino acid

<400> SEQUENCE: 329

Thr Ala Ser Xaa
1

<210> SEQ ID NO 330
<211> LENGTH: 4
<212> TYPE: PRT
<213> ORGANISM: Artificial Sequence
<220> FEATURE:
```

```
<223> OTHER INFORMATION: Synthetic
<220> FEATURE:
<221> NAME/KEY: MISC_FEATURE
<222> LOCATION: (4)..(4)
<223> OTHER INFORMATION: Xaa is any amino acid

<400> SEQUENCE: 330

His Ala Ser Xaa
1

<210> SEQ ID NO 331
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Xaa is any amino acid

<400> SEQUENCE: 331

Tyr Ala Ser Xaa
1

<210> SEQ ID NO 332
<211> LENGTH: 12
<212> TYPE: PRT
<213> ORGANISM: Artificial Sequence
<220> FEATURE:
<223> OTHER INFORMATION: Synthetic

<400> SEQUENCE: 332

Gln Gln Tyr Gly Tyr His His Ala Gly Leu Ile Thr
1               5                   10

<210> SEQ ID NO 333
<211> LENGTH: 12
<212> TYPE: PRT
<213> ORGANISM: Artificial Sequence
<220> FEATURE:
<223> OTHER INFORMATION: Synthetic

<400> SEQUENCE: 333

Gln Gln Tyr Gly Tyr His Asp Ala Gly Leu Ile Thr
1               5                   10

<210> SEQ ID NO 334
<211> LENGTH: 12
<212> TYPE: PRT
<213> ORGANISM: Artificial Sequence
<220> FEATURE:
<223> OTHER INFORMATION: Synthetic

<400> SEQUENCE: 334

Gln Gln Tyr Gly Tyr His Asn Ala Gly Leu Ile Thr
1               5                   10

<210> SEQ ID NO 335
<211> LENGTH: 12
<212> TYPE: PRT
<213> ORGANISM: Artificial Sequence
<220> FEATURE:
<223> OTHER INFORMATION: Synthetic

<400> SEQUENCE: 335

Gln Gln Tyr Gly Tyr His Gly Ala Gly Leu Ile Thr
1               5                   10
```

```
<210> SEQ ID NO 336
<211> LENGTH: 12
<212> TYPE: PRT
<213> ORGANISM: Artificial Sequence
<220> FEATURE:
<223> OTHER INFORMATION: Synthetic

<400> SEQUENCE: 336

Gln Gln Tyr Gly Tyr His Ser Ala Gly Leu Ile Thr
1               5                   10

<210> SEQ ID NO 337
<211> LENGTH: 9
<212> TYPE: PRT
<213> ORGANISM: Artificial Sequence
<220> FEATURE:
<223> OTHER INFORMATION: Synthetic

<400> SEQUENCE: 337

Gly Phe Thr Leu Tyr Tyr Ser Ser Met
1               5

<210> SEQ ID NO 338
<211> LENGTH: 9
<212> TYPE: PRT
<213> ORGANISM: Artificial Sequence
<220> FEATURE:
<223> OTHER INFORMATION: Synthetic

<400> SEQUENCE: 338

Gly Phe Asp Leu Tyr Tyr Ser Ser Met
1               5

<210> SEQ ID NO 339
<211> LENGTH: 9
<212> TYPE: PRT
<213> ORGANISM: Artificial Sequence
<220> FEATURE:
<223> OTHER INFORMATION: Synthetic

<400> SEQUENCE: 339

Gly Phe Ser Leu Tyr Tyr Ser Ser Met
1               5

<210> SEQ ID NO 340
<211> LENGTH: 10
<212> TYPE: PRT
<213> ORGANISM: Artificial Sequence
<220> FEATURE:
<223> OTHER INFORMATION: Synthetic

<400> SEQUENCE: 340

Ser Ile Tyr Ser Ser His Gly Arg Thr Gly
1               5                   10

<210> SEQ ID NO 341
<211> LENGTH: 10
<212> TYPE: PRT
<213> ORGANISM: Artificial Sequence
<220> FEATURE:
<223> OTHER INFORMATION: Synthetic

<400> SEQUENCE: 341

Ser Ile Tyr Ser Ser Ser Gly Tyr Thr Ser
1               5                   10
```

<210> SEQ ID NO 342
<211> LENGTH: 10
<212> TYPE: PRT
<213> ORGANISM: Artificial Sequence
<220> FEATURE:
<223> OTHER INFORMATION: Synthetic

<400> SEQUENCE: 342

Ser Ile Tyr Ser Ser Gly Ser Thr Cys
1               5                   10

<210> SEQ ID NO 343
<211> LENGTH: 10
<212> TYPE: PRT
<213> ORGANISM: Artificial Sequence
<220> FEATURE:
<223> OTHER INFORMATION: Synthetic

<400> SEQUENCE: 343

Ser Ile Tyr Ser Ser Gly Asp Thr His
1               5                   10

<210> SEQ ID NO 344
<211> LENGTH: 10
<212> TYPE: PRT
<213> ORGANISM: Artificial Sequence
<220> FEATURE:
<223> OTHER INFORMATION: Synthetic

<400> SEQUENCE: 344

Ser Ile Tyr Ser Ser His Gly Gly Thr Asn
1               5                   10

<210> SEQ ID NO 345
<211> LENGTH: 10
<212> TYPE: PRT
<213> ORGANISM: Artificial Sequence
<220> FEATURE:
<223> OTHER INFORMATION: Synthetic

<400> SEQUENCE: 345

Ser Ile Tyr Ser Ser His Gly Gly Thr Tyr
1               5                   10

<210> SEQ ID NO 346
<211> LENGTH: 10
<212> TYPE: PRT
<213> ORGANISM: Artificial Sequence
<220> FEATURE:
<223> OTHER INFORMATION: Synthetic

<400> SEQUENCE: 346

Ser Ile Tyr Ser Ser Asn Gly Arg Thr Tyr
1               5                   10

<210> SEQ ID NO 347
<211> LENGTH: 10
<212> TYPE: PRT
<213> ORGANISM: Artificial Sequence
<220> FEATURE:
<223> OTHER INFORMATION: Synthetic

<400> SEQUENCE: 347

Ser Ile Tyr Ser Ser Asn Gly Asn Thr Gly
1               5                   10

```
<210> SEQ ID NO 348
<211> LENGTH: 10
<212> TYPE: PRT
<213> ORGANISM: Artificial Sequence
<220> FEATURE:
<223> OTHER INFORMATION: Synthetic

<400> SEQUENCE: 348

Ser Ile Tyr Ser Ser Ser Gly Asp Thr Gly
1               5                   10

<210> SEQ ID NO 349
<211> LENGTH: 10
<212> TYPE: PRT
<213> ORGANISM: Artificial Sequence
<220> FEATURE:
<223> OTHER INFORMATION: Synthetic

<400> SEQUENCE: 349

Ser Ile Tyr Ser Ser His Gly Asn Thr Asp
1               5                   10

<210> SEQ ID NO 350
<211> LENGTH: 10
<212> TYPE: PRT
<213> ORGANISM: Artificial Sequence
<220> FEATURE:
<223> OTHER INFORMATION: Synthetic

<400> SEQUENCE: 350

Ser Ile Tyr Ser Ser Gly Gly Ser Thr Ser
1               5                   10

<210> SEQ ID NO 351
<211> LENGTH: 10
<212> TYPE: PRT
<213> ORGANISM: Artificial Sequence
<220> FEATURE:
<223> OTHER INFORMATION: Synthetic

<400> SEQUENCE: 351

Ser Ile Tyr Ser Ser Tyr Gly His Thr Ser
1               5                   10

<210> SEQ ID NO 352
<211> LENGTH: 10
<212> TYPE: PRT
<213> ORGANISM: Artificial Sequence
<220> FEATURE:
<223> OTHER INFORMATION: Synthetic

<400> SEQUENCE: 352

Ser Ile Tyr Ser Ser Ser Gly Ser Thr Ser
1               5                   10
```

HUMAN ANTIBODIES TO HUMAN INTERLEUKIN 18 RECEPTOR ALPHA OR BETA

CROSS-REFERENCE TO RELATED PATENT APPLICATIONS

This application is a U.S. National Stage Application under 35 U.S.C. 371 of International Application No. PCT/CN2019/091936, filed Jun. 19, 2019, which claims priority to PCT/CN2018/091780, filed on Jun. 19, 2018, the contents of all of which are incorporated herein by reference in their entirety in the present disclosure.

SEQUENCE LISTING

The instant application contains a sequence listing which has been submitted in ascii format via EFS-web and is hereby incorporated by reference in its entirety. Said ascii copy, created on Mar. 7, 2022, is named 267770_US_Reviv_ST25.TXT and is 278,528 bytes in size.

BACKGROUND

The interleukins (ILs) are a class of soluble cytokines used for leukocyte communication in shaping immune responses. Since their discovery in the late 1970's, more than 40 distinct proteins have been classified as ILs according to their sequence identity with other ILs or their functional activity.

IL-18 was originally discovered as a pro-inflammatory, IFN-γ-inducing cytokine that shares biological functions and acts synergistically with IL-12. As a member of the IL-1 family of cytokines, IL-18 is thought to play a role in early inflammatory responses and is synthesized by a range of both hematopoietic and non-hematopoietic cells (e.g., macrophages, dendritic cells, Kupffer cells, keratinocytes, osteoblasts, astrocytes, adrenal cortex cells, intestinal epithelial cells, microglial cells, and synovial fibroblasts) both constitutively and in response to lipopolysaccharide and other cytokines such as TNF-α, and is post-translationally cleaved by the caspase-1 for functional activity of the mature 18 kDa species. Active IL-18 then targets cells that express the IL-18 receptor which is widely expressed on both hematopoietic and non-hematopoietic tissues.

The IL-18 receptor is a heterodimeric transmembrane protein comprised of a ligand binding IL-18R alpha (IL-18Rα) subunit and a non-ligand binding IL-18R beta (IL-18Rβ) subunit that is essential for functional signaling. Ligand-induced activation of the receptor results in recruitment and activation of intracellular myeloid differentiation 88 (MyD88) and IL-1R-associated kinase (IRAK) that simultaneously triggers at least two divergent phosphorylation cascades that activate the PI3K pathway and the MAPK pathway including activation of Akt, p38 and SAPK/JNK. Activation of these pathways culminate in NF-κB activation and transcription of its downstream genes that includes IFN-γ, chemokines, transcription factors, G protein and cell surface receptors. IL-18 shares elements of its signaling pathway with IL-1 but also bears distinct elements.

On hematopoietic cells such as T cells, B cell, natural killer (NK) cells, macrophages, and neutrophils, IL-18 ligand stimulation can enhance T and NK cell maturation, cytokine secretion, cytotoxicity and adhesion. Differentiation of naive T cells induced by IL-18 can induce either Th1 or Th2 lineages independently of either IL-4 or IL-12. In differentiated Th1 clones, IL-18 can induce the production and secretion of IFN-γ, granulocyte-macrophage colony-stimulating factor (GM-CSF), or tumor necrosis factor (TNF); however, it does so primarily in synergy with IL-12. In neutrophils, IL-18 has been shown to induce the expression and secretion of cytokines and chemokines, up-regulate the expression of the cell surface adhesion molecule-CD11b, and potentiate the neutrophil respiratory burst. Importantly, the IL-18 receptor itself can be up-regulated on naive T, Th1 and B cells by IL-12 which explains, in part, the synergy between these two cytokines. IL-18 also acts synergistically with IL-2 inducing expression of IL-13 (in an IFN-γ-dependent manner) and IL-10 (in an IFN-γ independent manner). Together, these results underscore the role of IL-18 in both innate and adaptive immune responses.

In non-hematopoietic cells such as endothelial and epithelial cells, synovial fibroblasts and chondrocytes. IL-18 can up-regulate the expression of adhesion molecules (such as E-selectin, ICAM and VCAM), other cytokines, chemokines (CXCL8, CXCL5, CXCL1, CXCL12, CCL, CCL20) and angiogenic mediators such as vascular endothelial growth factor (VEGF) and thrombospondin. Overall, the effects of IL-18 induction of these effectors are to increase leukocyte recruitment, cellular adhesion, extravasation of immune cells, and promotion of cellular migration and formation of new blood vessels.

Mouse studies on IL-18 and its receptors have been facilitated by a reasonable degree of identity between both mouse and human ligands and their cognate receptors. Alignment of mouse and human IL-18 revealed a 63.5% identity between orthologs while alignment of mouse and human IL-18Rα and IL-18Rβ reveals a 64% and 65% sequence identity, respectively.

IL-18 can be induced by interaction of pattern recognition receptors with the repeating subunits of numerous different microbes including hepatitis C, chikungunya, *Mycobacterium tuberculosis*, human immunodeficiency virus, heliobacteria and more.

Mouse models of infection suggest that pathogen-associated molecular patterns (PAMPs) recognized by Toll receptors (TLRs) and Nod-like receptors (NLRs) can activate caspase-1 in the inflammasome leading to the cleavage and maturation of IL-18 (and IL-1B) which may help to limit immunopathologic responses. Studies of gram-negative bacterium *Burkholderia pseudomallei* in IL-18−/− mice suggest that IL-18-mediated production of IFN-γ is essential for survival. Alternately, studies on the obligate intracellular bacterium *Ixodes Ovatus Ehrlichia* (IOE) in IL-18R−/− mice revealed decreased immunopathogenic responses and enhanced control of infection suggesting that IL-18 may play a greater role in regulating the immune response rather than conferring protection against infection. Interestingly, a host of orthopoxviruses encodes a functional homolog of the naturally occurring inhibitor IL-18 binding protein (IL-18BP), which enhances virulence of these viruses by inhibiting IL-18 signals.

In the context of numerous inflammatory diseases, IL-18 has been shown to be upregulated, to correlate with disease or to be a risk factor for disease development. Examples include in Crohn's disease, rheumatoid arthritis, systemic lupus erythrites, cardiovascular disease. Increased IL-18 levels have been observed in individuals at risk of developing either Type I (T1D) or Type 2 diabetes (T2D). Elevated IL-18 has also been observed in the serum, urine and islets of juvenile and adult T1D and T2D patients, correlating with the severity of disease, and the development of sequelae such as diabetic nephropathy. Studies on Alzheimer's patients have revealed expression of IL-18 is increased in the brain and is thought to contribute to immune and inflammatory processes that enhance oxidative stress and alter the expression of proteins that contribute to amyloid beta (Aβ) formation.

Recognizing the potential role of IL-18 in immunopathogenesis of inflammatory diseases several studies have undertaken pre-clinical evaluation of IL-18 abrogation via either genetic knockout or anti-IL-18 antagonists. A mouse model of collagen-induced arthritis in which IL-18 levels increase within 4-8 days after collagen injection was used to obtain pre-clinical insights into the efficacy of two distinct modalities of IL-18 inhibition including an anti-mouse rabbit polyclonal antibody and a recombinant anti-IL-18-binding protein. The authors concluded that both modalities were capable of impeding gross measures of pathologic progression such as inflammatory paw swelling and histological measures of disease severity such as degree of cartilage erosion. These results were further confirmed by serological measures that noted a decrease in serum IFN-γ, IL-6, TNF-α and cartilage oligomeric matrix protein (COMP) with both treatments. This provides both strong rationale and a clear pathway for pre-clinical assessment.

In experimental mouse models of sepsis, dual genetic IL-18 and IL-1ß deficiencies were shown to protect mice from lethal doses of lipopolysaccharide (LPS), TNF-α or a surgical procedure that induces septic-like conditions referred to cecal ligation and puncture. Sepsis is often viewed as an 'unbridled hyper-inflammatory response' mediated by cytokines and is one of the leading causes of mortality in intensive care units. Importantly, the loss of either IL-1B or IL-18 provided only partial protection against septic lethality in contrast to the full protection offered by dual knockout, underscoring the complementary roles of these two pro-inflammatory cytokines.

Together, these studies suggest that inflammatory disorders may represent a class of pathologies that blockade of anti-IL-18-mediated signals through the use of antagonizing anti-IL-18 may show efficacy and for which there are ample opportunities for clearly defined pre-clinical study.

Studies in pre-clinical models of cancer suggest that anti-tumor activity of IL-18 arises from its ability to potentiate effector cells such as T cells and NK cells and have supported its use in clinical studies, though results thus far, provide modest support for a positive role for IL-18 in cancer. High IL-18 levels can be observed in numerous cancers either at the tumor site or systemically including breast, esophageal, gastrointestinal, lung, hepatic, ovarian and others.

SUMMARY

The present disclosure provides antibodies and antigen-binding fragments that are specific to IL-18 receptor alpha or beta subunits. These antibodies and fragments are capable of disrupting the IL-18 receptor linked downstream signaling pathway and thus can be used for treating certain diseases and conditions associated with expression or over-expression of IL-18 or the receptors, such as inflammatory and autoimmune diseases and cancer.

In one embodiment, therefore, the present disclosure provides an antibody or fragment thereof, wherein the antibody or fragment thereof has binding specificity to a human interleukin-18 receptor beta (IL-18Rβ) protein having the amino acid sequence of SEQ ID NO:1, wherein the binding comprises at least: an amino acid residue selected from the group consisting of L167, D213 and T242, an amino acid residue selected from the group consisting of V244, G245 and D246, and an amino acid residue selected from the group consisting of G278, F279, R281, V282, F283, N284, P285, S310, E315 and I317, of SEQ ID NO: 1.

In some embodiments, the binding comprises at least: an amino acid residue selected from the group consisting of D213 and T242, an amino acid residue selected from the group consisting of V244, G245 and D246, and an amino acid residue selected from the group consisting of G278, R281, V282, F283, N284, P285, S310, E315 and I317, of SEQ ID NO:1.

In some embodiments, the binding comprises at least: an amino acid residue selected from the group consisting of D213 and T242, the amino acid residue V244, and an amino acid residue selected from the group consisting of G278, R281, V282, F283, N284, P285, S310, E315 and I317, of SEQ ID NO:1. In some embodiments, the binding comprises at least the amino acid residues D213, T242, V244, G278, R281, V282, F283, N284, P285, S310, E315 and I317 of SEQ ID NO:1. In some embodiments, the binding comprises at least the amino acid residues L167, D213, T242, V244, G278, F279, R281, V282, F283, N284, P285, S310, E315 and I317 of SEQ ID NO:1.

In some embodiments, the antibody or fragment thereof further is capable of binding to a mouse IL-18Rβ protein.

Another embodiment of the present disclosure provides an antibody or fragment thereof, wherein the antibody or fragment thereof has binding specificity to a human interleukin-18 receptor beta (IL-18Rβ) protein, wherein the antibody or fragment thereof comprises a light chain variable region comprising light chain complementarity determining regions CDRL1, CDRL2, and CDRL3 and a heavy chain variable region comprising heavy chain complementarity determining regions CDRH1, CDRH2, and CDRH3, and wherein the CDRL3, CDRH1, CDRH2, and CDRH3, are selected from combinations 1-27 of Table B or each of the combinations 1-27 in which each of the CDRL3, CDRH1, CDRH2, and CDRH3 includes one, two, or three amino acid addition, deletion, conservative amino acid substitution or the combinations thereof.

In some embodiments, the CDRL3, CDRH1, CDRH2, and CDRH3 are selected from combination 1 of Table B or have one amino acid substitution. In some embodiments, the substitutions are selected from Table B1. In some embodiments, the CDRL3, CDRH1, CDRH2, and CDRH3 are selected from combinations 1-27 of Table B or any combination of Table 9. In some embodiments, the CDRL1 and CDRL2 have sequences of QSVSSA (SEQ ID NO: 45) and SAS (SEQ ID) NO: 46), respectively.

Yet another embodiment of the present disclosure provides an antibody or fragment thereof, wherein the antibody or fragment thereof has binding specificity to a human interleukin-18 receptor alpha (IL-18Rα) protein, wherein the antibody or fragment thereof comprises a light chain variable region comprising light chain complementarity determining regions CDRL1, CDRL2, and CDRL3 and a heavy chain variable region comprising heavy chain complementarity determining regions CDRH1, CDRH2, and CDRH3, and wherein the CDRL3, CDRH1, CDRH2, and CDRH3, are selected from combinations 1-12 of Table C or each of the combinations 1-12 in which each of the CDRL3, CDRH1, CDRH2, and CDRH3 includes one, two, or three amino acid addition, deletion, conservative amino acid substitution or the combinations thereof.

In some embodiments, the CDRL3, CDRH1, CDRH2, and CDRH3 are selected from combination 11 of Table C or have one amino acid substitution. In some embodiments, the substitutions are selected from Table C1. In some embodiments, the CDRL3, CDRH1, CDRH2, and CDRH3 are selected from combinations 1-12 of Table C. In some embodiments, the CDRL1 and CDRL2 have sequences of QSVSSA (SEQ ID NO:45) and SAS (SEQ ID NO:46), respectively.

In some embodiments, the antibody or fragment thereof of the present disclosure comprises a heavy chain variable region comprising an amino acid sequence selected from the group consisting of SEQ ID NO:2, 6, 10, 14, 18, 22, 26, 30, 34, 38, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, and 321 or a peptide having at least 90% sequence identity to an amino acid sequence selected from the group consisting of SEQ ID NO: 2, 6, 10, 14, 18, 22, 26, 30, 34, 38, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, and 321.

In some embodiments, the antibody or fragment thereof comprises a light chain variable region comprising an amino acid sequence selected from the group consisting of SEQ ID NO:4, 8, 12, 16, 20, 24, 28, 32, 36, 40, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, or a peptide having at least 90% sequence identity to an amino acid sequence selected from the group consisting of SEQ ID NO: 4, 8, 12, 16, 20, 24, 28, 32, 36, 40, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320.

In some embodiments, it comprises a heavy chain variable region comprising the amino acid sequence of SEQ ID NO:42, or a peptide having at least 90% sequence identity to the amino acid sequence of SEQ ID NO:42. In some embodiments, the antibody or fragment thereof comprises a light chain variable region comprising the amino acid sequence of SEQ ID NO: 44, or a peptide having at least 90% sequence identity to the amino acid sequence of SEQ ID NO:44.

In some embodiments, the antibody or fragment thereof further comprises a second specificity to a second target protein. In some embodiments, the second target protein can be other pro-inflammatory cytokines, including but not limited to, IL-1, IL-4, IL-5, IL-6, IL13, IL-17 and IL36. Other examples include but not limited to CD3, CD16, CD19, CD20, CD28, CD64, PD-1, CTLA-4, LAG-3 (also known as CD223), CD28, CD122, 4-1BB (also known as CD137), TIM3, OX-40 or OX40L, CD40 or CD40L, LIGHT, ICOS/ICOSL, GITR/GITRL, TIGIT, CD27, VISTA, B7H3, B7H4, HEVM or BTLA (also known as CD272), killer-cell immunoglobulin-like receptors (KIRs), and CD47.

Also provided, in one embodiment, is a composition comprising the antibody or fragment thereof of the present disclosure and a pharmaceutically acceptable carrier. Also provided is an isolated cell comprising one or more polynucleotide encoding the antibody or fragment thereof of the present disclosure.

Methods and uses of treatments are also provided. In one embodiment, provided is a method of treating an autoimmune or inflammatory disease in a patient in need thereof, comprising administering to the patient the antibody or fragment thereof of the present disclosure. In some embodiments, the autoimmune or inflammatory disease is selected from the group consisting of a Parkinson's disease, arthritis, rheumatoid arthritis, multiple sclerosis, psoriasis, psoriatic arthritis, Crohn's disease, inflammatory bowel disease, ulcerative colitis, lupus, systemic lupus erythematous, juvenile rheumatoid arthritis, juvenile idiopathic arthritis, Grave's disease, Hashimoto's thyroiditis, Addison's disease, celiac disease, dermatomyositis, multiple sclerosis, myasthenia gravis, pernicious anemia, Sjogren syndrome, type I diabetes, type II diabetes, vasculitis, uveitis, sepsis, atherosclerosis and ankylosing spondylitis.

In one embodiment, a method of treating cancer in a patient in need thereof is provided, comprising administering to the patient the antibody or fragment thereof of the present disclosure. In some embodiments, the cancer is selected from the group consisting of bladder cancer, liver cancer, colon cancer, rectal cancer, endometrial cancer, leukemia, lymphoma, pancreatic cancer, small cell lung cancer, non-small cell lung cancer, breast cancer, urethral cancer, head and neck cancer, gastrointestinal cancer, stomach cancer, oesophageal cancer, ovarian cancer, renal cancer, melanoma, prostate cancer and thyroid cancer.

Still further provided is a method of detecting expression of IL-18 receptor in a sample, comprising contacting the sample with an antibody or fragment thereof of the present disclosure under conditions for the antibody or fragment thereof to bind to the IL-18 receptor, and detecting the binding which indicates expression of IL-18 receptor in the sample.

In some embodiments, the sample is isolated from a human patient. In some embodiments, the detection indicates a disease associated with abnormal expression of the IL-18 receptor. In some embodiments, the disease is selected from the group consisting of infection, an autoimmune or inflammatory disease, or cancer.

BRIEF DESCRIPTION OF THE DRAWINGS

FIG. 2A-D. Antibody binding and epitope mapping. The $EC_{50}$ and $IC_{50}$ values of Fab binding to both IL-18Rα (red trace) and IL-18Rβ (black trace) were determined by A) multipoint direct binding and B) competitive binding ELISA following incubation with a two-fold dilutions series of soluble receptor. Generated curves were fit using appropriate models and values extracted from fit curves. C) The kinetics of anti Il-18Rβ Fab binding were determined to cognate human receptor by biolayer interferometry (BLI) to confirm $EC_{50}/IC_{50}$ estimates. Kinetics of the interaction between the anti-IL-18Rα Fab and its cognate human receptor was similarly determined by surface plasmon resonance (SPR). D) To assess overlap of the indicated anti-IL-18Rβ-binding Fabs, IgG binding to hIL-18Rβ was measured by ELISA (white bars) and compared with IgG-binding signals obtained in the presence of saturating Fab (black bars). Error bars represent standard deviation of replicate measurements.

FIG. 3A-D. IgG binding to ectopically-expressed, cell surface IL-18R by immunofluorescence and flow cytometry. Anti-IL18Rα IgGs or an isotype control IgG were used to immunostain HEK293 cells transfected with A) hIL-18Rα-GFP or B) hIL-18Rβ-GFP constructs. Fluorochrome signals from GFP expression (green) and IgG-binding (red) were measured in the Cy3 and Cy5 channels and merged in the far-right column vs DAPI-stained nuclei (blue). Cell binding was also characterized at 400 nM IgG by flow cytometry using receptor-expressing or non-transfected HEK293 cells versus isotype control IgG or secondary alone in (C) for hIL-18Rα and in (D) for hIL-18Rβ. Median fluorescence intensity of IgG or control binding was measured in the Cy3 (IgG), APC (control anti-18Rα), or PE3 (control IL-18β) channels and visualized as histograms.

FIG. 4A-F. IgG-mediated Inhibition of IL-18 signals and function A) IL-18-induced phospho-signals were assayed to assess the effects of cell pre-incubation with IgG and compared to levels of non-phosphorylated parent protein by Western blot. Band intensities determined by densitometry were used to calculate normalized ratios of phospho signals versus controls untreated with either IL-18 or antibody and plotted as bar graphs for phospho B) –IKKα/β, C) –p38 and D) SAPK/JNK. The statistical significance in the change of IL-18 induced phosphorylation of downstream effectors-IKK-α/β, p38 MARK and SAPK/JNK in comparison to no IL-18 control was assessed by t-test and * indicates a $p<0.05$. The cellular effects of antibody pre-incubation on IL-18-induced stimulation of IFN-γ secretion was assessed over a range of IgG concentrations on both E) KG-1 myeloblasts and F) isolated PBMCs.

DETAILED DESCRIPTION

Definitions

Figure 1A:
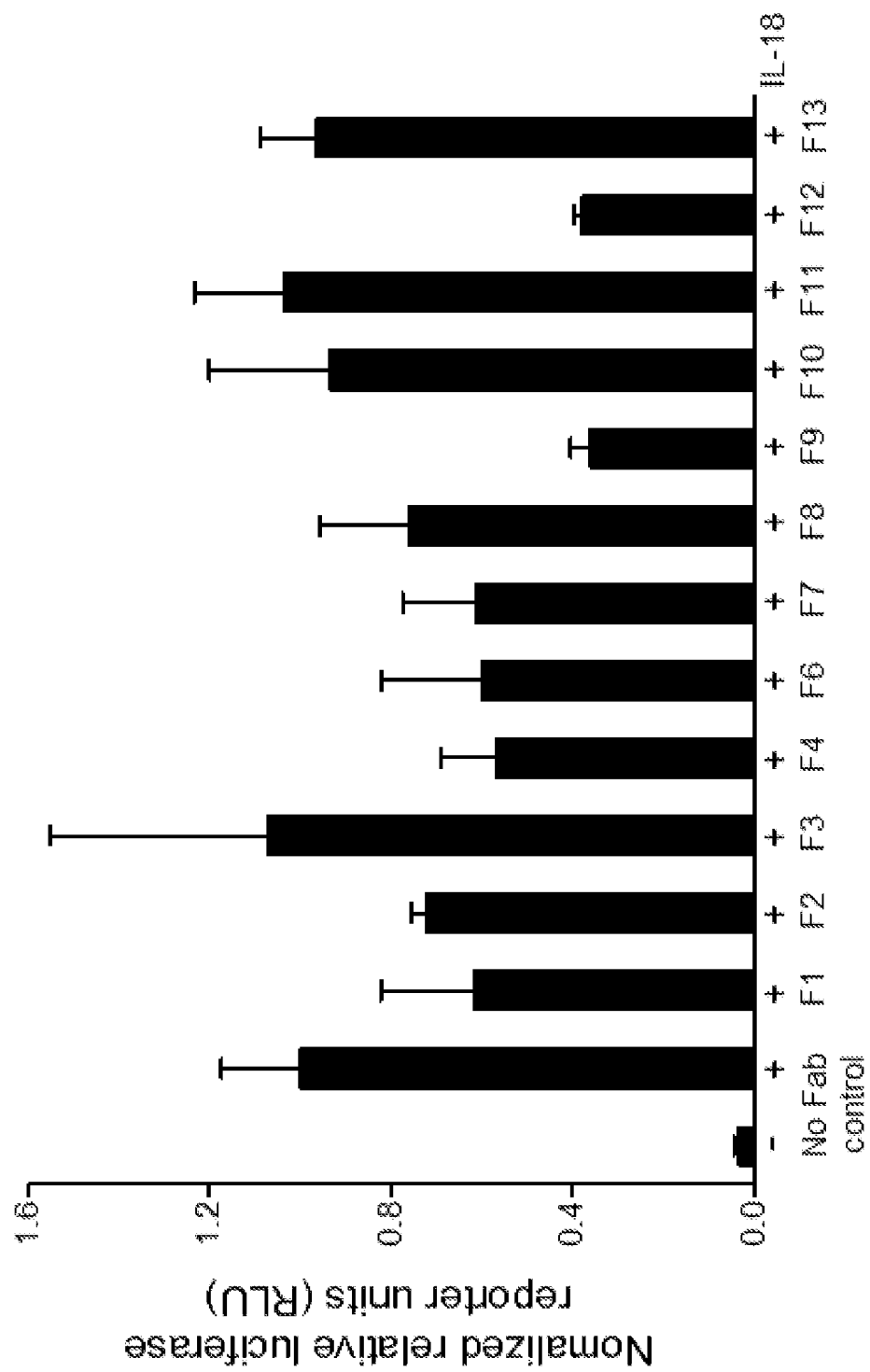
FIG. 1A-B. Evaluation of Fab-mediated inhibition of NF-κB signaling by luciferase assay. An IL-18 responsive luciferase reporter assay was used to assess the effects of A) anti-IL-18Rα- and B) anti-IL-18Rβ-binding Fabs on transcriptional activation of NF-κB by IL-18. NF-κB-induced luciferase signals by IL-18 (10 ng/mL) in transfected cells were compared to cells pre-treated with Fab and are expressed as normalized relative luciferase units. Errors bars represent standard deviation of replicate samples.

It is to be noted that the term "a" or "an" entity refers to one or more of that entity; for example, "an antibody," is understood to represent one or more antibodies. As such, the terms "a" (or "an"), "one or more," and "at least one" can be used interchangeably herein.

As used herein, the term "polypeptide" is intended to encompass a singular "polypeptide" as well as plural "polypeptides," and refers to a molecule composed of monomers (amino acids) linearly linked by amide bonds (also known as peptide bonds). The term "polypeptide" refers to any chain or chains of two or more amino acids, and does not refer to a specific length of the product. Thus, peptides, dipeptides, tripeptides, oligopeptides, "protein," "amino acid chain," or any other term used to refer to a chain or chains of two or more amino acids, are included within the definition of "polypeptide," and the term "polypeptide" may be used instead of, or interchangeably with any of these terms. The term "polypeptide" is also intended to refer to the products of post-expression modifications of the polypeptide, including without limitation glycosylation, acetylation, phosphorylation, amidation, derivatization by known protecting/blocking groups, proteolytic cleavage, or modification by non-naturally occurring amino acids. A polypeptide may be derived from a natural biological source or produced by recombinant technology, but is not necessarily translated from a designated nucleic acid sequence. It may be generated in any manner, including by chemical synthesis.

The term "isolated" as used herein with respect to cells, nucleic acids, such as DNA or RNA, refers to molecules separated from other DNAs or RNAs, respectively, that are present in the natural source of the macromolecule. The term "isolated" as used herein also refers to a nucleic acid or peptide that is substantially free of cellular material, viral material, or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state. The term "isolated" is also used herein to refer to cells or polypeptides which are isolated from other cellular proteins or tissues. Isolated polypeptides is meant to encompass both purified and recombinant polypeptides.

As used herein, the term "recombinant" as it pertains to polypeptides or polynucleotides intends a form of the polypeptide or polynucleotide that does not exist naturally, a non-limiting example of which can be created by combining polynucleotides or polypeptides that would not normally occur together.

"Homology" or "identity" or "similarity" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. An "unrelated" or "non-homologous" sequence shares less than 40% identity, though preferably less than 25% identity, with one of the sequences of the present disclosure.

A polynucleotide or polynucleotide region (or a polypeptide or polypeptide region) has a certain percentage (for example, 60%, 65%, 70%, 75%, 80%, 85%, 90%, 95%, 98% or 99%) of "sequence identity" to another sequence means that, when aligned, that percentage of bases (or amino acids) are the same in comparing the two sequences. This alignment and the percent homology or sequence identity can be determined using software programs known in the art, for example those described in Ausubel et al. eds. (2007) Current Protocols in Molecular Biology. Preferably, default parameters are used for alignment. One alignment program is BLAST, using default parameters. In particular, programs are BLASTN and BLASTP, using the following default parameters: Genetic code=standard; filter=none; strand=both; cutoff=60; expect=10; Matrix=BLOSUM62; Descriptions=50 sequences; sort by=HIGH SCORE; Databases=non-redundant, GenBank®+EMBL+DDBJ+PDB+GenBank® CDS translations+SwissProtein+SPupdate+PIR. Biologically equivalent polynucleotides are those having the above-noted specified percent homology and encoding a polypeptide having the same or similar biological activity.

The term "an equivalent nucleic acid or polynucleotide" refers to a nucleic acid having a nucleotide sequence having a certain degree of homology, or sequence identity, with the nucleotide sequence of the nucleic acid or complement thereof. A homolog of a double stranded nucleic acid is intended to include nucleic acids having a nucleotide sequence which has a certain degree of homology with or with the complement thereof. In one aspect, homologs of nucleic acids are capable of hybridizing to the nucleic acid or complement thereof. Likewise, "an equivalent polypeptide" refers to a polypeptide having a certain degree of homology, or sequence identity, with the amino acid sequence of a reference polypeptide. In some aspects, the sequence identity is at least about 70%, 75%, 80%, 85%, 90%, 95%, 98%, or 99%. In some aspects, the equivalent polypeptide or polynucleotide has one, two, three, four or five additions, deletions, substitutions and their combinations thereof as compared to the reference polypeptide or polynucleotide. In some aspects, the equivalent sequence retains the activity (e.g., epitope-binding) or structure (e.g., salt-bridge) of the reference sequence.

Hybridization reactions can be performed under conditions of different "stringency". In general, a low stringency hybridization reaction is carried out at about 40° C. in about 10×SSC or a solution of equivalent ionic strength/temperature. A moderate stringency hybridization is typically performed at about 50° C. in about 6×SSC, and a high stringency hybridization reaction is generally performed at about 60° C. in about 1×SSC. Hybridization reactions can also be performed under "physiological conditions" which is well known to one of skill in the art. A non-limiting example of a physiological condition is the temperature, ionic strength, pH and concentration of $Mg^{2+}$ normally found in a cell.

A polynucleotide is composed of a specific sequence of four nucleotide bases: adenine (A); cytosine (C); guanine (G); thymine (T); and uracil (U) for thymine when the polynucleotide is RNA. Thus, the term "polynucleotide sequence" is the alphabetical representation of a polynucleotide molecule. This alphabetical representation can be input into databases in a computer having a central processing unit and used for bioinformatics applications such as functional genomics and homology searching. The term "polymorphism" refers to the coexistence of more than one form of a gene or portion thereof. A portion of a gene of which there are at least two different forms, i.e., two different nucleotide sequences, is referred to as a "polymorphic region of a gene". A polymorphic region can be a single nucleotide, the identity of which differs in different alleles.

The terms "polynucleotide" and "oligonucleotide" are used interchangeably and refer to a polymeric form of nucleotides of any length, either deoxyribonucleotides or ribonucleotides or analogs thereof. Polynucleotides can have any three-dimensional structure and may perform any function, known or unknown. The following are non-limiting examples of polynucleotides: a gene or gene fragment (for example, a probe, primer, EST or SAGE tag), exons, introns, messenger RNA (mRNA), transfer RNA, ribosomal RNA, ribozymes, cDNA, dsRNA, siRNA, miRNA, recombinant polynucleotides, branched polynucleotides, plasmids, vectors, isolated DNA of any sequence, isolated RNA of any sequence, nucleic acid probes and primers. A polynucleotide can comprise modified nucleotides, such as methylated nucleotides and nucleotide analogs. If present, modifications to the nucleotide structure can be imparted before or after assembly of the polynucleotide. The sequence of nucleotides can be interrupted by non-nucleotide components. A polynucleotide can be further modified after polymerization, such as by conjugation with a labeling component. The term also refers to both double- and single-stranded molecules. Unless otherwise specified or required, any embodiment of this disclosure that is a polynucleotide encompasses both the double-stranded form and each of two complementary single-stranded forms known or predicted to make up the double-stranded form.

The term "encode" as it is applied to polynucleotides refers to a polynucleotide which is said to "encode" a polypeptide if, in its native state or when manipulated by methods well known to those skilled in the art, it can be transcribed and/or translated to produce the mRNA for the polypeptide and/or a fragment thereof. The antisense strand is the complement of such a nucleic acid, and the encoding sequence can be deduced therefrom.

As used herein, an "antibody" or "antigen-binding polypeptide" refers to a polypeptide or a polypeptide complex that specifically recognizes and binds to an antigen. An antibody can be a whole antibody and any antigen binding fragment or a single chain thereof. Thus the term "antibody" includes any protein or peptide containing molecule that comprises at least a portion of an immunoglobulin molecule having biological activity of binding to the antigen. Examples of such include, but are not limited to a complementarity determining region (CDR) of a heavy or light chain or a ligand binding portion thereof, a heavy chain or light chain variable region, a heavy chain or light chain constant region, a framework (FR) region, or any portion thereof, or at least one portion of a binding protein.

The terms "antibody fragment" or "antigen-binding fragment", as used herein, is a portion of an antibody such as $F(ab')_2$, $F(ab)_2$, Fab', Fab, Fv, scFv and the like. Regardless of structure, an antibody fragment binds with the same antigen that is recognized by the intact antibody. The term "antibody fragment" includes aptamers, spiegelmers, and diabodies. The term "antibody fragment" also includes any synthetic or genetically engineered protein that acts like an antibody by binding to a specific antigen to form a complex.

A "single-chain variable fragment" or "scFv" refers to a fusion protein of the variable regions of the heavy ($V_H$) and light chains ($V_L$) of immunoglobulins. In some aspects, the regions are connected with a short linker peptide of ten to about 25 amino acids. The linker can be rich in glycine for flexibility, as well as serine or threonine for solubility, and can either connect the N-terminus of the $V_H$ with the C-terminus of the $V_L$, or vice versa. This protein retains the specificity of the original immunoglobulin, despite removal of the constant regions and the introduction of the linker. ScFv molecules are known in the art and are described, e.g., in U.S. Pat. No. 5,892,019.

The term antibody encompasses various broad classes of polypeptides that can be distinguished biochemically. Those skilled in the art will appreciate that heavy chains are classified as gamma, mu, alpha, delta, or epsilon ($\gamma$, $\mu$, $\alpha$, $\delta$, $\epsilon$) with some subclasses among them (e.g., $\gamma 1$-$\gamma 4$). It is the nature of this chain that determines the "class" of the antibody as IgG, IgM, IgA IgD, or IgE, respectively. The immunoglobulin subclasses (isotypes) e.g., $IgG_1$, $IgG_2$, $IgG_3$ and $IgG_4$. are well characterized and are known to confer functional specialization. Modified versions of each of these classes and isotypes are readily discernable to the skilled artisan in view of the instant disclosure and, accordingly, are within the scope of the instant disclosure. All immunoglobulin classes are clearly within the scope of the present disclosure, the following discussion will generally be directed to the IgG class of immunoglobulin molecules. With regard to IgG, a standard immunoglobulin molecule comprises two identical light chain polypeptides of molecular weight approximately 23,000 Daltons, and two identical heavy chain polypeptides of molecular weight 53,000-70,000. The four chains are typically joined by disulfide bonds in a "Y" configuration wherein the light chains bracket the heavy chains starting at the mouth of the "Y" and continuing through the variable region.

Antibodies, antigen-binding polypeptides, variants, or derivatives thereof of the disclosure include, but are not limited to, polyclonal, monoclonal, multi-specific, human, humanized, primatized, or chimeric antibodies, single chain antibodies, epitope-binding fragments, e.g., Fab, Fab' and F(ab')$_2$, Fd, Fvs, single-chain Fvs (scFv), single-chain antibodies, disulfide-linked Fvs (sdFv), fragments comprising either a VK or VH domain, fragments produced by a Fab expression library, and anti-idiotypic (anti-Id) antibodies (including, e.g., anti-Id antibodies to LIGHT antibodies disclosed herein). Immunoglobulin or antibody molecules of the disclosure can be of any type (e.g., IgG, IgE, IgM, IgD, IgA, and IgY), class (e.g., IgG1, IgG2, IgG3, IgG4, IgA1 and IgA2) or subclass of immunoglobulin molecule.

Light chains are classified as either kappa or lambda ($\kappa$, $\lambda$). Each heavy chain class may be bound with either a kappa or lambda light chain. In general, the light and heavy chains are covalently bonded to each other, and the "tail" portions of the two heavy chains are bonded to each other by covalent disulfide linkages or non-covalent linkages when the immunoglobulins are generated either by hybridomas, B cells or genetically engineered host cells. In the heavy chain, the amino acid sequences run from an N-terminus at the forked ends of the Y configuration to the C-terminus at the bottom of each chain.

Both the light and heavy chains are divided into regions of structural and functional homology. The terms "constant" and "variable" are used functionally. In this regard, it will be appreciated that the variable domains of both the light (VK) and heavy (VH) chain portions determine antigen recognition and specificity. Conversely, the constant domains of the light chain (CK) and the heavy chain (CH1, CH2 or CH3) confer important biological properties such as secretion, transplacental mobility, Fc receptor binding, complement binding, and the like. By convention the numbering of the constant region domains increases as they become more distal from the antigen-binding site or amino-terminus of the antibody. The N-terminal portion is a variable region and at the C-terminal portion is a constant region; the CH3 and CK domains actually comprise the carboxy-terminus of the heavy and light chain, respectively.

As indicated above, the variable region allows the antibody to selectively recognize and specifically bind epitopes on antigens. That is, the VK domain and VH domain, or subset of the complementarity determining regions (CDRs), of an antibody combine to form the variable region that defines a three-dimensional antigen-binding site. This quaternary antibody structure forms the antigen-binding site present at the end of each arm of the Y. More specifically, the antigen-binding site is defined by three CDRs on each of the VH and VK chains (i.e. CDR-H1, CDR-H2, CDR-H3, CDR-L1, CDR-L2 and CDR-L3). In some instances, e.g., certain immunoglobulin molecules derived from camelid species or engineered based on camelid immunoglobulins, a complete immunoglobulin molecule may consist of heavy chains only, with no light chains. See, e.g., Hamers-Casterman et al., Nature 363:446-448 (1993).

In naturally occurring antibodies, the six "complementarity determining regions" or "CDRs" present in each antigen-binding domain are short, non-contiguous sequences of amino acids that are specifically positioned to form the antigen-binding domain as the antibody assumes its three-dimensional configuration in an aqueous environment. The remainder of the amino acids in the antigen-binding domains, referred to as "framework" regions, show less inter-molecular variability. The framework regions largely adopt a $\beta$-sheet conformation and the CDRs form loops which connect, and in some cases form part of, the $\beta$-sheet structure. Thus, framework regions act to form a scaffold that provides for positioning the CDRs in correct orientation by inter-chain, non-covalent interactions. The antigen-binding domain formed by the positioned CDRs defines a surface complementary to the epitope on the immuno-reactive antigen. This complementary surface promotes the non-covalent binding of the antibody to its cognate epitope. The amino acids comprising the CDRs and the framework regions, respectively, can be readily identified for any given heavy or light chain variable region by one of ordinary skill in the art, since they have been precisely defined (see "Sequences of Proteins of Immunological Interest," Kabat, E., et al., U.S. Department of Health and Human Services, (1983); and Chothia and Lesk, J. Mol. Biol., 196:901-917 (1987)).

In the case where there are two or more definitions of a term which is used and/or accepted within the art, the definition of the term as used herein is intended to include all such meanings unless explicitly stated to the contrary. A specific example is the use of the term "complementarity determining region" ("CDR") to describe the non-contiguous antigen combining sites found within the variable region of both heavy and light chain polypeptides. This particular region has been described by Kabat et al., U.S. Dept. of Health and Human Services, "Sequences of Proteins of Immunological Interest" (1983) and by Chothia et al., J. Mol. Biol. 196:901-917 (1987), which are incorporated herein by reference in their entireties. The CDR definitions according to Kabat and Chothia include overlapping or subsets of amino acid residues when compared against each other. Nevertheless, application of either definition to refer to a CDR of an antibody or variants thereof is intended to be within the scope of the term as defined and used herein. The appropriate amino acid residues which encompass the CDRs as defined by each of the above cited references are set forth in the table below as a comparison. The exact residue numbers which encompass a particular CDR will vary depending on the sequence and size of the CDR. Those skilled in the art can routinely determine which residues comprise a particular CDR given the variable region amino acid sequence of the antibody.

|        | Kabat  | Chothia |
|--------|--------|---------|
| CDR-H1 | 31-35  | 26-32   |
| CDR-H2 | 50-65  | 52-58   |
| CDR-H3 | 95-102 | 95-102  |
| CDR-L1 | 24-34  | 26-32   |
| CDR-L2 | 50-56  | 50-52   |
| CDR-L3 | 89-97  | 91-96   |

Kabat et al. also defined a numbering system for variable domain sequences that is applicable to any antibody. One of ordinary skill in the art can unambiguously assign this system of "Kabat numbering" to any variable domain sequence, without reliance on any experimental data beyond the sequence itself. As used herein, "Kabat numbering" refers to the numbering system set forth by Kabat et al., U.S. Dept. of Health and Human Services, "Sequence of Proteins of Immunological Interest" (1983).

In addition to table above, the Kabat number system describes the CDR regions as follows: CDR-H1 begins at approximately amino acid 31 (i.e., approximately 9 residues after the first cysteine residue), includes approximately 5-7 amino acids, and ends at the next tryptophan residue. CDR-H2 begins at the fifteenth residue after the end of CDR-H1, includes approximately 16-19 amino acids, and ends at the next arginine or lysine residue. CDR-H3 begins at approximately the thirty third amino acid residue after the end of CDR-H2; includes 3-25 amino acids. CDR-L1 begins at approximately residue 24 (i.e., following a cysteine residue); includes approximately 10-17 residues; and ends at the next tryptophan residue. CDR-L2 begins at approximately the sixteenth residue after the end of CDR-L1 and includes approximately 7 residues. CDR-L3 begins at approximately the thirty third residue after the end of CDR-L2 (i.e., following a cysteine residue); and includes approximately 7-11 residues.

Antibodies disclosed herein may be from any animal origin including birds and mammals. Preferably, the antibodies are human, murine, donkey, rabbit, goat, guinea pig, camel, llama, horse, or chicken antibodies. In another embodiment, the variable region may be condricthoid in origin (e.g., from sharks).

As used herein, the term "heavy chain constant region" includes amino acid sequences derived from an immunoglobulin heavy chain. A polypeptide comprising a heavy chain constant region comprises at least one of: a CH1 domain, a hinge (e.g., upper, middle, and/or lower hinge region) domain, a CH2 domain, a CH3 domain, or a variant or fragment thereof. For example, an antigen-binding polypeptide for use in the disclosure may comprise a polypeptide chain comprising a CH1 domain; a polypeptide chain comprising a CH1 domain, at least a portion of a hinge domain, and a CH2 domain; a polypeptide chain comprising a CH1 domain and a CH3 domain; a polypeptide chain comprising a CH1 domain, at least a portion of a hinge domain, and a CH3 domain, or a polypeptide chain comprising a CH1 domain, at least a portion of a hinge domain, a CH2 domain, and a CH3 domain. In another embodiment, a polypeptide of the disclosure comprises a polypeptide chain comprising a CH3 domain. Further, an antibody for use in the disclosure may lack at least a portion of a CH2 domain (e.g., all or part of a CH2 domain). As set forth above, it will be understood by one of ordinary skill in the art that the heavy chain constant region may be modified such that they vary in amino acid sequence from the naturally occurring immunoglobulin molecule.

The heavy chain constant region of an antibody disclosed herein may be derived from different immunoglobulin molecules. For example, a heavy chain constant region of a polypeptide may comprise a CH1 domain derived from an IgG$_1$ molecule and a hinge region derived from an IgG3 molecule. In another example, a heavy chain constant region can comprise a hinge region derived, in part, from an IgG1 molecule and, in part, from an IgG3 molecule. In another example, a heavy chain portion can comprise a chimeric hinge derived, in part, from an IgG$_1$ molecule and, in part, from an IgG4 molecule.

As used herein, the term "light chain constant region" includes amino acid sequences derived from antibody light chain. Preferably, the light chain constant region comprises at least one of a constant kappa domain or constant lambda domain.

A "light chain-heavy chain pair" refers to the collection of a light chain and heavy chain that can form a dimer through a disulfide bond between the CL domain of the light chain and the CH1 domain of the heavy chain.

As previously indicated, the subunit structures and three-dimensional configuration of the constant regions of the various immunoglobulin classes are well known. As used herein, the term "VH domain" includes the amino terminal variable domain of an immunoglobulin heavy chain and the term "CH1 domain" includes the first (most amino terminal) constant region domain of an immunoglobulin heavy chain. The CH1 domain is adjacent to the $V_H$ domain and is amino terminal to the hinge region of an immunoglobulin heavy chain molecule.

As used herein the term "CH2 domain" includes the portion of a heavy chain molecule that extends, e.g., from about residue 244 to residue 360 of an antibody using conventional numbering schemes (residues 244 to 360, Kabat numbering system; and residues 231-340, EU numbering system; see Kabat et al., U.S. Dept. of Health and Human Services, "Sequences of Proteins of Immunological Interest" (1983). The CH2 domain is unique in that it is not closely paired with another domain. Rather, two N-linked branched carbohydrate chains are interposed between the two CH2 domains of an intact native IgG molecule. It is also well documented that the CH3 domain extends from the CH2 domain to the C-terminal of the IgG molecule and comprises approximately 108 residues.

As used herein, the term "hinge region" includes the portion of a heavy chain molecule that joins the CH1 domain to the CH2 domain. This hinge region comprises approximately 25 residues and is flexible, thus allowing the two N-terminal antigen-binding regions to move independently. Hinge regions can be subdivided into three distinct domains: upper, middle, and lower hinge domains (Roux et al., *J. Immunol* 161:4083 (1998)).

As used herein the term "disulfide bond" includes the covalent bond formed between two sulfur atoms. The amino acid cysteine comprises a thiol group that can form a disulfide bond or bridge with a second thiol group. In most naturally occurring IgG molecules, the CH1 and CK regions are linked by a disulfide bond and the two heavy chains are linked by two disulfide bonds at positions corresponding to 239 and 242 using the Kabat numbering system (position 226 or 229, EU numbering system).

As used herein, the term "chimeric antibody" will be held to mean any antibody wherein the immuno-reactive region or site is obtained or derived from a first species and the constant region (which may be intact, partial or modified in accordance with the instant disclosure) is obtained from a second species. In certain embodiments, the target binding region or site will be from a non-human source (e.g. mouse or primate) and the constant region is human.

As used herein, "percent humanization" is calculated by determining the number of framework amino acid differences (i.e., non-CDR difference) between the humanized domain and the germline domain, subtracting that number from the total number of amino acids, and then dividing that by the total number of amino acids and multiplying by 100.

By "specifically binds" or "has specificity to," it is generally meant that an antibody binds to an epitope via its antigen-binding domain, and that the binding entails some complementarity between the antigen-binding domain and the epitope. According to this definition, an antibody is said to "specifically bind" to an epitope when it binds to that epitope, via its antigen-binding domain more readily than it would bind to a random, unrelated epitope. The term "specificity" is used herein to qualify the relative affinity by which a certain antibody binds to a certain epitope. For example, antibody "A" may be deemed to have a higher specificity for a given epitope than antibody "B," or antibody "A" may be said to bind to epitope "C" with a higher specificity than it has for related epitope "D."

As used herein, the terms "treat" or "treatment" refer to both therapeutic treatment and prophylactic or preventative measures, wherein the object is to prevent or slow down (lessen) an undesired physiological change or disorder, such as the progression of cancer. Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

By "subject" or "individual" or "animal" or "patient" or "mammal," is meant any subject, particularly a mammalian subject, for whom diagnosis, prognosis, or therapy is desired. Mammalian subjects include humans, domestic animals, farm animals, and zoo, sport, or pet animals such as dogs, cats, guinea pigs, rabbits, rats, mice, horses, cattle, cows, and so on.

As used herein, phrases such as "to a patient in need of treatment" or "a subject in need of treatment" includes subjects, such as mammalian subjects, that would benefit from administration of an antibody or composition of the present disclosure used, e.g., for detection, for a diagnostic procedure and/or for treatment.

Anti-IL-18R Alpha and Beta Antibodies

Some cytokine-directed therapies have been associated with an increase in infections. This might be less of a concern with anti-IL-18-directed antibodies. Nevertheless, recent clinical studies investigating the safety and efficacy of an anti-IL-18 monoclonal antibody with 30 pM affinity was used to evaluate its ability to restore fasting plasma glucose control, insulin levels and C-reactive peptide (a proxy for insulin levels) failed to show appreciable efficacy. It is therefore not surprising that no therapeutic antibodies have been developed targeting the receptors.

Various embodiments of the present disclosure provide antibodies specific to IL-18 receptor a or B. These antibodies can be effective therapeutic agents given their unique features. Often, antagonistic antibodies impede receptor-mediated signaling by steric blockade of the ligand binding site. The anti-IL-18Rβ antibody 3131 of the present disclosure, however, targets the non-ligand binding component of the receptor, as shown in the structural data obtained herein. This subunit of the receptor does not directly contact the ligand, but rather forms intermolecular contacts with the ligand-binding IL-18Rα subunit. In doing so, it mediates the signaling function of the receptor complex and without it, no transduction of ligand signals occurs. Antibody 3131 interaction with IL-18Rβ appears to occur at the hinge region between domains 2 (D2) and 3 (D3), distorting the relative angle between them into a conformation that cannot interact with IL-18Rα. This effectively impedes formation of a functional receptor-ligand complex and inhibits downstream signaling in a new manner.

It is also interesting that the IL-18Rβ antibody 3131 exhibited appreciable affinity for its mouse ortholog. This is useful as it will enable pre-clinical evaluation of its distribution, safety and activity in a mouse model against the endogenous receptor thus facilitating development and the path to clinical evaluation.

In accordance with one embodiment of the present disclosure, antibodies and fragments thereof are provided that specifically bind to the IL-18Rβ protein. These antibodies or fragments can have binding specificity to two or more of the following regions, (1) the D1-D2 domains, (2) the hinge region, and (3) the D3 domain of a human interleukin-18 receptor beta (IL-18Rβ) protein. The hinge regions can be illustrated with an example IL-18Rβ sequence, SEQ ID NO: 161 (UniProt ID 095256; Table A). In SEQ ID NO:1, amino acid residues 1-243 are the D1 and D2 domains. Amino acid residues 244-246 constitute the hinge region. Amino acid residues 247-356 constitute the D3 domain.

Amino acid residues in the D1-D2 domains that can be involved in binding the antibody or fragment include, without limitation, L167, D213, and T242. Amino acid residues in the hinge region that can be involved in binding the antibody or fragment include, without limitation, V244, G245 and D246. Amino acid residues in the D3 domain that can be involved in binding the antibody or fragment include, without limitation, G278, F279, R281, V282, F283, N284, P285, S310, E315 and I317.

In one embodiment, the antibody of fragment thereof binds to at least a residue in the D1-D2 domains (e.g., one of more of L167, D213, or T242, preferably one or more of D213 or T242) and at least a residue in the hinge region (e.g., one or more of V244, G245 or D246, preferably V244).

In one embodiment, the antibody of fragment thereof binds to at least a residue in the D1-D2 domains (e.g., one or more of L167, D213, and T242, preferably one or more of D213, and T242) and at least a residue in the D3 domain (one or more of G278, F279, R281, V282, F283, N284, P285, S310, E315 or I317, or preferably one or more of G278, R281, V282, F283, N284, P285, S310, E315 or I317).

In one embodiment, the antibody of fragment thereof binds to at least a residue in the hinge region (e.g., one or more of V244, G245 or D246, preferably V244) and at least a residue in the D3 domain (one or more of G278, F279, R281, V282, F283, N284, P285, S310, E315 or I317, or preferably one or more of G278, R281, V282, F283, N284, P285, S310, E315 or I317).

In one embodiment, the antibody of fragment thereof binds to at least a residue in the D1-D2 domains (e.g., one or more of L167, D213, or T242, preferably one or more of D213 or T242), at least a residue in the hinge region (e.g., one or more of V244, G245 or D246, preferably V244), and at least a residue in the D3 domain (one or more of G278, F279, R281, V282, F283, N284, P285, S310, E315 or I317, or preferably one or more of G278, R281, V282, F283, N284, P285, S310, E315 or I317).

In one embodiment, the antibody of fragment thereof binds to D213 and T242 of D1-D2, V244 of the hinge region, and at least two, three, four, five, six, seven or eight residues in the D3 domain selected from G278, F279, R281, V282, F283, N284, P285, S310, E315 and I317, or from G278, R281, V282, F283, N284, P285, S310, E315 and I317.

In one embodiment, the antibody of fragment thereof binds to amino acid residues D213, T242, V244, G278, R281, V282, F283, N284, P285, S310, E315 and I317. In one embodiment, the antibody of fragment thereof binds to amino acid residues L167, D213, T242, V244, G278, F279, R281, V282, F283, N284, P285, S310, E315 and I317.

TABLE A

Example IL-18Rβ sequence

| Name | Sequence |
|---|---|
| IL-18Rβ (SEQ ID NO: 161) | 1 MLCLGWIFLW LVAGERIKGF NISGCSTKKL LWTYSTRSEE EFVLFCDLPE |
| | 51 PQKSHFCHRN RLSPKQVPEH LPFMGSNDLS DVQWYQQPSN GDPLEDIRKS |
| | 101 YPHIIQDKCT LHFLTPGVNN SGSYICRPKM IKSPYDVACC VKMILEVKPQ |
| | 151 TNASCEYSAS HKQDLLLGST GSISCPSLSC QSDAQSPAVT WYKNGKLLSV |
| | 201 ERSNRIVVDE VYDYHQGTYV CDYTQSDTVS SWTVRAVVQV RTIVGDTKLK |
| | 251 PDILDPVEDT LEVELGKPLT ISCKARFGFE RVFNPVIKWY IKDSDLEWEV |
| | 301 SVPEAKSIKS TLKDEIIERN IILEKVTQRD LRRKFVCFVQ NSIGNTTQSV |
| | 351 QLKEKRGVVL LYILLGTIGT LVAVLAASAL LYRHWIEIVL LYRTYQSKDQ |
| | 401 TLGDKKDFDA FVSYAKWSSF PSEATSSLSE EHLALSLFPD VLENKYGYSL |
| | 451 CLLERDVAPG GVYAEDIVSI IKRSRRGIFI LSPNYVNGPS IFELQAAVNL |
| | 501 ALDDQTLKLI LIKFCYFQEP ESLPHLVKKA LRVLPTVTWR GLKSVPPNSR |
| | 551 FWAKMRYHMP VKNSQGFTWN QLRITSRIFQ WKGLSRTETT GRSSQPKEW |

In some embodiments, the antibody or fragment can bind to both human and mouse IL-18Rβ proteins.

Antibodies and fragments of the present disclosure are also described with respect to their CDR sequences. In one embodiment, an antibody or fragment thereof is provided that has binding specificity to a human interleukin-18 receptor beta (IL-18Rβ) protein, wherein the antibody or fragment thereof comprises a light chain variable region comprising light chain complementarity determining regions CDRL1, CDRL2, and CDRL3 and a heavy chain variable region comprising heavy chain complementarity determining regions CDRH1, CDRH2, and CDRH3, and wherein the CDRL3, CDRH1, CDRH2, and CDRH3, are selected from combinations 1-27 of Table B. The antibody or fragment disclosure herein can also include a CDRL1 and a CDRL2. A good variety of CDRL1 and CDRL2 sequences can be employed here. Non-limiting examples include QSVSSA (SEQ ID NO:45) and SAS (SEQ ID NO: 46), respectively, as well as them with substitutions as illustrated in Table B1.

TABLE B

CDR sequences for anti-IL-18Rβ antibodies

| Comb # | Fab ID | CDRL1 (SEQ ID NO:) | CDRL2 (SEQ ID NO:) | CDRL3 (SEQ ID NO:) | CDRH1 (SEQ ID NO:) | CDRH2 (SEQ ID NO:) | CDRH3 (SEQ ID NO:) |
|---|---|---|---|---|---|---|---|
| 1 | F3131 | QSVSSA 45 | SAS 46 | QQYGYHYAGLIT 47 | GFNLYYSSM 74 | SIYSSYGYTY 95 | ARSSFSHGYGWYGLDY 117 |
| 2 | F3132 | QSVSSA 45 | SAS 46 | QQHWWASVPPFT 48 | GFNISYYYI 75 | SIYSYSGYTS 96 | ARASAMDY 118 |

TABLE B-continued

CDR sequences for anti-IL-18Rβ antibodies

| Comb # | Fab ID | CDRL1 (SEQ ID NO:) | CDRL2 (SEQ ID NO:) | CDRL3 (SEQ ID NO:) | CDRH1 (SEQ ID NO:) | CDRH2 (SEQ ID NO:) | CDRH3 (SEQ ID NO:) |
|---|---|---|---|---|---|---|---|
| 3 | F3133 | QSVSSA 45 | SAS 46 | QQHYWGYLIT 49 | GFNLSYYSI 76 | SIYSSYGYTS 97 | ARSYGLDY 119 |
| 4 | F3134 | QSVSSA 45 | SAS 46 | QQHHWSYPIT 50 | GENIYSYSI 77 | SIYPSYGYTS 98 | ARSFGLDY 120 |
| 5 | F3135 | QSVSSA 45 | SAS 46 | QQHHHWAVLIT 51 | GFNFYSYSM 78 | YIYPYSGYTS 99 | ARSFAMDY 121 |
| 6 | F3136 | QSVSSA 45 | SAS 46 | QQHYWGGPIT 52 | GENISSYSM 79 | SIYSYYSYTS 100 | ARSYAMDY 122 |
| 7 | F3137 | QSVSSA 45 | SAS 46 | QQSWGWSWLIT 53 | GFNLSSYSI 80 | YIYPSYGSTY 101 | ARSYALDY 123 |
| 8 | F3138 | QSVSSA 45 | SAS 46 | QQHSFHSGLI 54 | GFNLYSYSM 81 | YIYSYSGYTS 102 | ARGFALDY 124 |
| 9 | F3139 | QSVSSA 45 | SAS 46 | QQSHGWWGFPFT 55 | GENISSYSI 82 | SIYPYYGYTY 103 | ARSWAMDY 125 |
| 10 | F3140 | QSVSSA 45 | SAS 46 | QQYYWASYPFT 56 | GFNFYSYSM 78 | SIYPSYGYTS 98 | ARSFGFDY 126 |
| 11 | F3141 | QSVSSA 45 | SAS 46 | QQYYYSAALIT 57 | GFNIYYSSM 83 | YIYPYSGYTS 99 | ARYFAMDY 127 |
| 12 | F3142 | QSVSSA 45 | SAS 46 | QQWWGGPYVLIT 58 | GFNLSYSSM 84 | SIYPSSSSTY 104 | ARSSHSGYYFGIDY 128 |
| 13 | F3143 | QSVSSA 45 | SAS 46 | QQYHWGSYYPFT 59 | GFNLSSYYM 85 | SIYPYYGYTY 103 | ARSSAMDY 129 |
| 14 | F3144 | QSVSSA 45 | SAS 46 | QQHWWGYPLIT 60 | GFNLSYYSI 76 | SIYSYSGYTS 96 | ARSSAMDY 129 |
| 15 | F3145 | QSVSSA 45 | SAS 46 | QQHYYGSFPPIT 61 | GFNFYSYSM 78 | SIYSYYGYTS 105 | ARSFGMDY 130 |
| 16 | F3147 | QSVSSA 45 | SAS 46 | QQHWWAALIT 62 | GFNLSSYSI 80 | YIYSSYGYTS 106 | ARSFGMDY 130 |
| 17 | F3148 | QSVSSA 45 | SAS 46 | QQHYYSSLIT 63 | GFNIYSYSM 86 | SIYPYYSSTY 107 | ARSSAMDY 129 |
| 18 | F3150 | QSVSSA 45 | SAS 46 | QQHSWAVPIT 64 | GFNLSSYSM 87 | SIYPYYGYTS 108 | ARSSAFDY 131 |
| 19 | F3152 | QSVSSA 45 | SAS 46 | QQHSYSAPLIT 65 | GFNIYSYSM 86 | SIYPSYGYTS 109 | ARSYAMDY 122 |
| 20 | FA3 | QSVSSA 45 | SAS 46 | QQSYFLIT 66 | GFNLYSSYI 88 | SIYSSSGYTY 110 | ARSVHSYYSSAAYYAMDY 132 |
| 21 | FE60 | QSVSSA 45 | SAS 46 | QQYPSASHYLIT 67 | GFNLYYYYM 89 | SIYSYYGYTS 105 | ARSYPSSSWGSVALDY 133 |
| 22 | 3131 AM1-1 | QSVSSA 45 | SAS 46 | QQYAYHEPGLLT 68 | GFNPYYSSI 90 | SISPSYSSTY 111 | ARSSCSHSCRFYGLDY 134 |
| 23 | 3131- AM1-2 | QSVSSA 45 | SAS 46 | QQWGYRYAPLVT 69 | GENFYYSSI 91 | SISSATGNTS 112 | ARSSYSHGHSWYGLDY 135 |
| 24 | 3144- AM1-3 | QSVSSA 45 | SAS 46 | QQHSWAYPMIT 70 | GFNLTWWSI 92 | TIFSGFSYTS 113 | ARSSAMDY 129 |
| 25 | 3144- AM1-4 | QSVSSA 45 | SAS 46 | QQHWFGYPAVT 71 | GFNISQYTI 93 | SIYARSRFTS 114 | ARSSRMDY 136 |
| 26 | 3144- AM1-5 | QSVSSA 45 | SAS 46 | QQHWWGYPMIT 72 | GENISYYTI 94 | SIYSYSLYTS 115 | ARSSAMDY 129 |

TABLE B-continued

CDR sequences for anti-IL-18Rβ antibodies

| Comb # | Fab ID | CDRL1 (SEQ ID NO:) | | CDRL2 (SEQ ID NO:) | | CDRL3 (SEQ ID NO:) | | CDRH1 (SEQ ID NO:) | | CDRH2 (SEQ ID NO:) | | CDRH3 (SEQ ID NO:) | |
|---|---|---|---|---|---|---|---|---|---|---|---|---|---|
| 27 | 3144-AM1-6 | QSVSSA | 45 | SAS | 46 | QQHSWRYPLIT | 73 | GFNLSSYSI | 80 | AIYAGFGSTT | 116 | ARSSAMDY | 129 |

It can be readily appreciated that certain modification (e.g., one, two, or three amino acid additions, deletions, conservative amino acid substitutions) to one or more of the CDR sequences can be made while retaining the binding activity of the antibody or fragment. In some embodiments, the modifications are amino acid substitution of one, two, or three residues.

In some embodiments, the modification is substitution at no more than one hot spot position from each of the CDRs. In some embodiments, the modification is substitution at one, two or three such hot spot positions. In one embodiment, the modification is substitution at one of the hot spot positions. Such substitutions, in some embodiments, are conservative substitutions.

A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a nonessential amino acid residue in an immunoglobulin polypeptide is preferably replaced with another amino acid residue from the same side chain family. In another embodiment, a string of amino acids can be replaced with a structurally similar string that differs in order and/or composition of side chain family members.

Non-limiting examples of conservative amino acid substitutions are provided in the table below, where a similarity score of 0 or higher indicates conservative substitution between the two amino acids.

Amino Acid Similarity Matrix

|   | C | G | P | S | A | T | D | E | N | Q | H | K | R | V | M | I | L | F | Y | W |
|---|---|---|---|---|---|---|---|---|---|---|---|---|---|---|---|---|---|---|---|---|
| W | -8 | -7 | -6 | -2 | -6 | -5 | -7 | -7 | -4 | -5 | -3 | -3 | 2 | -6 | -4 | -5 | -2 | 0 | 0 | 17 |
| Y | 0 | -5 | -5 | -3 | -3 | -3 | -4 | -4 | -2 | -4 | 0 | -4 | -5 | -2 | -2 | -1 | -1 | 7 | 10 | |
| F | -4 | -5 | -5 | -3 | -4 | -3 | -6 | -5 | -4 | -5 | -2 | -5 | -4 | -1 | 0 | 1 | 2 | 9 | | |
| L | -6 | -4 | -3 | -3 | -2 | -2 | -4 | -3 | -3 | -2 | -2 | -3 | -3 | 2 | 4 | 2 | 6 | | | |
| I | -2 | -3 | -2 | -1 | -1 | 0 | -2 | -2 | -2 | -2 | -2 | -2 | -2 | 4 | 2 | 5 | | | | |
| M | -5 | -3 | -2 | -2 | -1 | -1 | -3 | -2 | 0 | -1 | -2 | 0 | 0 | 2 | 6 | | | | | |
| V | -2 | -1 | -1 | -1 | 0 | 0 | -2 | -2 | -2 | -2 | -2 | -2 | -2 | 4 | | | | | | |
| R | -4 | -3 | 0 | 0 | -2 | -1 | -1 | -1 | 0 | 1 | 2 | 3 | 6 | | | | | | | |
| K | -5 | -2 | -1 | 0 | -1 | 0 | 0 | 0 | 1 | 1 | 0 | 5 | | | | | | | | |
| H | -3 | -2 | 0 | -1 | -1 | -1 | 1 | 1 | 2 | 3 | 6 | | | | | | | | | |
| Q | -5 | -1 | 0 | -1 | 0 | -1 | 2 | 2 | 1 | 4 | | | | | | | | | | |
| N | -4 | 0 | -1 | 1 | 0 | 0 | 2 | 1 | 2 | | | | | | | | | | | |
| E | -5 | 0 | -1 | 0 | 0 | 0 | 3 | 4 | | | | | | | | | | | | |
| D | -5 | 1 | -1 | 0 | 0 | 0 | 4 | | | | | | | | | | | | | |
| T | -2 | 0 | 0 | 1 | 1 | 3 | | | | | | | | | | | | | | |
| A | -2 | 1 | 1 | 1 | 2 | | | | | | | | | | | | | | | |
| S | 0 | 1 | 1 | 1 | | | | | | | | | | | | | | | | |
| P | -3 | -1 | 6 | | | | | | | | | | | | | | | | | |
| G | -3 | 5 | | | | | | | | | | | | | | | | | | |
| C | 12 | | | | | | | | | | | | | | | | | | | |

Conservative Amino Acid Substitutions

| For Amino Acid | Substitution With |
|---|---|
| Alanine | D-Ala, L-Gly, Aib, β-Ala, L-Cys, D-Cys |
| Arginine | D-Arg, L-Lys, D-Lys, Orn, D-Orn |
| Asparagine | D-Asn, L-Asp, D-Asp, L-Glu, D-Glu, L-Gln, D-Gln |
| Aspartic Acid | D-Asp, D-Asn, L-Asn, L-Glu, D-Glu, L-Gln, D-Gln |
| Cysteine | D-Cys, L-S-Me-Cys, Seleno-Cys (Sec), L-Met, D-Met, L-Thr, D-Thr, L-Ser, D-Ser |
| Glutamine | D-Gln, L-Asn, D-Asn, L-Glu, D-Glu, L-Asp, D-Asp |
| Glutamic Acid | D-Glu, D-Asp, L-Asp, L-Asn, D-Asn, L-Gln, D-Gln |
| Glycine | L-Ala, D-Ala, L-Pro, D-Pro, Aib, β-Ala |
| Isoleucine | D-Ile, L-Val, D-Val, L-Leu, D-Leu, L-Met, D-Met |
| Leucine | L-Val, D-Val, L-Met, D-Met, D-Ile, D-Leu, L-Ile |
| Lysine | D-Lys, L-Arg, D-Arg, L-Orn, D-Orn |
| Methionine | D-Met, L-S-Me-Cys, L-Ile, D-Ile, L-Leu, D-Leu, L-Val, D-Val |
| Phenylalanine | D-Phe, L-Tyr, D-Tyr, L-His, D-His, L-Trp, D-Trp |
| Proline | D-Pro |

-continued

| For Amino Acid | Substitution With |
|---|---|
| Serine | D-Ser, L-Thr, D-Thr, allo-Thr, L-Cys, D-Cys, Seleno-Cys (Sec) |
| Threonine | D-Thr, L-Ser, D-Ser, allo-Thr, L-Met, D-Met, L-Val, D-Val |
| Tyrosine | D-Tyr, L-Phe, D-Phe, L-His, D-His, L-Trp, D-Trp |
| Valine | D-Val, L-Leu, D-Leu, L-Ile, D-Ile, L-Met, D-Met |

Specific examples of CDRs (from F3131, #1 in Table B) with suitable substitutions are provided in the table below.

TABLE B1

Substitutions of CDR Residues

| CDR | No.* | Residue | Can be substituted with |
|---|---|---|---|
| CDRL1 | 27 | Q | N, D, E, S, T, Y, W, H, K, R |
|  | 28 | S | N, D, E, Q, T, Y, W, H, K, R |
|  | 29 | V | A, I, L, M, P, F |
|  | 36 | S | N, D, E, Q, T, Y, W, H, K, R |
|  | 37 | S | N, D, E, Q, T, Y, W, H, K, R |
|  | 38 | A | V, I, L, M, P, F |
| CDRL2 | 56 | S | N, D, E, Q, T, Y, W, H, K, R |
|  | 57 | A | V, I, L, M, P, F |
|  | 65 | S | N, D, E, Q, T, Y, W, H, K, R |
| CDRL3 | 105 | Q | N, D, E, S, T, Y, W, H, K, R |
|  | 106 | Q | N, D, E, S, T, Y, W, H, K, R |
|  | 107 | Y | N, D, E, S, T, Q, W, H, K, R, V, I, L, M, P, F, A |
|  | 108 | G | N, D, E, S, T, Q, W, H, K, R |
|  | 109 | Y | N, D, E, S, T, Q, W, H, K, R, V, I, L, M, P, F, A |
|  | 110 | H | N, D, E, S, T, Y, W, Q, K, R |
|  | 112 | Y | N, D, E, S, T, Q, W, H, K, R, V, I, L, M, P, F, A |
|  | 113 | A | V, I, L, M, P, F |
|  | 114 | G | V, I, L, M, P, F |
|  | 115 | L | V, I, A, M, P, F |
|  | 116 | I | V, L, A, M, P, F |
|  | 117 | T | N, D, E, Q, S, Y, W, H, K, R |
| CDRH1 | 27 | G | N, D, E, S, T, Q, W, H, K, R, V, I, L, M, P, F, A, Y |
|  | 28 | F | A, I, L, M, P, V |
|  | 29 | N | Q, D, E, S, T, Y, W, H, K, R |
|  | 30 | L | V, I, A, M, P, F |
|  | 35 | Y | N, D, E, S, T, Q, W, H, K, R, V, I, L, M, P, F, A |
|  | 36 | Y | N, D, E, S, T, Q, W, H, K, R, V, I, L, M, P, F, A |
|  | 37 | S | N, D, E, Q, T, Y, W, H, K, R |
|  | 38 | S | N, D, E, Q, T, Y, W, H, K, R |
|  | 39 | M | V, L, A, I, P, F |
| CDRH2 | 55 | S | N, D, E, Q, T, Y, W, H, K, R |
|  | 56 | I | V, L, A, M, P, F |
|  | 57 | Y | N, D, E, S, T, Q, W, H, K, R, V, I, L, M, P, F, A |
|  | 58 | S | N, D, E, Q, T, Y, W, H, K, R |
|  | 59 | S | N, D, E, Q, T, Y, W, H, K, R |
|  | 62 | Y | N, D, E, S, T, Q, W, H, K, R, V, I, L, M, P, F, A |
|  | 63 | G | N, D, E, S, T, Q, W, H, K, R, V, I, L, M, P, F, A, Y |
|  | 64 | Y | N, D, E, S, T, Q, W, H, K, R, V, I, L, M, P, F, A |
|  | 65 | T | N, D, E, Q, S, Y, W, H, K, R |
|  | 66 | Y | N, D, E, S, T, Q, W, H, K, R, V, I, L, M, P, F, A |
| CDRH3 | 105 | A | V, I, L, M, P, F |
|  | 106 | R | N, D, E, Q, T, Y, W, H, K, S |
|  | 107 | S | N, D, E, Q, T, Y, W, H, K, R |
|  | 108 | S | N, D, E, Q, T, Y, W, H, K, R |
|  | 109 | F | A, I, L, M, P, V |
|  | 110 | S | N, D, E, Q, T, Y, W, H, K, R |
|  | 111 | H | N, D, E, S, T, Y, W, Q, K, R |
|  | 111.1 | G | N, D, E, S, T, Q, W, H, K, R, V, I, L, M, P, F, A, Y |
|  | 112.2 | Y | N, D, E, S, T, Q, W, H, K, R, V, I, L, M, P, F, A |
|  | 112.1 | G | N, D, E, S, T, Q, W, H, K, R, V, I, L, M, P, F, A, Y |
|  | 112 | W | A, I, L, M, P, V, F |
|  | 113 | Y | N, D, E, S, T, Q, W, H, K, R, V, I, L, M, P, F, A |
|  | 114 | G | N, D, E, S, T, Q, W, H, K, R, V, I, L, M, P, F, A, Y |
|  | 115 | L | V, I, A, M, P, F |
|  | 116 | D | N, Q, E, S, T, Y, W, H, K, R |
|  | 117 | Y | N, D, E, S, T, Q, W, H, K, R, V, I, L, M, P, F, A |

*IMGT numbering system

Specific example antibodies include those that have a heavy chain sequence of SEQ ID NO: 2, 6, 10, 14, 18, 22, 26, 30, 34, or 38 and/or a light chain sequence of SEQ ID NO:4, 8, 12, 16, 20, 24, 28, 32, 36, and 40, and their respective biological variants.

Antibody 3131 (with a heavy chain variable region of SEQ ID NO:2, and a light chain variable region of SEQ ID NO:4) went through a few rounds of affinity maturations, resulting in the generation of 3131 AM1-1 and AM1-2 (see Table 2), and those provided in Table 8. Each of these affinity maturated antibodies, their Fab fragments, variable regions and CDRs are also within the scope of the present disclosure.

In some embodiments, an antibody or fragment of the present disclosure includes CDRL3, CDRH1, CDRH2, and CDRH3 of 3131 or each of its affinity maturated variants (e.g., Table 9). In some embodiments, an antibody or fragment of the present disclosure includes CDRL1, CDRL2, CDRL3, CDRH1, CDRH2, and CDRH3 of 3131 or each of its affinity maturated variants (e.g., Table 9).

In some embodiments, an antibody or fragment of the present disclosure includes a heavy chain variable region and a light chain variable region of an affinity maturated variant of Table 8, such as AM2-1, AM2-1, AM2-2, AM2-2, AM2-3, AM2-3, AM2-4, AM2-4, AM2-5, AM2-5, AM2-6, AM2-6, AM2-7, AM2-7, AM2-8, AM2-8, AM2-9, AM2-9, AM2-10, AM2-10, AM2-11, AM2-11, AM2-13, AM2-13, AM2-14, AM2-14, AM2-15, AM2-15, AM2-16, AM2-16, AM2-17, AM2-17, AM2-18, AM2-18, AM2-21, AM2-21, AM2-24, AM2-24, AM2-25, AM2-25, AM2-26, AM2-26, AM2-28, AM2-28, AM2-29, AM2-29, AM2-30, AM2-30, AM2-31, AM2-31, AM2-32, AM2-32, AM2-33, AM2-33, AM2-35, AM2-35, AM2-36, AM2-36, AM2-37, AM2-37, AM2-S-G, AM2-S-G, AM2-S-T, AM2-S-T, AM2-S-H, AM2-S-H, AM2-S-Y, AM2-S-T, AM2-O-01, AM2-O-01, AM2-O-02, AM2-O-02, AM2-O-03, AM2-O-03, AM2-O-04, AM2-O-04, AM2-O-05, AM2-O-05, AM2-O-06, AM2-O-06, AM2-O-07, AM2-O-07, AM2-O-08, AM2-O-08, AM2-O-09, AM2-O-09, AM2-O-10, AM2-O-10, AM2-O-11, AM2-O-11, AM2-O-12, AM2-O-12, AM2-O-13, AM2-O-13, AM2-O-14, AM2-O-14, AM2-O-15, AM2-O-15, AM2-O-16, AM2-O-16, AM2-O-17, AM2-0-17, AM2-O-18, AM2-O-18, AM2-O-19, AM2-O-19, AM2-O-20, AM2-O-20, AM2-O-21, AM2-O-21, AM2-O-22, AM2-O-22, AM2-O-23, AM2-O-23, AM2-O-24, AM2-O-24, AM2-O-25, AM2-O-25, AM2-O-26, AM2-O-26, AM2-O-27, AM2-O-27, AM2-O-28, AM2-O-28, AM2-O-29, AM2-O-29, AM2-O-30, AM2-O-30, AM2-O-31, AM2-O-31, AM2-O-32, AM2-0-32, AM2-O-33, AM2-O-33. AM2-O-34, AM2-O-34, AM2-O-35, AM2-O-35, AM2-O-36, AM2-O-36, AM2-O-37, AM2-O-37, AM2-O-38, AM2-O-38, AM2-O-39, AM2-O-39, AM2-0-40, AM2-O-40, AM2-O-41, AM2-O-41, AM2-O-42, AM2-O-42, AM2-O-43, AM2-O-43, AM2-O-44, AM2-O-44, AM2-O-45, AM2-O-45, AM2-O-46, and AM2-O-46.

In some embodiments, an antibody or fragment of the present disclosure includes the CDRs of an affinity maturated variant of Table 8, such as AM2-1, AM2-1, AM2-2, AM2-2, AM2-3, AM2-3, AM2-4, AM2-4, AM2-5, AM2-5, AM2-6, AM2-6, AM2-7, AM2-7, AM2-8, AM2-8, AM2-9, AM2-9, AM2-10, AM2-10, AM2-11, AM2-11, AM2-13, AM2-13, AM2-14, AM2-14, AM2-15, AM2-15, AM2-16, AM2-16, AM2-17, AM2-17, AM2-18, AM2-18, AM2-21, AM2-21, AM2-24, AM2-24, AM2-25, AM2-25, AM2-26, AM2-26, AM2-28, AM2-28, AM2-29, AM2-29, AM2-30, AM2-30, AM2-31, AM2-31, AM2-32, AM2-32, AM2-33, AM2-33, AM2-35, AM2-35, AM2-36, AM2-36, AM2-37, AM2-37, AM2-S-G, AM2-S-G, AM2-S-T, AM2-S-T, AM2-S-H, AM2-S-H, AM2-S-Y, AM2-S-T, AM2-O-01, AM2-O-01, AM2-O-02, AM2-O-02, AM2-O-03, AM2-O-03, AM2-O-04, AM2-O-04, AM2-O-05, AM2-O-05, AM2-O-06, AM2-O-06, AM2-O-07, AM2-O-07, AM2-O-08, AM2-O-08, AM2-O-09, AM2-O-09, AM2-O-10, AM2-O-10, AM2-O-11, AM2-O-11, AM2-O-12, AM2-O-12, AM2-O-13, AM2-O-13, AM2-O-14, AM2-O-14, AM2-O-15, AM2-O-15, AM2-O-16, AM2-O-16, AM2-O-17, AM2-O-17, AM2-O-18, AM2-O-18, AM2-O-19, AM2-O-19, AM2-O-20, AM2-O-20, AM2-O-21, AM2-O-21, AM2-O-22, AM2-O-22, AM2-O-23, AM2-O-23, AM2-O-24, AM2-O-24, AM2-O-25, AM2-O-25, AM2-O-26, AM2-O-26, AM2-O-27, AM2-O-27, AM2-O-28, AM2-O-28, AM2-O-29, AM2-O-29, AM2-O-30, AM2-O-30, AM2-O-31, AM2-O-31, AM2-O-32, AM2-O-32, AM2-O-33, AM2-O-33, AM2-O-34, AM2-O-34, AM2-0-35, AM2-O-35, AM2-O-36, AM2-O-36, AM2-O-37, AM2-O-37, AM2-O-38, AM2-O-38, AM2-O-39, AM2-O-39, AM2-O-40, AM2-O-40, AM2-O-41, AM2-O-41, AM2-O-42, AM2-0-42, AM2-O-43, AM2-O-43, AM2-O-44, AM2-O-44, AM2-O-45, AM2-O-45, AM2-O-46, and AM2-O-46.

Examples of such CDR combinations include, without limitation, for CDRL1, CDRL2, CDRL3, CDRH1, CDRH2, and CDRH3, SEQ ID NO:45, 46, 332, 74, 95, and 117 (AM2-1), SEQ ID NO:45, 46, 47, 74, 340, and 117 (AM2-2), SEQ ID NO:45, 46, 47, 74, 341, and 117 (AM2-3), SEQ ID NO:45, 46, 47, 74, 342, and 117 (AM2-4), SEQ ID NO:45, 46, 47, 74, 343, and 117 (AM2-5), SEQ ID NO:45, 46, 47, 74, 344, and 117 (AM2-6), SEQ ID NO: 45, 46, 333, 74, 345, and 117 (AM2-7), SEQ ID NO:45, 46, 47, 74, 346, and 117 (AM2-8), SEQ ID NO:45, 46, 334, 74, 95, and 117 (AM2-9), SEQ ID NO:45, 46, 47, 74, 347, and 117 (AM2-10), SEQ ID NO:45, 46, 47, 74, 347, and 117 (AM2-11), SEQ ID NO: 45, 46, 333, 74, 95, and 117 (AM2-13), SEQ ID NO:45, 46, 335, 74, 95, and 117 (AM2-14), SEQ ID NO:45, 46, 47, 74, 348, and 117 (AM2-15), SEQ ID NO:45, 322, 47, 74, 95, and 117 (AM2-16), SEQ ID NO:45, 46, 47, 74, 349, and 117 (AM2-17), SEQ ID NO:45, 46, 47, 74, 350, and 117 (AM2-18), SEQ ID NO:45, 323, 47, 74, 95, and 117 (AM2-21), SEQ ID NO: 45, 324, 47, 74, 95, and 117 (AM2-24), SEQ ID NO:45, 46, 47, 74, 95, and 117 (AM2-25), SEQ ID NO:45, 325, 47, 74, 95, and 117 (AM2-26), SEQ ID NO:45, 326, 47, 74, 95, and 117 (AM2-28), SEQ ID NO:45, 322, 47, 74, 95, and 117 (AM2-29), SEQ ID NO:45, 46, 47, 74, 95, and 117 (AM2-30), SEQ ID NO:45, 325, 47, 74, 95, and 117 (AM2-31), SEQ ID NO: 45, 327, 47, 74, 95, and 117 (AM2-32), SEQ ID NO:45, 46, 47, 74, 351, and 117 (AM2-33), SEQ ID NO:45, 46, 336, 74, 95, and 117 (AM2-35), SEQ ID NO:45, 46, 47, 74, 352, and 117 (AM2-36), SEQ ID NO:45, 46, 336, 74, 352, and 117 (AM2-37), SEQ ID NO:45, 328, 47, 74, 95, and 117 (AM2-S-G), SEQ ID NO:45, 329, 47, 74, 95, and 117 (AM2-S-T), SEQ ID NO:45, 330, 47, 74, 95, and 117 (AM2-S-H), SEQ ID NO:45, 331, 47, 74, 95, and 117 (AM2-S-Y), SEQ ID NO:45, 46, 47, 337, 350, and 117 (AM2-O-01), SEQ ID NO:45, 46, 47, 338, 350, and 117 (AM2-O-02), SEQ ID NO:45, 46, 47, 339, 350, and 117 (AM2-O-03), SEQ ID NO:45, 46, 47, 337, 343, and 117 (AM2-O-04), SEQ ID NO:45, 46, 47, 338, 343, and 117 (AM2-O-05), SEQ ID NO:45, 46, 47, 339, 343, and 117 (AM2-O-06), SEQ ID NO: 45, 328, 47, 74, 350, and 117 (AM2-O-07), SEQ ID NO:45, 328, 47, 337, 350, and 117 (AM2-O-08), SEQ ID NO:45, 328, 47, 338, 350, and 117 (AM2-O-09), SEQ ID NO:45, 328, 47, 339, 350, and 117 (AM2-O-10), SEQ ID NO:45, 328, 47, 74, 343, and 117 (AM2-O-11), SEQ ID NO:45, 328, 47, 337, 343, and 117 (AM2-O-12), SEQ ID NO:45, 328, 47, 338, 343, and 117 (AM2-O-13), SEQ ID NO:45, 328, 47, 339, 343, and 117 (AM2-O-14), SEQ ID NO: 45, 46, 333, 74, 350, and 117 (AM2-O-15), SEQ ID NO:45, 46, 333, 337, 350, and 117 (AM2-O-16), SEQ ID NO:45, 46, 333, 338, 350, and 117 (AM2-O-17), SEQ ID NO:45, 46, 333, 339, 350, and 117 (AM2-O-18), SEQ ID NO:45, 46, 333, 74, 343, and 117 (AM2-O-19), SEQ ID NO:45, 46, 333, 337, 343, and 117 (AM2-O-20), SEQ ID NO:45, 46, 333, 338, 343, and 117 (AM2-O-21), SEQ ID NO:45, 46, 333, 339, 343, and 117

(AM2-O-22), SEQ ID NO: 45, 328, 333, 74, 350, and 117
(AM2-O-23), SEQ ID NO:45, 328, 333, 337, 350, and 117
(AM2-O-24), SEQ ID NO:45, 328, 333, 338, 350, and 117
(AM2-O-25), SEQ ID NO:45, 328, 333, 339, 350, and 117
(AM2-O-26), SEQ ID NO:45, 328, 333, 74, 343, and 117
(AM2-O-27), SEQ ID NO:45, 328, 333, 337, 343, and 117
(AM2-O-28), SEQ ID NO:45, 328, 333, 338, 343, and 117
(AM2-O-29), SEQ ID NO:45, 328, 333, 339, 343, and 117
(AM2-O-30), SEQ ID NO:45, 46, 335, 74, 350, and 117
(AM2-O-31), SEQ ID NO:45, 46, 335, 337, 350, and 117
(AM2-O-32), SEQ ID NO:45, 46, 335, 338, 350, and 117
(AM2-O-33), SEQ ID NO: 45, 46, 335, 339, 350, and 117
(AM2-O-34), SEQ ID NO:45, 46, 335, 74, 343, and 117
(AM2-O-35), SEQ ID NO:45, 46, 335, 337, 343, and 117
(AM2-O-36), SEQ ID NO:45, 46, 335, 338, 343, and 117

The present disclosure likewise provides antibodies and fragments thereof that specifically bind to a human interleukin-18 receptor alpha (IL-18Rα) protein. In some embodiments, the antibody or fragment thereof comprises a light chain variable region comprising light chain complementarity determining regions CDRL1, CDRL2, and CDRL3 and a heavy chain variable region comprising heavy chain complementarity determining regions CDRH1, CDRH2, and CDRH3, and wherein the CDRL3, CDRH1, CDRH2, and CDRH3, are selected from combinations 1-12 of Table C. The antibody or fragment disclosure herein can also include a CDRL1 and a CDRL2. A good variety of CDRL1 and CDRL2 sequences can be employed here. Non-limiting examples include QSVSSA (SEQ ID NO: 45) and SAS (SEQ ID NO:46), respectively, as well as their biological equivalents as illustrated in Table C1.

TABLE C

CDR sequences for anti-IL-18Rα antibodies

| Comb # | Fab ID | CDRL1 (SEQ ID NO:) | CDRL2 (SEQ ID NO:) | CDRL3 | (SEQ ID NO:) | CDRH1 | (SEQ ID NO:) | CDRH2 | (SEQ ID NO:) | CDRH3 | (SEQ ID NO:) |
|---|---|---|---|---|---|---|---|---|---|---|---|
| 1 | F1 | QSVSSA 45 | SAS 46 | QQYYSPFT | 137 | GFNIYYSSM | 83 | SISSYYGSTY | 150 | ARGAFDY | 156 |
| 2 | F2 | QSVSSA 45 | SAS 46 | QQYASPFT | 138 | GFNIYYSSI | 145 | SISSSYSSTS | 151 | ARGAFDY | 156 |
| 3 | F3 | QSVSSA 45 | SAS 46 | QQYASPFT | 138 | GFNIYYSSM | 83 | SISSSYGSTY | 152 | ARGAMDY | 157 |
| 4 | F4 | QSVSSA 45 | SAS 46 | QQYVPFT | 139 | GFNISSSSM | 146 | SISSSYGSTY | 152 | ARGAMDY | 157 |
| 5 | F6 | QSVSSA 45 | SAS 46 | QQYHPFT | 140 | GFNLSSSSI | 147 | SISSYYGSTY | 150 | ARGAMDY | 157 |
| 6 | F7 | QSVSSA 45 | SAS 46 | QQYASPFT | 138 | GFNIYYSSI | 145 | SISSSYSSTS | 151 | ARGAFDY | 156 |
| 7 | F8 | QSVSSA 45 | SAS 46 | QQYHPFT | 140 | GFNISSSSM | 146 | SISSYYGSTY | 150 | ARGAMDY | 157 |
| 8 | F9 | QSVSSA 45 | SAS 46 | QQYASPFT | 138 | GFNLSSSSI | 147 | SISSYYGSTY | 150 | ARGAMDY | 157 |
| 9 | F10 | QSVSSA 45 | SAS 46 | QQYFHPFT | 141 | GFNLSYSSM | 84 | SISSSYSSTY | 153 | ARGALDY | 158 |
| 10 | F11 | QSVSSA 45 | SAS 46 | QQGFFHPIT | 142 | GFNIYYSSM | 83 | SIYSYYGSTS | 154 | ARYYHGYWGSYSAGSSAWGFDY | 159 |
| 11 | F12 | QSVSSA 45 | SAS 46 | QQYWHPFT | 143 | GFNISSSSI | 148 | SISSSYSSTY | 153 | ARGAFDY | 156 |
| 12 | F13 | QSVSSA 45 | SAS 46 | QQAGYSIT | 144 | GFNFSSSSI | 149 | YISSYYGSTS | 155 | ARSVVYGYWYGGWVGFDY | 160 |

(AM2-O-37), SEQ ID NO:45, 46, 335, 339, 343, and 117
(AM2-O-38), SEQ ID NO:45, 328, 335, 74, 350, and 117
(AM2-O-39), SEQ ID NO:45, 328, 335, 337, 350, and 117
(AM2-O-40), SEQ ID NO:45, 328, 335, 338, 350, and 117
(AM2-O-41), SEQ ID NO: 45, 328, 335, 339, 350, and 117
(AM2-O-42), SEQ ID NO:45, 328, 335, 74, 343, and 117
(AM2-O-43), SEQ ID NO:45, 328, 335, 337, 343, and 117
(AM2-O-44), SEQ ID NO:45, 328, 335, 338, 343, and 117
(AM2-O-45), and SEQ ID NO:45, 328, 335, 339, 343, and 117 (AM2-O-46).

Non-limiting examples of such antibodies or fragments include those having the heavy chain variable region and light chain variable region of each of the variants in Table 8, as well as those having about at least 75%, 80%, 85%, 90%, 95%, 98%, or 99% sequence identity to each of the heavy chain variable region and light chain variable region of each of the variants in Table 8, while retaining the respective CDR sequences (see, e.g., Table 9).

It can be readily appreciated that certain modification (e.g., one, two, or three amino acid additions, deletions, conservative amino acid substitutions) to one or more of the CDR sequences can be made while retaining the binding activity of the antibody or fragment. In some embodiments, the modifications are amino acid substitution of one, two, or three residues.

In some embodiments, the modification is substitution at no more than one hot spot position from each of the CDRs. In some embodiments, the modification is substitution at one, two or three such hot spot positions. In one embodiment, the modification is substitution at one of the hot spot positions. Such substitutions, in some embodiments, are conservative substitutions.

Specific examples of CDRs (from CDR Combination #11 in Table C) with suitable substitutions are provided in the table below.

TABLE C1

Substitutions of CDR Residues

| CDR | No.* | Residue | Can be substituted with |
|---|---|---|---|
| CDRL1 | 27 | Q | N, D, E, S, T, Y, W, H, K, R |
|  | 28 | S | N, D, E, Q, T, Y, W, H, K, R |
|  | 29 | V | A, I, L, M, P, F |
|  | 36 | S | N, D, E, Q, T, Y, W, H, K, R |
|  | 37 | S | N, D, E, Q, T, Y, W, H, K, R |
|  | 38 | A | V, I, L, M, P, F |
| CDRL2 | 56 | S | N, D, E, Q, T, Y, W, H, K, R |
|  | 57 | A | V, I, L, M, P, F |
|  | 65 | S | N, D, E, Q, T, Y, W, H, K, R |
| CDRL3 | 105 | Q | N, D, E, S, T, Y, W, H, K, R |
|  | 106 | Q | N, D, E, S, T, Y, W, H, K, R |
|  | 107 | Y | N, D, E, S, T, Q, W, H, K, R, V, I, L, M, P, F, A |
|  | 108 | W | A, I, L, M, P, V, F |
|  | 114 | H | N, D, E, S, T, Y, W, Q, K, R |
|  | 115 | P | V, I, A, M, L, F |
|  | 116 | F | A, I, L, M, P, V |
|  | 117 | T | N, D, E, Q, S, Y, W, H, K, R |
| CDRH1 | 27 | G | N, D, E, S, T, Q, W, H, K, R, V, I, L, M, P, F, A, Y |
|  | 28 | F | A, I, L, M, P, V |
|  | 29 | N | Q, D, E, S, T, Y, W, H, K, R |
|  | 30 | I | V, L, A, M, P, F |
|  | 35 | S | N, D, E, Q, T, Y, W, H, K, R |
|  | 36 | S | N, D, E, Q, T, Y, W, H, K, R |
|  | 37 | S | N, D, E, Q, T, Y, W, H, K, R |
|  | 38 | S | N, D, E, Q, T, Y, W, H, K, R |
|  | 39 | I | V, L, A, M, P, F |
| CDRH2 | 55 | S | N, D, E, Q, T, Y, W, H, K, R |
|  | 56 | I | V, L, A, M, P, F |
|  | 57 | S | N, D, E, Q, T, Y, W, H, K, R |
|  | 58 | S | N, D, E, Q, T, Y, W, H, K, R |
|  | 59 | S | N, D, E, Q, T, Y, W, H, K, R |
|  | 62 | Y | N, D, E, S, T, Q, W, H, K, R, V, I, L, M, P, F, A |
|  | 63 | S | N, D, E, Q, T, Y, W, H, K, R |
|  | 64 | S | N, D, E, Q, T, Y, W, H, K, R |
|  | 65 | T | N, D, E, Q, S, Y, W, H, K, R |
|  | 66 | Y | N, D, E, S, T, Q, W, H, K, R, V, I, L, M, P, F, A |
| CDRH3 | 105 | A | V, I, L, M, P, F |
|  | 106 | R | N, D, E, Q, T, Y, W, H, K, S |
|  | 107 | G | N, D, E, S, T, Q, W, H, K, R, V, I, L, M, P, F, A, Y |
|  | 114 | A | V, I, L, M, P, F |
|  | 115 | F | A, I, L, M, P, V |
|  | 116 | D | N, Q, E, S, T, Y, W, H, K, R |
|  | 117 | Y | N, D, E, S, T, Q, W, H, K, R, V, I, L, M, P, F, A |

*IMGT numbering system

Specific example antibodies include those that have a heavy chain sequence of SEQ ID NO: 42, and/or a light chain sequence of SEQ ID NO:44, and their respective biological variants.

It will also be understood by one of ordinary skill in the art that antibodies as disclosed herein may be modified such that they vary in amino acid sequence from the naturally occurring binding polypeptide from which they were derived. For example, a polypeptide or amino acid sequence derived from a designated protein may be similar, e.g., have a certain percent identity to the starting sequence, e.g., it may be 60%, 70%, 75%, 80%, 85%, 90%, 95%, 98%, or 99% identical to the starting sequence.

In certain embodiments, the antibody comprises an amino acid sequence or one or more moieties not normally associated with an antibody. Exemplary modifications are described in more detail below. For example, an antibody of the disclosure may comprise a flexible linker sequence or may be modified to add a functional moiety (e.g., PEG, a drug, a toxin, or a label).

Antibodies, variants, or derivatives thereof of the disclosure include derivatives that are modified, i.e., by the covalent attachment of any type of molecule to the antibody such that covalent attachment does not prevent the antibody from binding to the epitope. For example, but not by way of limitation, the antibodies can be modified, e.g., by glycosylation, acetylation, pegylation, phosphorylation, phosphorylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the antibodies may contain one or more non-classical amino acids.

In some embodiments, the antibodies may be conjugated to therapeutic agents, prodrugs, peptides, proteins, enzymes, viruses, lipids, biological response modifiers, pharmaceutical agents, or PEG.

The antibodies may be conjugated or fused to a therapeutic agent, which may include detectable labels such as radioactive labels, an immunomodulator, a hormone, an enzyme, an oligonucleotide, a photoactive therapeutic or diagnostic agent, a cytotoxic agent, which may be a drug or a toxin, an ultrasound enhancing agent, a non-radioactive label, a combination thereof and other such agents known in the art.

The antibodies can be detectably labeled by coupling it to a chemiluminescent compound. The presence of the chemiluminescent-tagged antigen-binding polypeptide is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

The antibodies can also be detectably labeled using fluorescence emitting metals such as $^{152}$Eu, or others of the lanthanide series. These metals can be attached to the antibody using such metal chelating groups as diethylenetriaminepentacetic acid (DTPA) or ethylenediaminetetraacetic acid (EDTA). Techniques for conjugating various moieties to an antibody are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. (1985); Hellstrom et al., "Antibodies For Drug Delivery", in Controlled Drug Delivery (2nd Ed.), Robinson et al., (eds.), Marcel Dekker, Inc., pp. 623-53 (1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), Academic Press pp. 303-16 (1985), and Thorpe et al., "The Preparation And Cytotoxic Properties Of Antibody-Toxin Conjugates", *Immunol. Rev.* (52:119-58 (1982)).

Bi-Functional Molecules

IL-18 is a pro-inflammatory, IFN-γ-inducing cytokine. As a member of the IL-1 family of cytokines, it is thought to play a role in early inflammatory responses and is synthesized by a range of both hematopoietic and non-hematopoietic cells (e.g., macrophages, dendritic cells, Kuppfer cells, keratinocytes, osteoblasts, astrocytes, adrenal cortex cells, intestinal epithelial cells, microglial cells, and synovial fibroblasts) both constitutively and in response to lipopolysaccharide and other cytokines such as TNF-α. It is contemplated that bi-functional molecules that combine an anti-IL-18R alpha or beta antibody or fragment with another molecule or fragment that has specificity (second specificity) to a cytokine, an immune checkpoint, or a cancer antigen would have synergistic effect in treatments.

In some embodiments, the second specificity is to a molecule selected from IL-1, CD3, CD16, CD19, CD28, and CD64. Other examples include PD-1, CTLA-4, LAG-3 (also known as CD223), CD28, CD122, 4-1BB (also known as CD137), TIM3, OX-40 or OX40L, CD40 or CD40L, LIGHT, ICOS/ICOSL, GITR/GITRL, TIGIT, CD27, VISTA, B7H3, B7H4, HEVM or BTLA (also known as CD272), killer-cell immunoglobulin-like receptors (KIRs), and CD47.

As an immune checkpoint inhibitor, an antibody or antigen-binding fragment specific to IL-18 receptor can be combined with a second antigen-binding fragment specific to a tumor antigen to generate a bispecific antibody. A "tumor antigen" is an antigenic substance produced in tumor cells, i.e., it triggers an immune response in the host. Tumor antigens are useful in identifying tumor cells and are potential candidates for use in cancer therapy. Normal proteins in the body are not antigenic. Certain proteins, however, are produced or overexpressed during tumorigenesis and thus appear "foreign" to the body. This may include normal proteins that are well sequestered from the immune system, proteins that are normally produced in extremely small quantities, proteins that are normally produced only in certain stages of development, or proteins whose structure is modified due to mutation.

An abundance of tumor antigens are known in the art and new tumor antigens can be readily identified by screening. Non-limiting examples of tumor antigens include EGFR, Her2, EpCAM, CD20, CD30, CD33, CD47, CD52, CD133, CD73, CEA, gpA33, Mucins, TAG-72, CIX, PSMA, folate-binding protein, GD2, GD3, GM2, VEGF, VEGFR, Integrin, αVβ3, α5β1, ERBB2, ERBB3, MET, IGF1R, EPHA3, TRAILR1, TRAILR2, RANKL, FAP and Tenascin.

Different formats of bispecific antibodies are also provided. In some embodiments, each of the anti-IL-18 receptor fragment and the second fragment each is independently selected from a Fab fragment, a single-chain variable fragment (scFv), or a single-domain antibody. In some embodiments, the bispecific antibody further includes a Fc fragment.

Bifunctional molecules that include not just antibody or antigen binding fragment are also provided. As a tumor antigen-targeting molecule, an antibody or antigen-binding fragment specific to IL-18R alpha or beta, such as those described here, can be combined with an immune cytokine or ligand optionally through a peptide linker. The linked immune cytokines or ligands include, but not limited to, IL-1, IL-2, IL-3, IL-4, IL-5, IL-6, IL-7, IL-10, IL-12, IL-13, IL-15, GM-CSF, TNF-α, CD40L, OX40L, CD27L, CD30L, 4-1BBL, LIGHT and GITRL. Such bi-functional molecules can combine the immune checkpoint blocking effect with tumor site local immune modulation.

Polynucleotides Encoding the Antibodies and Methods of Preparing the Antibodies

The present disclosure also provides isolated polynucleotides or nucleic acid molecules (e.g., SEQ ID NO:41 and 43) encoding the antibodies, variants or derivatives thereof of the disclosure. The polynucleotides of the present disclosure may encode the entire heavy and light chain variable regions of the antigen-binding polypeptides, variants or derivatives thereof on the same polynucleotide molecule or on separate polynucleotide molecules. Additionally, the polynucleotides of the present disclosure may encode portions of the heavy and light chain variable regions of the antigen-binding polypeptides, variants or derivatives thereof on the same polynucleotide molecule or on separate polynucleotide molecules.

Methods of making antibodies are well known in the art and described herein. In certain embodiments, both the variable and constant regions of the antigen-binding polypeptides of the present disclosure are fully human. Fully human antibodies can be made using techniques described in the art and as described herein. For example, fully human antibodies against a specific antigen can be prepared by administering the antigen to a transgenic animal which has been modified to produce such antibodies in response to antigenic challenge, but whose endogenous loci have been disabled. Exemplary techniques that can be used to make such antibodies are described in U.S. Pat. Nos. 6,150,584; 6,458,592; 6,420,140 which are incorporated by reference in their entireties.

Autoimmune and Inflammatory Diseases

As provided, IL-18 has been shown to be upregulated or to be a risk factor for the development of various autoimmune and inflammatory diseases, such as Crohn's disease, rheumatoid arthritis, systemic lupus erythrites, and cardiovascular disease.

Further, increased IL-18 levels have been observed in individuals at risk of developing either Type I (T1D) or Type 2 diabetes (T2D). Elevated IL-18 has also been observed in the serum, urine and islets of juvenile and adult T1D and T2D patients, correlating with the severity of disease, and the development of sequelae such as diabetic nephropathy. Moreover, studies on Alzheimer's patients have revealed expression of IL-18 is increased in the brain and is thought to contribute to immune and inflammatory processes that enhance oxidative stress and alter the expression of proteins that contribute to AB formation.

In one embodiment, therefore, provided are methods of using the antibodies and fragments thereof for treating autoimmune and inflammatory diseases. Non-limiting examples include Parkinson's disease, arthritis, rheumatoid arthritis, multiple sclerosis, psoriasis, psoriatic arthritis, Crohn's disease, inflammatory bowel disease, ulcerative colitis, lupus, systemic lupus erythematous, juvenile rheumatoid arthritis, juvenile idiopathic arthritis, Grave's disease, Hashimoto's thyroiditis, Addison's disease, celiac disease, dermatomyositis, multiple sclerosis, myasthenia gravis, pernicious anemia, Sjogren syndrome, type I diabetes, type II diabetes, vasculitis, uveitis, sepsis, atherosclerosis and ankylosing spondylitis.

Cancer Treatment

As described above, high IL-18 levels have been observed in numerous cancers either at the tumor site or systemically. Such cancers include breast, esophageal, gastrointestinal, lung, hepatic, and ovarian cancers. It is believed that administration of the presently described antibodies can be useful for treating or inhibit cancer, and studies in pre-clinical models of cancer suggest that anti-tumor activity of IL-18 arises from its ability to potentiate effector cells such as T cells and NK cells.

Accordingly, in some embodiments, provided are methods for treating a cancer in a patient in need thereof. The method, in one embodiment, entails administering to the patient an effective amount of an antibody of the present disclosure. In some embodiments, at least one of the cancer cells (e.g., stromal cells) in the patient expresses, overexpress, or is induced to express IL-18 or one of its receptors.

Cancers that can be suitably treated include bladder cancer, non-small cell lung cancer, renal cancer, breast cancer, urethral cancer, colorectal cancer, head and neck cancer, squamous cell cancer, Merkel cell carcinoma, gastrointestinal cancer, stomach cancer, oesophageal cancer, ovarian cancer, renal cancer, and small cell lung cancer. Accordingly, the presently disclosed antibodies can be used for treating any one or more such cancers. In some embodiments, the cancer is selected from breast, esophageal, gastrointestinal, lung, hepatic, and ovarian cancers.

Cellular therapies, such as chimeric antigen receptor (CAR) T-cell therapies, are also provided in the present disclosure. A suitable cell can be used, that is put in contact with an anti-IL-18R alpha or beta antibody of the present disclosure. Upon such contact or engineering, the cell can then be introduced to a cancer patient in need of a treatment. The cancer patient may have a cancer of any of the types as disclosed herein. The cell (e.g., T cell) can be, for instance, a tumor-infiltrating T lymphocyte, a CD4+ T cell, a CD8+ T cell, or the combination thereof, without limitation.

In some embodiments, the cell was isolated from the cancer patient him- or her-self. In some embodiments, the cell was provided by a donor or from a cell bank. When the cell is isolated from the cancer patient, undesired immune reactions can be minimized.

Additional diseases or conditions associated with increased cell survival, that may be treated, prevented, diagnosed and/or prognosed with the antibodies or variants, or derivatives thereof of the disclosure include, but are not limited to, progression, and/or metastases of malignancies and related disorders such as leukemia (including acute leukemias (e.g., acute lymphocytic leukemia, acute myelocytic leukemia (including myeloblastic, promyelocytic, myelomonocytic, monocytic, and erythroleukemia)) and chronic leukemias (e.g., chronic myelocytic (granulocytic) leukemia and chronic lymphocytic leukemia)), polycythemia vera, lymphomas (e.g., Hodgkin's disease and non-Hodgkin's disease), multiple myeloma, Waldenstrom's macroglobulinemia, heavy chain disease, and solid tumors including, but not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyo sarcoma, colon carcinoma, pancreatic cancer, breast cancer, thyroid cancer, endometrial cancer, melanoma, prostate cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma and retinoblastoma.

Combination Therapies

In a further embodiment, the compositions of the disclosure are administered in combination with an antineoplastic agent, an antiviral agent, antibacterial or antibiotic agent or antifungal agents. Any of these agents known in the art may be administered in the compositions of the current disclosure. Such combinations can be useful for treating various cancers.

In another embodiment, compositions of the disclosure are administered in combination with a chemotherapeutic agent. Chemotherapeutic agents that may be administered with the compositions of the disclosure include, but are not limited to, antibiotic derivatives (e.g., doxorubicin, bleomycin, daunorubicin, and dactinomycin); antiestrogens (e.g., tamoxifen); antimetabolites (e.g., fluorouracil, 5-FU, methotrexate, floxuridine, interferon alpha-2b, glutamic acid, plicamycin, mercaptopurine, and 6-thioguanine); cytotoxic agents (e.g., carmustine, BCNU, lomustine, CCNU, cytosine arabinoside, cyclophosphamide, estramustine, hydroxyurea, procarbazine, mitomycin, busulfan, cis-platin, and vincristine sulfate); hormones (e.g., medroxyprogesterone, estramustine phosphate sodium, ethinyl estradiol, estradiol, megestrol acetate, methyltestosterone, diethylstilbestrol diphosphate, chlorotrianisene, and testolactone); nitrogen mustard derivatives (e.g., mephalen, chorambucil, mechlorethamine (nitrogen mustard) and thiotepa); steroids and combinations (e.g., bethamethasone sodium phosphate); and others (e.g., dicarbazine, asparaginase, mitotane, vincristine sulfate, vinblastine sulfate, and etoposide).

In an additional embodiment, the compositions of the disclosure are administered in combination with cytokines. Cytokines that may be administered with the compositions of the disclosure include, but are not limited to, IL-1, IL-2, IL-3, IL-4, IL-5, IL-6, IL-7, IL-10, IL-12, IL-13, IL-15, anti-CD40, CD40L, and TNF-α.

In additional embodiments, the compositions of the disclosure are administered in combination with other therapeutic or prophylactic regimens, such as, for example, radiation therapy.

Diagnostic Methods

Over-expression of IL-18 or its receptors is observed in certain tumor samples, and such patients are likely responsive to treatments with the anti-IL-18 receptor antibodies of the present disclosure. Accordingly, the antibodies of the present disclosure can also be used for diagnostic and prognostic purposes.

A sample that preferably includes a cell can be obtained from a patient, which can be a cancer patient or a patient desiring diagnosis. The cell be a cell of a tumor tissue or a tumor block, a blood sample, a urine sample or any sample from the patient. Upon optional pre-treatment of the sample, the sample can be incubated with an antibody of the present disclosure under conditions allowing the antibody to interact with an IL-18 receptor protein potentially present in the sample. Methods such as ELISA can be used, taking advantage of the anti-IL-18 receptor antibody, to detect the presence of the IL-18 receptor protein in the sample.

Presence of the IL-18 receptor protein in the sample (optionally with the amount or concentration) can be used for diagnosis of cancer, as an indication that the patient is suitable for a treatment with the antibody, or as an indication that the patient has (or has not) responded to a cancer treatment. For a prognostic method, the detection can be done at once, twice or more, at certain stages, upon initiation of a cancer treatment to indicate the progress of the treatment.

Compositions

The present disclosure also provides pharmaceutical compositions. Such compositions comprise an effective amount of an antibody, and an acceptable carrier. In some embodiments, the composition further includes a second anticancer agent (e.g., an immune checkpoint inhibitor).

In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. Further, a "pharmaceutically acceptable carrier" will generally be a non-toxic solid, semisolid or liquid filler, diluent, encapsulating material or formulation auxiliary of any type.

The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents such as acetates, citrates or phosphates. Antibacterial agents such as benzyl alcohol or methyl parabens; antioxidants such as ascorbic acid or sodium bisulfite; chelating agents such as ethylenediaminetetraacetic acid; and agents for the adjustment of tonicity such as sodium chloride or dextrose are also envisioned. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in Remington's Pharmaceutical Sciences by E. W. Martin, incorporated herein by reference. Such compositions will contain a therapeutically effective amount of the antigen-binding polypeptide, preferably in purified form, together with a suitable amount of carrier so as to provide the form for proper administration to the patient. The formulation should suit the mode of administration. The parental preparation can be enclosed in ampoules, disposable syringes or multiple dose vials made of glass or plastic.

In an embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compounds of the disclosure can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

EXAMPLES

Example 1: Selection, Characterization and Optimization of Il-18R Alpha and Beta Antibodies By panning against purified, Fc-tagged versions of either the human IL-18Rα or Rβ receptors (R&D) in vitro, this example isolated high affinity antibody binders to each receptor. Specifically, receptor-binding Fab-phage clones to each were sequenced, converted to IgG and evaluated for apparent affinity, cell binding and ability to inhibit functional IL-18 signaling.

Selections against the human IL-18Rα ECD Fc fusion (816-LR-100; R&D Systems) yielded 12 unique receptor-binding Fab sequences (Table 1), whereas selections against the IL-18Rβ ECD Fc fusion (118-AP-100, R&D Systems) yielded 21 unique sequences (Table 2). The CDR-encoding regions of Fab-phage clones were sub-cloned into expression constructs for expression and purification of Fab protein.

TABLE 1

CDRs in IL-18Rα-binding Fab sequences

| Fab ID | CDRL3 | | | | | | | | | | | | CDRH1 | | | | | | | | |
|---|---|---|---|---|---|---|---|---|---|---|---|---|---|---|---|---|---|---|---|---|---|
| | 105 | 106 | 107 | 108 | 109 | 110 | 112 | 113 | 114 | 115 | 116 | 117 | 27 | 28 | 29 | 30 | 35 | 36 | 37 | 38 | 39 |
| F1 | Q | Q | Y | Y | . | . | . | . | S | P | F | T | G | F | N | I | Y | Y | S | S | M |
| F2 | Q | Q | Y | A | . | . | . | . | S | P | F | T | G | F | N | I | Y | Y | S | S | I |
| F3 | Q | Q | Y | A | . | . | . | . | S | P | F | T | G | F | N | I | Y | Y | S | S | M |
| F4 | Q | Q | Y | Y | . | . | . | . | V | P | F | T | G | F | N | I | S | S | S | S | M |
| F6 | Q | Q | Y | Y | . | . | . | . | H | P | F | T | G | F | N | L | S | S | S | S | I |
| F7 | Q | Q | Y | A | . | . | . | . | S | P | F | T | G | F | N | I | Y | Y | S | S | I |
| F8 | Q | Q | Y | Y | . | . | . | . | H | P | F | T | G | F | N | I | S | S | S | S | M |
| F8 | Q | Q | Y | A | . | . | . | . | S | P | F | T | G | F | N | L | S | S | S | S | I |
| F10 | Q | Q | Y | F | . | . | . | . | H | P | F | T | G | F | N | L | S | Y | S | S | M |
| F11 | Q | Q | G | F | F | . | . | . | H | P | I | T | G | F | N | I | Y | Y | S | S | M |
| F12 | Q | Q | Y | W | . | . | . | . | H | P | F | T | G | F | N | I | S | S | S | S | I |
| F13 | Q | Q | A | G | . | . | . | . | Y | S | I | T | G | F | N | F | S | S | S | S | I |

| Fab ID | CDRH2 | | | | | | | | | | CDRH3 | | | | | | | | | |
|---|---|---|---|---|---|---|---|---|---|---|---|---|---|---|---|---|---|---|---|---|
| | 55 | 56 | 57 | 58 | 59 | 62 | 63 | 64 | 65 | 66 | 105 | 106 | 107 | 108 | 109 | 110 | 111 | 111.1 | 111.2 | 111.3 | 111.4 |
| F1 | S | I | S | S | Y | Y | G | S | T | Y | A | R | G | . | . | . | . | . | . | . | . |
| F2 | S | I | S | P | S | Y | S | S | T | S | A | R | G | . | . | . | . | . | . | . | . |
| F3 | S | I | S | P | S | Y | G | S | T | Y | A | R | G | . | . | . | . | . | . | . | . |
| F4 | S | I | S | P | S | Y | G | S | T | Y | A | R | G | . | . | . | . | . | . | . | . |
| F6 | S | I | S | P | Y | Y | G | S | T | Y | A | R | G | . | . | . | . | . | . | . | . |
| F7 | S | I | S | P | S | Y | S | S | T | S | A | R | G | . | . | . | . | . | . | . | . |
| F8 | S | I | S | P | Y | Y | G | S | T | Y | A | R | G | . | . | . | . | . | . | . | . |
| F8 | S | I | S | P | Y | Y | G | S | T | Y | A | R | G | . | . | . | . | . | . | . | . |
| F10 | S | I | S | P | S | Y | S | S | T | Y | A | R | G | . | . | . | . | . | . | . | . |
| F11 | S | I | Y | S | Y | Y | G | S | T | S | A | R | Y | Y | H | G | Y | W | G | S | Y |
| F12 | S | I | S | P | S | Y | S | S | T | Y | A | R | G | . | . | . | . | . | . | . | . |
| F13 | Y | I | S | S | Y | Y | G | S | T | S | A | R | G | V | V | Y | G | Y | W | . | . |

| Fab ID | CDRH3 | | | | | | | | | |
|---|---|---|---|---|---|---|---|---|---|---|
| | 112.5 | 112.4 | 112.3 | 112.2 | 112.1 | 112 | 113 | 114 | 115 | 116 | 117 |
| F1 | . | . | . | . | . | . | . | A | F | D | Y |
| F2 | . | . | . | . | . | . | . | A | F | D | Y |
| F3 | . | . | . | . | . | . | . | A | M | D | Y |
| F4 | . | . | . | . | . | . | . | A | M | D | Y |
| F6 | . | . | . | . | . | . | . | A | M | D | Y |
| F7 | . | . | . | . | . | . | . | A | F | D | Y |
| F8 | . | . | . | . | . | . | . | A | M | D | Y |
| F8 | . | . | . | . | . | . | . | A | M | D | Y |
| F10 | . | . | . | . | . | . | . | G | L | D | Y |

TABLE 1-continued

CDRs in IL-18Rα-binding Fab sequences

| | | | | | | | | | | |
|---|---|---|---|---|---|---|---|---|---|---|
| F11 | S | A | G | S | S | A | W | G | F | D | Y |
| F12 | . | . | . | . | . | . | . | A | F | D | Y |
| F13 | . | . | Y | G | G | W | V | G | F | D | Y |

TABLE 2

CDRs in IL-18Rβ-binding Fab sequences

| Fab ID | CDRL3 | | | | | | | | | | | | CDRH1 | | | | | | | |
|---|---|---|---|---|---|---|---|---|---|---|---|---|---|---|---|---|---|---|---|---|
| | 105 | 106 | 107 | 108 | 109 | 110 | 112 | 113 | 114 | 115 | 116 | 117 | 27 | 28 | 29 | 30 | 35 | 36 | 37 | 38 | 39 |
| F3131 | Q | Q | Y | G | Y | H | Y | A | G | L | I | T | G | F | N | L | Y | Y | S | S | M |
| F3132 | Q | Q | H | W | W | A | S | V | P | P | F | T | G | F | N | I | S | Y | Y | Y | I |
| F3133 | Q | Q | H | Y | W | . | . | G | Y | L | I | T | G | F | N | L | S | Y | Y | S | I |
| F3134 | Q | Q | H | H | W | . | . | S | Y | P | I | T | G | F | N | I | Y | S | Y | S | I |
| F3135 | Q | Q | H | H | H | . | W | A | V | L | I | T | G | F | N | F | Y | S | Y | S | M |
| F3136 | Q | Q | H | Y | W | . | . | G | G | P | I | T | G | F | N | I | S | S | Y | S | M |
| F3137 | Q | Q | S | W | G | . | W | S | W | L | I | T | G | F | N | L | S | S | Y | S | I |
| F3138 | Q | Q | H | S | F | . | H | S | G | L | I | T | G | F | N | L | Y | S | Y | S | M |
| F3139 | Q | Q | S | H | G | W | W | G | F | P | F | T | G | F | N | I | S | S | Y | S | I |
| F3140 | Q | Q | Y | Y | W | . | A | S | Y | P | F | T | G | F | N | F | Y | S | Y | S | M |
| F3141 | Q | Q | Y | Y | Y | . | S | A | A | L | I | T | G | F | N | I | Y | Y | S | S | M |
| F3142 | Q | Q | W | W | G | G | P | Y | V | L | I | T | G | F | N | L | S | Y | S | S | M |
| F3143 | Q | Q | Y | H | W | G | S | Y | Y | P | F | T | G | F | N | L | S | S | Y | Y | M |
| F3144 | Q | Q | H | W | W | . | G | Y | P | L | I | T | G | F | N | L | S | Y | Y | S | I |
| F3145 | Q | Q | H | Y | Y | G | S | F | P | P | I | T | G | F | N | F | Y | S | Y | S | M |
| F3147 | Q | Q | H | W | W | . | . | A | A | L | I | T | G | F | N | L | S | Y | Y | S | I |
| F3148 | Q | Q | H | Y | Y | . | . | S | S | L | I | T | G | F | N | I | Y | S | Y | S | M |
| F3150 | Q | Q | H | S | W | . | . | A | V | P | I | T | G | F | N | L | S | Y | Y | S | M |
| F3152 | Q | Q | H | S | Y | . | S | A | P | L | I | T | G | F | N | I | Y | S | Y | S | M |
| FA3 | Q | Q | S | Y | . | . | . | . | F | L | I | T | G | F | N | L | Y | S | S | Y | I |
| FE60 | Q | Q | Y | P | S | A | S | H | Y | L | I | T | G | F | N | L | Y | Y | Y | Y | M |
| 3131 AM1-1 | Q | Q | Y | A | Y | H | E | P | G | L | L | T | G | F | N | P | Y | Y | S | S | I |
| 3131-AM1-2 | Q | Q | W | G | Y | R | Y | A | P | L | V | T | G | F | N | F | Y | Y | S | S | I |
| 3144-AM1-3 | Q | Q | H | S | W | A | . | Y | P | M | I | T | G | F | N | L | T | W | W | S | I |
| 3144-AM1-4 | Q | Q | H | W | F | G | . | Y | P | A | V | T | G | F | N | I | S | Q | Y | T | I |
| 3144-AM1-5 | Q | Q | H | W | W | G | . | Y | P | M | I | T | G | F | N | I | S | Y | Y | T | I |
| 3144-AM1-6 | Q | Q | H | S | W | R | . | Y | P | L | I | T | G | F | N | L | S | S | Y | S | I |

TABLE 2-continued

CDRs in IL-18Rβ-binding Fab sequences

| Fab | CDRH2 | | | | | | | | | | CDRH3 | | | | | | | | | | |
|---|---|---|---|---|---|---|---|---|---|---|---|---|---|---|---|---|---|---|---|---|---|
| ID | 55 | 56 | 57 | 58 | 59 | 62 | 63 | 64 | 65 | 66 | 105 | 106 | 107 | 108 | 109 | 110 | 111 | 111.1 | 111.2 | 112.3 | 112.2 |
| F3131 | S | I | Y | S | S | Y | G | Y | T | Y | A | R | S | S | F | S | H | G | . | . | Y |
| F3132 | S | I | Y | S | Y | S | G | Y | T | S | A | R | A | S | . | . | . | . | . | . | . |
| F3133 | S | I | Y | S | S | Y | G | Y | T | S | A | R | S | Y | . | . | . | . | . | . | . |
| F3134 | S | I | Y | P | S | Y | G | Y | T | S | A | R | S | F | . | . | . | . | . | . | . |
| F3135 | Y | I | Y | P | Y | S | G | Y | T | S | A | R | S | F | . | . | . | . | . | . | . |
| F3136 | S | I | Y | S | Y | Y | S | Y | T | S | A | R | S | Y | . | . | . | . | . | . | . |
| F3137 | Y | I | Y | P | S | Y | G | S | T | Y | A | R | S | Y | . | . | . | . | . | . | . |
| F3138 | Y | I | Y | S | Y | S | G | Y | T | S | A | R | G | F | . | . | . | . | . | . | . |
| F3139 | S | I | Y | P | Y | Y | G | Y | T | Y | A | R | S | W | . | . | . | . | . | . | . |
| F3140 | S | I | Y | P | S | Y | G | Y | T | S | A | R | S | F | . | . | . | . | . | . | . |
| F3141 | Y | I | Y | P | Y | S | G | Y | T | S | A | R | Y | F | . | . | . | . | . | . | . |
| F3142 | S | I | Y | P | S | S | S | S | T | Y | A | R | S | S | H | B | H | G | . | . | Y |
| F3143 | S | I | Y | P | Y | Y | G | Y | T | Y | A | R | S | S | . | . | . | . | . | . | . |
| F3144 | S | I | Y | S | Y | S | G | Y | T | S | A | R | S | S | . | . | . | . | . | . | . |
| F3145 | S | I | Y | S | Y | Y | G | Y | T | S | A | R | S | F | . | . | . | . | . | . | . |
| F3147 | Y | I | Y | S | S | Y | G | Y | T | S | A | R | S | F | . | . | . | . | . | . | . |
| F3148 | S | I | Y | P | Y | Y | S | S | T | Y | A | R | S | S | . | . | . | . | . | . | . |
| F3150 | S | I | Y | P | Y | Y | G | Y | T | S | A | R | S | S | . | . | . | . | . | . | . |
| F3152 | S | I | Y | P | S | Y | S | Y | T | S | A | R | S | Y | . | . | . | . | . | . | . |
| FA3 | S | I | Y | S | S | S | G | Y | T | Y | A | R | S | V | H | S | Y | Y | S | S | A |
| FE60 | S | I | Y | S | Y | Y | G | Y | T | S | A | R | S | Y | P | S | S | . | . | S | W |
| 3131 AM1-1 | S | I | S | P | S | Y | S | S | T | Y | A | R | S | S | C | S | H | S | . | . | C |
| 3131-AM1-2 | S | I | S | S | A | T | G | N | T | S | A | R | S | S | Y | S | H | G | . | . | H |
| 3144-AM1-3 | T | I | F | S | G | F | S | Y | T | S | A | R | S | S | . | . | . | . | . | . | . |
| 3144-AM1-4 | S | I | Y | A | R | S | R | F | T | S | A | R | S | S | . | . | . | . | . | . | . |
| 3144-AM1-5 | S | I | Y | S | Y | S | L | Y | T | S | A | R | S | S | . | . | . | . | . | . | . |
| 3144-AM1-6 | A | I | Y | A | G | F | G | S | T | T | A | R | S | S | . | . | . | . | . | . | . |

| Fab | CDRH3 | | | | | | |
|---|---|---|---|---|---|---|---|
| ID | 112.1 | 112 | 113 | 114 | 115 | 116 | 117 |
| F3131 | G | W | Y | G | L | D | Y |
| F3132 | . | . | . | A | M | D | Y |
| F3133 | . | . | . | G | L | D | Y |
| F3134 | . | . | . | G | L | D | Y |
| F3135 | . | . | . | A | M | D | Y |

TABLE 2-continued

CDRs in IL-18Rβ-binding Fab sequences

| Name | | | | | | | |
|---|---|---|---|---|---|---|---|
| F3136 | . | . | . | A | M | D | Y |
| F3137 | . | . | . | A | L | D | Y |
| F3138 | . | . | . | A | L | D | Y |
| F3139 | . | . | . | A | M | D | Y |
| F3140 | . | . | . | G | F | D | Y |
| F3141 | . | . | . | A | M | D | Y |
| F3142 | Y | F | Y | G | I | D | Y |
| F3143 | . | . | . | A | M | D | Y |
| F3144 | . | . | . | A | M | D | Y |
| F3145 | . | . | . | G | M | D | Y |
| F3147 | . | . | . | G | M | D | Y |
| F3148 | . | . | . | A | M | D | Y |
| F3150 | . | . | . | A | F | D | Y |
| F3152 | . | . | . | A | M | D | Y |
| FA3 | A | Y | Y | A | M | D | Y |
| FE60 | G | S | V | A | L | D | Y |
| 3131_AM1-1 | R | F | Y | G | L | D | Y |
| 3131-AM1-2 | S | W | Y | G | L | D | Y |
| 3144-AM1-3 | . | . | . | A | M | D | Y |
| 3144-AM1-4 | . | . | . | R | M | D | Y |
| 3144-AM1-5 | . | . | . | A | M | D | Y |
| 3144-AM1-6 | . | . | . | A | M | D | Y |

The amino acid and nucleotide sequences of representative Fab fragments are provided in Tables 3 and 4 below.

TABLE 3

IL-18Rα-binding Fab sequences

| Name (SEQ ID NO:) | Sequence |
|---|---|
| Fab 12 Heavy chain nucleotide sequence (SEQ ID NO: 41) | GAGGTTCAGCTGGTGGAGTCTGGCGGTGGCCTGGTGCAGCCAGGGGGCTCACTCCGTTTG TCCTGTGCAGCTTCTGGCTTCAACATCTCTTCTTCTTCTATCCACTGGGTGCGTCAGGCC CCGGGTAAGGGCCTGGAATGGGTTGCATCTATTTCTCCTTCTTATAGCTCTACTTATTAT GCCGATAGCGTCAAGGGCCGTTTCACTATAAGCGCAGACACATCCAAAAACACAGCCTAC CTACAAATGAACAGCTTAAGAGCTGAGGACACTGCCGTCTATTATTGTGCTCGCGGTGCT TTTGACTACTGGGGTCAAGGAACCCTGGTCACCGTCTCCTCGGCCTCCACCAAGGGTCCA TCGGTCTTCCCCCTGGCACCCTCCTCCAAGAGCACCTCTGGGGGCACAGCGGCCCTGGGC TGCCTGGTCAAGGACTACTTCCCCGAACCGGTGACGGTGTCGTGGAACTCAGGCGCCCTG ACCAGCGGCGTGCACACCTTCCCGGCTGTCCTACAGTCCTCAGGACTCTACTCCCTCAGC AGCGTGGTGACCGTGCCCTCCAGCAGCTTGGGCACCCAGACCTACATCTGCAACGTGAAT CACAAGCCCAGCAACACCAAGGTCGACAAGAAAGTTGAGCCCAAATCTTGTGACAAAACT CACACATAA |
| Fab 12 Heavy chain amino acid sequence (SEQ ID NO: 42) | EVQLVESGGGLVQPGGSLRLSCAASGFNISSSSIHWVRQAPGKGLEWVASISPSYSSTYY ADSVKGRFTISADTSKNTAYLQMNSERAEDTAVYYCARGAFDYWGQGTLVTVSSASTKGP SVFPLAPSSKSTSGGTAALGCLVKDYFPEPVTVSWNSGALTSGVHTFPAVLQSSGLYSLS SVVTVPSSSLGTQTYICNVNHKPSNTKVDKKVEPKSCDKTHT |
| Fab 12 Light chain nucleotide sequence (SEQ ID NO: 43) | GATATCCAGATGACCCAGTCCCCGAGCTCCCTGTCCGCCTCTGTGGGCGATAGGGTCACC ATCACCTGCCGTGCCAGTCAGTCCGTGTCCAGCGCTGTAGCCTGGTATCAACAGAAACCA GGAAAAGCTCCGAAGCTTCTGATTTACTCGGCATCCAGCCTCTACTCTGGAGTCCCTTCT CGCTTCTCTGGTAGCCGTTCCGGGACGGATTTCACTCTGACCATCAGCAGTCTGCAGCCG |

TABLE 3-continued

IL-18Rα-binding Fab sequences

| Name (SEQ ID NO:) | Sequence |
|---|---|
| | GAAGACTTCGCAACTTATTACTGTCAGCAATACTGGCATCCGTTCACGTTCGGACAGGGT<br>ACCAAGGTGGAGATCAAACGAACTGTGGCTGCACCATCTGTCTTCATCTTCCCGCCATCT<br>GATTCACAGTTGAAATCTGGAACTGCCTCTGTTGTGTGCCTGCTGAATAACTTCTATCCC<br>AGAGAGGCCAAAGTACAGTGGAAGGTGGATAACGCCCTCCAATCGGGTAACTCCCAGGAG<br>AGTGTCACAGAGCAGGACAGCAAGGACAGCACCTACAGCCTCAGCAGCACCCTGACGCTG<br>AGCAAAGCAGACTACGAAAAACATAAAGTCTACGCCTGCGAAGTCACCCATCAGGGCCTG<br>AGCTCGCCCGTCACAAAGAGCTTCAACAGGGGAGAGTGTGGTGGTTCTGATTACAAAGAT<br>GACGATGACAAATAA |
| Fab 12 Light chain<br>amino acid sequence<br>(SEQ ID NO: 44) | DIQMTQSPSSLSASVGDRVTITCRASQSVSSAVAWYQQKPGKAPKLLIYSASSLYSGVPS<br>RFSGSRSGIDFILTISSLQPEDFATYYCQQYWHPFTEGQGTKVEIKRTVAAPSVFIFPPS<br>DSQLKSGTASVVCLLNNFYPREAKVQWKVDNALQSGNSQESVTEQDSKDSTYSLSSTLTL<br>SKADYEKHKVYACEVTHQGLSSPVIKSENRGECGGSDYKDDDDK |

TABLE 4

IL-18Rβ-binding Fab sequences

| Name (SEQ ID NO:) | Sequence |
|---|---|
| Fab 3131 Heavy chain<br>nucleotide sequence<br>(SEQ ID NO: 1) | GAGGTTCAGCTGGTGGAGTCTGGCGGTGGCCTGGTGCAGCCAGGGGGCTCACTCCGTTTG<br>TCCTGTGCAGCTTCTGGCTTCAACCTCTATTATTCTTCTATGCACTGGGTGCGTCAGGCC<br>CCGGGTAAGGGCCTGGAATGGGTTGCATCTATTTATTCTTATGGCTATACTTATTAT<br>GCCGATAGCGTCAAGGGCCGTTTCACTATAAGCGCAGACACATCCAAAAACACAGCCTAC<br>CTACAAATGAACAGCTTAAGAGCTGAGGACACTGCCGTCTATTATTGTGCTCGCTCTTCT<br>TTCTCTCATGGTTACGGTTGGTACGGTTTGGACTACTGGGGTCAAGGAACCCTGGTCACC<br>GTCTCCTCGGCCTCCACCAAGGGTCCATCGGTCTTCCCCCTGGCACCCTCCTCCAAGAGC<br>ACCTCTGGGGGCACAGCGGCCCTGGGCTGCCTGGTCAAGGACTACTTCCCCGAACCGGTG<br>ACGGTGTCGTGGAACTCAGGCGCCCTGACCAGCGGCGTGCACACCTTCCCGGCTGTCCTA<br>CAGTCCTCAGGACTCTACTCCCTCAGCAGCGTGGTGACCGTGCCCTCCAGCAGCTTGGGC<br>ACCCAGACCTACATCTGCAACGTGAATCACAAGCCCAGCAACACCAAGGTCGACAAGAAA<br>GTTGAGCCCAAATCTTGTGACAAAACTCACACATAA |
| Fab 3131 Heavy chain<br>amino acid sequence<br>(SEQ ID NO: 2) | EVQLVESGGGLVQPGGSLRLSCAASGENLYYSSMHWVRQAPGKGLEWVASIYSYGYTYY<br>ADSVKGRFTISADISKNTAYLQMNSLRAEDTAVYYCARSSFSHGYGWYGLDYWGQGTLVT<br>VSSASTKGPSVFPLAPSSKSTSGGTAALGCLVKDYFPEPVTVSWNSGALTSGVHTFPAVL<br>QSSGLYSLSSVVTVPSSSLGTQTYICNVNHKPSNTKVDKKVEPKSCDKTHT |
| Fab 3131 Light chain<br>nucleotide sequence<br>(SEQ ID NO: 3) | GATATCCAGATGACCCAGTCCCCGAGCTCCCTGTCCGCCTCTGTGGGCGATAGGGTCACC<br>ATCACCTGCCGTGCCAGTCAGTCCGTGTCCAGCGCTGTAGCCTGGTATCAACAGAAACCA<br>GGAAAAGCTCCGAAGCTTCTGATTTACTCGGCATCCAGCCTCTACTCTGGAGTCCCTTCT<br>CGCTTCTCTGGTAGCCGTTCCGGGACGGATTTCACTCTGACCATCAGCAGTCTGCAGCCG<br>GAAGACTTCGCAACTTATTACTGTCAGCAATACGGTTACCATTACGCTGGTCTGATCACG<br>TTCGGACAGGGTACCAAGGTGGAGATCAAACGAACTGTGGCTGCACCATCTGTCTTCATC<br>TTCCCCCCATCTGATTCACAGTTGAAATCTGGAACTGCCTCTGTTGTGTGCCTGCTGAAT<br>AACTTCTATCCCAGAGAGGCCAAAGTACAGTGGAAGGTGGATAACGCCCTCCAATCGGGT<br>AACTCCCAGGAGAGTGTCACAGAGCAGGACAGCAAGGACAGCACCTACAGCCTCAGCAGC<br>ACCCTGACGCTGAGCAAAGCAGACTACGAAAAACATAAAGTCTACGCCTGCGAAGTCACC<br>CATCAGGGCCTGAGCTCGCCCGTCACAAAGAGCTTCAACAGGGGAGAGTGTGGTGGTTCT<br>GATTACAAAGATGACGATGACAAATAA |
| Fab 3131 Light chain<br>amino acid sequence<br>(SEQ ID NO: 4) | DIQMTQSPSSLSASVGDRVTITCRASQSVSSAVAWYQQKPGKAPKLLIYSASSLYSGVPS<br>RFSGSRSGIDFILTISSLQPEDFATYYCQQYGYHYAGLITFGQGTKVEIKRIVAAPSVFI<br>FPPSDSQLKSGTASVVCLLNNFYPREAKVQWKVDNALQSGNSQESVTEQDSKDSTYSLSS<br>ILTLSKADYEKHKVYACEVTHQGLSSPVTKSENRGECGGSDYKDDDDK |
| Fab 3132 Heavy chain<br>nucleotide sequence<br>(SEQ ID NO: 5) | GAGGTTCAGCTGGTGGAGTCTGGCGGTGGCCTGGTGCAGCCAGGGGGCTCACTCCGTTTG<br>TCCTGTGCAGCTTCTGGCTTCAACATCTCTTATTATTATATCCACTGGGTGCGTCAGGCC<br>CCGGGTAAGGGCCTGGAATGGGTTGCATCTATTTATTCTTATTCGGCTATACTTCTTAT<br>GCCGATAGCGTCAAGGGCCGTTTCACTATAAGCGCAGACACATCCAAAAACACAGCCTAC<br>CTACAAATGAACAGCTTAAGAGCTGAGGACACTGCCGTCTATTATTGTGCTCGCGCTTCT<br>GCTATGGACTACTGGGGTCAAGGAACCCTGGTCACCGTCTCCTCGGCCTCCACCAAGGGT<br>CCATCGGTCTTCCCCCTGGCACCCTCCTCCAAGAGCACCTCTGGGGGCACAGCGGCCCTG<br>GGCTGCCTGGTCAAGGACTACTTCCCCGAACCGGTGACGGTGTCGTGGAACTCAGGCGCC<br>CTGACCAGCGGCGTGCACACCTTCCCGGCTGTCCTACAGTCCTCAGGACTCTACTCCCTC<br>AGCAGCGTGGTGACCGTGCCCTCCAGCAGCTTGGGCACCCAGACCTACATCTGCAACGTG<br>AATCACAAGCCCAGCAACACCAAGGTCGACAAGAAAGTTGAGCCCAAATCTTGTGACAAA<br>ACTCACACATAA |
| Fab 3132 Heavy chain<br>amino acid sequence<br>(SEQ ID NO: 6) | EVQLVESGGGLVQPGGSLRLSCAASGENISYYYIHWVRQAPGKGLEWVASIYSYGYTSY<br>ADSVKGRFTISADTSKNTAYLQMNSLRAEDTAVYYCARASAMDYWGQGTLVTVSSASTKG<br>PSVFPLAPSSKSTSGGTAALGCLVKDYFPEPVTVSWNSGALISGVHTFPAVLQSSGLYSL<br>SSVVTVPSSSLGTQTYICNVNHKPSNTKVDKKVEPKSCDKTHT |

TABLE 4-continued

IL-18Rβ-binding Fab sequences

| Name (SEQ ID NO:) | Sequence |
|---|---|
| Fab 3132 Light chain nucleotide sequence (SEQ ID NO: 7) | GATATCCAGATGACCCAGTCCCCGAGCTCCCTGTCCGCCTCTGTGGGCGATAGGGTCACC ATCACCTGCCGTGCCAGTCAGTCCGTGTCCAGCGCTGTAGCCTGGTATCAACAGAAACCA GGAAAAGCTCCGAAGCTTCTGATTTACTCGGCATCCAGCCTCTACTCTGGAGTCCCTTCT CGCTTCTCTGGTAGCCGTTCCGGGACGGATTTCACTCTGACCATCAGCAGTCTGCAGCCG GAAGACTTCGCAACTTATTACTGTCAGCAACATTGGTGGGCTTCTGTTCCGCCGTTCACG TTCGGACAGGGTACCAAGGTGGAGATCAAACGAACTGTGGCTGCACCATCTGTCTTCATC TTCCCGCCATCTGATTCACAGTTGAAATCTGGAACTGCCTCTGTTGTGTGCCTGCTGAAT AACTTCTATCCCAGAGAGGCCAAAGTACAGTGGAAGGTGGATAACGCCCTCCAATCGGGT AACTCCCAGGAGAGTGTCACAGAGCAGGACAGCAAGGACAGCACCTACAGCCTCAGCAGC ACCCTGACGCTGAGCAAAGCAGACTACGAAAAACATAAAGTCTACGCCTGCGAAGTCACC CATCAGGGCCTGAGCTCGCCCGTCACAAAGAGCTTCAACAGGGGAGAGTGTGGTGGTTCT GATTACAAAGATGACGATGACAAATAA |
| Fab 3132 Light chain amino acid sequence (SEQ ID NO: 8) | DIQMTQSPSSLSASVGDRVTITCRASQSVSSAVAWYQQKPGKAPKLLIYSASSLYSGVPS RFSGSRSGTDFILTISSLQPEDFATYYCQQHWWASVPPFTFGQGTKVEIKRIVAAPSVFI FPPSDSQLKSGTASVVCLLNNFYPREAKVQWKVDNALQSGNSQESVTEQDSKDSTYSLSS TLTLSKADYEKHKVYACEVTHQGLSSPVIKSENRGECGGSDYKDDDDK |
| Fab 3144 Heavy chain nucleotide sequence (SEQ ID NO: 9) | GAGGTTCAGCTGGTGGAGTCTGGCGGTGGCCTGGTGCAGCCAGGGGGCTCACTCCGTTTG TCCTGTGCAGCTTCTGGCTTCAACCTCTCTTATTATTCTATCCACTGGGTGCGTCAGGCC CCGGGTAAGGGCCTGGAATGGGTTGCATCTATTTATTCTTATTCTGGCTATACTTCTTAT GCCGATAGCGTCAAGGGCCGTTTCACTATAAGCGCAGACACATCCAAAAACACAGCCTAC CTACAAATGAACAGCTTAAGAGCTGAGGACACTGCCGTCTATTATTGTGCTCGCTCTTCT GCTATGGACTACTGGGGTCAAGGAACCCTGGTCACCGTCTCCTCGGCCTCCACCAAGGGT CCATCGGTCTTCCCCCTGGCACCCTCCTCCAAGAGCACCTCTGGGGGCACAGGGCCCTG GCTGCCTGGTCAAGGACTACTTCCCCGAACCGGTGACGGTGTCGTGGAACTCAGGCGCC CTGACCAGCGGCGTGCACACCTTCCCGGCTGTCCTACAGTCCTCAGGACTCTACTCCCTC AGCAGCGTGGTGACCGTGCCCTCCAGCAGCTTGGGCACCCAGACCTACATCTGCAACGTG AATCACAAGCCCAGCAACACCAAGGTCGACAAGAAAGTTGAGCCCAAATCTTGTGACAAA ACTCACACATAA |
| Fab 3144 Heavy chain amino acid sequence (SEQ ID NO: 10) | EVQLVESGGGLVQPGGSLRLSCAASGENLSYYSIHWVRQAPGKGLEWVASIYSYSGYTSY ADSVKGRFTISADISKNTAYLQMNSLRAEDTAVYYCARSSAMDYWGQGTLVTVSSASTKG PSVFPLAPSSKSTSGGTAALGCLVKDYFPEPVTVSWNSGALISGVHTFPAVLQSSGLYSL SSVVTVPSSSLGTQTYICNVNHKPSNTKVDKKVEPKSCDKTHT |
| Fab 3144 Light chain nucleotide sequence (SEQ ID NO: 11) | GATATCCAGATGACCCAGTCCCCGAGCTCCCTGTCCGCCTCTGTGGGCGATAGGGTCACC ATCACCTGCCGTGCCAGTCAGTCCGTGTCCAGCGCTGTAGCCTGGTATCAACAGAAACCA GGAAAAGCTCCGAAGCTTCTGATTTACTCGGCATCCAGCCTCTACTCTGGAGTCCCTTCT CGCTTCTCTGGTAGCCGTTCCGGGACGGATTTCACTCTGACCATCAGCAGTCTGCAGCCG GAAGACTTCGCAACTTATTACTGTCAGCAACATTGGTGGGGTTACCCGCTGATCACGTTC GGACAGGGTACCAAGGTGGAGATCAAACGAACTGTGGCTGCACCATCTGTCTTCATCTTC CCGCCATCTGATTCACAGTTGAAATCTGGAACTGCCTCTGTTGTGTGCCTGCTGAATAAC TTCTATCCCAGAGAGGCCAAAGTACAGTGGAAGGTGGATAACGCCCTCCAATCGGGTAAC TCCCAGGAGAGTGTCACAGAGCAGGACACCAAGGACAGCACCTACAGCCTCAGCAGCACC CTGACGCTGAGCAAAGCAGACTACGAAAAACATAAAGTCTACGCCTGCGAAGTCACCCAT CAGGGCCTGAGCTCGCCCGTCACAAAGAGCTTCAACAGGGGAGAGTGTGGTGGTTCTGAT TACAAAGATGACGATGACAAATAA |
| Fab 3144 Light chain amino acid sequence (SEQ ID NO: 12) | DIQMTQSPSSLSASVGDRVTITCRASQSVSSAVAWYQQKPGKAPKLLIYSASSLYSGVPS RFSGSRSGIDFILTISSLQPEDFATYYCQQHWWGYPLITEGQGTKVEIKRTVAAPSVFIF PPSDSQLKSGTASVVCLLNNFYPREAKVQWKVDNALQSGNSQESVTEQDSKDSTYSLSST TLTLSKADYEKHKVYACEVTHQGLSSPVTKSFNRGECGGSDYKDDDDK |
| Fab A3 Heavy chain nucleotide sequence (SEQ ID NO: 13) | GAGGTTCAGCTGGTGGAGTCTGGCGGTGGCCTGGTGCAGCCAGGGGGCTCACTCCGTTTG TCCTGTGCAGCTTCTGGCTTCAACCTCTATTCTTCTTATATCCACTGGGTGCGTCAGGCC CCGGGTAAGGGCCTGGAATGGGTTGCATCTATTTATTCTTCTGGCTATACTTATTAT GCCGATAGCGTCAAGGGCCGTTTCACTATAAGCGCAGACACATCCAAAAACACAGCCTAC CTACAAATGAACAGCTTAAGAGCTGAGGACACTGCCGTCTATTATTGTGCTCGCTCTGTT CATTCTTACTACTCTTCTGCTGCTTACTACGCTATGGACTACTGGGGTCAAGGAACCCTG GTCACCGTCTCCTCGGCCTCCACCAAGGGTCCATCGGTCTTCCCCCTGGCACCCTCCTCC AAGAGCACCTCTGGGGGCACAGCGGCCCTGGGCTGCCTGGTCAAGGACTACTTCCCCGAA CCGGTGACGGTGTCGTGGAACTCAGGCGCCCTGACCAGCGGCGTGCACACCTTCCCGGCT GTCCTACAGTCCTCAGGACTCTACTCCCTCAGCAGCGTGGTGACCGTGCCCTCCAGCAGC TTGGGCACCCAGACCTACATCTGCAACGTGAATCACAAGCCCAGCAACACCAAGGTCGAC AAGAAAGTTGAGCCCAAATCTTGTGACAAAACTCACACATAA |
| Fab A3 Heavy chain amino acid sequence (SEQ ID NO: 14) | EVQLVESGGGLVQPGGSLRLSCAASGENLSYYIHWVRQAPGKGLEWVASIYSSSGYTYY ADSVKGRFTISADTSKNTAYLQMNSLRAEDTAVYYCARSVHSYYSSAAYYAMDYWGQGTL VTVSSASTKGPSVFPLAPSSKSTSGGTAALGCLVKDYFPEPVTVSWNSGALTSGVHTFPA VLQSSGLYSLSSVVTVPSSSLGTQTYICNVNHKPSNTKVDKKVEPKSCDKTHT |
| Fab A3 Light chain nucleotide sequence (SEQ ID NO: 15) | GATATCCAGATGACCCAGTCCCCGAGCTCCCTGTCCGCCTCTGTGGGCGATAGGGTCACC ATCACCTGCCGTGCCAGTCAGTCCGTGTCCAGCGCTGTAGCCTGGTATCAACAGAAACCA GGAAAAGCTCCGAAGCTTCTGATTTACTCGGCATCCAGCCTCTACTCTGGAGTCCCTTCT |

TABLE 4-continued

IL-18Rβ-binding Fab sequences

| Name (SEQ ID NO:) | Sequence |
| --- | --- |
| | CGCTTCTCTGGTAGCCGTTCCGGGACGGATTTCACTCTGACCATCAGCAGTCTGCAGCCG<br>GAAGACTTCGCAACTTATTACTGTCAGCAATCTTACTTCCTGATCACGTTCGGACAGGGT<br>ACCAAGGTGGAGATCAAACGAACTGTGGCTGCACCATCTGTCTTCATCTTCCCGCCATCT<br>GATTCACAGTTGAAATCTGGAACTGCCTCTGTTGTGTGCCTGCTGAATAACTTCTATCCC<br>AGAGAGGCCAAAGTACAGTGGAAGGTGGATAACGCCCTCCAATCGGGTAACTCCCAGGAG<br>AGTGTCACAGAGCAGGACAGCAAGGACAGCACCTACAGCCTCAGCAGCACCCTGACGCTG<br>AGCAAAGCAGACTACGAAAAACATAAAGTCTACGCCTGCGAAGTCACCCATCAGGGCCTG<br>AGCTCGCCCGTCACAAAGAGCTTCAACAGGGGAGAGTGTGGTGGTTCTGATTACAAAGAT<br>GACGATGACAAATAA |
| Fab A3 Light chain<br>amino acid sequence<br>(SEQ ID NO: 16) | DIQMTQSPSSLSASVGDRVTITCRASQSVSSAVAWYQQKPGKAPKLLIYSASSLYSGVPS<br>RFSGSRSGTDFTLTISSLQPEDFATYYCQQSYFLITFGQGTKVEIKRTVAAPSVFIFPPS<br>DSQLKSGTASVVCLLNNFYPREAKVQWKVDNALQSGNSQESVTEQDSKDSTYSLSSTLTL<br>SKADYEKHKVYACEVTHQGLSSPVTKSFNRGECGGSDYKDDDDK |
| Fab AM1-1 Heavy<br>chain nucleotide<br>sequence (SEQ ID<br>NO: 17) | GAGGTTCAGCTGGTGGAGTCTGGCGGTGGCCTGGTGCAGCCAGGGGGCTCACTCCGTTTG<br>TCCTGTGCAGCTTCTGGCTTCAACCCCTATTATTCTTCCATTCACTGGGTGCGTCAGGCC<br>CCGGGTAAGGGCCTGGAATGGGTTGCATCTATTTCTCCTTCTTATAGCTCTACTTATTAT<br>GCCGATAGCGTCAAGGGCCGTTTCACTATAAGCGCAGACACATCCAAAAACACAGCCTAC<br>CTACAAATGAACAGCTTAAGAGCTGAGGACACTGCCGTCTATTATTGTGCTCGCTCTTCT<br>TGCTCTCATAGTTGCCGTTTTTACGGTTTGGACTACTGGGGTCAAGGAACCCTGGTCACC<br>GTCTCCTCGGCCTCCACCAAGGGTCCATCGGTCTTCCCCCTGGCACCCTCCTCCAAGAGC<br>ACCTCTGGGGGCACAGCGGCCCTGGGCTGCCTGGTCAAGGACTACTTCCCCGAACCGGTG<br>ACGGTGTCGTGGAACTCAGGCGCCCTGACCAGCGGCGTGCACACCTTCCCGGCTGTCCTA<br>CAGTCCTCAGGACTCTACTCCCTCAGCAGCGTGGTGACCGTGCCCTCCAGCAGCTTGGGC<br>ACCCAGACCTACATCTGCAACGTGAATCACAAGCCCAGCAACACCAAGGTCGACAAGAAA<br>GTTGAGCCCAAATCTTGTGACAAAACTCACACATAA |
| Fab AM1-1 Heavy<br>chain amino acid<br>sequence (SEQ ID<br>NO: 18) | EVQLVESGGGLVQPGGSLRLSCAASGFNPYYSSIHWVRQAPGKGLEWVASISPSYSSTYY<br>ADSVKGRFTISADTSKNIAYLQMNSLRAEDTAVYYCARSSCSHSCRFYGLDYWGQGTLVT<br>VSSASTKGPSVFPLAPSSKSTSGGTAALGCLVKDYFPEPVTVSWNSGALTSGVHTFPAVL<br>QSSGLYSLSSVVTVPSSSLGTQTYICNVNHKPSNIKVDKKVEPKSCDKTHT |
| Fab AM1-1 Light<br>chain nucleotide<br>sequence (SEQ ID<br>NO: 19) | GATATCCAGATGACCCAGTCCCCGAGCTCCCTGTCCGCCTCTGTGGGCGATAGGGTCACC<br>ATCACCTGCCGTGCCAGTCAGTCCGTGTCCAGCGCTGTAGCCTGGTATCAACAGAAACCA<br>GGAAAAGCTCCGAAGCTTCTGATTTACTCGGCATCCAGCCTCTACTCTGGAGTCCCTTCT<br>CGCTTCTCTGGTAGCCGTTCCGGGACGGATTTCACTCTGACCATCAGCAGTCTGCAGCCG<br>GAAGACTTCGCAACTTATTACTGTCAGCAATACGCTTACATGAGCCCGGTTTGCTCTCT<br>TCTTATTCTCTGATCACGTTCGGACAGGGTACCAAGGTGGAGATCAAACGAACTGTGGCT<br>GCACCATCTGTCTTCATCTTCCCGCCATCTGATTCACAGTTGAAATCTGGAACTGCCTCT<br>GTTGTGTGCCTGCTGAATAACTTCTATCCCAGAGAGGCCAAAGTACAGTGGAAGGTGGAT<br>AACGCCCTCCAATCGGGTAACTCCCAGGAGAGTGTCACAGAGCAGGACAGCAAGGACAGC<br>ACCTACAGCCTCAGCAGCACCCTGACGCTGAGCAAAGCAGACTACGAAAAACATAAAGTC<br>TACGCCTGCGAAGTCACCCATCAGGGCCTGAGCTCGCCCGTCACAAAGAGCTTCAACAGG<br>GGAGAGTGTGGTGGTTCTGATTACAAAGATGACGATGACAAATAA |
| Fab AM1-1 Light<br>chain amino acid<br>sequence (SEQ ID<br>NO: 20) | DIQMTQSPSSLSASVGDRVTITCRASQSVSSAVAWYQQKPGKAPKLLIYSASSLYSGVPS<br>RESGSRSGTDFTLTISSLQPEDFATYYCQQYAYHEPLLTFGQGIKVEIKRTVAAPSVFI<br>FPPSDSQLKSGTASVVCLLNNFYPREAKVQWKVDNALQSGNSQESVTEQDSKDSTYSLSS<br>TLILSKADYEKHKVYACEVTHQGLSSPVTKSFNRGECGGSDYKDDDDK |
| Fab AM1-2 Heavy<br>chain nucleotide<br>sequence (SEQ ID<br>NO: 21) | GAGGTTCAGCTGGTGGAGTCTGGCGGTGGCCTGGTGCAGCCAGGGGGCTCACTCCGTTTG<br>TCCTGTGCAGCTTCTGGCTTCAACTTCTATTATTCTTCGATTCACTGGGTGCGTCAGGCC<br>CCGGGTAAGGGCCTGGAATGGGTTGCATCTTCGATTTCTTCGGCTACTGGAAATACTTCT<br>TATGCCGATAGCGTCAAGGGCCGTTTCACTATAAGCGCAGACACATCCAAAAACACAGCC<br>TACCTACAAATGAACAGCTTAAGAGCTGAGGACACTGCCGTCTATTATTGTGCTCGCTCT<br>TCTTACTCTCATGGTCATAGTTGGTACGGTTTGGACTACTGGGGTCAAGGAACCCTGGTC<br>ACCGTCTCCTCGGCCTCCACCAAGGGTCCATCGGTCTTCCCCCTGGCACCCTCCTCCAAG<br>AGCACCTCTGGGGGCACAGCGGCCCTGGGCTGCCTGGTCAAGGACTACTTCCCCGAACCG<br>GTGACGGTGTCGTGGAACTCAGGCGCCCTGACCAGCGGCGTGCACACCTTCCCGGCTGTC<br>CTACAGTCCTCAGGACTCTACTCCCTCAGCAGCGTGGTGACCGTGCCCTCCAGCAGCTTG<br>GGCACCCAGACCTACATCTGCAACGTGAATCACAAGCCCAGCAACACCAAGGTCGACAAG<br>AAAGTTGAGCCCAAATCTTGTGACAAAACTCACACATAA |
| Fab AM1-2 Heavy<br>chain amino acid<br>sequence (SEQ ID<br>NO: 22) | EVQLVESGGGLVQPGGSLRLSCAASGFNFYYSSIHWVRQAPGKGLEWVASSISSATGNTS<br>YADSVKGRFTISADISKNTAYLQMNSLRAEDTAVYYCARSSYSHGHSWYGLDYWGQGTLV<br>TVSSASTKGPSVFPLAPSSKSTSGGTAALGCLVKDYFPEPVTVSWNSGALTSGVHTEPAV<br>LQSSGLYSLSSVVTVPSSSLGTQTYICNVNHKPSNTKVDKKVEPKSCDKTHT |
| Fab AM1-2 Light<br>chain nucleotide<br>sequence (SEQ ID<br>NO: 23) | GATATCCAGATGACCCAGTCCCCGAGCTCCCTGTCCGCCTCTGTGGGCGATAGGGTCACC<br>ATCACCTGCCGTGCCAGTCAGTCCGTGTCCAGCGCTGTAGCCTGGTATCAACAGAAACCA<br>GGAAAAGCTCCGAAGCTTCTGATTTACTCGGCATCCAGCCTCTACTCTGGAGTCCCTTCT<br>CGCTTCTCTGGTAGCCGTTCCGGGACGGATTTCACTCTGACCATCAGCAGTCTGCAGCCG<br>GAAGACTTCGCAACTTATTACTGTCAGCAATGGGTTACCGGTACGCACCCCTGGTCACG<br>TTCGGACAGGGTACCAAGGTGGAGATCAAACGAACTGTGGCTGCACCATCTGTCTTCATC<br>TTCCCGCCATCTGATTCACAGTTGAAATCTGGAACTGCCTCTGTTGTGTGCCTGCTGAAT |

TABLE 4-continued

IL-18Rβ-binding Fab sequences

| Name (SEQ ID NO:) | Sequence |
|---|---|
| | AACTTCTATCCCAGAGAGGCCAAAGTACAGTGGAAGGTGGATAACGCCCTCCAATCGGGT<br>AACTCCCAGGAGAGTGTCACAGAGCAGGACAGCAAGGACAGCACCTACAGCCTCAGCAGC<br>ACCCTGACGCTGAGCAAAGCAGACTACGAAAAACATAAAGTCTACGCCTGCGAAGTCACC<br>CATCAGGGCCTGAGCTCGCCCGTCACAAAGAGCTTCAACAGGGGAGAGTGTGGTGGTTCT<br>GATTACAAAGATGACGATGACAAATAA |
| Fab AM1-2 Light chain amino acid sequence (SEQ ID NO: 24) | DIQMTQSPSSLSASVGDRVTITCRASQSVSSAVAWYQQRPGKAPKLLIYSASSLYSGVPS<br>RFSGSRSGTDFTLTISSLQPEDFATYYCQQWGYRYAPLVIFGQGTKVEIKRIVAAPSVFI<br>FPPSDSQLKSGTASVVCLLNNFYPREAKVQWKVDNALQSGNSQESVTEQDSKDSTYSLSS<br>TLILSKADYEKHKVYACEVTHQGLSSPVIKSENRGECGGSDYKDDDDK |
| Fab AM1-3 Heavy chain nucleotide sequence (SEQ ID NO: 25) | GAGGTTCAGCTGGTGGAGTCTGGCGGTGGCCTGGTGCAGCCAGGGGGCTCACTCCGTTTG<br>TCCTGTGCAGCTTCTGGCTTCAACCTCACTTGGTGGTCTATCCTCCACTTGGGTGGTCTA<br>TCCACTGGGTGCGTCAGGCCCCGGGTAAGGGCCTGGAATGGGTTGCATCTACTATTTTTT<br>CTGGTTTTTCCTATACTTCTTATGCCGATAGCGTCAAGGGCCGTTTCACTATAAGCGCAG<br>ACACATCCAAAAACACAGCCTACCTACAAATGAACAGCTTAAGAGCTGAGGACACTGCCG<br>TCTATTATTGTGCTCGCTCTTCTGCTATGGACTACTGGGGTCAAGGAACCCTGGTCACCG<br>TCTCCTCGGCCTCCACCAAGGGTCCATCGGTCTTCCCCCTGGCACCCTCCTCCAAGAGCA<br>CCTCTGGGGGCACAGCGGCCCTGGGCTGCCTGGTCAAGGACTACTTCCCCGAACCGGTGA<br>CGGTGTCGTGGAACTCAGGCGCCCTGACCAGCGGCGTGCACACCTTCCCGGCTGTCCTAC<br>AGTCCTCAGGACTCTACTCCCTCAGCAGCGTTGGTGACCGTGCCCTCCAGCAGCTTGGGCA<br>CCCAGACCTACATCTGCAACGTGAATCACAAGCCCAGCAACACCAAGGTCGACAAGAAAG<br>TTGAGCCCAAATCTTGTGACAAAACTCACACATAA |
| Fab AM1-3 Heavy chain amino acid sequence (SEQ ID NO: 26) | EVQLVESGGGLVQPGGSLRLSCAASGENLTWWSIHWVRQAPGKGLEWVASTIFSGESYTS<br>YADSVKGRFTISADISKNTAYLQMNSLRAEDTAVYYCARSSAMDYWGQGTLVTVSSASTK<br>GPSVFPLAPSSKSTSGGTAALGCLVKDYFPEPVTVSWNSGALTSGVHIFPAVLQSSGLYS<br>LSSVVTVPSSSLGTQTYICNVNHKPSNTKVDKKVEPKSCDKIHT |
| Fab AM1-3 Light chain nucleotide sequence (SEQ ID NO: 27) | GATATCCAGATGACCCAGTCCCCGAGCTCCCTGTCCGCCTCTGTGGGCGATAGGGTCACC<br>ATCACCTGCCGTGCCAGTCAGTCCGTGTCCAGCGCTGTAGCCTGGTATCAACAGAAACCA<br>GGAAAAGCTCCGAAGCTTCTGATTTACTCGGCATCCAGCCTCTACTCTGGAGTCCCTTCT<br>CGCTTCTCTGGTAGCCGTTCCGGGACGGATTTCACTCTGACCATCAGCAGTCTGCAGCCG<br>GAAGACTTCGCAACTTATTACTGTCAGCAACATTCATGGGCATACCCGATGATAACGTTC<br>GGACAGGGTACCAAGGTGGAGATCAAACGAACTGTGGCTGCACCATCTGTCTTCATCTTC<br>CCGCCATCTGATTCACAGTTGAAATCTGGAACTGCCTCTGTTGTGTGCCTGCTGAATAAC<br>TTCTATCCCAGAGAGGCCAAAGTACAGTGGAAGGTGGATAACGCCCTCCAATCGGGTAAC<br>TCCCAGGAGAGTGTCACAGAGCAGGACAGCAAGGACAGCACCTACAGCCTCAGCAGCACC<br>CTGACGCTGAGCAAAGCAGACTACGAAAAACATAAAGTCTACGCCTGCGAAGTCACCCAT<br>CAGGGCCTGAGCTCGCCCGTCACAAAGAGCTTCAACAGGGGAGAGTGTGGTGGTTCTGAT<br>TACAAAGATGACGATGACAAATAA |
| Fab AM1-3 Light chain amino acid sequence (SEQ ID NO: 28) | DIQMTQSPSSLSASVGDRVTITCRASQSVSSAVAWYQQKPGKAPKLLIYSASSLYSGVPS<br>RESGSRSGIDFILTISSLQPEDFATYYCQQHSWAYPMITFGQGTKVEIKRTVAAPSVFIF<br>PPSDSQLKSGTASVVCLLNNFYPREAKVQWKVDNALQSGNSQESVTEQDSKDSTYSLSST<br>LTLSKADYEKHKVYACEVTHQGLSSPVTKSENRGECGGSDYKDDDDK |
| Fab AM1-4 Heavy chain nucleotide sequence (SEQ ID NO: 29) | GAGGTTCAGCTGGTGGAGTCTGGCGGTGGCCTGGTGCAGCCAGGGGGCTCACTCCGTTTG<br>TCCTGTGCAGCTTCTGGCTTCAACATCTCTCAGTATACTATCCACTGGGTGCGTCAGGCC<br>CCGGGTAAGGGCCTGGAATGGGTTGCATCTATTTATGCTCGTTCTAGGTTTACTTCTTAT<br>GCCGATAGCGTCAAGGGCCGTTTCACTATAAGCGCAGACACATCCAAAAACACAGCCTAC<br>CTACAAATGAACAGCTTAAGAGCTGAGGACACTGCCGTCTATTATTGTGCTCGCTCTTCT<br>CGTATGGACTACTGGGGTCAAGGAACCCTGGTCACCGTCTCCTCGGCCTCCACCAAGGGT<br>CCATCGGTCTTCCCCCTGGCACCCTCCTCCAAGAGCACCTCTGGGGGCACAGCGGCCCTG<br>GGCTGCCTGGTCAAGGACTACTTCCCCGAACCGGTGACGGTGTCGTGGAACTCAGGCGCC<br>CTGACCAGCGGCGTGCACACCTTCCCGGCTGTCCTACAGTCCTCAGGACTCTACTCCCTC<br>AGCAGCGTGGTGACCGTGCCCTCCAGCAGCTTGGGCACCCAGACCTACATCTGCAACGTG<br>AATCACAAGCCCAGCAACACCAAGGTCGACAAGAAAGTTGAGCCCAAATCTTGTGACAAA<br>ACTCACACATAA |
| Fab AM1-4 Heavy chain amino acid sequence (SEQ ID NO: 30) | EVQLVESGGGLVQPGGSLRLSCAASGENISQYTIHWVRQAPGKGLEWVASIYARSRFTSY<br>ADSVKGRFTISADTSKNIAYLQMNSLRAEDTAVYYCARSSRMDYWGQGILVTVSSASTKG<br>PSVFPLAPSSKSTSGGTAALGCLVKDYFPEPVTVSWNSGALTSGVHTFPAVLQSSGLYSL<br>SSVVTVPSSSLGTQTYICNVNHKPSNTKVDKKVEPKSCDKTHT |
| Fab AM1-4 Light chain nucleotide sequence (SEQ ID NO: 31) | GATATCCAGATGACCCAGTCCCCGAGCTCCCTGTCCGCCTCTGTGGGCGATAGGGTCACC<br>ATCACCTGCCGTGCCAGTCAGTCCGTGTCCAGCGCTGTAGCCTGGTATCAACAGAAACCA<br>GGAAAAGCTCCGAAGCTTCTGATTTACTCGGCATCCAGCCTCTACTCTGGAGTCCCTTCT<br>CGCTTCTCTGGTAGCCGTTCCGGGACGGATTTCACTCTGACCATCAGCAGTCTGCAGCCG<br>GAAGACTTCGCAACTTATTACTGTCAGCAACATTGGTTTGGATACCCAGCGGTATCTTCT<br>TATTCTCTGATCACGTTCGGACAGGGTACCAAGGTGGAGATCAAACGAACTGTGGCTGCA<br>CCATCTGTCTTCATCTTCCCGCCATCTGATTCACAGTTGAAATCTGGAACTGCCTCTGTT<br>GTGTGCCTGCTGAATAACTTCTATCCCAGAGAGGCCAAAGTACAGTGGAAGGTGGATAAC<br>GCCCTCCAATCGGGTAACTCCCAGGAGAGTGTCACAGAGCAGGACAGCAAGGACAGCACC |

TABLE 4-continued

IL-18Rβ-binding Fab sequences

| Name (SEQ ID NO:) | Sequence |
|---|---|
| | TACAGCCTCAGCAGCACCCTGACGCTGAGCAAAGCAGACTACGAAAAACATAAAGTCTAC<br>GCCTGCGAAGTCACCCATCAGGGCCTGAGCTCGCCCGTCACAAAGAGCTTCAACAGGGGA<br>GAGTGTGGTGGTTCTGATTACAAAGATGACGATGACAAATAA |
| Fab AM1-4 Light chain amino acid sequence (SEQ ID NO: 32) | DIQMTQSPSSLSASVGDRVTITCRASQSVSSAVAWYQQKPGKAPKLLIYSASSLYSGVPS<br>RFSGSRSGIDFILTISSLQPEDFATYYCQQHWEGYPAVTEGQGTKVEIKRTVAAPSVEIF<br>PPSDSQLKSGTASVVCLLNNFYPREAKVQWKVDNALQSGNSQESVTEQDSKDSTYSLSST<br>LTLSKADYEKHKVYACEVTHQGLSSPVTKSFNRGECGGSDYKDDDDK |
| Fab AM1-5 Heavy chain nucleotide sequence (SEQ ID NO: 33) | GAGGTTCAGCTGGTGGAGTCTGGCGGTGGCCTGGTGCAGCCAGGGGGCTCACTCCGTTTG<br>TCCTGTGCAGCTTCTGGCTTCAACATCTCTTATTATACTATCCACTGGGTGCGTCAGGCC<br>CCGGGTAAGGGCCTGGAATGGGTTGCATCCTCTATTTATTCTTATTCTCTCTATACTTCT<br>TATGCCGATAGCGTCAAGGGCCGTTTCACTATAAGCGCAGACACATCCAAAAACACAGCC<br>TACCTACAAATGAACAGCTTAAGAGCTGAGGACACTGCCGTCTATTATTGTGCTCGCTCT<br>TCTGCTATGGACTACTGGGGTCAAGGAACCCTGGTCACCGTCTCCTCGGCCTCCACCAAG<br>GGTCCATCGGTCTTCCCCCTGGCACCCTCCTCCAAGAGCACCTCTGGGGGCACAGCGGCC<br>CTGGGCTGCCTGGTCAAGGACTACTTCCCCGAACCGGTGACGGTGTCGTGGAACTCAGGC<br>GCCCTGACCAGCGGCGTGCACACCTTCCCGGCTGTCCTACAGTCCTCAGGACTCTACTCC<br>CTCAGCAGCGTGGTGACCGTGCCCTCCAGCAGCTTGGGCACCCAGACCTACATCTGCAAC<br>GTGAATCACAAGCCCAGCAACACCAAGGTCGACAAGAAAGTTGAGCCCAAATCTTGTGAC<br>AAAACTCACACATAA |
| Fab AM1-5 Heavy chain amino acid sequence (SEQ ID NO: 34) | EVQLVESGGGLVQPGGSLRLSCAASGFNISYYTIHWVRQAPGKGLEWVASSIYSYSLYTS<br>YADSVKGRFTISADTSKNTAYLQMNSLRAEDTAVYYCARSSAMDYWGQGTLVTVSSASTK<br>GPSVFPLAPSSKSTSGGTAALGCLVKDYFPEPVTVSWNSGALTSGVHTFPAVLQSSGLYS<br>LSSVVTVPSSSLGTQTYICNVNHKPSNTKVDKKVERKSCDKTHT |
| Fab AM1-5 Light chain nucleotide sequence (SEQ ID NO: 35) | GATATCCAGATGACCCAGTCCCCGAGCTCCCTGTCCGCCTCTGTGGGCGATAGGGTCACC<br>ATCACCTGCCGTGCCAGTCAGTCCGTGTCCAGCGCTGTAGCCTGGTATCAACAGAAACCA<br>GGAAAAGCTCCGAAGCTTCTGATTTACTCGGCATCCAGCCTCTACTCTGGAGTCCCTTCT<br>CGCTTCTCTGGTAGCCGTTCCGGGACGGATTTCACTCTGACCATCAGCAGTCTGCAGCCG<br>GAAGACTTCGCAACTTATTACTGTCAGCAACATTGGTGGGGTTACCCTATGATCACGTTC<br>GGACAGGGTACCAAGGTGGAGATCAAACGAACTGTGGCTGCACCATCTGTCTTCATCTTC<br>CCGCCATCTGATTCACAGTTGAAATCTGGAACTGCCTCTGTTGTGTGCCTGCTGAATAAC<br>TTCTATCCCAGAGAGGCCAAAGTACAGTGGAAGGTGGATAACGCCCTCCAATCGGGTAAC<br>TCCCAGGAGAGTGTCACAGAGCAGGACAGCAAGGACAGCACCTACAGCCTCAGCAGCACC<br>CTGACGCTGAGCAAAGCAGACTACGAAAAACATAAAGTCTACGCCTGCGAAGTCACCCAT<br>CAGGGCCTGAGCTCGCCCGTCACAAAGAGCTTCAACAGGGGAGAGTGTGGTGGTTCTGAT<br>TACAAAGATGACGATGACAAATAA |
| Fab AM1-5 Light chain amino acid sequence (SEQ ID NO: 36) | DIQMTQSPSSLSASVGDRVTITCRASQSVSSAVAWYQQKPGKAPKLLIYSASSLYSGVPS<br>RESGSRSGTDFTLTISSLQPEDFATYYCQQHWWGYPMITFGQGTKVEIKRTVAAPSVFIF<br>PPSDSQLKSGTASVVCLLNNFYPREAKVQWKVDNALQSGNSQESVTEQDSKDSTYSLSST<br>LTLSKADYEKHKVYACEVTHQGLSSPVTKSFNRGECGGSDYKDDDDK |
| Fab AM1-6 Heavy chain nucleotide sequence (SEQ ID NO: 37) | GAGGTTCAGCTGGTGGAGTCTGGCGGTGGCCTGGTGCAGCCAGGGGGCTCACTCCGTTTG<br>TCCTGTGCAGCTTCTGGCTTCAACCTCTCTTCTTATTCTATCCACTGGGTGCGTCAGGCC<br>CCGGGTAAGGGCCTGGAATGGGTTGCATCTGCAATTTATGCTGGTTTCGGCTCAACTACG<br>TATGCCGATAGCGTCAAGGGCCGTTTCACTATAAGCGCAGACACATCCAAAAACACAGCC<br>TACCTACAAATGAACAGCTTAAGAGCTGAGGACACTGCCGTCTATTATTGTGCTCGCTCT<br>TCAGCTATGGACTACTGGGGTCAAGGAACCCTGGTCACCGTCTCCTCGGCCTCCACCAAG<br>GGTCCATCGGTCTTCCCCCTGGCACCCTCCTCCAAGAGCACCTCTGGGGGCACAGCGGCC<br>CTGGGCTGCCTGGTCAAGGACTACTTCCCCGAACCGGTGACGGTGTCGTGGAACTCAGGC<br>GCCCTGACCAGCGGCGTGCACACCTTCCCGGCTGTCCTACAGTCCTCAGGACTCTACTCC<br>CTCAGCAGCGTGGTGACCGTGCCCTCCAGCAGCTTGGGCACCCAGACCTACATCTGCAAC<br>GTGAATCACAAGCCCAGCAACACCAAGGTCGACAAGAAAGTTGAGCCCAAATCTTGTGAC<br>AAAACTCACACATAA |
| Fab AM1-6 Heavy chain amino acid sequence (SEQ ID NO: 38) | EVQLVESGGGLVQPGGSERLSCAASGENLSSYSIHWVRQAPGKGLEWVASAIYAGFGSTT<br>YADSVKGRETISADISKNTAYLQMNSLRAEDTAVYYCARSSAMDYWGQGTLVTVSSASTK<br>GPSVFPLAPSSKSTSGGIAALGCLVKDYFPEPVTVSWNSGALTSGVHTFPAVLQSSGLYS<br>LSSVVTVPSSSLGTQTYICNVNHKPSNTKVDKKVEPKSCDKTHT |
| Fab AM1-6 Light chain nucleotide sequence (SEQ ID NO: 39) | GATATCCAGATGACCCAGTCCCCGAGCTCCCTGTCCGCCTCTGTGGGCGATAGGGTCACC<br>ATCACCTGCCGTGCCAGTCAGTCCGTGTCCAGCGCTGTAGCCTGGTATCAACAGAAACCA<br>GGAAAAGCTCCGAAGCTTCTGATTTACTCGGCATCCAGCCTCTACTCTGGAGTCCCTTCT<br>CGCTTCTCTGGTAGCCGTTCCGGGACGGATTTCACTCTGACCATCAGCAGTCTGCAGCCG<br>GAAGACTTCGCAACTTATTACTGTCAGCAACATTCTTGGCGGTACCCGCTGATTACGTTC<br>GGACAGGGTACCAAGGTGGAGATCAAACGAACTGTGGCTGCACCATCTGTCTTCATCTTC<br>CCGCCATCTGATTCACAGTTGAAATCTGGAACTGCCTCTGTTGTGTGCCTGCTGAATAAC<br>TTCTATCCCAGAGAGGCCAAAGTACAGTGGAAGGTGGATAACGCCCTCCAATCGGGTAAC<br>TCCCAGGAGAGTGTCACAGAGCAGGACAGCAAGGACAGCACCTACAGCCTCAGCAGCACC<br>CTGACGCTGAGCAAAGCAGACTACGAAAAACATAAAGTCTACGCCTGCGAAGTCACCCAT<br>CAGGGCCTGAGCTCGCCCGTCACAAAGAGCTTCAACAGGGGAGAGTGTGGTGGTTCTGAT<br>TACAAAGATGACGATGACAAATAA |

TABLE 4-continued

IL-18Rβ-binding Fab sequences

| Name (SEQ ID NO:) | Sequence |
|---|---|
| Fab AM1-6 Light chain amino acid sequence (SEQ ID NO: 40) | DIQMTQSPSSLSASVGDRVTITCRASQSVSSAVAWYQQKPGKAPKLLIYSASSLYSGVPS RFSGSRSGIDFILTISSLQPEDFATYYCQQHSWRYPLITEGQGTKVEIKRTVAAPSVFIE PPSDSQLKSGTASVVCLLNNFYPREAKVQWKVDNALQSGNSQESVTEQDSKDSTYSLSST LTLSKADYEKHKVYACEVTHQGLSSPVTKSENRGECGGSDYKDDDDK |

Example 2. Functional Characterization of IL-18R-Binding Antibodies

Figure 1B:
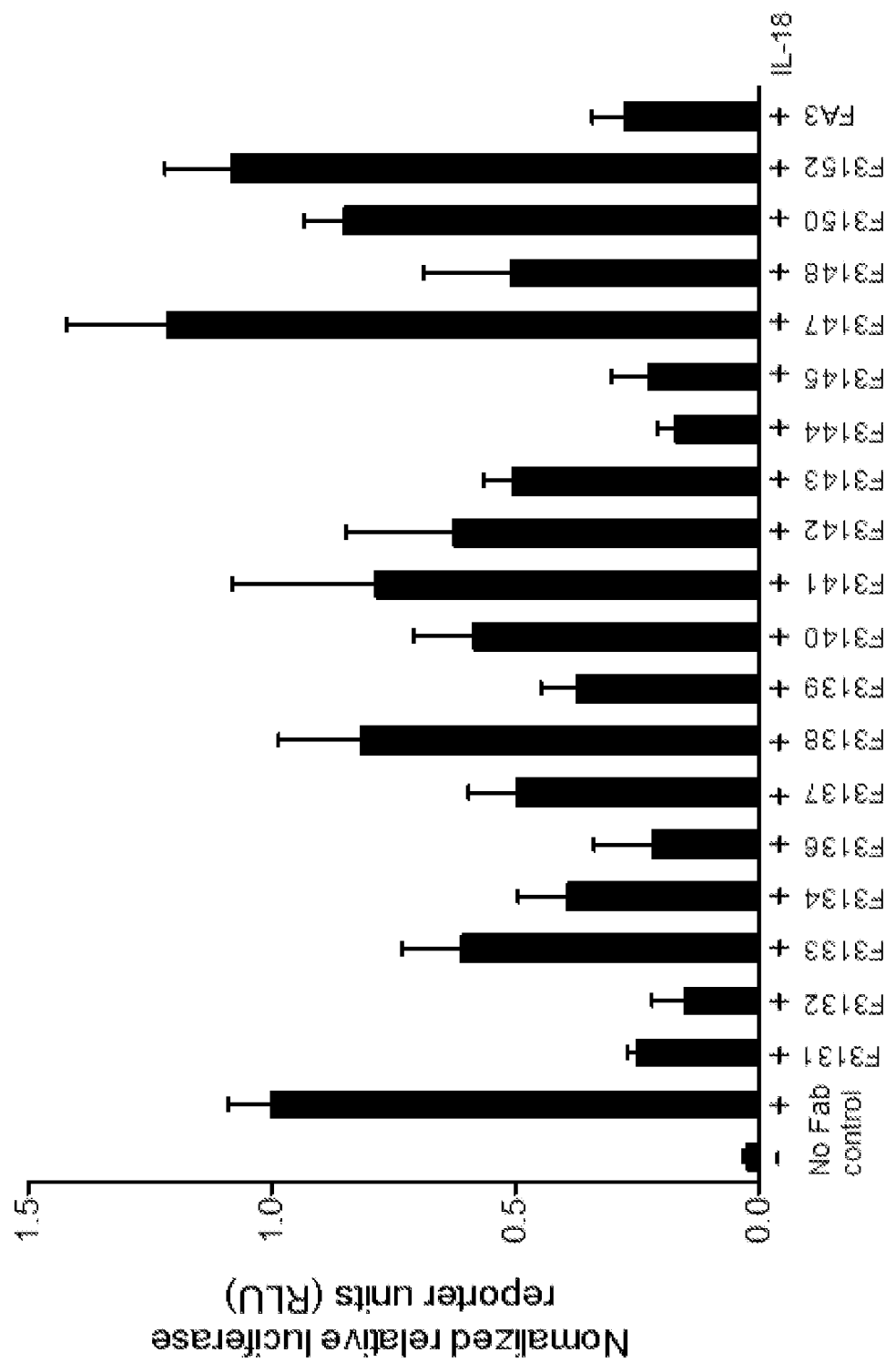

Evaluation of expressed and purified Fab protein in an IL-18-dependent NF-κB cellular luciferase reporter assay inhibition of IL-18 induced luciferase signals >60% 2 anti-IL-18Rα Fabs (Fab 9 and 12) (FIG. 1A) and >80% by 7 anti-IL-18Rβ Fabs (FIG. 1B). In light of the sequence identity and high likelihood of similar epitopes, Fab CDR regions for five Fabs (1 anti-IL-18Rα and 4 anti-IL-18Rβ) were sub-cloned in to IgG expression constructs, transfected and expressed in 293F cells and then purified from the media to homogeneity over a Sepharose™ A chromatography column. In vitro binding of each IgG to receptor was then evaluated over a range of concentrations revealing in all cases, $EC_{50}$ values in the low double-digit nanomolar binding to IL-18Rβ with virtually no binding to either negative control protein ($F_c$, BSA) at all concentrations tested (FIG. 2, panel A). Additional estimation of binding affinity by multi-point competitive ELISA revealed affinities in the 100 nM and sub-100 nM range (FIG. 2, panel B). SPR analysis of the same Fabs confirmed these estimates and enabled the determined of kinetics constants and equilibrium binding affinity (Table 5).

encoding either full length IL-18Rα or IL-18Rβ and cultivated for 24 hrs prior to IgG labeling. Both untransfected cells and cells transiently transfected with the receptor-GFP fusion were incubated with saturating concentrations of IL-18R-binding IgG (or an isotype control) before washing and fluorostaining with a Cy3-labeled secondary antibody. After removal of the secondary antibody and fixation, cells were imaged by fluorescence microscopy (FIG. 3, panels A and B). Images obtained by staining with each IgG of the anti-IL-18R antibodies revealed co-incident GFP expression (taken as confirmation of receptor expression) and antibody staining that was not apparent in the control IgG-stained cells. Similar analysis of GFP-expressing cells by flow cytometry revealed a distinct population of IL-18R-expressing (based on GFP expression) cells that stained positively with each of the IgGs and a positive commercially-sourced control.

HEK293 cells transfected in the same manner for expression of individual receptors were used to further test binding by flow cytometry. Cells expressing IL-18R-GFP fusions were stained with saturating IgG concentrations (red histograms) and compared to receptor-expressing cells stained with a non-receptor binding isotype control IgG (dark grey histograms) or anti-human Alexa® 488 dye-labeled second-

TABLE 5

Fab kinetics of binding versus mouse and human IL-18R by surface plasmon resonance (SPR)

| | Target | Human receptor | | | Mouse receptor | | |
|---|---|---|---|---|---|---|---|
| Fab ID | Receptor | $k_a$ ($10^4 M^{-1} s^{-1}$) | $k_d$ ($10^{-4} s^{-1}$) | $K_D$ (nM) | $k_a$ ($10^4 M^{-1} s^{-1}$) | $k_d$ ($10^{-4} s^{-1}$) | $K_D$ (nM) |
| 3131 | IL-18Rβ | 21 ± 0.1 | 12.7 ± 0.1 | 6.2± | 12 ± 0.1 | 6.2 ± 0.5 | 5.2± |
| 3132 | IL-18Rβ | | | | | | |
| 3144 | IL-18Rβ | 32 ± 0.1 | 5.8 ± 0.2 | 1.8± | 9.3 ± 0.1 | 12 ± 0.4 | 12.9± |
| A3 | IL-18Rβ | 2 ± 0.1 | 16.0 ± 0.2 | 78± | ND | ND | ND |
| 12 | IL-18Rα | 11 ± 0.1 | 2.0 ± 0.2 | 1.9± | ND | ND | ND |

To determine whether IgGs bound unique or overlapping epitopes, binding experiments were conducted using by pre-incubating IgGs with immobilized receptor to block epitopes, the testing Fab binding by co-incubation with IgG-blocked receptor. Results showed that Fab clone FA3 was blocked only by its corresponding IgG (suggesting a unique epitope), whereas the remaining three Fabs (F3131, F3132, F3144) could be blocked by any of the IgG molecules (I3131, I3132, I3144) except the IA3 clone (corresponding to Fab FA3) (FIG. 2, panel D), suggesting a shared or overlapping epitope.

Example 3. Cell Binding of IL-18R-Binding Antibodies by Fluorescence Microscopy and Flow Cytometry To assess IgG binding to its target cellular receptor, HEK293 cells were transiently transfected with a construct ary antibody alone (blue histograms) (FIG. 3, panels C and D). These results confirmed a significant shift in receptor-expressing cells that was not apparent with either secondary antibody alone or with the isotype control. Though controls IgGs targeting IL-18Rα and IL-18Rβ, also exhibited respective binding to cells expressing their cognate receptor, they also showed some binding to non-expressing HEK293 cells (pink histograms), despite the absence of binding of secondary alone controls (green histogram). Since these cells are not expected to express either of the IL-18 receptors, this may simply represent a stickiness to non-expressing cells evident in only one of our antibodies to IL-18Rβ (IgG 3132) and the single antibody to IL-18Rα (IgG A3).

To test cell binding to endogenously expressed IL-18Rβ, macrophage-derived KG-1 myeloblast cells, known to express both IL-18Rs, were similarly immuno-stained with each IgG over a range of concentrations in comparison to a non-binding isotype control antibody (this needs to be added in). Plots of the median fluorescence intensity of staining versus a range of antibody concentrations revealed clear and saturable binding that enabled the fitting of the various binding curves and estimation of $EC_{50}$s for cell binding (FIG. 4).

Example 4. Functional Consequence of IL-18R IgG Binding by Phospho-Western Analysis and IFN-γ ELISA To evaluate the functional consequences of anti-IL18Rβ binding by IgG, IL-18-induced phospho-signaling was first assessed in KG-1 cells for several downstream effectors of IL-18R activation including IKKα/IKKβ, p38 MAPK and SAPK/JNK using phosphospecific antibodies in Western blots that quantify phosphorylation of specific residues within each protein. Antibodies specific for their respective non-phosphorylated parent proteins were also used to probe blots prepared from the same lysates for comparison as load controls (FIG. 4, panel A). Initially, KG-1 cells were incubated with saturating concentrations of IL-18R-binding antibodies for 1 hr prior to stimulation. Cells were then stimulated with IL-18 (10 ng/ml., R&D Systems) for 24 hrs in the presence of antibody prior to collection of cell lysates for Western blot analysis and compared with cells in the absence of antibody and cells incubated with antibody but not stimulated with IL-18. Following stimulation, cell lysates were collected on ice and separated by SDS-PAGE before transfer to a solid PVDF support. Transferred proteins were probed separately with antibodies to rabbit anti-human p-IKKα/β (Ser176/180) (#2078; Cell Signaling), p-p38 MAPK (Thr180/Tyr182) (#4631; Cell Signaling), or phospho p44/42 MAPK (Thr202/Tyr204) (#4370; Cell Signaling) monoclonal antibodies developing with an anti-rabbit-HRP fusion secondary antibody (#7074; Cell Signaling) and enhanced chemi-luminescence reagent (ECL; #34095, Thermo).

Intensity results from both were quantified by densitometry to calculate the ratio of phosphorylated to non-phosphorylated protein, normalized to no antibody, no-IL-18 controls and ratios plotted versus the antibody treatment with or without IL-18 stimulation. Results show IL-18-induced phosphorylation of IKKα/B, p38 MAPK and SAPK/JNK that could be inhibited by pre-incubation with any of the four anti-IL-18Rβ antibodies such that phospho-signal were virtually indistinguishable from no IL-18 controls, suggesting potent inhibition (FIG. 4, panels B-D).

To corroborate these results, secretion of IFN-γ was additionally used as a phenotypic readout to assess activity and quantified from cell supernatants by ELISA. KG-1 cells or isolated PBMCs were incubated with a range of concentrations of anti-IL-18Rβ IgG, then stimulated with 10 ng/ml IL-18 for 24 hours. Quantification of secreted IFN-γ revealed for each antibody tested revealed a similar dose-dependent reduction in secreted IFN-γ in both KG-1 cells and isolated PBMCs to approximately 50% of maximal at a range of ~0.5-2 pM for IgGs 3131, 3132 and 3144 and ~4-6 μM IgG A3 (lesser activity corresponding to its lesser affinity), in KG-1 cells (FIG. 4, panel E). Similar results were obtained in PBMCs, in which IgGs 3131, 3132 and 3144 inhibited ~50% of maximal signals at ~0.5-2 pM with substantially higher levels of IgG A3 required for similar inhibition (FIG. 4, panel F). Additionally, anti-IL-18Rα-binding IgG 12 was shown to possess similar potency to the Il-18Rβ-binding antibodies, inhibiting ~50% of IFN-γ secreted at ~1 μM IgG in PBMCs.

Example 5. Structural Characterization of the Anti-IL-18Rα/IL-18Rβ Complex

Figure 5:
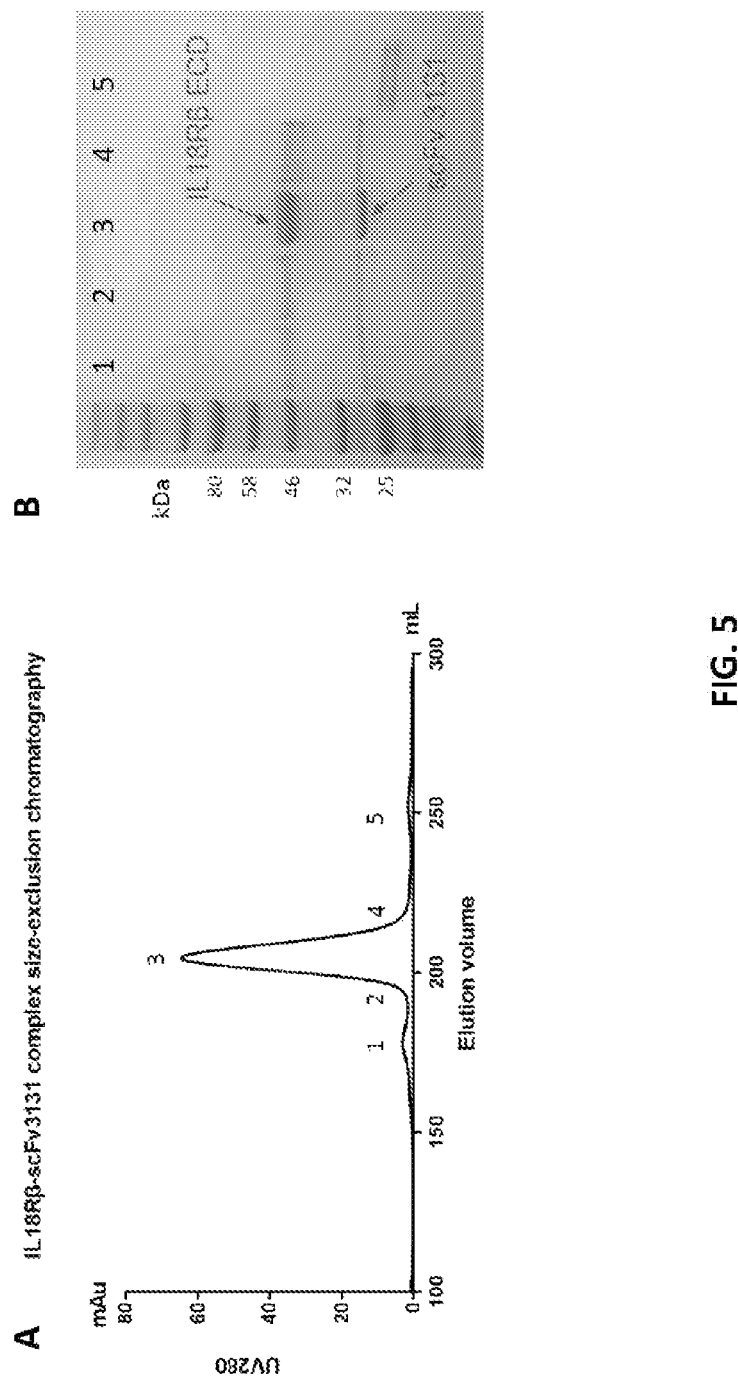
FIG. 5. Purification of the extracellular domain (ECD) of IL-18Rβ in complex with scFv 3131. A) The ECD of IL-18Rβ in complex with scFv 3131 was purified from size exclusion chromatography column (S200 26/600, GE). B) SDS-PAGE profile of size exclusion chromatography.

To glean additional insight into how the anti-IL-18Rβ-binding Fab 3131 inhibited the non-ligand-binding receptor component of the IL-18R, crystallographic studies were undertaken to structurally characterize the interactions between the scFv format of Fab 3131 and the extracellular domain (ECD) of receptor IL-18Rβ. IL-18Rβ was expressed as an N-terminal HisX6 tag fusion from baculovirus expression vector pFastBac™ Dual in High Five insect cells. scFv format of 3131 was constructed from Fab 3131 by fusion of VH and VL with a linker of 17 amino acids. scFv 3131 was expressed in *E. coli* as an N-terminal HisX6 tag fusion protein and purified to homogeneity using a TALON® Metal Affinity Resin. The ECD of IL-18Rβ receptor was purified to homogeneity using a TALON® Metal Affinity Resin and mixed 1:2 molar ratio with purified scFv 3131; the mixture was then loaded onto size exclusion chromatography column for purification of complex (FIG. 5). The complex was concentrated to 10 mg/mL before screening for crystals with a battery of crystallization suites. Ultimately crystals were generated from a buffer comprised of 0.2 M Ammonium iodide and 20% (w/v) PEG 3350 and isolated crystals were stored in cryosolution in liquid N2 prior to X-ray diffraction.

X-ray diffraction data were collected at the Shanghai Synchrotron Radiation Facility (SSRF) with a resolution of 3.3 Å. The crystal belonged to $P3_1$ with the unit cell a=163.160, b=163.160, c=64.145, α=90°, β=90°, γ=120°.

Figure 6:
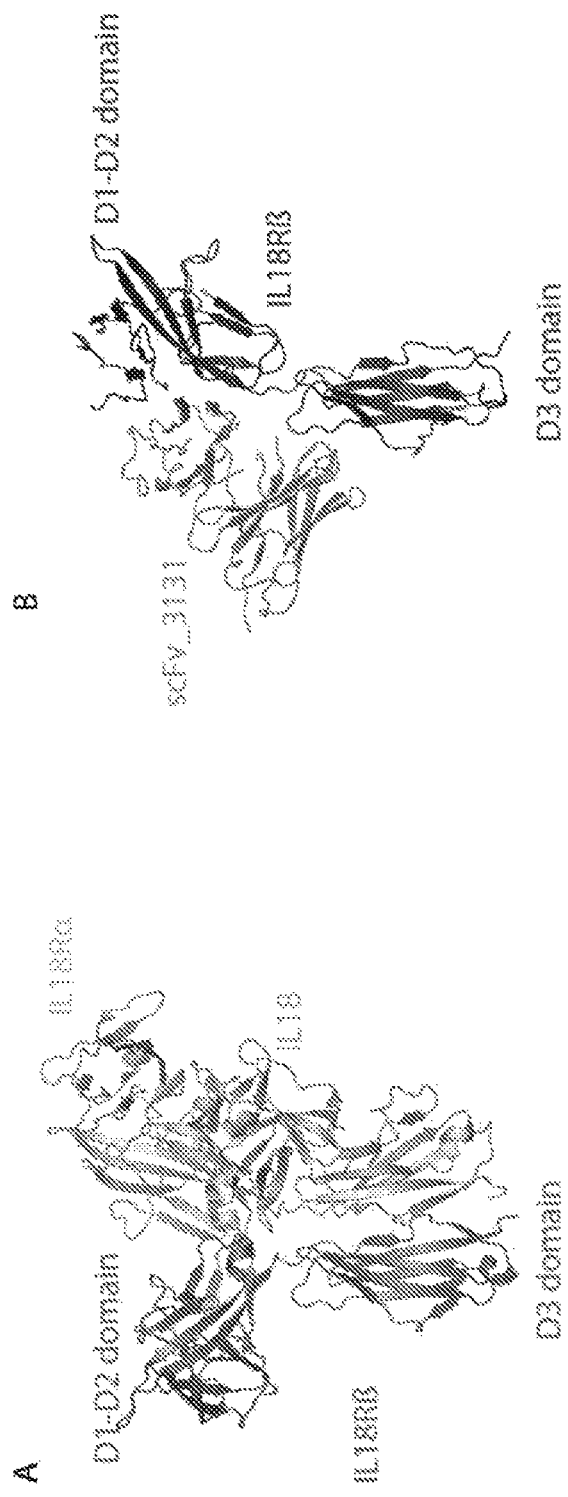
FIG. 6. Structural analysis of antibody binding reveals a novel mode of non-competitive antagonism. A) The structure of the IL-18 ternary signaling complex from PDB ID 3WO4 is shown for reference. B) A refined model of IgG 3131 reformatted as scFv in complex with IL-18Rβ (PDB ID 5ZX7) reveals a novel mode of inhibition in which binding to the hinge region of the receptor between domains 2 and 3 locks IL-18Rβ into a non-binding conformation for IL-18Rα. The D3 domain of IL-18Rβ in both structures is shown in the same orientation.

A refined model revealed a novel mode of non-competitive antagonism in which the antibody binds to the face opposite the ligand binding site, locking the receptor into a non-functional conformation in which the geometry of the ligand-biding site is disrupted (FIG. 6). These results provide mechanistic insight into the mode of antagonism of signaling via the non-ligand binding component of the receptor that suggests that antagonism arises from locking the receptor into a confirmation that impeded interaction with the IL-18Rα-ligand complex.

Example 6. Characterization of IgG 3131 Binding to Monkey IL-18Rβ

This example tested the binding of antibody 313 to monkey IL-18Rβ.

Figure 7:
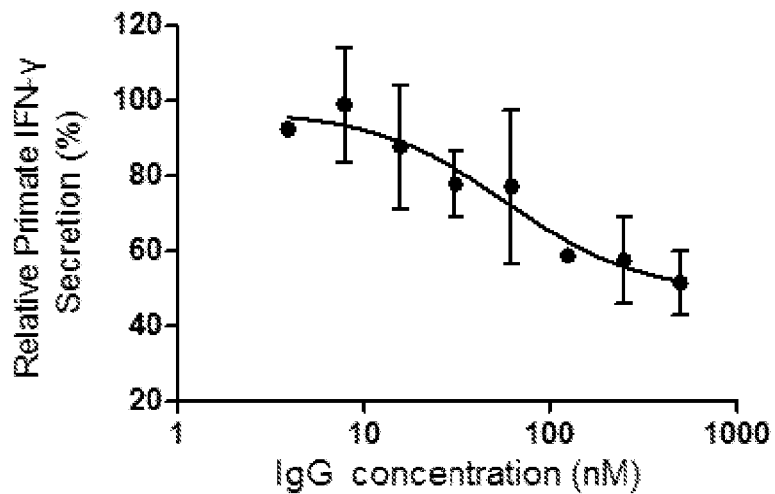
FIG. 7 shows the cellular effects of IgG 3131 pre-incubation on rhesus IL-18 (50 ng/ml) plus rhesus IL-12 (5 ng/ml) induced stimulation of IFN-γ secretion which was assessed over a range of IgG concentrations on isolated fresh cynomolgus monkey PBMCs. The mean and the standard deviation (SD) were calculated from three different monkeys. $IC_{50}$ values were estimated from the dose response curves by curve fitting in GraphPad Prism (Version 5.0).

$EC_{50}$ value of IgG 3131 binding to rhesus IL-18Rβ was determined by multipoint direct binding ELISA. The kinetics of IgG 3131 binding was determined to rhesus IL-18 receptor beta by Surface Plasmon Resonance (SPR) to confirm $EC_{50}$ estimates. The cellular effects of IgG 3131 pre-incubation on rhesus IL-18 (50 ng/ml) plus rhesus IL-12 (5 ng/ml) induced stimulation of IFN-γ secretion was assessed over a range of IgG concentrations on isolated fresh cynomolgus monkey PBMCs. The mean and the standard deviation (SD) were calculated from three different monkeys. $IC_{50}$ values were estimated from the dose response curves by curve fitting in GraphPad Prism (Version5.0). The summary results are shown below and the dose-dependency is plotted in FIG. 7.

| IgG ID | Target | $EC_{50}$ (nM) | $k_a$ ($10^4$ $M^{-1}$ $s^{-1}$) | $k_d$ ($10^{-4}$ $s^{-1}$) | $K_D$ (nM) |
|---|---|---|---|---|---|
| 3131 | Rhesus IL-18Rβ | 11.5 ± 0.4 | 3.8 ± 0.1 | 1.5 ± 0.1 | 3.9 ± 0.1 |

Figure 8:
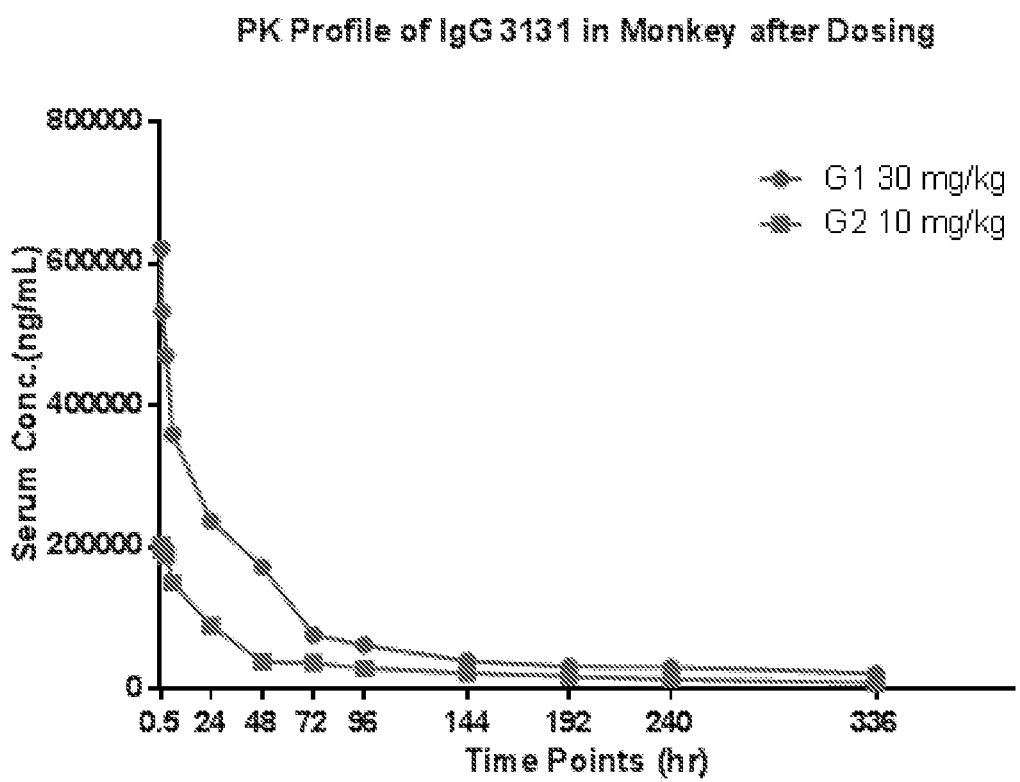
FIG. 8 shows the individual serum concentration-time curve of IgG 3131 in male monkey following dosing of IgG 3131.

IgG 3131 serum concentration from individual monkeys. Following intravenous administration of IgG 3131 at a dose of 30 mg/kg (group 1, or G1) or 10 mg/kg (group 2, or G2), 2 ml whole blood were collected at pre-dose, 0.5, 1, 3, 6, 24, 48 h, 3 d, 4 d, 144 h (6 d), 192 h (8 d), 240 h (10 d) and 336 h (14 d). After serum isolation, analysis of sample IgG was conducted by ELISA. The results are shown in Table 6 and FIG. 8.

TABLE 6

IgG 3131 serum concentration from individual male monkeys.

| Time points(hr) predose | G1 30 mg/kg Mean Single Conc.(ng/mL) | CV % | G2 10 mg/kg Mean Single Conc.(ng/ml) | CV % |
|---|---|---|---|---|
| | BQL | NA | BQL | NA |
| 0.5 hr | 621501.346 | 8.2 | 203564.463 | 4.4 |
| 1 hr | 532472.449 | 6.6 | 196796.426 | 5.2 |
| 3 hr | 470342.688 | 5.1 | 189477.094 | 4.8 |
| 6 hr | 359419.118 | 5.7 | 150558.530 | 2.4 |
| 24 hr | 237529.252 | 5.1 | 89643.134 | 0.5 |
| 48 hr | 172548.375 | 10.6 | 51125.427 | 17.1 |
| Day3 | 76872.242 | 0.1 | 37305.556 | 25.4 |
| Day4 | 62353.833 | 4.5 | 29332.824 | 13.3 |
| Day6 | 39732.496 | 2.4 | 22742.962 | 23.8 |
| Day8 | 32240.520 | 1.5 | 18363.603 | 17.4 |
| Day10 | 31031.273 | 1.0 | 13901.55 | 14.6 |
| Day14 | 22526.709 | 0.9 | 9022.943 | 7.7 |
| DAY21 | 15808.016 | 1.7 | 2641.525 | 1.2 |
| Day 28 | 9866.219 | 0.4 | 1705.89 | 1.5 |

BLQ: below the limit of quantitation; N/A: not available

Table 7 shows selected pharmacokinetics parameters of IgG 3131 in male monkeys.

TABLE 7

Pharmacokinetics parameters of IgG 3131 in rhesus

| Group | G1 | G2 |
|---|---|---|
| Dose (mg/kg) | 30 | 10 |
| $\lambda_z$ (1/day) | 0.0613 | 0.127 |
| $T_{1/2}$ (day) | 11.3 | 5.46 |
| $T_{max}$ (day) | 0.0208333 | 0.0208333 |
| $C_{max}$ (ng/ml) | 621501.35 | 203564.46 |
| $AUC_{0-t}$ (day*ng/mL) | 1311391.3 | 511163.9 |
| $AUC_{0-\infty}$ (day*ng/ml) | 1472301.3 | 524605.3 |
| AUC_% Extrap_obs ({%}) | 10.93 | 2.56 |
| Vz_obs (mL/kg) | 332.32 | 150.2 |
| MRTlast (day) | 6.22 | 5.33 |
| Vss_obs (mL/kg) | 211.51 | 116.43 |

Example 7. Further Affinity Maturation of IgG 3131

This example presents antibody Fab sequences derived from affinity maturation of antibody 3131. Affinity maturation libraries were subject to rounds of affinity-based solution-phase phage display selection with decreasing concentration of antigen at each round. Antibodies with improved affinity are listed in Table 8.

TABLE 8

Affinity matured sequences

| Seq ID | Sequence | Name | VH/VL |
|---|---|---|---|
| 162 | DIQMTQSPSSLSASVGDRVTITCRASQSVSSAVAWYQQKPGKAPKLLIY SASSLYSGVPSRFSGSRSGTDFTLTISSLQPEDFATYYCQQYGYHHAGL ITFGQGTKVEIK | 3131 AM2-1 | VL |
| 163 | EVQLVESGGGLVQPGGSLRLSCAASGFNLYYSSMHWVRQAPGKGLEWVA SIYSSYGYTYYADSVKGRFTISADTSKNTAYLQMNSLRAEDTAVYYCAR SSFSHGYGWYGLDYWGQGTLVTVSS | 3131 AM2-1 | VH |
| 164 | DIQMTQSPSSLSASVGDRVTITCRASQSVSSAVAWYQQKPGKAPKLLIY SASSRDSGVPSRFSGSRSGTDFTLTISSLQPEDFATYYCQQYGYHYAGL ITFGQGTKVEIK | 3131 AM2-2 | VL |
| 165 | EVQLVESGGGLVQPGGSLRLSCAASGENLYYSSMHWVRQAPGKGLEWVA SIYSSHGRTGYADSVKGRFTISADTSKNTAYLQMNSLRAEDTAVYYCAR SSFSHGYGWYGLDYWGQGTLVTVSS | 3131 AM2-2 | VE |
| 166 | DIQMTQSPSSLSASVGDRVTITCRASQSVSSAVAWYQQKPGKAPKLLIY SASSLYSGVPSRFSGSRSGTDFTLTISSLQPEDFATYYCQQYGYHYAGL ITFGQGTKVEIK | 3131 AM2-3 | VL |
| 167 | EVQLVESGGGLVQPGGSLRLSCAASGFNLYYSSMHWVRQAPGKGLEWVA SIYSSSGYTSYADSVKGRFTISADTSKNTAYLQMNSLRAEDTAVYYCAR SSFSHGYGWYGLDYWGQGTLVTVSS | 3131 AM2-3 | VH |
| 168 | DIQMTQSPSSLSASVGDRVTITCRASQSVSSAVAWYQQKPGKAPKLLIY SASSLYSGVPSRFSGSRSGTDFTLTISSLQPEDFATYYCQQYGYHYAGL ITFGQGTKVEIK | 3131 AM2-4 | VL |

TABLE 8-continued

Affinity matured sequences

| Seq ID | Sequence | Name | VH/VL |
|---|---|---|---|
| 169 | EVQLVESGGGLVQPGGSLRLSCAASGENLYYSSMHWVRQAPGKGLEWVASIYSSSGSTCYADSVKGRFTISADTSKNTAYLQMNSLRAEDTAVYYCARSSFSHGYGWYGLDYWGQGTLVTVSS | 3131 AM2-4 | VH |
| 170 | DIQMTQSPSSLSASVGDRVTITCRASQSVSSAVAWYQQKPGKAPKLLIYSASSLYSGVPSRFSGSRSGTDFTLTISSLQPEDFATYYCQQYGYHYAGLITFGQGTKVEIK | 3131 AM2-5 | VL |
| 171 | EVQLVESGGGLVQPGGSLRLSCAASGFNLYYSSMHWVRQAPGKGLEWVASIYSSSGDTHYADSVKGRFTISADTSKNTAYLQMNSLRAEDTAVYYCARSSFSHGYGWYGLDYWGQGTLVTVSS | 3131 AM2-5 | VH |
| 172 | DIQMTQSPSSLSASVGDRVTITCRASQSVSSAVAWYQQKPGKAPKLLIYSASSLYSGVPSRFSGSRSGTDFTLTISSLQPEDFATYYCQQYGYHYAGLITFGQGTKVEIK | 3131 AM2-6 | VL |
| 173 | EVQLVESGGGLVQPGGSLRLSCAASGFNLYYSSMHWVRQAPGKGLEWVASIYSSHGGTNYADSVKGRFTISADTSKNTAYLQMNSLRAEDTAVYYCARSSFSHGYGWYGLDYWGQGTLVTVSS | 3131 AM2-6 | VH |
| 174 | DIQMTQSPSSLSASVGDRVTITCRASQSVSSAVAWYQQKPGKAPKLLIYSASSLYSGVPSRFSGSRSGTDETLTISSLQPEDFATYYCQQYGYHDAGLITFGQGIKVEIK | 3131 AM2-7 | VL |
| 175 | EVQLVESGGGLVQPGGSLRLSCAASGENLYYSSMHWVRQAPGKGLEWVASIYSSHGGTYYADSVKGRFTISADTSKNTAYLQMNSLRAEDTAVYYCARSSFSHGYGWYGLDYWGQGTLVTVSS | 3131 AM2-7 | VH |
| 176 | DIQMTQSPSSLSASVGDRVTITCRASQSVSSAVAWYQQKPGKAPKLLIYSASSLYSGVPSRFSGSRSGTDFTLTISSLQPEDFATYYCQQYGYHYAGLITFGQGTKVEIK | 3131 AM2-8 | VL |
| 177 | EVQLVESGGGLVQPGGSLRISCAASGENLYYSSMHWVRQAPGKGLEWVASIYSSNGRIYYADSVKGRETISADISKNTAYLQMNSLRAEDTAVYYCARSSFSHGYGWYGLDYWGQGTLVTVSS | 3131 AM2-8 | VH |
| 178 | DIQMTQSPSSLSASVGDRVTITCRASQSVSSAVAWYQQKPGKAPKLLIYSASSLYSGVPSRFSGSRSGTDFTLTISSLQPEDFATYYCQQYGYHNAGLITFGQGTKVEIK | 3131 AM2-9 | VL |
| 179 | EVQLVESGGGLVQPGGSLRLSCAASGFNLYYSSMHWVRQAPGKGLEWVASIYSSYGYTYYADSVKGRFTISADTSKNTAYLQMNSLRAEDTAVYYCARSSFSHGYGWYGLDYWGQGTLVTVSS | 3131 AM2-9 | VH |
| 180 | DIQMTQSPSSLSASVGDRVTITCRASQSVSSAVAWYQQKPGKAPKLLIYSASSLYSGVPSRFSGSRSGTDFTLTISSLQPEDFATYYCQQYGYHYAGLITFGQGTKVEIK | 3131 AM2-10 | VL |
| 181 | EVQLVESGGGLVQPGGSLRLSCAASGENLYYSSMHWVRQAPGKGLEWVASIYSSNGNTGYADSVKGRFTISADTSKNTAYLQMNSLRAEDTAVYYCARSSFSHGYGWYGLDYWGQGTLVTVSS | 3131 AM2-10 | VH |
| 182 | DIQMTQSPSSLSASVGDRVTITCRASQSVSSAVAWYQQKPGKAPKLLIYSASSLYSGVPSRFSGSRSGTDFTLTISSLQPEDFATYYCQQYGYHYAGLITFGQGTKVEIK | 3131 AM2-11 | VL |
| 183 | EVQLVESGGGLVQPGGSLRLSCAASGENLYYSSMHWVRQAPGKGLEWVASIYSSNGNTGYADSVKGRFTISADTSKNTAYLQMNSLRAEDTAVYYCARSSFSHGYGWYGLDYWGQGTLVTVSS | 3131 AM2-11 | VH |
| 184 | DIQMTQSPSSLSASVGDRVTITCRASQSVSSAVAWYQQKPGKAPKLLIYSASSLYSGVPSRESGSRSGTDFILTISSLQPEDFATYYCQQYGYHDAGLITEGQGIKVEIK | 3131 AM2-13 | VL |
| 185 | EVQLVESGGGLVQPGGSLRLSCAASGENLYYSSMHWVRQAPGKGLEWVASIYSSYGYTYYADTSKNTAYLQMNSLRAEDTAVYYCARSSFSHGYGWYGLDYWGQGTLVTVSS | 3131 AM2-13 | VH |
| 186 | DIQMTQSPSSLSASVGDRVTITCRASQSVSSAVAWYQQKPGKAPKLLIYSASSLYSGVPSRFSGSRSGTDFTLTISSLQPEDFATYYCQQYGYHGAGLITFGQGTKVEIK | 3131 AM2-14 | VL |
| 187 | EVQLVESGGGLVQPGGSLRLSCAASGENLYYSSMHWVRQAPGKGLEWVASIYSSYGYTYYADSVKGRFTISADTSKNTAYLQMNSLRAEDTAVYYCARSSFSHGYGWYGLDYWGQGTLVTVSS | 3131 AM2-14 | VH |

TABLE 8-continued

Affinity matured sequences

| Seq ID | Sequence | Name | VH/VL |
|---|---|---|---|
| 188 | DIQMTQSPSSLSASVGDRVTITCRASQSVSSAVAWYQQKPGKAPKLLIY SASSLYSGVPSRFSGSRSGTDFTLTISSLQPEDFATYYCQQYGYHYAGL ITFGQGTKVEIK | 3131 AM2-15 | VL |
| 189 | EVQLVESGGGLVQPGGSLRLSCAASGFNLYYSSMHWVRQAPGKGLEWVA SIYSSSGDTGYADSVKGRFTISADTSKNTAYLQMNSLRAEDTAVYYCAR SSFSHGYGWYGLDYWGQGTLVTVSS | 3131 AM2-15 | VH |
| 190 | DIQMTQSPSSLSASVGDRVTITCRASQSVSSAVAWYQQKPGKAPKLLIY STSSLYSGVPSRFSGSRSGTDFTLTISSLQPEDFATYYCQQYGYHYAGL ITFGQGTKVEIK | 3131 AM2-16 | VL |
| 191 | EVQLVESGGGLVQPGGSLRLSCAASGFNLYYSSMHWVRQAPGKGLEWVA SIYSSYGYTYYADSVKGRFTISADTSKNTAYLQMNSLRAEDTAVYYCAR SSFSHGYGWYGLDYWGQGTLVTVSS | 3131 AM2-16 | VH |
| 192 | DIQMTQSPSSLSASVGDRVTITCRASQSVSSAVAWYQQKPGKAPKLLIY SASSLYSGVPSRFSGSRSGTDFTLTISSLQPEDFATYYCQQYGYHYAGL ITFGQGTKVEIK | 3131 AM2-17 | VL |
| 193 | EVQLVESGGGLVQPGGSLRLSCAASGENLYYSSMHWVRQAPGKGLEWVA SIYSSHGNTDYADSVKGRFTISADTSKNTAYLQMNSLRAEDTAVYYCAR SSFSHGYGWYGLDYWGQGTLVTVSS | 3131 AM2-17 | VH |
| 194 | DIQMTQSPSSLSASVGDRVTITCRASQSVSSAVAWYQQKPGKAPKLLIY SASSLYSGVPSRFSGSRSGTDFTLTISSLQPEDFATYYCQQYGYHYAGL ITFGQGTKVEIK | 3131 AM2-18 | VL |
| 195 | EVQLVESGGGLVQPGGSLRLSCAASGFNLYYSSMHWVRQAPGKGLEWVA SIYSSGGSTSYADSVKGRFTISADTSKNTAYLQMNSLRAEDTAVYYCAR SSFSHGYGWYGLDYWGQGTLVTVSS | 3131 AM2-18 | VH |
| 196 | DIQMTQSPSSLSASVGDRVTITCRASQSVSSAVAWYQQKPGKAPKLLIY SGSSGRSGVPSRFSGSRSGTDFTLTISSLQPEDFATYYCQQYGYHYAGL ITFGQGTKVEIK | 3131 AM2-21 | VL |
| 197 | EVQLVESGGGLVQPGGSLRLSCAASGENLYYSSMHWVRQAPGKGLEWVA SIYSSYGYTYYADSVKGRFTISADTSKNTAYLQMNSLRAEDTAVYYCAR SSFSHGYGWYGLDYWGQGTLVTVSS | 3131 AM2-21 | VH |
| 198 | DIQMTQSPSSLSASVGDRVTITCRASQSVSSAVAWYQQKPGKAPKLLIY SDSSLYSGVPSRFSGSRSGTDFTLTISSLQPEDFATYYCQQYGYHYAGL ITFGQGTKVEIK | 3131 AM2-24 | VL |
| 199 | EVQLVESGGGLVQPGGSLRLSCAASGFNLYYSSMHWVRQAPGKGLEWVA SIYSSYGYTYYADSVKGRFTISADTSKNTAYLQMNSLRAEDTAVYYCAR SSFSHGYGWYGLDYWGQGTLVTVSS | 3131 AM2-24 | VH |
| 200 | DIQMTQSPSSLSASVGDRVTITCRASQSVSSAVAWYQQKPGKAPKLLIY SASSRDSGVPSRFSGSRSGTDFTLTISSLQPEDFATYYCQQYGYHYAGL ITFGQGTKVEIK | 3131 AM2-25 | VL |
| 201 | EVQLVESGGGLVQPGGSLRLSCAASGFNLYYSSMHWVRQAPGKGLEWVA SIYSSYGYTYYADSVKGRFTISADTSKNTAYLQMNSLRAEDTAVYYCAR SSFSHGYGWYGLDYWGQGTLVTVSS | 3131 AM2-25 | VH |
| 202 | DIQMTQSPSSLSASVGDRVTITCRASQSVSSAVAWYQQKPGKAPKLLIY SESSLSSGVPSRFSGSRSGTDFTLTISSLQPEDFATYYCQQYGYHYAGL ITFGQGTKVEIK | 3131 AM2-26 | VL |
| 203 | EVQLVESGGGLVQPGGSLRLSCAASGENLYYSSMHWVRQAPGKGLEWVA SIYSSYGYTYYADSVKGRFTISADTSKNTAYLQMNSLRAEDTAVYYCAR SSFSHGYGWYGLDYWGQGTLVTVSS | 3131 AM2-26 | VH |
| 204 | DIQMTQSPSSLSASVGDRVTITCRASQSVSSAVAWYQQKPGKAPKLLIY SRSSDSSGVPSRFSGSRSGTDFTLTISSLQPEDFATYYCQQYGYHYAGL ITFGQGTKVEIK | 3131 AM2-28 | VL |
| 205 | EVQLVESGGGLVQPGGSLRLSCAASGFNLYYSSMHWVRQAPGKGLEWVA SIYSSYGYTYYADSVKGRFTISADTSKNTAYLQMNSLRAEDTAVYYCAR SSFSHGYGWYGLDYWGQGTLVTVSS | 3131 AM2-28 | VH |
| 206 | DIQMTQSPSSLSASVGDRVTITCRASQSVSSAVAWYQQKPGKAPKLLIY STSSLYSGVPSRFSGSRSGTDFTLTISSLQPEDFATYYCQQYGYHYAGL ITFGQGTKVEIK | 3131 AM2-29 | VL |

TABLE 8-continued

Affinity matured sequences

| Seq ID | Sequence | Name | VH/VL |
|---|---|---|---|
| 207 | EVQLVESGGGLVQPGGSLRLSCAASGENLYYSSMHWVRQAPGKGLEWVA SIYSSYGYTYYADSVKGRFTISADTSKNTAYLQMNSLRAEDTAVYYCAR SSFSHGYGWYGLDYWGQGTLVTVSS | 3131 AM2-29 | VH |
| 208 | DIQMTQSPSSLSASVGDRVTITCRASQSVSSAVAWYQQKPGKAPKLLIY SASSERSGVPSRFSGSRSGTDFTLTISSLQPEDFATYYCQQYGYHYAGL ITFGQGTKVEIK | 3131 AM2-30 | VL |
| 209 | EVQLVESGGGLVQPGGSLRLSCAASGFNLYYSSMHWVRQAPGKGLEWVA SIYSSYGYTYYADSVKGRFTISADTSKNTAYLQMNSLRAEDTAVYYCAR SSFSHGYGWYGLDYWGQGTLVTVSS | 3131 AM2-30 | VH |
| 210 | DIQMTQSPSSLSASVGDRVTITCRASQSVSSAVAWYQQKPGKAPKLLIY SESSLYSGVPSRFSGSRSGTDFTLTISSLQPEDFATYYCQQYGYHYAGL ITFGQGTKVEIK | 3131 AM2-31 | VL |
| 211 | EVQLVESGGGLVQPGGSLRLSCAASGENLYYSSMHWVRQAPGKGLEWVA SIYSSYGYTYYADSVKGRFTISADTSKNTAYLQMNSLRAEDTAVYYCAR SSFSHGYGWYGLDYWGQGTLVTVSS | 3131 AM2-31 | VH |
| 212 | DIQMTQSPSSLSASVGDRVTITCRASQSVSSAVAWYQQKPGKAPKLLIY SSSSVYSGVPSRFSGSRSGTDFTLTISSLQPEDFATYYCQQYGYHYAGL ITFGQGTKVEIK | 3131 AM2-32 | VL |
| 213 | EVQLVESGGGLVQPGGSLRLSCAASGENLYYSSMHWVRQAPGKGLEWVA SIYSSYGYTYYADSVKGRFTISADTSKNTAYLQMNSLRAEDTAVYYCAR SSFSHGYGWYGLDYWGQGTLVTVSS | 3131 AM2-32 | VH |
| 214 | DIQMTQSPSSLSASVGDRVTITCRASQSVSSAVAWYQQKPGKAPKLLIY SASSLYSGVPSRFSGSRSGTDFTLTISSLQPEDFATYYCQQYGYHYAGL ITFGQGTKVEIK | 3131 AM2-33 | VL |
| 215 | EVQLVESGGGLVQPGGSLRLSCAASGFNLYYSSMHWVRQAPGKGLEWVA SIYSSYGHTSYADSVKGRFTISADTSKNTAYLQMNSLRAEDTAVYYCAR SSFSHGYGWYGLDYWGQGTLVTVSS | 3131 AM2-33 | VH |
| 216 | DIQMTQSPSSLSASVGDRVTITCRASQSVSSAVAWYQQKPGKAPKLLIY SASSLYSGVPSRFSGSRSGTDFTLTISSLQPEDFATYYCQQYGYHSAGL ITFGQGTKVEIK | 3131 AM2-35 | VL |
| 217 | EVQLVESGGGLVQPGGSLRLSCAASGENLYYSSMHWVRQAPGKGLEWVA SIYSSYGYTYYADSVKGRFTISADTSKNTAYLQMNSLRAEDTAVYYCAR SSFSHGYGWYGLDYWGQGTLVTVSS | 3131 AM2-35 | VH |
| 218 | DIQMTQSPSSLSASVGDRVTITCRASQSVSSAVAWYQQKPGKAPKLLIY SASSLYSGVPSRFSGSRSGTDFTLTISSLQPEDFATYYCQQYGYHYAGL ITFGQGTKVEIK | 3131 AM2-36 | VL |
| 219 | EVQLVESGGGLVQPGGSLRLSCAASGENLYYSSMHWVRQAPGKGLEWVA SIYSSSGSTSYADSVKGRFTISADISKNTAYLQMNSLRAEDTAVYYCAR SSESHGYGWYGLDYWGQGTLVIVSS | 3131 AM2-36 | VH |
| 220 | DIQMTQSPSSLSASVGDRVTITCRASQSVSSAVAWYQQKPGKAPKLLIY SASSLYSGVPSRFSGSRSGTDFTLTISSLQPEDFATYYCQQYGYHSAGL ITFGQGTKVEIK | 3131 AM2-37 | VL |
| 221 | EVQLVESGGGLVQPGGSLRLSCAASGENLYYSSMHWVRQAPGKGLEWVA SIYSSSGSTSYADSVKGRETISADTSKNTAYLQMNSLRAEDTAVYYCAR SSFSIIGYGWYGLDYWGQGTLVTVSS | 3131 AM2-37 | VH |
| 222 | DIQMTQSPSSLSASVGDRVTITCRASQSVSSAVAWYQQKPGKAPKLLIY GASSLYSGVPSRFSGSRSGTDFTLTISSLQPEDFATYYCQQYGYHYAGL ITFGQGTKVEIK | 3131 AM2-S-G | VL |
| 223 | EVQLVESGGGLVQPGGSLRLSCAASGENLYYSSMHWVRQAPGKGLEWVA SIYSSYGYTYYADSVKGRFTISADTSKNTAYLQMNSLRAEDTAVYYCAR SSFSHGYGWYGLDYWGQGTLVTVSS | 3131 AM2-S-G | VH |
| 224 | DIQMTQSPSSLSASVGDRVTITCRASQSVSSAVAWYQQKPGKAPKLLIY TASSLYSGVPSRFSGSRSGTDFTLTISSLQPEDFATYYCQQYGYHYAGL ITFGQGTKVEIK | 3131 AM2-S-T | VL |
| 225 | EVQLVESGGGLVQPGGSLRLSCAASGFNLYYSSMHWVRQAPGKGLEWVA SIYSSYGYTYYADSVKGRFTISADTSKNTAYLQMNSLRAEDTAVYYCAR SSFSHGYGWYGLDYWGQGTLVTVSS | 3131 AM2-S-T | VH |

TABLE 8-continued

Affinity matured sequences

| Seq ID | Sequence | Name | VH/VL |
|---|---|---|---|
| 226 | DIQMTQSPSSLSASVGDRVTITCRASQSVSSAVAWYQQKPGKAPKLLIY HASSLYSGVPSRFSGSRSGTDFTLTISSLQPEDFATYYCQQYGYHYAGL ITFGQGTKVEIK | 3131 AM2-S-H | VL |
| 227 | EVQLVESGGGLVQPGGSLRLSCAASGFNLYYSSMHWVRQAPGKGLEWVA SIYSSYGYTYYADSVKGRFTISADTSKNTAYLQMNSLRAEDTAVYYCAR SSFSHGYGWYGLDYWGQGTLVTVSS | 3131 AM2-S-H | VH |
| 228 | DIQMTQSPSSLSASVGDRVTITCRASQSVSSAVAWYQQKPGKAPKLLIY YASSLYSGVPSRFSGSRSGTDFTLTISSLQPEDFATYYCQQYGYHYAGL ITFGQGTKVEIK | 3131 AM2-S-Y | VL |
| 229 | EVQLVESGGGLVQPGGSLRLSCAASGENLYYSSMHWVRQAPGKGLEWVA SIYSSYGYTYYADSVKGRFTISADTSKNTAYLQMNSLRAEDTAVYYCAR SSFSHGYGWYGLDYWGQGTLVTVSS | 3131 AM2-S-T | VH |
| 230 | DIQMTQSPSSLSASVGDRVTITCRASQSVSSAVAWYQQKPGKAPRLLIY SASSLYSGVPSRFSGSRSGTDFTLTISSLQPEDFATYYCQQYGYHYAGL ITFGQGTKVEIK | 3131 AM2-O-01 | VL |
| 231 | EVQLVESGGGLVQPGGSLRLSCAASGFTLYYSSMHWVRQAPGKGLEWVA SIYSSGGSTSYADSVKGRFTISADTSKNTAYLQMNSLRAEDTAVYYCAR SSFSHGYGWYGLDYWGQGTLVTVSS | 3131 AM2-O-01 | VH |
| 232 | DIQMTQSPSSLSASVGDRVTITCRASQSVSSAVAWYQQKPGKAPRLLIY SASSLYSGVPSRFSGSRSGTDFTLTISSLQPEDFATYYCQQYGYHYAGL ITFGQGTKVEIK | 3131 AM2-O-02 | VL |
| 233 | EVQLVESGGGLVQPGGSLRLSCAASGFDLYYSSMHWVRQAPGKGLEWVA SIYSSGGSTSYADSVKGRFTISADTSKNTAYLQMNSLRAEDTAVYYCAR SSFSHGYGWYGLDYWGQGTLVTVSS | 3131 AM2-O-02 | VH |
| 234 | DIQMTQSPSSLSASVGDRVTITCRASQSVSSAVAWYQQKPGKAPRLLIY SASSLYSGVPSRFSGSRSGTDFTLTISSLQPEDFATYYCQQYGYHYAGL ITFGQGTKVEIK | 3131 AM2-O-03 | VL |
| 235 | EVQLVESGGGLVQPGGSLRLSCAASGFSLYYSSMHWVRQAPGKGLEWVA SIYSSGGSTSYADSVKGRFTISADTSKNTAYLQMNSLRAEDTAVYYCAR SSFSHGYGWYGLDYWGQGTLVTVSS | 3131 AM2-O-03 | VH |
| 236 | DIQMTQSPSSLSASVGDRVTITCRASQSVSSAVAWYQQKPGKAPRLLIY SASSLYSGVPSRFSGSRSGTDFTLTISSLQPEDFATYYCQQYGYHYAGL ITFGQGTKVEIK | 3131 AM2-O-04 | VL |
| 237 | EVQLVESGGGLVQPGGSLRLSCAASGFTLYYSSMHWVRQAPGKGLEWVA SIYSSSGDTHYADSVKGRFTISADTSKNTAYLQMNSLRAEDTAVYYCAR SSFSHGYGWYGLDYWGQGTLVTVSS | 3131 AM2-O-04 | VH |
| 238 | DIQMTQSPSSLSASVGDRVTITCRASQSVSSAVAWYQQKPGKAPRLLIY SASSLYSGVPSRFSGSRSGTDFTLTISSLQPEDFATYYCQQYGYHYAGL ITFGQGTKVEIK | 3131 AM2-O-05 | VL |
| 239 | EVQLVESGGGLVQPGGSLRLSCAASGFDLYYSSMHWVRQAPGKGLEWVA SIYSSSGDTHYADSVKGRFTISADTSKNTAYLQMNSLRAEDTAVYYCAR SSFSHGYGWYGLDYWGQGTLVTVSS | 3131 AM2-O-05 | VH |
| 240 | DIQMTQSPSSLSASVGDRVTITCRASQSVSSAVAWYQQKPGKAPRLLIY SASSLYSGVPSRFSGSRSGTDFTLTISSLQPEDFATYYCQQYGYHYAGL ITFGQGTKVEIK | 3131 AM2-O-06 | VL |
| 241 | EVQLVESGGGLVQPGGSLRLSCAASGFSLYYSSMHWVRQAPGKGLEWVA SIYSSSGDTHYADSVKGRFTISADTSKNTAYLQMNSLRAEDTAVYYCAR SSFSHGYGWYGLDYWGQGTLVTVSS | 3131 AM2-O-06 | VH |
| 242 | DIQMTQSPSSLSASVGDRVTITCRASQSVSSAVAWYQQKPGKAPRLLIY GASSLYSGVPSRFSGSRSGTDFTLTISSLQPEDFATYYCQQYGYHYAGL ITFGQGTKVEIK | 3131 AM2-O-07 | VL |
| 243 | EVQLVESGGGLVQPGGSLRLSCAASGENLYYSSMHWVRQAPGKGLEWVA SIYSSGGSTSYADSVKGRFTISADTSKNTAYLQMNSLRAEDTAVYYCAR SSFSHGYGWYGLDYWGQGTLVTVSS | 3131 AM2-O-07 | VH |
| 244 | DIQMTQSPSSLSASVGDRVTITCRASQSVSSAVAWYQQKPGKAPRLLIY GASSLYSGVPSRFSGSRSGTDFTLTISSLQPEDFATYYCQQYGYHYAGL ITFGQGTKVEIK | 3131 AM2-O-08 | VL |

TABLE 8-continued

Affinity matured sequences

| Seq ID | Sequence | Name | VH/VL |
|---|---|---|---|
| 245 | EVQLVESGGGLVQPGGSLRLSCAASGFTLYYSSMHWVRQAPGKGLEWVA SIYSSGGSTSYADSVKGRFTISADTSKNTAYLQMNSLRAEDTAVYYCAR SSFSHGYGWYGLDYWGQGTLVTVSS | 3131 AM2-O-08 | VH |
| 246 | DIQMTQSPSSLSASVGDRVTITCRASQSVSSAVAWYQQKPGKAPRLLIY GASSLYSGVPSRFSGSRSGTDFTLTISSLQPEDFATYYCQQYGYHYAGL ITFGQGTKVEIK | 3131 AM2-O-09 | VL |
| 247 | EVQLVESGGGLVQPGGSLRLSCAASGFDLYYSSMHWVRQAPGKGLEWVA SIYSSGGSTSYADSVKGRFTISADTSKNTAYLQMNSLRAEDTAVYYCAR SSFSHGYGWYGLDYWGQGTLVTVSS | 3131 AM2-O-09 | VH |
| 248 | DIQMTQSPSSLSASVGDRVTITCRASQSVSSAVAWYQQKPGKAPRLLIY GASSLYSGVPSRFSGSRSGTDFTLTISSLQPEDFATYYCQQYGYHYAGL ITFGQGTKVEIK | 3131 AM2-O-10 | VL |
| 249 | EVQLVESGGGLVQPGGSLRLSCAASGFSLYYSSMHWVRQAPGKGLEWVA SIYSSGGSTSYADSVKGRFTISADTSKNTAYLQMNSLRAEDTAVYYCAR SSFSHGYGWYGLDYWGQGTLVTVSS | 3131 AM2-O-10 | VH |
| 250 | DIQMTQSPSSLSASVGDRVTITCRASQSVSSAVAWYQQKPGKAPRLLIY GASSLYSGVPSRFSGSRSGTDFTLTISSLQPEDFATYYCQQYGYHYAGL ITFGQGTKVEIK | 3131 AM2-O-11 | VL |
| 251 | EVQLVESGGGLVQPGGSLRLSCAASGENLYYSSMHWVRQAPGKGLEWVA SIYSSSGDTHYADSVKGRFTISADTSKNTAYLQMNSLRAEDTAVYYCAR SSFSHGYGWYGLDYWGQGTLVTVSS | 3131 AM2-O-11 | VH |
| 252 | DIQMTQSPSSLSASVGDRVTITCRASQSVSSAVAWYQQKPGKAPRLLIY GASSLYSGVPSRFSGSRSGTDFTLTISSLQPEDFATYYCQQYGYHYAGL ITFGQGTKVEIK | 3131 AM2-O-12 | VL |
| 253 | EVQLVESGGGLVQPGGSLRLSCAASGFTLYYSSMHWVRQAPGKGLEWVA SIYSSSGDTHYADSVKGRFTISADTSKNTAYLQMNSLRAEDTAVYYCAR SSFSHGYGWYGLDYWGQGTLVTVSS | 3131 AM2-O-12 | VH |
| 254 | DIQMTQSPSSLSASVGDRVTITCRASQSVSSAVAWYQQKPGKAPRLLIY GASSLYSGVPSRFSGSRSGTDFTLTISSLQPEDFATYYCQQYGYHYAGL ITFGQGTKVEIK | 3131 AM2-O-13 | VL |
| 255 | EVQLVESGGGLVQPGGSLRLSCAASGFDLYYSSMHWVRQAPGKGLEWVA SIYSSSGDTHYADSVKGRFTISADTSKNTAYLQMNSLRAEDTAVYYCAR SSFSHGYGWYGLDYWGQGTLVTVSS | 3131 AM2-O-13 | VH |
| 256 | DIQMTQSPSSLSASVGDRVTITCRASQSVSSAVAWYQQKPGKAPRLLIY GASSLYSGVPSRFSGSRSGTDFTLTISSLQPEDFATYYCQQYGYHYAGL ITFGQGTKVEIK | 3131 AM2-O-14 | VL |
| 257 | EVQLVESGGGLVQPGGSLRLSCAASGFSLYYSSMHWVRQAPGKGLEWVA SIYSSSGDTHYADSVKGRFTISADTSKNTAYLQMNSLRAEDTAVYYCAR SSFSHGYGWYGLDYWGQGTLVTVSS | 3131 AM2-O-14 | VH |
| 258 | DIQMTQSPSSLSASVGDRVTITCRASQSVSSAVAWYQQKPGKAPRLLIY SASSLYSGVPSRFSGSRSGTDFTLTISSLQPEDFATYYCQQYGYHDAGL ITFGQGTKVEIK | 3131 AM2-O-15 | VL |
| 259 | EVQLVESGGGLVQPGGSLRLSCAASGENLYYSSMHWVRQAPGKGLEWVA SIYSSGGSTSYADSVKGRFTISADTSKNTAYLQMNSLRAEDTAVYYCAR SSFSHGYGWYGLDYWGQGTLVTVSS | 3131 AM2-O-15 | VH |
| 260 | DIQMTQSPSSLSASVGDRVTITCRASQSVSSAVAWYQQKPGKAPRLLIY SASSLYSGVPSRFSGSRSGTDFTLTISSLQPEDFATYYCQQYGYHDAGL ITFGQGTKVEIK | 3131 AM2-O-16 | VL |
| 261 | EVQLVESGGGLVQPGGSLRLSCAASGFTLYYSSMHWVRQAPGKGLEWVA SIYSSGGSTSYADSVKGRFTISADTSKNTAYLQMNSLRAEDTAVYYCAR SSFSHGYGWYGLDYWGQGTLVTVSS | 3131 AM2-O-16 | VH |
| 262 | DIQMTQSPSSLSASVGDRVTITCRASQSVSSAVAWYQQKPGKAPRLLIY SASSLYSGVPSRFSGSRSGTDFTLTISSLQPEDFATYYCQQYGYHDAGL ITFGQGTKVEIK | 3131 AM2-O-17 | VL |
| 263 | EVQLVESGGGLVQPGGSLRLSCAASGFDLYYSSMHWVRQAPGKGLEWVA SIYSSGGSTSYADSVKGRFTISADTSKNTAYLQMNSLRAEDTAVYYCAR SSFSHGYGWYGLDYWGQGTLVTVSS | 3131 AM2-O-17 | VH |

TABLE 8-continued

Affinity matured sequences

| Seq ID | Sequence | Name | VH/VL |
|---|---|---|---|
| 264 | DIQMTQSPSSLSASVGDRVTITCRASQSVSSAVAWYQQKPGKAPRLLIY SASSLYSGVPSRFSGSRSGTDFTLTISSLQPEDFATYYCQQYGYHDAGL ITFGQGTKVEIK | 3131 AM2-O-18 | VL |
| 265 | EVQLVESGGGLVQPGGSLRLSCAASGFSLYYSSMHWVRQAPGKGLEWVA SIYSSGGSTSYADSVKGRFTISADTSKNTAYLQMNSLRAEDTAVYYCAR SSFSHGYGWYGLDYWGQGTLVTVSS | 3131 AM2-O-18 | VH |
| 266 | DIQMTQSPSSLSASVGDRVTITCRASQSVSSAVAWYQQKPGKAPRLLIY SASSLYSGVPSRFSGSRSGTDFTLTISSLQPEDFATYYCQQYGYHDAGL ITFGQGTKVEIK | 3131 AM2-O-19 | VL |
| 267 | EVQLVESGGGLVQPGGSLRLSCAASGENLYYSSMHWVRQAPGKGLEWVA SIYSSGDTHYADSVKGRFTISADTSKNTAYLQMNSLRAEDTAVYYCAR SSFSHGYGWYGLDYWGQGTLVTVSS | 3131 AM2-O-19 | VH |
| 268 | DIQMTQSPSSLSASVGDRVTITCRASQSVSSAVAWYQQKPGKAPRLLIY SASSLYSGVPSRFSGSRSGTDFTLTISSLQPEDFATYYCQQYGYHDAGL ITFGQGTKVEIK | 3131 AM2-O-20 | VL |
| 269 | EVQLVESGGGLVQPGGSLRLSCAASGFTLYYSSMHWVRQAPGKGLEWVA SIYSSGDTHYADSVKGRFTISADTSKNTAYLQMNSLRAEDTAVYYCAR SSFSHGYGWYGLDYWGQGTLVTVSS | 3131 AM2-O-20 | VH |
| 270 | DIQMTQSPSSLSASVGDRVTITCRASQSVSSAVAWYQQKPGKAPRLLIY SASSLYSGVPSRFSGSRSGTDFTLTISSLQPEDFATYYCQQYGYHDAGL ITFGQGTKVEIK | 3131 AM2-O-21 | VL |
| 271 | EVQLVESGGGLVQPGGSLRLSCAASGFDLYYSSMHWVRQAPGKGLEWVA SIYSSGDTHYADSVKGRFTISADTSKNTAYLQMNSLRAEDTAVYYCAR SSFSHGYGWYGLDYWGQGTLVTVSS | 3131 AM2-O-21 | VH |
| 272 | DIQMTQSPSSLSASVGDRVTITCRASQSVSSAVAWYQQKPGKAPRLLIY SASSLYSGVPSRFSGSRSGTDFTLTISSLQPEDFATYYCQQYGYHDAGL ITFGQGTKVEIK | 3131 AM2-O-22 | VL |
| 273 | EVQLVESGGGLVQPGGSLRLSCAASGFSLYYSSMHWVRQAPGKGLEWVA SIYSSGDTHYADSVKGRFTISADTSKNTAYLQMNSLRAEDTAVYYCAR SSFSHGYGWYGLDYWGQGTLVTVSS | 3131 AM2-O-22 | VH |
| 274 | DIQMTQSPSSLSASVGDRVTITCRASQSVSSAVAWYQQKPGKAPRLLIY GASSLYSGVPSRFSGSRSGTDFTLTISSLQPEDFATYYCQQYGYHDAGL ITFGQGTKVEIK | 3131 AM2-O-23 | VL |
| 275 | EVQLVESGGGLVQPGGSLRLSCAASGFNLYYSSMHWVRQAPGKGLEWVA SIYSSGGSTSYADSVKGRFTISADTSKNTAYLQMNSLRAEDTAVYYCAR SSFSHGYGWYGLDYWGQGTLVTVSS | 3131 AM2-O-23 | VH |
| 276 | DIQMTQSPSSLSASVGDRVTITCRASQSVSSAVAWYQQKPGKAPRLLIY GASSLYSGVPSRFSGSRSGTDFTLTISSLQPEDFATYYCQQYGYHDAGL ITFGQGTKVEIK | 3131 AM2-O-24 | VL |
| 277 | EVQLVESGGGLVQPGGSLRLSCAASGFTLYYSSMHWVRQAPGKGLEWVA SIYSSGGSTSYADSVKGRFTISADTSKNTAYLQMNSLRAEDTAVYYCAR SSFSHGYGWYGLDYWGQGTLVTVSS | 3131 AM2-O-24 | VH |
| 278 | DIQMTQSPSSLSASVGDRVTITCRASQSVSSAVAWYQQKPGKAPRLLIY GASSLYSGVPSRFSGSRSGTDFTLTISSLQPEDFATYYCQQYGYHDAGL ITFGQGTKVEIK | 3131 AM2-O-25 | VL |
| 279 | EVQLVESGGGLVQPGGSLRLSCAASGFDLYYSSMHWVRQAPGKGLEWVA SIYSSGGSTSYADSVKGRFTISADTSKNTAYLQMNSLRAEDTAVYYCAR SSFSHGYGWYGLDYWGQGTLVTVSS | 3131 AM2-O-25 | VH |
| 280 | DIQMTQSPSSLSASVGDRVTITCRASQSVSSAVAWYQQKPGKAPRLLIY GASSLYSGVPSRFSGSRSGTDFTLTISSLQPEDFATYYCQQYGYHDAGL ITFGQGTKVEIK | 3131 AM2-O-26 | VL |
| 281 | EVQLVESGGGLVQPGGSLRLSCAASGFSLYYSSMHWVRQAPGKGLEWVA SIYSSGGSTSYADSVKGRFTISADTSKNTAYLQMNSLRAEDTAVYYCAR SSFSHGYGWYGLDYWGQGTLVTVSS | 3131 AM2-O-26 | VH |
| 282 | DIQMTQSPSSLSASVGDRVTITCRASQSVSSAVAWYQQKPGKAPRLLIY GASSLYSGVPSRFSGSRSGTDFTLTISSLQPEDFATYYCQQYGYHDAGL ITFGQGTKVEIK | 3131 AM2-O-27 | VL |

TABLE 8-continued

Affinity matured sequences

| Seq ID | Sequence | Name | VH/VL |
|---|---|---|---|
| 283 | EVQLVESGGGLVQPGGSLRLSCAASGFNLYYSSMHWVRQAPGKGLEWVA SIYSSSGDTHYADSVKGRFTISADTSKNTAYLQMNSLRAEDTAVYYCAR SSFSHGYGWYGLDYWGQGTLVTSS | 3131 AM2-O-27 | VH |
| 284 | DIQMTQSPSSLSASVGDRVTITCRASQSVSSAVAWYQQKPGKAPRLLIY GASSLYSGVPSRFSGSRSGTDFTLTISSLQPEDFATYYCQQYGYHDAGL ITFGQGTKVEIK | 3131 AM2-O-28 | VL |
| 285 | EVQLVESGGGLVQPGGSLRLSCAASGFTLYYSSMHWVRQAPGKGLEWVA SIYSSSGDTHYADSVKGRFTISADTSKNTAYLQMNSLRAEDTAVYYCAR SSFSHGYGWYGLDYWGQGTLVTSS | 3131 AM2-O-28 | VH |
| 286 | DIQMTQSPSSLSASVGDRVTITCRASQSVSSAVAWYQQKPGKAPRLLIY GASSLYSGVPSRFSGSRSGTDFTLTISSLQPEDFATYYCQQYGYHDAGL ITFGQGTKVEIK | 3131 AM2-O-29 | VL |
| 287 | EVQLVESGGGLVQPGGSLRLSCAASGFDLYYSSMHWVRQAPGKGLEWVA SIYSSSGDTHYADSVKGRFTISADTSKNTAYLQMNSLRAEDTAVYYCAR SSFSHGYGWYGLDYWGQGTLVTSS | 3131 AM2-O-29 | VH |
| 288 | DIQMTQSPSSLSASVGDRVTITCRASQSVSSAVAWYQQKPGKAPRLLIY GASSLYSGVPSRFSGSRSGTDFTLTISSLQPEDFATYYCQQYGYHDAGL ITFGQGTKVEIK | 3131 AM2-O-30 | VL |
| 289 | EVQLVESGGGLVQPGGSLRLSCAASGFSLYYSSMHWVRQAPGKGLEWVA SIYSSSGDTHYADSVKGRFTISADTSKNTAYLQMNSLRAEDTAVYYCAR SSFSHGYGWYGLDYWGQGTLVTSS | 3131 AM2-O-30 | VH |
| 290 | DIQMTQSPSSLSASVGDRVTITCRASQSVSSAVAWYQQKPGKAPRLLIY SASSLYSGVPSRFSGSRSGTDFTLTISSLQPEDFATYYCQQYGYHGAGL ITFGQGTKVEIK | 3131 AM2-O-31 | VL |
| 291 | EVQLVESGGGLVQPGGSLRLSCAASGENLYYSSMHWVRQAPGKGLEWVA SIYSSGGSTSYADSVKGRFTISADTSKNTAYLQMNSLRAEDTAVYYCAR SSFSHGYGWYGLDYWGQGTLVTSS | 3131 AM2-O-31 | VH |
| 292 | DIQMTQSPSSLSASVGDRVTITCRASQSVSSAVAWYQQKPGKAPRLLIY SASSLYSGVPSRFSGSRSGTDFTLTISSLQPEDFATYYCQQYGYHGAGL ITFGQGTKVEIK | 3131 AM2-O-32 | VL |
| 293 | EVQLVESGGGLVQPGGSLRLSCAASGFTLYYSSMHWVRQAPGKGLEWVA SIYSSGGSTSYADSVKGRFTISADTSKNTAYLQMNSLRAEDTAVYYCAR SSFSHGYGWYGLDYWGQGTLVTSS | 3131 AM2-O-32 | VH |
| 294 | DIQMTQSPSSLSASVGDRVTITCRASQSVSSAVAWYQQKPGKAPRLLIY SASSLYSGVPSRFSGSRSGTDFTLTISSLQPEDFATYYCQQYGYHGAGL ITFGQGTKVEIK | 3131 AM2-O-33 | VL |
| 295 | EVQLVESGGGLVQPGGSLRLSCAASGFDLYYSSMHWVRQAPGKGLEWVA SIYSSGGSTSYADSVKGRFTISADTSKNTAYLQMNSLRAEDTAVYYCAR SSFSHGYGWYGLDYWGQGTLVTSS | 3131 AM2-O-33 | VH |
| 296 | DIQMTQSPSSLSASVGDRVTITCRASQSVSSAVAWYQQKPGKAPRLLIY SASSLYSGVPSRFSGSRSGTDFTLTISSLQPEDFATYYCQQYGYHGAGL ITFGQGTKVEIK | 3131 AM2-O-34 | VL |
| 297 | EVQLVESGGGLVQPGGSLRLSCAASGFSLYYSSMHWVRQAPGKGLEWVA SIYSSGGSTSYADSVKGRFTISADTSKNTAYLQMNSLRAEDTAVYYCAR SSFSHGYGWYGLDYWGQGTLVTSS | 3131 AM2-O-34 | VH |
| 298 | DIQMTQSPSSLSASVGDRVTITCRASQSVSSAVAWYQQKPGKAPRLLIY SASSLYSGVPSRFSGSRSGTDFTLTISSLQPEDFATYYCQQYGYHGAGL ITFGQGTKVEIK | 3131 AM2-O-35 | VL |
| 299 | EVQLVESGGGLVQPGGSLRLSCAASGFNLYYSSMHWVRQAPGKGLEWVA SIYSSSGDTHYADSVKGRFTISADTSKNTAYLQMNSLRAEDTAVYYCAR SSFSHGYGWYGLDYWGQGTLVTSS | 3131 AM2-O-35 | VH |
| 300 | DIQMTQSPSSLSASVGDRVTITCRASQSVSSAVAWYQQKPGKAPRLLIY SASSLYSGVPSRFSGSRSGTDFTLTISSLQPEDFATYYCQQYGYHGAGL ITFGQGTKVEIK | 3131 AM2-O-36 | VL |
| 301 | EVQLVESGGGLVQPGGSLRLSCAASGFTLYYSSMHWVRQAPGKGLEWVA SIYSSSGDTHYADSVKGRFTISADTSKNTAYLQMNSLRAEDTAVYYCAR SSFSHGYGWYGLDYWGQGTLVTSS | 3131 AM2-O-36 | VH |

TABLE 8-continued

Affinity matured sequences

| Seq ID | Sequence | Name | VH/VL |
|---|---|---|---|
| 302 | DIQMTQSPSSLSASVGDRVTITCRASQSVSSAVAWYQQKPGKAPRLLIY SASSLYSGVPSRFSGSRSGTDFTLTISSLQPEDFATYYCQQYGYHGAGL ITFGQGTKVEIK | 3131 AM2-O-37 | VL |
| 303 | EVQLVESGGGLVQPGGSLRLSCAASGFDLYYSSMHWVRQAPGKGLEWVA SIYSSSGDTHYADSVKGRFTISADTSKNTAYLQMNSLRAEDTAVYYCAR SSFSHGYGWYGLDYWGQGTLVTVSS | 3131 AM2-O-37 | VH |
| 304 | DIQMTQSPSSLSASVGDRVTITCRASQSVSSAVAWYQQKPGKAPRLLIY SASSLYSGVPSRFSGSRSGTDFTLTISSLQPEDFATYYCQQYGYHGAGL ITFGQGTKVEIK | 3131 AM2-O-38 | VL |
| 305 | EVQLVESGGGLVQPGGSLRLSCAASGFSLYYSSMHWVRQAPGKGLEWVA SIYSSSGDTHYADSVKGRFTISADTSKNTAYLQMNSLRAEDTAVYYCAR SSFSHGYGWYGLDYWGQGTLVTVSS | 3131 AM2-O-38 | VH |
| 306 | DIQMTQSPSSLSASVGDRVTITCRASQSVSSAVAWYQQKPGKAPRLLIY GASSLYSGVPSRFSGSRSGTDFTLTISSLQPEDFATYYCQQYGYHGAGL ITFGQGTKVEIK | 3131 AM2-O-39 | VL |
| 307 | EVQLVESGGGLVQPGGSLRLSCAASGFNLYYSSMHWVRQAPGKGLEWVA SIYSSGGSTSYADSVKGRFTISADTSKNTAYLQMNSLRAEDTAVYYCAR SSFSHGYGWYGLDYWGQGTLVTVSS | 3131 AM2-O-39 | VH |
| 308 | DIQMTQSPSSLSASVGDRVTITCRASQSVSSAVAWYQQKPGKAPRLLIY GASSLYSGVPSRFSGSRSGTDFTLTISSLQPEDFATYYCQQYGYHGAGL ITFGQGTKVEIK | 3131 AM2-O-40 | VL |
| 309 | EVQLVESGGGLVQPGGSLRLSCAASGFTLYYSSMHWVRQAPGKGLEWVA SIYSSGGSTSYADSVKGRFTISADTSKNTAYLQMNSLRAEDTAVYYCAR SSFSHGYGWYGLDYWGQGTLVTVSS | 3131 AM2-O-40 | VH |
| 310 | DIQMTQSPSSLSASVGDRVTITCRASQSVSSAVAWYQQKPGKAPRLLIY GASSLYSGVPSRFSGSRSGTDFTLTISSLQPEDFATYYCQQYGYHGAGL ITFGQGTKVEIK | 3131 AM2-O-41 | VL |
| 311 | EVQLVESGGGLVQPGGSLRLSCAASGFDLYYSSMHWVRQAPGKGLEWVA SIYSSGGSTSYADSVKGRFTISADTSKNTAYLQMNSLRAEDTAVYYCAR SSFSHGYGWYGLDYWGQGTLVTVSS | 3131 AM2-O-41 | VH |
| 312 | DIQMTQSPSSLSASVGDRVTITCRASQSVSSAVAWYQQKPGKAPRLLIY GASSLYSGVPSRFSGSRSGTDFTLTISSLQPEDFATYYCQQYGYHGAGL ITFGQGTKVEIK | 3131 AM2-O-42 | VL |
| 313 | EVQLVESGGGLVQPGGSLRLSCAASGFSLYYSSMHWVRQAPGKGLEWVA SIYSSGGSTSYADSVKGRFTISADTSKNTAYLQMNSLRAEDTAVYYCAR SSFSHGYGWYGLDYWGQGTLVTVSS | 3131 AM2-O-42 | VH |
| 314 | DIQMTQSPSSLSASVGDRVTITCRASQSVSSAVAWYQQKPGKAPRLLIY GASSLYSGVPSRFSGSRSGTDFTLTISSLQPEDFATYYCQQYGYHGAGL ITFGQGTKVEIK | 3131 AM2-O-43 | VL |
| 315 | EVQLVESGGGLVQPGGSLRLSCAASGFNLYYSSMHWVRQAPGKGLEWVA SIYSSSGDTHYADSVKGRFTISADTSKNTAYLQMNSLRAEDTAVYYCAR SSFSHGYGWYGLDYWGQGTLVTVSS | 3131 AM2-O-43 | VH |
| 316 | DIQMTQSPSSLSASVGDRVTITCRASQSVSSAVAWYQQKPGKAPRLLIY GASSLYSGVPSRFSGSRSGTDFTLTISSLQPEDFATYYCQQYGYHGAGL ITFGQGTKVEIK | 3131 AM2-O-44 | VL |
| 317 | EVQLVESGGGLVQPGGSLRLSCAASGFTLYYSSMHWVRQAPGKGLEWVA SIYSSSGDTHYADSVKGRFTISADTSKNTAYLQMNSLRAEDTAVYYCAR SSFSHGYGWYGLDYWGQGTLVTVSS | 3131 AM2-O-44 | VH |
| 318 | DIQMTQSPSSLSASVGDRVTITCRASQSVSSAVAWYQQKPGKAPRLLIY GASSLYSGVPSRFSGSRSGTDFTLTISSLQPEDFATYYCQQYGYHGAGL ITFGQGTKVEIK | 3131 AM2-O-45 | VL |
| 319 | EVQLVESGGGLVQPGGSLRLSCAASGFDLYYSSMHWVRQAPGKGLEWVA SIYSSSGDTHYADSVKGRFTISADTSKNTAYLQMNSLRAEDTAVYYCAR SSFSHGYGWYGLDYWGQGTLVTVSS | 3131 AM2-O-45 | VH |
| 320 | DIQMTQSPSSLSASVGDRVTITCRASQSVSSAVAWYQQKPGKAPRLLIY GASSLYSGVPSRFSGSRSGTDFTLTISSLQPEDFATYYCQQYGYHGAGL ITFGQGTKVEIK | 3131 AM2-O-46 | VL |

TABLE 8-continued

Affinity matured sequences

| Seq ID | Sequence | Name | VH/VL |
|---|---|---|---|
| 321 | EVQLVESGGGLVQPGGSLRLSCAASGFSLYYSSMHWVRQAPGKGLEWVA SIYSSSGDTHYADSVKGRFTISADTSKNTAYLQMNSLRAEDTAVYYCAR SSFSHGYGWYGLDYWGQGTLVTVSS | 3131 AM2-O-46 | VH |

The CDRs are summarized in Table 9 below.

TABLE 9

CDRs of the affinity matured variants

| Name | CDRL1 (SEQ ID NO:) | | CDRL2 (SEQ ID NO:) | | CDRL3 (SEQ ID NO:) | | CDRH1 (SEQ ID NO:) | | CDRH2 (SEQ ID NO:) | | CDRH3 (SEQ ID NO:) | |
|---|---|---|---|---|---|---|---|---|---|---|---|---|
| AM2-1 | QSVSSA | 45 | SAS | 46 | QQYGYHH AGLIT | 332 | GFNLYYS SM | 74 | SIYSSYG YTY | 95 | ARSSFSH GYGWYGL DY | 117 |
| AM2-2 | QSVSSA | 45 | SAS | 46 | QQYGYHY AGLIT | 47 | GFNLYYS SM | 74 | SIYSSHG RTG | 340 | ARSSFSH GYGWYGL DY | 117 |
| AM2-3 | QSVSSA | 45 | SAS | 46 | QQYGYHY AGLIT | 47 | GFNLYYS SM | 74 | SIYSSSG YTS | 341 | ARSSFSH GYGWYGL DY | 117 |
| AM2-4 | QSVSSA | 45 | SAS | 46 | QQYGYHY AGLIT | 47 | GFNLYYS SM | 74 | SIYSSSG STC | 342 | ARSSFSH GYGWYGL DY | 117 |
| AM2-5 | QSVSSA | 45 | SAS | 46 | QQYGYHY AGLIT | 47 | GFNLYYS SM | 74 | SIYSSSG DTH | 343 | ARSSFSH GYGWYGL DY | 117 |
| AM2-6 | QSVSSA | 45 | SAS | 46 | QQYGYHY AGLIT | 47 | GFNLYYS SM | 74 | SIYSSHG GTN | 344 | ARSSFSH GYGWYGL DY | 117 |
| AM2-7 | QSVSSA | 45 | SAS | 46 | QQYGYHD AGLIT | 333 | GFNLYYS SM | 74 | SIYSSHG GTY | 345 | ARSSFSH GYGWYGL DY | 117 |
| AM2-8 | QSVSSA | 45 | SAS | 46 | QQYGYHY AGLIT | 47 | GFNLYYS SM | 74 | SIYSSNG RTY | 346 | ARSSFSH GYGWYGL DY | 117 |
| AM2-9 | QSVSSA | 45 | SAS | 46 | QQYGYHN AGLIT | 334 | GFNLYYS SM | 74 | SIYSSYG YTY | 95 | ARSSFSH GYGWYGL DY | 117 |
| AM2-10 | QSVSSA | 45 | SAS | 46 | QQYGYHY AGLIT | 47 | GFNLYYS SM | 74 | SIYSSNG NTG | 347 | ARSSFSH GYGWYGL DY | 117 |
| AM2-11 | QSVSSA | 45 | SAS | 46 | QQYGYHY AGLIT | 47 | GFNLYYS SM | 74 | SIYSSNG NTG | 347 | ARSSFSH GYGWYGL DY | 117 |
| AM2-13 | QSVSSA | 45 | SAS | 46 | QQYGYHD AGLIT | 333 | GFNLYYS SM | 74 | SIYSSYG YTY | 95 | ARSSFSH GYGWYGL DY | 117 |
| AM2-14 | QSVSSA | 45 | SAS | 46 | QQYGYHG AGLIT | 335 | GFNLYYS SM | 74 | SIYSSYG YTY | 95 | ARSSFSH GYGWYGL DY | 117 |
| AM2-15 | QSVSSA | 45 | SAS | 46 | QQYGYHY AGLIT | 47 | GFNLYYS SM | 74 | SIYSSSG DTG | 348 | ARSSFSH GYGWYGL DY | 117 |
| AM2-16 | QSVSSA | 45 | STS | 322 | QQYGYHY AGLIT | 47 | GFNLYYS SM | 74 | SIYSSYG YTY | 95 | ARSSFSH GYGWYGL DY | 117 |

TABLE 9-continued

CDRs of the affinity matured variants

| Name | CDRL1 (SEQ ID NO:) | | CDRL2 (SEQ ID NO:) | | CDRL3 (SEQ ID NO:) | | CDRH1 (SEQ ID NO:) | | CDRH2 (SEQ ID NO:) | | CDRH3 (SEQ ID NO:) | |
|---|---|---|---|---|---|---|---|---|---|---|---|---|
| AM2-17 | QSVSSA | 45 | SAS | 46 | QQYGYHYAGLIT | 47 | GFNLYYSM | 74 | SIYSSHGNTD | 349 | ARSSFSHGYGWYGLDY | 117 |
| AM2-18 | QSVSSA | 45 | SAS | 46 | QQYGYHYAGLIT | 47 | GFNLYYSM | 74 | SIYSSGGSTS | 350 | ARSSFSHGYGWYGLDY | 117 |
| AM2-21 | QSVSSA | 45 | SGS | 323 | QQYGYHYAGLIT | 47 | GFNLYYSM | 74 | SIYSSYGYTY | 95 | ARSSFSHGYGWYGLDY | 117 |
| AM2-24 | QSVSSA | 45 | SDS | 324 | QQYGYHYAGLIT | 47 | GFNLYYSM | 74 | SIYSSYGYTY | 95 | ARSSFSHGYGWYGLDY | 117 |
| AM2-25 | QSVSSA | 45 | SAS | 46 | QQYGYHYAGLIT | 47 | GFNLYYSM | 74 | SIYSSYGYTY | 95 | ARSSFSHGYGWYGLDY | 117 |
| AM2-26 | QSVSSA | 45 | SES | 325 | QQYGYHYAGLIT | 47 | GFNLYYSM | 74 | SIYSSYGYTY | 95 | ARSSFSHGYGWYGLDY | 117 |
| AM2-28 | QSVSSA | 45 | SRS | 326 | QQYGYHYAGLIT | 47 | GFNLYYSM | 74 | SIYSSYGYTY | 95 | ARSSFSHGYGWYGLDY | 117 |
| AM2-29 | QSVSSA | 45 | STS | 322 | QQYGYHYAGLIT | 47 | GFNLYYSM | 74 | SIYSSYGYTY | 95 | ARSSFSHGYGWYGLDY | 117 |
| AM2-30 | QSVSSA | 45 | SAS | 46 | QQYGYHYAGLIT | 47 | GFNLYYSM | 74 | SIYSSYGYTY | 95 | ARSSFSHGYGWYGLDY | 117 |
| AM2-31 | QSVSSA | 45 | SES | 325 | QQYGYHYAGLIT | 47 | GFNLYYSM | 74 | SIYSSYGYTY | 95 | ARSSFSHGYGWYGLDY | 117 |
| AM2-32 | QSVSSA | 45 | SSS | 327 | QQYGYHYAGLIT | 47 | GFNLYYSM | 74 | SIYSSYGYTY | 95 | ARSSFSHGYGWYGLDY | 117 |
| AM2-33 | QSVSSA | 45 | SAS | 46 | QQYGYHYAGLIT | 47 | GFNLYYSM | 74 | SIYSSYGHTS | 351 | ARSSFSHGYGWYGLDY | 117 |
| AM2-35 | QSVSSA | 45 | SAS | 46 | QQYGYHSAGLIT | 336 | GFNLYYSM | 74 | SIYSSYGYTY | 95 | ARSSFSHGYGWYGLDY | 117 |
| AM2-36 | QSVSSA | 45 | SAS | 46 | QQYGYHYAGLIT | 47 | GFNLYYSM | 74 | SIYSSSGSTS | 352 | ARSSFSHGYGWYGLDY | 117 |
| AM2-37 | QSVSSA | 45 | SAS | 46 | QQYGYHSAGLIT | 336 | GFNLYYSM | 74 | SIYSSSGSTS | 352 | ARSSFSHGYGWYGLDY | 117 |
| AM2-S-G | QSVSSA | 45 | GAS | 328 | QQYGYHYAGLIT | 47 | GFNLYYSM | 74 | SIYSSYGYTY | 95 | ARSSFSHGYGWYGLDY | 117 |
| AM2-S-T | QSVSSA | 45 | TAS | 329 | QQYGYHYAGLIT | 47 | GFNLYYSM | 74 | SIYSSYGYTY | 95 | ARSSFSHGYGWYGLDY | 117 |
| AM2-S-H | QSVSSA | 45 | HAS | 330 | QQYGYHYAGLIT | 47 | GFNLYYSM | 74 | SIYSSYGYTY | 95 | ARSSFSHGYGWYGLDY | 117 |

TABLE 9-continued

CDRs of the affinity matured variants

| Name | CDRL1 (SEQ ID NO:) | | CDRL2 (SEQ ID NO:) | | CDRL3 (SEQ ID NO:) | | CDRH1 (SEQ ID NO:) | | CDRH2 (SEQ ID NO:) | | CDRH3 (SEQ ID NO:) | |
|---|---|---|---|---|---|---|---|---|---|---|---|---|
| AM2-S-Y | QSVSSA | 45 | YAS | 331 | QQYGYHYAGLIT | 47 | GFNLYYSM | 74 | SIYSSYGYTY | 95 | ARSSFSHGYGWYGLDY | 117 |
| AM2-O-01 | QSVSSA | 45 | SAS | 46 | QQYGYHYAGLIT | 47 | GFTLYYSM | 337 | SIYSSGGSTS | 350 | ARSSFSHGYGWYGLDY | 117 |
| AM2-O-02 | QSVSSA | 45 | SAS | 46 | QQYGYHYAGLIT | 47 | GFDLYYSM | 338 | SIYSSGGSTS | 350 | ARSSFSHGYGWYGLDY | 117 |
| AM2-O-03 | QSVSSA | 45 | SAS | 46 | QQYGYHYAGLIT | 47 | GFSLYYSM | 339 | SIYSSGGSTS | 350 | ARSSFSHGYGWYGLDY | 117 |
| AM2-O-04 | QSVSSA | 45 | SAS | 46 | QQYGYHYAGLIT | 47 | GFTLYYSM | 337 | SIYSSSGDTH | 343 | ARSSFSHGYGWYGLDY | 117 |
| AM2-O-05 | QSVSSA | 45 | SAS | 46 | QQYGYHYAGLIT | 47 | GFDLYYSM | 338 | SIYSSSGDTH | 343 | ARSSFSHGYGWYGLDY | 117 |
| AM2-O-06 | QSVSSA | 45 | SAS | 46 | QQYGYHYAGLIT | 47 | GFSLYYSM | 339 | SIYSSSGDTH | 343 | ARSSFSHGYGWYGLDY | 117 |
| AM2-O-07 | QSVSSA | 45 | GAS | 328 | QQYGYHYAGLIT | 47 | GFNLYYSM | 74 | SIYSSGGSTS | 350 | ARSSFSHGYGWYGLDY | 117 |
| AM2-O-08 | QSVSSA | 45 | GAS | 328 | QQYGYHYAGLIT | 47 | GFTLYYSM | 337 | SIYSSGGSTS | 350 | ARSSFSHGYGWYGLDY | 117 |
| AM2-O-09 | QSVSSA | 45 | GAS | 328 | QQYGYHYAGLIT | 47 | GFDLYYSM | 338 | SIYSSGGSTS | 350 | ARSSFSHGYGWYGLDY | 117 |
| AM2-O-10 | QSVSSA | 45 | GAS | 328 | QQYGYHYAGLIT | 47 | GFSLYYSM | 339 | SIYSSGGSTS | 350 | ARSSFSHGYGWYGLDY | 117 |
| AM2-O-11 | QSVSSA | 45 | GAS | 328 | QQYGYHYAGLIT | 47 | GFNLYYSM | 74 | SIYSSSGDTH | 343 | ARSSFSHGYGWYGLDY | 117 |
| AM2-O-12 | QSVSSA | 45 | GAS | 328 | QQYGYHYAGLIT | 47 | GFTLYYSM | 337 | SIYSSSGDTH | 343 | ARSSFSHGYGWYGLDY | 117 |
| AM2-O-13 | QSVSSA | 45 | GAS | 328 | QQYGYHYAGLIT | 47 | GFDLYYSM | 338 | SIYSSSGDTH | 343 | ARSSFSHGYGWYGLDY | 117 |
| AM2-O-14 | QSVSSA | 45 | GAS | 328 | QQYGYHYAGLIT | 47 | GFSLYYSM | 339 | SIYSSSGDTH | 343 | ARSSFSHGYGWYGLDY | 117 |
| AM2-O-15 | QSVSSA | 45 | SAS | 46 | QQYGYHDAGLIT | 333 | GFNLYYSM | 74 | SIYSSGGSTS | 350 | ARSSFSHGYGWYGLDY | 117 |
| AM2-O-16 | QSVSSA | 45 | SAS | 46 | QQYGYHDAGLIT | 333 | GFTLYYSM | 337 | SIYSSGGSTS | 350 | ARSSFSHGYGWYGLDY | 117 |
| AM2-O-17 | QSVSSA | 45 | SAS | 46 | QQYGYHDAGLIT | 333 | GFDLYYSM | 338 | SIYSSGGSTS | 350 | ARSSFSHGYGWYGLDY | 117 |

TABLE 9-continued

CDRs of the affinity matured variants

| Name | CDRL1 (SEQ ID NO:) | | CDRL2 (SEQ ID NO:) | | CDRL3 (SEQ ID NO:) | | CDRH1 (SEQ ID NO:) | | CDRH2 (SEQ ID NO:) | | CDRH3 (SEQ ID NO:) | |
|---|---|---|---|---|---|---|---|---|---|---|---|---|
| AM2-O-18 | QSVSSA | 45 | SAS | 46 | QQYGYHDAGLIT | 333 | GFSLYYSM | 339 | SIYSSGGSTS | 350 | ARSSFSHGYGWYGLDY | 117 |
| AM2-O-19 | QSVSSA | 45 | SAS | 46 | QQYGYHDAGLIT | 333 | GFNLYYSM | 74 | SIYSSGDTH | 343 | ARSSFSHGYGWYGLDY | 117 |
| AM2-O-20 | QSVSSA | 45 | SAS | 46 | QQYGYHDAGLIT | 333 | GFTLYYSM | 337 | SIYSSGDTH | 343 | ARSSFSHGYGWYGLDY | 117 |
| AM2-O-21 | QSVSSA | 45 | SAS | 46 | QQYGYHDAGLIT | 333 | GFDLYYSM | 338 | SIYSSSGDTH | 343 | ARSSFSHGYGWYGLDY | 117 |
| AM2-O-22 | QSVSSA | 45 | SAS | 46 | QQYGYHDAGLIT | 333 | GFSLYYSM | 339 | SIYSSSGDTH | 343 | ARSSFSHGYGWYGLDY | 117 |
| AM2-O-23 | QSVSSA | 45 | GAS | 328 | QQYGYHDAGLIT | 333 | GFNLYYSM | 74 | SIYSSGGSTS | 350 | ARSSFSHGYGWYGLDY | 117 |
| AM2-O-24 | QSVSSA | 45 | GAS | 328 | QQYGYHDAGLIT | 333 | GFTLYYSM | 337 | SIYSSGGSTS | 350 | ARSSFSHGYGWYGLDY | 117 |
| AM2-O-25 | QSVSSA | 45 | GAS | 328 | QQYGYHDAGLIT | 333 | GFDLYYSM | 338 | SIYSSGGSTS | 350 | ARSSFSHGYGWYGLDY | 117 |
| AM2-O-26 | QSVSSA | 45 | GAS | 328 | QQYGYHDAGLIT | 333 | GFSLYYSM | 339 | SIYSSGGSTS | 350 | ARSSFSHGYGWYGLDY | 117 |
| AM2-O-27 | QSVSSA | 45 | GAS | 328 | QQYGYHDAGLIT | 333 | GFNLYYSM | 74 | SIYSSGGDTH | 343 | ARSSFSHGYGWYGLDY | 117 |
| AM2-O-28 | QSVSSA | 45 | GAS | 328 | QQYGYHDAGLIT | 333 | GFTLYYSM | 337 | SIYSSGGDTH | 343 | ARSSFSHGYGWYGLDY | 117 |
| AM2-O-29 | QSVSSA | 45 | GAS | 328 | QQYGYHDAGLIT | 333 | GFDLYYSM | 338 | SIYSSSGDTH | 343 | ARSSFSHGYGWYGLDY | 117 |
| AM2-O-30 | QSVSSA | 45 | GAS | 328 | QQYGYHDAGLIT | 333 | GFSLYYSM | 339 | SIYSSSGDTH | 343 | ARSSFSHGYGWYGLDY | 117 |
| AM2-O-31 | QSVSSA | 45 | SAS | 46 | QQYGYHGAGLIT | 335 | GFNLYYSM | 74 | SIYSSGGSTS | 350 | ARSSFSHGYGWYGLDY | 117 |
| AM2-O-32 | QSVSSA | 45 | SAS | 46 | QQYGYHGAGLIT | 335 | GFTLYYSM | 337 | SIYSSGGSTS | 350 | ARSSFSHGYGWYGLDY | 117 |
| AM2-O-33 | QSVSSA | 45 | SAS | 46 | QQYGYHGAGLIT | 335 | GFDLYYSM | 338 | SIYSSGGSTS | 350 | ARSSFSHGYGWYGLDY | 117 |
| AM2-O-34 | QSVSSA | 45 | SAS | 46 | QQYGYHGAGLIT | 335 | GFSLYYSM | 339 | SIYSSGGSTS | 350 | ARSSFSHGYGWYGLDY | 117 |

TABLE 9-continued

CDRs of the affinity matured variants

| Name | CDRL1 (SEQ ID NO:) | | CDRL2 (SEQ ID NO:) | | CDRL3 (SEQ ID NO:) | | CDRH1 (SEQ ID NO:) | | CDRH2 (SEQ ID NO:) | | CDRH3 (SEQ ID NO:) | |
|---|---|---|---|---|---|---|---|---|---|---|---|---|
| AM2-O-35 | QSVSSA | 45 | SAS | 46 | QQYGYHGAGLIT | 335 | GFNLYYSSM | 74 | SIYSSSGDTH | 343 | ARSSFSHGYGWYGLDY | 117 |
| AM2-O-36 | QSVSSA | 45 | SAS | 46 | QQYGYHGAGLIT | 335 | GFTLYYSSM | 337 | SIYSSSGDTH | 343 | ARSSFSHGYGWYGLDY | 117 |
| AM2-O-37 | QSVSSA | 45 | SAS | 46 | QQYGYHGAGLIT | 335 | GFDLYYSSM | 338 | SIYSSSGDTH | 343 | ARSSFSHGYGWYGLDY | 117 |
| AM2-O-38 | QSVSSA | 45 | SAS | 46 | QQYGYHGAGLIT | 335 | GFSLYYSSM | 339 | SIYSSSGDTH | 343 | ARSSFSHGYGWYGLDY | 117 |
| AM2-O-39 | QSVSSA | 45 | GAS | 328 | QQYGYHGAGLIT | 335 | GFNLYYSSM | 74 | SIYSSGGSTS | 350 | ARSSFSHGYGWYGLDY | 117 |
| AM2-O-40 | QSVSSA | 45 | GAS | 328 | QQYGYHGAGLIT | 335 | GFTLYYSSM | 337 | SIYSSGGSTS | 350 | ARSSFSHGYGWYGLDY | 117 |
| AM2-O-41 | QSVSSA | 45 | GAS | 328 | QQYGYHGAGLIT | 335 | GFDLYYSSM | 338 | SIYSSGGSTS | 350 | ARSSFSHGYGWYGLDY | 117 |
| AM2-O-42 | QSVSSA | 45 | GAS | 328 | QQYGYHGAGLIT | 335 | GFSLYYSSM | 339 | SIYSSGGSTS | 350 | ARSSFSHGYGWYGLDY | 117 |
| AM2-O-43 | QSVSSA | 45 | GAS | 328 | QQYGYHGAGLIT | 335 | GFNLYYSSM | 74 | SIYSSSGDTH | 343 | ARSSFSHGYGWYGLDY | 117 |
| AM2-O-44 | QSVSSA | 45 | GAS | 328 | QQYGYHGAGLIT | 335 | GFTLYYSSM | 337 | SIYSSSGDTH | 343 | ARSSFSHGYGWYGLDY | 117 |
| AM2-O-45 | QSVSSA | 45 | GAS | 328 | QQYGYHGAGLIT | 335 | GFDLYYSSM | 338 | SIYSSSGDTH | 343 | ARSSFSHGYGWYGLDY | 117 |
| AM2-O-46 | QSVSSA | 45 | GAS | 328 | QQYGYHGAGLIT | 335 | GFSLYYSSM | 339 | SIYSSSGDTH | 343 | ARSSFSHGYGWYGLDY | 117 |

Example 8. Binding Competition Assay of the Affinity Maturated Antibodies

This example assessed the epitopes of the affinity matured antibody variants of Example 7 (AM2) relative to the parent 3131 antibody.

Figure 9:
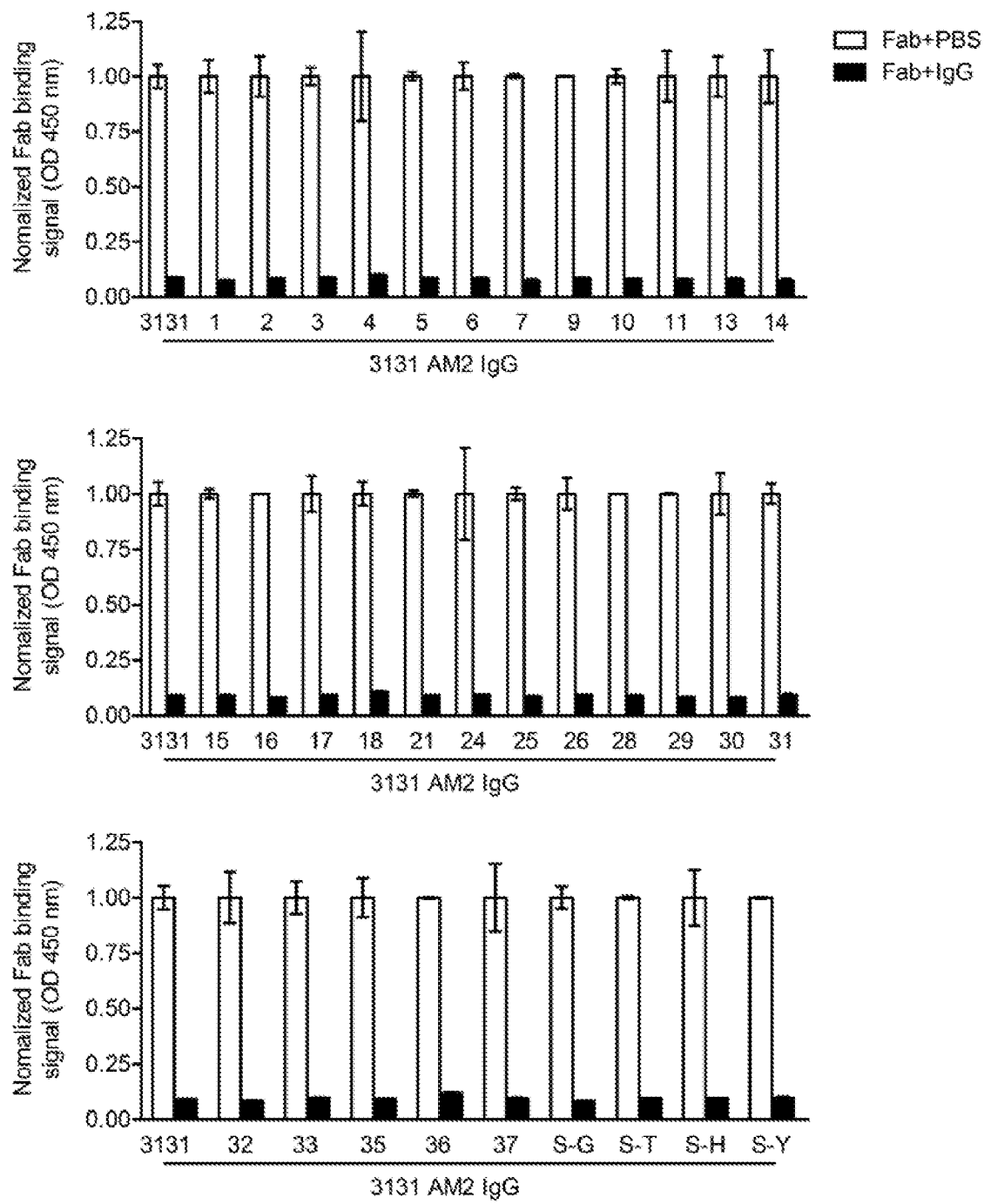
FIG. 9 shows the binding competition results for assessing the epitopes of AM2 antibody variants developed in Example 7 relative to parent 3131 antibody. The binding signals for purified AM2 Fab clones (white bars) to recombinant human IL-18Rb were compared to those obtained in the presence of saturating IgG 3131 (black bars). Fab 3131 was used as a positive control. Error bars represent standard deviation of replicate measurements.

The results are presented in FIG. 9, in which the binding signals for purified AM2 Fab clones (white bars) to recombinant human IL-18Rb were evaluated by ELISA and compared to those obtained in the presence of saturating IgG 3131 (black bars). Fab 3131 was used as a positive control, to observe self-blocking by IgG 3131 (top plot, far left). Error bars represent standard deviation of replicate measurements. The results demonstrate that these affinity matured antibody variants bind to the same epitope as the parent 3131 antibody.

The present disclosure is not to be limited in scope by the specific embodiments described which are intended as single illustrations of individual aspects of the disclosure, and any compositions or methods which are functionally equivalent are within the scope of this disclosure. It will be apparent to those skilled in the art that various modifications and variations can be made in the methods and compositions of the present disclosure without departing from the spirit or scope of the disclosure. Thus, it is intended that the present disclosure cover the modifications and variations of this disclosure provided they come within the scope of the appended claims and their equivalents.

All publications and patent applications mentioned in this specification are herein incorporated by reference to the same extent as if each individual publication or patent application was specifically and individually indicated to be incorporated by reference.

What is claimed is:

1. An antibody or antigen-binding fragment thereof having binding specificity to a human interleukin-18 receptor beta (IL-18Rβ) protein, wherein the antibody or fragment thereof comprises a light chain variable region (VL) comprising light chain complementarity determining regions CDRL1, CDRL2, and CDRL3 and a heavy chain variable region (VH) comprising heavy chain complementarity determining regions CDRH1, CDRH2, and CDRH3, and wherein the CDRL1, CDRL2, CDRL3, CDRH1, CDRH2 and CDRH3 comprise the amino acid sequences of SEQ ID NO:45, 46, 333, 74, 346 and 117, respectively.

2. An antibody or antigen-binding fragment thereof having binding specificity to a human interleukin-18 receptor beta (IL-18Rβ) protein, wherein the antibody or fragment thereof comprises a light chain variable region (VL) comprising light chain complementarity determining regions CDRL1, CDRL2, and CDRL3 and a heavy chain variable region (VH) comprising heavy chain complementarity determining regions CDRH1, CDRH2, and CDRH3, and wherein the CDRL1, CDRL2, CDRL3, CDRH1, CDRH2 and CDRH3 comprise the amino acid sequences of SEQ ID NO:45, 46, 333, 74, 352 and 117, respectively.

3. The antibody or antigen-binding fragment thereof of claim 1, wherein the VL comprises the amino acid sequence of SEQ ID NO:174 and the VH comprises the amino acid sequence of SEQ ID NO:177.

4. The antibody or antigen-binding fragment thereof of claim 2, wherein the VL comprises the amino acid sequence of SEQ ID NO: 174 and the VH comprises the amino acid sequence of SEQ ID NO:219.

5. An antibody or antigen-binding fragment thereof having binding specificity to a human interleukin-18 receptor beta (IL-18Rβ) protein, wherein the antibody or fragment thereof comprises a light chain variable region (VL) comprising light chain complementarity determining regions CDRL1, CDRL2, and CDRL3 and a heavy chain variable region (VH) comprising heavy chain complementarity determining regions CDRH1, CDRH2, and CDRH3, and wherein the CDRL1, CDRL2, CDRL3, CDRH1, CDRH2 and CDRH3 comprise the amino acid sequences of SEQ ID NO: 45, 46, 336, 74, 346 and 117, respectively.

6. The antibody or antigen-binding fragment thereof of claim 5, wherein the VL comprises the amino acid sequence of SEQ ID NO:216 and the VH comprises the amino acid sequence of SEQ ID NO:177.

* * * * *